US012497458B2

(12) United States Patent
Sun et al.

(10) Patent No.: US 12,497,458 B2
(45) Date of Patent: *Dec. 16, 2025

(54) ANTI-GAL3 ANTIBODIES AND USES THEREOF

(71) Applicant: TrueBinding, Inc., Santa Clara, CA (US)

(72) Inventors: Dongxu Sun, Palo Alto, CA (US); Yan Wang, Concord, CA (US); Yinan Wu, San Carlos, CA (US); Catherine A. Gordon, Seattle, WA (US); Samuel A. F. Williams, Burlingame, CA (US)

(73) Assignee: TrueBinding, Inc., Santa Clara, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 17/813,578

(22) Filed: Jul. 19, 2022

(65) Prior Publication Data

US 2022/0380473 A1 Dec. 1, 2022

Related U.S. Application Data

(63) Continuation of application No. 17/384,542, filed on Jul. 23, 2021, now Pat. No. 11,427,638, which is a continuation of application No. PCT/US2020/015692, filed on Jan. 29, 2020.

(60) Provisional application No. 62/798,945, filed on Jan. 30, 2019, provisional application No. 62/798,949, filed on Jan. 30, 2019.

(51) Int. Cl.
*C07K 16/28* (2006.01)
*A61K 39/395* (2006.01)
*A61P 35/00* (2006.01)

(52) U.S. Cl.
CPC ...... *C07K 16/2851* (2013.01); *A61K 39/3955* (2013.01); *A61P 35/00* (2018.01); *C07K 2317/24* (2013.01); *C07K 2317/565* (2013.01)

(58) Field of Classification Search
None
See application file for complete search history.

(56) References Cited

U.S. PATENT DOCUMENTS 4,179,337 A 12/1979 Davis et al.
4,301,144 A 11/1981 Iwashita et al.
4,495,285 A 1/1985 Shimizu et al.
4,496,689 A 1/1985 Mitra
4,609,546 A 9/1986 Hiratani
4,640,835 A 2/1987 Shimizu et al.
4,670,417 A 6/1987 Iwasaki et al.
4,766,106 A 8/1988 Katre et al.
4,791,192 A 12/1988 Nakagawa et al.
5,208,020 A 5/1993 Chari et al.
5,229,275 A 7/1993 Goroff
5,270,202 A 12/1993 Raychaudhuri
5,405,783 A 4/1995 Pirrung et al.
5,416,064 A 5/1995 Chari et al.
5,445,934 A 8/1995 Fodor et al.
5,567,610 A 10/1996 Borrebaeck et al.
5,624,659 A 4/1997 Bigner et al.
5,695,937 A 12/1997 Kinzler et al.
5,928,885 A 7/1999 Nixon et al.
5,936,078 A 8/1999 Kuga et al.
5,948,626 A 9/1999 Hawkins et al.
5,968,797 A 10/1999 Ni et al.
5,969,108 A 10/1999 McCafferty et al.
5,985,660 A 11/1999 Galy
5,994,084 A 11/1999 Anderton et al.
6,087,153 A 7/2000 Greenwald et al.
6,150,584 A 11/2000 Kucherlapati et al.
6,156,311 A 12/2000 Strickland et al.
6,162,963 A 12/2000 Kucherlapati et al.
6,174,708 B1 1/2001 Sodoyer et al.
6,187,287 B1 2/2001 Leung et al.
6,242,421 B1 6/2001 Bowen et al.
6,255,054 B1 7/2001 Hugon et al.
6,303,576 B1 10/2001 Blaschuk et al.
6,562,806 B1 5/2003 Thurston et al.
6,576,607 B1 6/2003 Schachner
6,608,192 B1 8/2003 Thurston et al.
6,677,116 B1 1/2004 Blaschuk et al.
6,716,821 B2 4/2004 Zhao et al.
6,727,075 B2 4/2004 Fitzgerald et al.
6,821,783 B1 11/2004 Comely et al.
6,825,164 B1 11/2004 Stern et al.
6,852,482 B1 2/2005 Chrysler et al.
6,884,869 B2 4/2005 Senter et al.
6,982,089 B2 1/2006 Tobinick et al.
7,014,855 B2 3/2006 Schenk
7,029,860 B2 4/2006 Ota et al.
7,049,311 B1 5/2006 Thurston et al.
7,067,511 B2 6/2006 Thurston et al.
(Continued)

FOREIGN PATENT DOCUMENTS

CN 1957082 5/2007
EP 0 329 400 8/1989
(Continued)

OTHER PUBLICATIONS

US 10,308,710 B2, 06/2019, Grueninger et al. (withdrawn)
(Continued)

*Primary Examiner* — Nora M Rooney
(74) *Attorney, Agent, or Firm* — KNOBBE, MARTENS, OLSON & BEAR LLP

(57) ABSTRACT

Disclosed herein are antibodies that specifically bind to Gal3 and methods of use thereof. In some embodiments, also described herein are methods of inducing immune activation or promoting T cell or Natural Killer cell proliferation with an antibody that specifically binds to Gal3. Also disclosed herein are methods and compositions of reducing fibrosis or propensity thereof in a tissue with antibodies that specifically bind to Gal3. In some cases, the anti-Gal3 antibody also disrupts the interaction between Gal3 and TIM-3.

5 Claims, 64 Drawing Sheets

Specification includes a Sequence Listing.

(56) References Cited

U.S. PATENT DOCUMENTS

| | | | |
|---|---|---|---|
| 7,115,260 | B2 | 10/2006 | Dixit et al. |
| 7,186,681 | B2 | 3/2007 | Liu et al. |
| 7,214,715 | B2 | 5/2007 | Beck et al. |
| 7,244,724 | B2 | 7/2007 | Liu et al. |
| 7,270,818 | B2 | 9/2007 | Averback |
| 7,276,497 | B2 | 10/2007 | Chari et al. |
| 7,409,040 | B2 | 8/2008 | Cyrulnik |
| 7,416,855 | B2 | 8/2008 | He et al. |
| 7,485,712 | B2 | 2/2009 | Mandelkow et al. |
| 7,498,298 | B2 | 3/2009 | Doronina et al. |
| 7,528,126 | B2 | 5/2009 | Howard et al. |
| 7,582,732 | B2 | 9/2009 | Horie et al. |
| 7,611,910 | B2 | 11/2009 | Balin et al. |
| 7,612,062 | B2 | 11/2009 | Gregson et al. |
| 7,659,241 | B2 | 2/2010 | Senter et al. |
| 7,662,816 | B2 | 2/2010 | Cumming et al. |
| 7,700,823 | B2 | 4/2010 | Casas et al. |
| 7,704,924 | B2 | 4/2010 | Thurston et al. |
| 7,732,568 | B2 | 6/2010 | Mattner |
| 7,750,116 | B1 | 7/2010 | Doronina et al. |
| 7,846,679 | B2 | 12/2010 | St. George-Hyslop et al. |
| 7,858,642 | B2 | 12/2010 | John et al. |
| 7,910,590 | B2 | 3/2011 | Huang et al. |
| 7,935,252 | B2 | 5/2011 | Mattner et al. |
| 7,935,348 | B2 | 5/2011 | Mattner et al. |
| 7,951,373 | B2 | 5/2011 | Schachner |
| 7,955,812 | B2 | 6/2011 | Moir et al. |
| 7,964,566 | B2 | 6/2011 | Doronina et al. |
| 7,989,597 | B2 | 8/2011 | Chang et al. |
| 8,008,449 | B2 | 8/2011 | Korman et al. |
| 8,022,180 | B2 | 9/2011 | Mattner et al. |
| 8,034,353 | B2 | 10/2011 | Yano et al. |
| 8,060,179 | B1 | 11/2011 | Flynn |
| 8,105,597 | B2 | 1/2012 | Davies et al. |
| 8,105,839 | B2 | 1/2012 | Urakami et al. |
| 8,163,736 | B2 | 4/2012 | Gauzy et al. |
| 8,168,188 | B1 | 5/2012 | Hoshi et al. |
| 8,173,775 | B2 | 5/2012 | Iwatsubo et al. |
| 8,192,954 | B2 | 6/2012 | Klass et al. |
| 8,222,002 | B2 | 7/2012 | Sugimura et al. |
| 8,232,373 | B2 | 7/2012 | Wang |
| 8,257,740 | B1 | 9/2012 | Sung et al. |
| 8,263,558 | B2 | 9/2012 | Holzman et al. |
| 8,288,352 | B2 | 10/2012 | Doronina et al. |
| 8,318,171 | B2 | 11/2012 | Bush et al. |
| 8,318,687 | B2 | 11/2012 | Tabira et al. |
| 8,323,925 | B2 | 12/2012 | Chakravarthy |
| 8,338,379 | B2 | 12/2012 | Yamaguchi et al. |
| 8,343,493 | B2 | 1/2013 | VanMechelen et al. |
| 8,349,579 | B2 | 1/2013 | Raz et al. |
| 8,357,781 | B2 | 1/2013 | Johnson-Wooed et al. |
| 8,394,380 | B2 | 3/2013 | Manucharyan et al. |
| 8,404,678 | B2 | 3/2013 | Bouchard et al. |
| 8,409,575 | B2 | 4/2013 | Lannfelt et al. |
| 8,426,402 | B2 | 4/2013 | Li et al. |
| 8,481,701 | B2 | 7/2013 | Jarrige et al. |
| 8,487,099 | B2 | 7/2013 | Greenlee et al. |
| 8,501,934 | B2 | 8/2013 | Howard et al. |
| 8,518,975 | B2 | 8/2013 | Aslanian et al. |
| 8,613,920 | B2 | 12/2013 | Lieberburg et al. |
| 8,617,549 | B2 | 12/2013 | Sierks et al. |
| 8,618,123 | B2 | 12/2013 | Sasikumar et al. |
| 8,623,365 | B2 | 1/2014 | Davies et al. |
| 8,633,185 | B2 | 1/2014 | Howard et al. |
| 8,642,044 | B2 | 2/2014 | Schenk et al. |
| 8,663,650 | B2 | 3/2014 | Nicolau et al. |
| 8,664,411 | B2 | 3/2014 | Wu et al. |
| 8,672,857 | B2 | 3/2014 | Muntendam |
| 8,697,688 | B2 | 4/2014 | Howard et al. |
| 8,703,714 | B2 | 4/2014 | Doronina et al. |
| 8,710,193 | B2 | 4/2014 | Irie et al. |
| 8,722,042 | B2 | 5/2014 | Relkin |
| 8,748,386 | B2 | 6/2014 | Sigurdsson |
| 8,764,695 | B2 | 7/2014 | Eliaz |
| 8,778,885 | B2 | 7/2014 | Cashman et al. |
| 8,784,810 | B2 | 7/2014 | Lieberburg et al. |
| 8,796,319 | B2 | 8/2014 | Combs et al. |
| 8,802,667 | B2 | 8/2014 | Li et al. |
| 8,809,010 | B2 | 8/2014 | Hoffmann et al. |
| 8,809,320 | B2 | 8/2014 | Li et al. |
| 8,852,874 | B2 | 10/2014 | Olas et al. |
| 8,871,720 | B2 | 10/2014 | Doronina et al. |
| 8,877,192 | B2 | 11/2014 | Mjalli et al. |
| 8,877,207 | B2 | 11/2014 | Cimini et al. |
| 8,912,145 | B2 | 12/2014 | Terakawa et al. |
| 8,933,295 | B2 | 1/2015 | Jung et al. |
| 8,936,910 | B2 | 1/2015 | Mitsch et al. |
| 8,951,747 | B2 | 2/2015 | Demotte et al. |
| 8,993,833 | B2 | 3/2015 | Colton et al. |
| 9,034,334 | B2 | 5/2015 | Gellerfors et al. |
| 9,066,928 | B1 | 6/2015 | Estus et al. |
| 9,089,614 | B2 | 7/2015 | Lin et al. |
| 9,133,267 | B2 | 9/2015 | Lee et al. |
| 9,163,062 | B2 | 10/2015 | Sarasa Barrio |
| 9,173,928 | B2 | 11/2015 | Matsumoto |
| 9,217,036 | B2 | 12/2015 | Strittmatter et al. |
| 9,234,038 | B2 | 1/2016 | Jung et al. |
| 9,239,333 | B2 | 1/2016 | Snider |
| 9,242,013 | B2 | 1/2016 | Howard et al. |
| 9,295,707 | B2 | 3/2016 | Shashoua |
| 9,320,436 | B2 | 4/2016 | Russmann et al. |
| 9,347,085 | B2 | 5/2016 | Gan et al. |
| 9,382,316 | B2 | 7/2016 | Yoon |
| 9,580,494 | B2 | 2/2017 | Shafer et al. |
| 9,618,511 | B2 | 4/2017 | Querfurth |
| 9,637,552 | B2 | 5/2017 | Cashman et al. |
| 9,645,155 | B2 | 5/2017 | Cai et al. |
| 9,737,505 | B2 | 8/2017 | Denis et al. |
| 9,751,912 | B2 | 9/2017 | Hoshi |
| 9,757,398 | B2 | 9/2017 | Vigo et al. |
| 9,777,056 | B2 | 10/2017 | Sigurdsson et al. |
| 9,790,253 | B2 | 10/2017 | Shair et al. |
| 9,821,114 | B2 | 11/2017 | Cabrera Aquino et al. |
| 9,879,076 | B2 | 1/2018 | Samira et al. |
| 9,903,855 | B2 | 2/2018 | Cheresh et al. |
| 9,907,485 | B2 | 3/2018 | Hartlep et al. |
| 9,921,230 | B2 | 3/2018 | Chodobski et al. |
| 9,933,440 | B2 | 4/2018 | Goetzl |
| 9,937,248 | B2 | 4/2018 | Arya |
| 9,999,624 | B2 | 6/2018 | May et al. |
| 10,011,653 | B2 | 7/2018 | Hayashi et al. |
| 10,028,962 | B2 | 7/2018 | Brodney et al. |
| 10,117,895 | B2 | 11/2018 | Monsonego |
| 10,131,708 | B2 | 11/2018 | Nitsch et al. |
| 10,203,342 | B2 | 2/2019 | Goetzl |
| 10,213,462 | B2 | 2/2019 | Eliaz |
| 10,232,056 | B2 | 3/2019 | Uchida et al. |
| 10,282,349 | B2 | 5/2019 | Jaffee |
| 10,323,084 | B2 | 6/2019 | Hillen et al. |
| 10,358,503 | B2 | 7/2019 | Sigurdsson |
| 10,364,286 | B2 | 7/2019 | Fog et al. |
| 10,377,834 | B2 | 8/2019 | De Strooper et al. |
| 10,393,757 | B2 | 8/2019 | Hashimoto et al. |
| 10,420,923 | B1 | 9/2019 | Katz |
| 10,421,958 | B2 | 9/2019 | Poma et al. |
| 10,472,414 | B2 | 11/2019 | Christensen et al. |
| 10,473,672 | B2 | 11/2019 | Lin et al. |
| 10,532,104 | B2 | 1/2020 | Elmaleh |
| 10,570,196 | B2 | 2/2020 | Ghochikyan et al. |
| 10,654,917 | B2 | 5/2020 | Volker et al. |
| 10,662,226 | B2 | 5/2020 | Nowick et al. |
| 10,662,239 | B2 | 5/2020 | Groves et al. |
| 10,662,246 | B2 | 5/2020 | Wisniewski et al. |
| 10,670,613 | B2 | 6/2020 | Umek et al. |
| 10,718,785 | B2 | 7/2020 | Pike et al. |
| 10,730,937 | B2 | 8/2020 | Okazawa et al. |
| 10,738,107 | B2 | 8/2020 | Gnauer et al. |
| 10,792,349 | B2 | 10/2020 | Jaffee |
| 10,815,230 | B2 | 10/2020 | Pike et al. |
| 10,815,469 | B2 | 10/2020 | Poma et al. |
| 10,822,402 | B2 | 11/2020 | Dengl et al. |
| 10,828,413 | B2 | 11/2020 | Eliaz |
| 10,836,814 | B2 | 11/2020 | Goshima et al. |
| 10,837,966 | B2 | 11/2020 | Hodi et al. |

(56) References Cited

U.S. PATENT DOCUMENTS 10,842,871 B2 11/2020 Ferrero et al.
10,851,156 B2 12/2020 Mercken et al.
10,859,582 B2 12/2020 Sigurdsson et al.
10,874,725 B2 12/2020 Henco et al.
10,888,600 B2 1/2021 Tanzi et al.
10,894,822 B2 1/2021 Chain
10,919,971 B2 2/2021 Collinge et al.
10,934,348 B2 3/2021 Pedersen et al.
10,941,205 B2 3/2021 Duerr et al.
10,941,215 B2 3/2021 Dennis et al.
10,954,306 B2 3/2021 Greenfield et al.
10,976,319 B2 4/2021 Pugia
10,981,989 B2 4/2021 Eisenbach et al.
10,988,528 B2 4/2021 Sigurdsson
11,084,873 B2 8/2021 Shie et al.
11,085,935 B2 8/2021 Barthelemy et al.
11,091,552 B2 8/2021 Fontayne et al.
11,098,106 B2 8/2021 Novák et al.
11,111,290 B2 9/2021 Pedersen et al.
11,135,313 B2 10/2021 Wilson et al.
11,181,533 B2 11/2021 Shi et al.
11,214,835 B1 1/2022 Patel et al.
11,219,627 B2 1/2022 Davis et al.
11,236,155 B2 2/2022 Van et al.
11,278,620 B2 3/2022 Liang et al.
11,286,297 B2 3/2022 Groves et al.
11,312,751 B2 4/2022 Poma et al.
11,319,372 B2 5/2022 Calzone et al.
11,365,223 B2 6/2022 Poma et al.
11,370,833 B2 6/2022 Le et al.
11,389,476 B2 7/2022 Eliaz
11,395,796 B2 7/2022 Romanelli et al.
11,396,553 B2 7/2022 Oostindie et al.
11,413,282 B2 8/2022 Sampath et al.
11,427,638 B2 * 8/2022 Sun .................... A61K 39/3955
11,434,302 B2 9/2022 Raum et al.
11,439,665 B2 9/2022 Yao et al.
11,446,398 B2 9/2022 Barrett et al.
11,459,404 B2 10/2022 Bacac et al.
11,459,405 B2 10/2022 Sasisekharan et al.
11,466,099 B2 10/2022 Garcia et al.
11,471,490 B2 10/2022 Andresen et al.
11,472,858 B2 10/2022 Yao et al.
11,478,554 B2 10/2022 Lerchen et al.
11,505,609 B2 11/2022 Qin et al.
11,512,137 B2 11/2022 Oostindie et al.
11,518,810 B2 12/2022 Song et al.
11,525,007 B2 12/2022 Bruenker et al.
11,535,838 B2 12/2022 Rosenblum et al.
11,583,594 B2 2/2023 Xie
11,584,793 B2 2/2023 Dengl et al.
11,590,128 B2 2/2023 Sampath et al.
11,596,699 B2 3/2023 Fotin-Mleczek
11,597,772 B2 3/2023 Oestergaard et al.
11,603,411 B2 3/2023 Duerr et al.
11,608,369 B2 3/2023 Yao et al.
11,608,376 B2 3/2023 Georges et al.
11,618,778 B2 4/2023 Yao et al.
11,633,430 B2 4/2023 Yao et al.
11,634,486 B2 4/2023 Jefferies et al.
11,654,143 B2 5/2023 Hamdy et al.
11,660,351 B2 5/2023 Lerchen et al.
11,666,642 B2 6/2023 Suri et al.
11,679,127 B2 6/2023 Stubenrauch et al.
11,685,714 B2 6/2023 Lerchen et al.
11,713,358 B2 8/2023 Schellenberger et al.
11,718,680 B2 8/2023 Bacac et al.
11,746,161 B2 9/2023 Chen et al.
11,753,466 B2 9/2023 West et al.
11,768,203 B2 9/2023 Chaudhary
11,771,696 B2 10/2023 Hamdy et al.
11,788,205 B2 10/2023 Klein et al.
11,833,214 B2 12/2023 Hilderbrand et al.
11,857,628 B2 1/2024 Poma et al.
11,866,507 B2 1/2024 Eckelman
11,867,696 B2 1/2024 Schwartz
11,873,332 B2 1/2024 Soto et al.
11,873,342 B2 1/2024 Li et al.
11,891,444 B2 2/2024 Gauthier et al.
11,912,759 B2 2/2024 Liu et al.
11,913,945 B2 2/2024 Schaefer et al.
12,227,567 B2 * 2/2025 Sun ...................... G01N 33/505
2002/0076738 A1 6/2002 Woo
2002/0155513 A1 10/2002 Hsu et al.
2003/0133939 A1 7/2003 Ledbetter et al.
2004/0223971 A1 11/2004 Chang et al.
2005/0032673 A1 2/2005 John et al.
2005/0084915 A1 4/2005 Woo
2005/0158321 A1 7/2005 Hurez et al.
2006/0148712 A1 7/2006 Liu et al.
2006/0240551 A1 10/2006 Jiang
2006/0246496 A1 11/2006 Ahmed et al.
2006/0257359 A1 11/2006 Francois et al.
2006/0257946 A1 11/2006 Ding et al.
2008/0219973 A1 9/2008 Sasaki et al.
2009/0269779 A1 10/2009 Raz et al.
2009/0280116 A1 11/2009 Smith et al.
2009/0311193 A1 12/2009 Mauro et al.
2010/0061992 A1 3/2010 Anderson et al.
2010/0098683 A1 4/2010 Kufe
2010/0104587 A1 4/2010 Chavan et al.
2010/0143954 A1 6/2010 Muntendam
2010/0196882 A1 8/2010 Raz et al.
2010/0330602 A1 12/2010 Van Meir et al.
2011/0038861 A1 2/2011 Rosenthal et al.
2011/0293608 A1 12/2011 Jaffee
2012/0046181 A1 2/2012 Harb et al.
2012/0225114 A1 9/2012 Francois et al.
2012/0253160 A1 10/2012 Mauro et al.
2013/0017998 A1 1/2013 Nishi et al.
2013/0029900 A1 1/2013 Widdison
2013/0029955 A1 1/2013 Muntendam
2013/0045882 A1 2/2013 Klass et al.
2013/0065258 A1 3/2013 Watanabe et al.
2013/0323268 A1 12/2013 Chari et al.
2014/0086836 A1 3/2014 Burnham et al.
2014/0086932 A1 3/2014 Traber
2014/0099254 A1 4/2014 Chang et al.
2014/0105997 A1 4/2014 Eliaz
2014/0235495 A1 8/2014 Pugia
2014/0286970 A1 9/2014 Jeffrey et al.
2014/0294862 A1 10/2014 Chavan et al.
2014/0294868 A1 10/2014 Howard et al.
2014/0370521 A1 12/2014 Porter et al.
2015/0105539 A1 4/2015 Miao et al.
2015/0105540 A1 4/2015 Miao et al.
2015/0150945 A1 6/2015 Francois et al.
2015/0218274 A1 8/2015 Sabatos-Peyton et al.
2015/0301058 A1 10/2015 Schettini et al.
2015/0329636 A1 11/2015 Dennis et al.
2015/0377905 A1 12/2015 Burns et al.
2016/0068577 A1 3/2016 Poma et al.
2016/0166686 A1 6/2016 McNeel et al.
2016/0177284 A1 6/2016 Poma et al.
2016/0199470 A1 7/2016 Chavan et al.
2016/0376328 A1 12/2016 Poma et al.
2017/0002046 A1 1/2017 Poma et al.
2017/0014446 A1 1/2017 Rolke et al.
2017/0056498 A1 3/2017 Krause et al.
2017/0153241 A1 6/2017 Pugia
2017/0275353 A1 9/2017 Sheng et al.
2017/0355756 A1 12/2017 Julien
2017/0363620 A1 12/2017 Beshiri et al.
2017/0363637 A1 12/2017 Takata et al.
2017/0370944 A1 12/2017 Muntendam et al.
2018/0000899 A1 1/2018 Francois et al.
2018/0243432 A1 8/2018 Poma et al.
2018/0256747 A1 9/2018 Hawthorne et al.
2018/0291359 A1 10/2018 Poma et al.
2019/0153044 A1 5/2019 Poma et al.
2019/0175649 A1 6/2019 Novik
2019/0218300 A1 7/2019 Del Rio et al.
2019/0248902 A1 8/2019 Nioi
2019/0265235 A1 8/2019 Schwartz et al.

(56) References Cited

U.S. PATENT DOCUMENTS

| | | | |
|---|---|---|---|
| 2019/0374650 | A1 | 12/2019 | Moon et al. |
| 2020/0024312 | A1 | 1/2020 | Poma et al. |
| 2020/0055938 | A1 | 2/2020 | Desai |
| 2020/0078398 | A1 | 3/2020 | Eliaz |
| 2020/0085866 | A1 | 3/2020 | Eliaz |
| 2020/0085867 | A1 | 3/2020 | Eliaz |
| 2020/0223921 | A1* | 7/2020 | Sun .................. G01N 33/57492 |
| 2021/0001032 | A1 | 1/2021 | Eliaz |
| 2021/0032350 | A1 | 2/2021 | Spriggs et al. |
| 2021/0102948 | A1 | 4/2021 | Hodi et al. |
| 2021/0115123 | A1 | 4/2021 | Sheng et al. |
| 2021/0132067 | A1 | 5/2021 | Schwartz |
| 2021/0177794 | A1 | 6/2021 | Steineger et al. |
| 2021/0246211 | A1 | 8/2021 | Goldberg et al. |
| 2021/0324056 | A1 | 10/2021 | Luthman et al. |
| 2021/0363255 | A1 | 11/2021 | Sun et al. |
| 2021/0371533 | A1 | 12/2021 | Sun et al. |
| 2021/0401985 | A1 | 12/2021 | Biel et al. |
| 2022/0025071 | A1 | 1/2022 | Capon |
| 2022/0040172 | A1 | 2/2022 | Li et al. |
| 2022/0088013 | A1 | 3/2022 | Hamdy et al. |
| 2022/0088195 | A1 | 3/2022 | Klein et al. |
| 2022/0098329 | A1 | 3/2022 | Santich et al. |
| 2022/0125942 | A1 | 4/2022 | Musick et al. |
| 2022/0127366 | A1 | 4/2022 | Fotakis et al. |
| 2022/0133711 | A1 | 5/2022 | Chari et al. |
| 2022/0135678 | A1 | 5/2022 | Chaudhary |
| 2022/0162316 | A1 | 5/2022 | Pandit et al. |
| 2022/0168418 | A1 | 6/2022 | Haefel et al. |
| 2022/0184127 | A1 | 6/2022 | Wang et al. |
| 2022/0195043 | A1 | 6/2022 | Li et al. |
| 2022/0195057 | A1 | 6/2022 | Li et al. |
| 2022/0195071 | A1 | 6/2022 | Jones |
| 2022/0204582 | A1 | 6/2022 | Chaudhary |
| 2022/0211696 | A1 | 7/2022 | Sampath et al. |
| 2022/0211865 | A1 | 7/2022 | Fischer et al. |
| 2022/0226514 | A1 | 7/2022 | Vasiljeva et al. |
| 2022/0233705 | A1 | 7/2022 | Le Scolan et al. |
| 2022/0242936 | A1 | 8/2022 | Feng et al. |
| 2022/0242949 | A1 | 8/2022 | Desnoyers et al. |
| 2022/0244271 | A1 | 8/2022 | Reed et al. |
| 2022/0251231 | A1 | 8/2022 | Oostindie et al. |
| 2022/0257762 | A1 | 8/2022 | Liang et al. |
| 2022/0259306 | A1 | 8/2022 | Duan et al. |
| 2022/0259321 | A1 | 8/2022 | Cascino |
| 2022/0265642 | A1 | 8/2022 | Sampath et al. |
| 2022/0267460 | A1 | 8/2022 | Lansing et al. |
| 2022/0275067 | A1 | 9/2022 | Dolan, III et al. |
| 2022/0281945 | A1 | 9/2022 | Yao et al. |
| 2022/0288123 | A1 | 9/2022 | Yao et al. |
| 2022/0289173 | A1 | 9/2022 | Sun et al. |
| 2022/0289858 | A1 | 9/2022 | Benatuil et al. |
| 2022/0306761 | A1 | 9/2022 | Duerr et al. |
| 2022/0324940 | A1 | 10/2022 | Yao et al. |
| 2022/0332757 | A1 | 10/2022 | Zhang et al. |
| 2022/0340640 | A1 | 10/2022 | Yao et al. |
| 2022/0340677 | A1 | 10/2022 | Zhang et al. |
| 2022/0354938 | A1 | 11/2022 | Poma et al. |
| 2022/0357340 | A1 | 11/2022 | Brady et al. |
| 2022/0370441 | A1 | 11/2022 | Sampath et al. |
| 2022/0372142 | A1 | 11/2022 | Baliga et al. |
| 2022/0372156 | A1 | 11/2022 | Lechner et al. |
| 2022/0380480 | A1 | 12/2022 | Lechner et al. |
| 2022/0389116 | A1 | 12/2022 | Klein et al. |
| 2022/0389449 | A1 | 12/2022 | Paul et al. |
| 2022/0396632 | A1 | 12/2022 | Novobrantseva et al. |
| 2022/0402998 | A1 | 12/2022 | Liu et al. |
| 2022/0403001 | A1 | 12/2022 | Suri et al. |
| 2022/0403027 | A1 | 12/2022 | Ast et al. |
| 2022/0411514 | A1 | 12/2022 | Sun et al. |
| 2023/0036181 | A1 | 2/2023 | Sun et al. |
| 2023/0039927 | A1 | 2/2023 | Cascino |
| 2023/0046007 | A1 | 2/2023 | Bauer et al. |
| 2023/0048390 | A1 | 2/2023 | Liebowitz |
| 2023/0052521 | A1 | 2/2023 | Bacac et al. |
| 2023/0074330 | A1 | 3/2023 | Suri et al. |
| 2023/0074657 | A1 | 3/2023 | Song et al. |
| 2023/0081117 | A1 | 3/2023 | Oakes et al. |
| 2023/0082273 | A1 | 3/2023 | Song et al. |
| 2023/0084763 | A1 | 3/2023 | Chen et al. |
| 2023/0091653 | A1 | 3/2023 | Bindman et al. |
| 2023/0094463 | A1 | 3/2023 | Sun et al. |
| 2023/0094471 | A1 | 3/2023 | Chari et al. |
| 2023/0099756 | A1 | 3/2023 | Hirata et al. |
| 2023/0103667 | A1 | 4/2023 | Muntendam et al. |
| 2023/0104705 | A1 | 4/2023 | Yao et al. |
| 2023/0107479 | A1 | 4/2023 | Muntendam |
| 2023/0121775 | A1 | 4/2023 | Schellenberger et al. |
| 2023/0140802 | A1 | 5/2023 | Chaudhary |
| 2023/0151104 | A1 | 5/2023 | Yan et al. |
| 2023/0190638 | A1 | 6/2023 | Romanelli et al. |
| 2023/0192884 | A1 | 6/2023 | Raum et al. |
| 2023/0192898 | A1 | 6/2023 | Zhou et al. |
| 2023/0197278 | A1 | 6/2023 | Griffin et al. |
| 2023/0201364 | A1 | 6/2023 | Pattabiraman et al. |
| 2023/0201365 | A1 | 6/2023 | Kreft et al. |
| 2023/0203117 | A1 | 6/2023 | Gorby et al. |
| 2023/0203169 | A1 | 6/2023 | Qin et al. |
| 2023/0203199 | A1 | 6/2023 | Wei et al. |
| 2023/0203467 | A1 | 6/2023 | Rosenblum et al. |
| 2023/0203532 | A1 | 6/2023 | Ilkow et al. |
| 2023/0212255 | A1 | 7/2023 | Yao et al. |
| 2023/0212303 | A1 | 7/2023 | Umana et al. |
| 2023/0212319 | A1 | 7/2023 | Chaudhary |
| 2023/0220071 | A1 | 7/2023 | Dengl et al. |
| 2023/0220113 | A1 | 7/2023 | Garcia et al. |
| 2023/0220115 | A1 | 7/2023 | Capon |
| 2023/0220116 | A1 | 7/2023 | Capon |
| 2023/0221333 | A1 | 7/2023 | Sandoval et al. |
| 2023/0226045 | A1 | 7/2023 | Sampath et al. |
| 2023/0227553 | A1 | 7/2023 | Wei et al. |
| 2023/0235075 | A1 | 7/2023 | Chen et al. |
| 2023/0235092 | A1 | 7/2023 | Wei et al. |
| 2023/0242613 | A1 | 8/2023 | Yao et al. |
| 2023/0255959 | A1 | 8/2023 | Sampath et al. |
| 2023/0256092 | A1 | 8/2023 | Tanaka et al. |
| 2023/0265204 | A1 | 8/2023 | Shao |
| 2023/0270875 | A1 | 8/2023 | Hirata et al. |
| 2023/0272092 | A1 | 8/2023 | Paller et al. |
| 2023/0279120 | A1 | 9/2023 | Sun et al. |
| 2023/0285588 | A1 | 9/2023 | Shahar et al. |
| 2023/0287040 | A1 | 9/2023 | Schellenberger et al. |
| 2023/0287118 | A1 | 9/2023 | Ast et al. |
| 2023/0295327 | A1 | 9/2023 | Lee et al. |
| 2023/0295334 | A1 | 9/2023 | Schellenberger et al. |
| 2023/0295336 | A1 | 9/2023 | Eckelman et al. |
| 2023/0322935 | A1 | 10/2023 | Chen et al. |
| 2023/0322950 | A1 | 10/2023 | Darowski et al. |
| 2023/0324389 | A1 | 10/2023 | Schellenberger et al. |
| 2023/0331839 | A1 | 10/2023 | Jefferies et al. |
| 2023/0338559 | A1 | 10/2023 | Lerchen et al. |
| 2023/0340155 | A1 | 10/2023 | Chen et al. |
| 2023/0340160 | A1 | 10/2023 | Ast et al. |
| 2023/0348600 | A1 | 11/2023 | Timmer et al. |
| 2023/0348611 | A1 | 11/2023 | Oestergaard |
| 2023/0348612 | A1 | 11/2023 | Lin et al. |
| 2023/0348628 | A1 | 11/2023 | Meux et al. |
| 2023/0348995 | A1 | 11/2023 | Paulson et al. |
| 2023/0357431 | A1 | 11/2023 | Darowski et al. |
| 2023/0365705 | A1 | 11/2023 | Chen et al. |
| 2023/0366884 | A1 | 11/2023 | Zettl et al. |
| 2023/0372479 | A1 | 11/2023 | Bacac et al. |
| 2023/0381321 | A1 | 11/2023 | Lyski et al. |
| 2023/0390338 | A1 | 12/2023 | Stubenrauch et al. |
| 2023/0399414 | A1 | 12/2023 | Oostindie et al. |
| 2023/0406930 | A1 | 12/2023 | Ji et al. |
| 2023/0414750 | A1 | 12/2023 | Filippou-Frye et al. |
| 2023/0416365 | A1 | 12/2023 | Georges et al. |
| 2023/0416412 | A1 | 12/2023 | Leclercq-Cohen et al. |
| 2024/0000776 | A1 | 1/2024 | Sampath et al. |
| 2024/0002546 | A1 | 1/2024 | Codarri et al. |
| 2024/0018204 | A1 | 1/2024 | Kim et al. |
| 2024/0018260 | A1 | 1/2024 | Schellenberger et al. |
| 2024/0026009 | A1 | 1/2024 | Spriggs et al. |

(56) References Cited

U.S. PATENT DOCUMENTS

| | | | |
|---|---|---|---|
| 2024/0033351 A1 | 2/2024 | Brunetta | |
| 2024/0043379 A1 | 2/2024 | Lerchen et al. | |
| 2024/0043535 A1 | 2/2024 | Amann et al. | |
| 2024/0043554 A1 | 2/2024 | Maller et al. | |
| 2024/0050562 A1 | 2/2024 | Fujimura et al. | |
| 2024/0058443 A1 | 2/2024 | Haegel et al. | |
| 2024/0059785 A1 | 2/2024 | Liu et al. | |
| 2024/0059798 A1 | 2/2024 | Xu et al. | |
| 2024/0158512 A1 | 5/2024 | Sun et al. | |
| 2024/0182564 A1 | 6/2024 | Sun et al. | |
| 2024/0352131 A1 | 10/2024 | Sun et al. | |
| 2025/0145722 A1 | 5/2025 | Sun et al. | |
| 2025/0171539 A1 | 5/2025 | Sun et al. | |

FOREIGN PATENT DOCUMENTS

| | | |
|---|---|---|
| EP | 0 404 097 | 12/1990 |
| EP | 1 074 634 B1 | 2/2001 |
| EP | 0 651 809 B1 | 12/2001 |
| EP | 0 728 215 B1 | 2/2002 |
| EP | 0 817 969 B1 | 7/2002 |
| EP | 0 935 457 B1 | 1/2004 |
| EP | 0 610 254 B1 | 9/2004 |
| EP | 0 783 523 B1 | 10/2004 |
| EP | 0 792 458 B1 | 10/2004 |
| EP | 1 221 480 B1 | 5/2005 |
| EP | 0 846 171 B1 | 9/2005 |
| EP | 1 156 811 B1 | 12/2005 |
| EP | 1 490 692 B1 | 1/2006 |
| EP | 0 699 755 | 3/2006 |
| EP | 1 104 307 B1 | 6/2006 |
| EP | 0 909 316 B1 | 8/2006 |
| EP | 0 890 105 B1 | 11/2006 |
| EP | 1 481 007 B1 | 1/2007 |
| EP | 1 161 524 B1 | 2/2007 |
| EP | 1 172 377 B1 | 4/2007 |
| EP | 1 697 370 B1 | 4/2007 |
| EP | 0 970 203 B1 | 5/2007 |
| EP | 1 379 546 B1 | 6/2007 |
| EP | 1 402 034 B1 | 6/2007 |
| EP | 1 485 410 B1 | 6/2007 |
| EP | 1 392 728 B1 | 8/2007 |
| EP | 1 516 189 B1 | 11/2007 |
| EP | 1 385 531 B1 | 5/2008 |
| EP | 1 781 644 B1 | 5/2008 |
| EP | 1 617 849 B1 | 6/2008 |
| EP | 0 932 674 B1 | 7/2008 |
| EP | 1 379 882 B1 | 7/2008 |
| EP | 1 521 774 B1 | 8/2008 |
| EP | 1 353 691 B1 | 1/2009 |
| EP | 1 476 757 B1 | 1/2009 |
| EP | 1 590 673 B1 | 4/2009 |
| EP | 1 623 719 B1 | 7/2009 |
| EP | 0 911 390 B1 | 8/2009 |
| EP | 0 966 533 B1 | 9/2009 |
| EP | 1 891 215 B1 | 10/2009 |
| EP | 1 497 661 B1 | 11/2009 |
| EP | 1 721 008 B1 | 2/2010 |
| EP | 1 180 938 B1 | 3/2010 |
| EP | 1 355 949 B1 | 3/2010 |
| EP | 1 797 123 B1 | 3/2010 |
| EP | 1 255 824 B1 | 4/2010 |
| EP | 1 423 704 B1 | 4/2010 |
| EP | 0 996 463 B1 | 5/2010 |
| EP | 1 596 809 B1 | 5/2010 |
| EP | 1 896 430 B1 | 11/2010 |
| EP | 1 891 241 B1 | 1/2011 |
| EP | 1 524 994 B1 | 4/2011 |
| EP | 1 404 710 B1 | 6/2011 |
| EP | 1 879 613 B1 | 11/2011 |
| EP | 1 885 886 B1 | 11/2011 |
| EP | 1 636 268 | 2/2012 |
| EP | 1 480 666 B1 | 6/2012 |
| EP | 1 554 311 B1 | 6/2012 |
| EP | 2 140 247 B1 | 6/2012 |
| EP | 1 838 854 B1 | 10/2012 |
| EP | 2 297 196 B1 | 11/2012 |
| EP | 1 842 859 B1 | 1/2013 |
| EP | 2 185 592 B1 | 1/2013 |
| EP | 1 765 388 B1 | 4/2013 |
| EP | 2 240 602 B1 | 5/2013 |
| EP | 2 356 996 B1 | 6/2013 |
| EP | 2 380 583 B1 | 8/2013 |
| EP | 1 776 591 B1 | 10/2013 |
| EP | 2 165 714 B1 | 10/2013 |
| EP | 2 345 411 B1 | 10/2013 |
| EP | 1 670 943 B1 | 11/2013 |
| EP | 2 207 885 B1 | 11/2013 |
| EP | 2 364 719 B1 | 11/2013 |
| EP | 1 976 877 B1 | 1/2014 |
| EP | 2 423 311 B1 | 1/2014 |
| EP | 1 937 720 B1 | 4/2014 |
| EP | 2 182 983 B1 | 5/2014 |
| EP | 2 379 563 B1 | 7/2014 |
| EP | 1 678 505 B1 | 8/2014 |
| EP | 1 891 234 B1 | 12/2014 |
| EP | 2 354 795 B1 | 12/2014 |
| EP | 1 669 085 B1 | 1/2015 |
| EP | 2 365 976 B1 | 4/2015 |
| EP | 1 594 969 B1 | 5/2015 |
| EP | 1 781 703 B1 | 5/2015 |
| EP | 2 441 847 B1 | 9/2015 |
| EP | 1 420 032 B2 | 12/2015 |
| EP | 2 262 526 B1 | 12/2015 |
| EP | 2 470 211 B1 | 1/2016 |
| EP | 2 116 556 B1 | 3/2016 |
| EP | 2 500 361 B1 | 3/2016 |
| EP | 2 593 475 B1 | 3/2016 |
| EP | 2 470 911 B1 | 4/2016 |
| EP | 2 454 599 B1 | 5/2016 |
| EP | 2 238 160 B1 | 6/2016 |
| EP | 2 330 113 B1 | 6/2016 |
| EP | 1 877 442 B1 | 8/2016 |
| EP | 2 443 149 B1 | 8/2016 |
| EP | 2 104 682 B1 | 9/2016 |
| EP | 2 011 513 B1 | 10/2016 |
| EP | 2 051 734 B1 | 10/2016 |
| EP | 2 842 967 B1 | 11/2016 |
| EP | 2 819 700 B1 | 12/2016 |
| EP | 2 694 124 B1 | 1/2017 |
| EP | 2 550 361 B1 | 2/2017 |
| EP | 2 462 161 B1 | 3/2017 |
| EP | 1 989 308 B1 | 5/2017 |
| EP | 2 207 568 B1 | 5/2017 |
| EP | 2 299 812 B1 | 7/2017 |
| EP | 2 149 584 B1 | 12/2017 |
| EP | 2 828 660 B1 | 12/2017 |
| EP | 2 463 368 B1 | 1/2018 |
| EP | 2 788 761 B1 | 2/2018 |
| EP | 2 740 744 B1 | 3/2018 |
| EP | 3 043 802 B1 | 4/2018 |
| EP | 3 121 277 B1 | 4/2018 |
| EP | 2 514 823 B1 | 5/2018 |
| EP | 2 307 457 B1 | 6/2018 |
| EP | 2 356 144 B1 | 7/2018 |
| EP | 3 050 898 B1 | 8/2018 |
| EP | 3 056 510 B1 | 10/2018 |
| EP | 2 758 077 B1 | 12/2018 |
| EP | 2 802 602 B1 | 3/2019 |
| EP | 2 994 160 B1 | 7/2019 |
| EP | 3 003 356 B1 | 7/2019 |
| EP | 3 066 475 B1 | 7/2019 |
| EP | 3 013 355 B1 | 8/2019 |
| EP | 2 789 695 B1 | 10/2019 |
| EP | 2 834 270 B1 | 10/2019 |
| EP | 2 961 426 B1 | 10/2019 |
| EP | 3 274 010 B1 | 10/2019 |
| EP | 3 269 736 B1 | 11/2019 |
| EP | 3 339 323 B1 | 11/2019 |
| EP | 3 083 680 B1 | 1/2020 |
| EP | 3 164 152 B1 | 2/2020 |
| EP | 3 225 251 B1 | 2/2020 |
| EP | 2 814 963 B1 | 4/2020 |
| EP | 2 224 000 B1 | 5/2020 |

(56) References Cited

FOREIGN PATENT DOCUMENTS

| | | | | |
|---|---|---|---|---|
| EP | 2 831 584 B1 | 6/2020 | | |
| EP | 2 968 548 B1 | 9/2020 | | |
| EP | 3 324 186 B1 | 9/2020 | | |
| EP | 3 221 349 B1 | 11/2020 | | |
| EP | 2 448 968 B1 | 1/2021 | | |
| EP | 3 166 970 B1 | 3/2021 | | |
| EP | 3 436 010 B1 | 3/2021 | | |
| EP | 3 102 230 B1 | 4/2021 | | |
| EP | 3 197 445 B1 | 4/2021 | | |
| EP | 3 281 614 B1 | 6/2021 | | |
| EP | 2 408 807 B1 | 7/2021 | | |
| EP | 3 070 100 B1 | 7/2021 | | |
| EP | 3 353 214 B1 | 8/2021 | | |
| EP | 1 812 062 B1 | 3/2022 | | |
| EP | 4 129 335 A1 | 2/2023 | | |
| EP | 4 176 900 A1 | 5/2023 | | |
| EP | 4 186 926 A1 | 5/2023 | | |
| FR | 2994803 | 3/2014 | | |
| WO | WO 93/011161 | 6/1993 | | |
| WO | WO 94/013804 | 6/1994 | | |
| WO | WO 00/24782 | 5/2000 | | |
| WO | WO 02/026246 A2 | 4/2002 | | |
| WO | WO 05/033144 | 4/2005 | | |
| WO | WO 06/067198 A2 | 6/2006 | | |
| WO | WO 08/068048 | 6/2008 | | |
| WO | WO 08/085564 | 7/2008 | | |
| WO | WO 08/112559 | 9/2008 | | |
| WO | WO 10/005858 A1 | 1/2010 | | |
| WO | WO 10/056722 A1 | 5/2010 | | |
| WO | WO 10/095042 A2 | 8/2010 | | |
| WO | WO 10/147969 A2 | 12/2010 | | |
| WO | WO 13/017891 | 2/2013 | | |
| WO | WO 13/169890 | 11/2013 | | |
| WO | WO 14/140317 | 9/2014 | | |
| WO | WO 15/038426 | 3/2015 | | |
| WO | WO 15/051850 | 4/2015 | | |
| WO | WO 15/052345 | 4/2015 | | |
| WO | WO 15/117002 | 8/2015 | | |
| WO | WO 15/138438 | 9/2015 | | |
| WO | WO 16/004093 | 1/2016 | | |
| WO | WO 16/059453 A1 | 4/2016 | | |
| WO | WO 17/080973 | 5/2017 | | |
| WO | WO 18/058098 A1 | 3/2018 | | |
| WO | WO 18/115003 | 6/2018 | | |
| WO | WO 18/119351 | 7/2018 | | |
| WO | WO 18/129188 | 7/2018 | | |
| WO | WO 18/209276 | 11/2018 | | |
| WO | WO 2019/023247 | 1/2019 | * | A61K 38/17 |
| WO | WO 19/024784 A1 | 2/2019 | | |
| WO | WO 19/028357 | 2/2019 | | |
| WO | WO 19/074840 A1 | 4/2019 | | |
| WO | WO 19/079496 A2 | 4/2019 | | |
| WO | WO 19/084332 A1 | 5/2019 | | |
| WO | WO 19/089080 | 5/2019 | | |
| WO | WO 19/094679 A1 | 5/2019 | | |
| WO | WO 19/134481 A1 | 7/2019 | | |
| WO | WO 19/137922 A1 | 7/2019 | | |
| WO | WO 19/143125 A1 | 7/2019 | | |
| WO | WO 19/150183 A1 | 8/2019 | | |
| WO | WO 19/152895 | 8/2019 | | |
| WO | WO 19/161384 A1 | 8/2019 | | |
| WO | WO 19/165233 | 8/2019 | | |
| WO | WO 19/165240 A1 | 8/2019 | | |
| WO | WO 19/165421 | 8/2019 | | |
| WO | WO 19/168403 A2 | 9/2019 | | |
| WO | WO 19/173795 A2 | 9/2019 | | |
| WO | WO 19/186276 | 10/2019 | | |
| WO | WO 19/191518 A1 | 10/2019 | | |
| WO | WO 19/195621 | 10/2019 | | |
| WO | WO 19/198825 A1 | 10/2019 | | |
| WO | WO 19/207159 A1 | 10/2019 | | |
| WO | WO 19/222441 A1 | 11/2019 | | |
| WO | WO 19/243453 A1 | 12/2019 | | |
| WO | WO 19/246422 A1 | 12/2019 | | |
| WO | WO 20/023530 | 1/2020 | | |
| WO | WO 20/037258 A1 | 2/2020 | | |
| WO | WO 20/045646 A1 | 3/2020 | | |
| WO | WO 20/055975 A1 | 3/2020 | | |
| WO | WO 20/059847 A1 | 3/2020 | | |
| WO | WO 20/069621 A1 | 4/2020 | | |
| WO | WO 20/070225 A1 | 4/2020 | | |
| WO | WO 20/079244 A1 | 4/2020 | | |
| WO | WO 20/084346 A1 | 4/2020 | | |
| WO | WO 20/092107 A1 | 5/2020 | | |
| WO | WO 20/092202 A2 | 5/2020 | | |
| WO | WO 20/112889 | 6/2020 | | |
| WO | WO 20/117560 A1 | 6/2020 | | |
| WO | WO 20/123492 A1 | 6/2020 | | |
| WO | WO 20/138402 A1 | 7/2020 | | |
| WO | WO 20/139960 | 7/2020 | | |
| WO | WO 20/154475 | 7/2020 | | |
| WO | WO 20/163730 A2 | 8/2020 | | |
| WO | WO 20/165453 A1 | 8/2020 | | |
| WO | WO 20/171724 | 8/2020 | | |
| WO | WO 20/172621 | 8/2020 | | |
| WO | WO 20/185676 A1 | 9/2020 | | |
| WO | WO 20/219646 A1 | 10/2020 | | |
| WO | WO 20/219868 A1 | 10/2020 | | |
| WO | WO 20/225799 A2 | 11/2020 | | |
| WO | WO 20/227376 | 11/2020 | | |
| WO | WO 20/257745 A1 | 12/2020 | | |
| WO | WO 20/263862 A1 | 12/2020 | | |
| WO | WO 20/264211 A1 | 12/2020 | | |
| WO | WO 21/002312 A1 | 1/2021 | | |
| WO | WO 21/007110 A1 | 1/2021 | | |
| WO | WO 21/011673 | 1/2021 | | |
| WO | WO 21/012082 A1 | 1/2021 | | |
| WO | WO 21/028590 A1 | 2/2021 | | |
| WO | WO 21/048619 A2 | 3/2021 | | |
| WO | WO 21/055583 A1 | 3/2021 | | |
| WO | WO 21/062361 A2 | 4/2021 | | |
| WO | WO 21/068879 A1 | 4/2021 | | |
| WO | WO 21/071830 A1 | 4/2021 | | |
| WO | WO 21/078942 A1 | 4/2021 | | |
| WO | WO 21/081101 A1 | 4/2021 | | |
| WO | WO 21/084274 A1 | 5/2021 | | |
| WO | WO 21/108809 A1 | 6/2021 | | |
| WO | WO 21/113527 | 6/2021 | | |
| WO | WO 21/146218 | 7/2021 | | |
| WO | WO 21/157634 A1 | 8/2021 | | |
| WO | WO 21/163346 A2 | 8/2021 | | |
| WO | WO 21/163681 A2 | 8/2021 | | |
| WO | WO 21/167723 A1 | 8/2021 | | |
| WO | WO 21/184404 A1 | 9/2021 | | |
| WO | WO 21/186079 A1 | 9/2021 | | |
| WO | WO 21/190558 A1 | 9/2021 | | |
| WO | WO 21/190562 A1 | 9/2021 | | |
| WO | WO 21/195020 | 9/2021 | | |
| WO | WO 21/195770 A1 | 10/2021 | | |
| WO | WO 21/207273 A1 | 10/2021 | | |
| WO | WO 21/207312 | 10/2021 | | |
| WO | WO 21/236809 A2 | 11/2021 | | |
| WO | WO 21/242545 A1 | 12/2021 | | |
| WO | WO 21/242776 | 12/2021 | | |
| WO | WO 21/247217 | 12/2021 | | |
| WO | WO 21/248081 A1 | 12/2021 | | |
| WO | WO 21/256710 A1 | 12/2021 | | |
| WO | WO 21/260193 A1 | 12/2021 | | |
| WO | WO 22/005590 A1 | 1/2022 | | |
| WO | WO 22/026740 A1 | 2/2022 | | |
| WO | WO 22/031342 A1 | 2/2022 | | |
| WO | WO 22/032166 A1 | 2/2022 | | |
| WO | WO 22/060424 A1 | 3/2022 | | |
| WO | WO 22/060488 A1 | 3/2022 | | |
| WO | WO 22/072538 | 4/2022 | | |
| WO | WO 22/150642 | 7/2022 | | |
| WO | WO 22/150644 | 7/2022 | | |
| WO | WO 22/164886 | 8/2022 | | |
| WO | WO 22/178367 | 8/2022 | | |
| WO | WO 22/198232 | 9/2022 | | |
| WO | WO 22/200412 | 9/2022 | | |
| WO | WO 22/200478 | 9/2022 | | |
| WO | WO 22/200525 | 9/2022 | | |
| WO | WO 22/204282 | 9/2022 | | |

(56) References Cited

FOREIGN PATENT DOCUMENTS

| | | |
|---|---|---|
| WO | WO 22/212918 | 10/2022 |
| WO | WO 22/226100 | 10/2022 |
| WO | WO 22/231978 | 11/2022 |
| WO | WO 22/235622 | 11/2022 |
| WO | WO 22/240741 | 11/2022 |
| WO | WO 22/241148 | 11/2022 |
| WO | WO 22/241446 | 11/2022 |
| WO | WO 22/251850 | 12/2022 |
| WO | WO 22/253867 | 12/2022 |
| WO | WO 22/258015 | 12/2022 |
| WO | WO 22/258662 | 12/2022 |
| WO | WO 22/258673 | 12/2022 |
| WO | WO 22/258678 | 12/2022 |
| WO | WO 22/258691 | 12/2022 |
| WO | WO 22/261113 | 12/2022 |
| WO | WO 22/266539 | 12/2022 |
| WO | WO 22/266540 | 12/2022 |
| WO | WO 22/268050 | 12/2022 |
| WO | WO 22/268192 | 12/2022 |
| WO | WO 23/001884 | 1/2023 |
| WO | WO 23/288252 | 1/2023 |
| WO | WO 23/288267 | 1/2023 |
| WO | WO 23/019216 | 2/2023 |
| WO | WO 23/051727 | 4/2023 |
| WO | WO 23/056969 | 4/2023 |
| WO | WO 23/061388 | 4/2023 |
| WO | WO 23/068818 A1 | 4/2023 |
| WO | WO 23/077099 A1 | 5/2023 |
| WO | WO 23/086768 | 5/2023 |
| WO | WO 23/094413 A1 | 6/2023 |
| WO | WO 23/109942 | 6/2023 |
| WO | WO 23/116880 | 6/2023 |
| WO | WO 23/125611 | 7/2023 |
| WO | WO 23/138551 | 7/2023 |
| WO | WO 23/141611 | 7/2023 |
| WO | WO 23/153759 | 8/2023 |
| WO | WO 23/163187 | 8/2023 |
| WO | WO 23/166322 | 9/2023 |
| WO | WO 23/174396 | 9/2023 |
| WO | WO 23/180533 | 9/2023 |
| WO | WO 23/183923 | 9/2023 |
| WO | WO 23/196785 | 10/2023 |
| WO | WO 23/196786 | 10/2023 |
| WO | WO 23/196996 | 10/2023 |
| WO | WO 23/198195 | 10/2023 |
| WO | WO 23/198635 | 10/2023 |
| WO | WO 23/215674 | 11/2023 |
| WO | WO 23/215740 | 11/2023 |
| WO | WO 23/227660 | 11/2023 |
| WO | WO 23/232752 | 12/2023 |
| WO | WO 24/001641 | 1/2024 |
| WO | WO 24/015830 | 1/2024 |
| WO | WO 24/026407 | 2/2024 |
| WO | WO 24/030577 | 2/2024 |
| WO | WO 24/036148 | 2/2024 |
| WO | WO 24/036329 | 2/2024 |
| WO | WO 24/040194 | 2/2024 |

OTHER PUBLICATIONS

US 11,331,347 B2, 05/2022, Yao et al. (withdrawn)
US 11,339,200 B2, 05/2022, Yao et al. (withdrawn)
US 11,732,039 B2, 08/2023, Sun et al. (withdrawn)
Agarwal et al., Jan. 2, 2013, A Pictet-Spengler ligation for protein chemical modification, PNAS, 110(1): 46-51.
Ajjan et al., 2006, Coagulation and atherothrombotic disease, Atherosclerosis, 186:240-259.
Andrade et al., 2009, Rechallenge in drug-induced liver injury: the attractive hazard, Expert Opin. Drug Saf., 8(6):709-714.
Ashraf et al., Jun. 2018, Investigation of Gal-3 expression pattern in serum and cerebrospinal fluid of patients suffering from neurodegenerative disorders, Frontiers in Neuroscience, 12:Article 430, 8 pp.
Axup et al., Oct. 2, 2012, Synthesis of site-specific antibody-drug conjugates using unnatural amino acids, PNAS 109(40):16101-16106.
Baines et al., 1992, Purification of Immunoglobulin G (IgG), in Methods in Molecular Biology, 10:79-104, The Humana Press, Inc., Totowa, NJ.
Balan et al., Dec. 15, 2008, Racial disparity in breast cancer and functional germ line mutation in galectin-3 (rs4644): a pilot study, Cancer Res. 68(24)10045-10050.
Banks et al., Mar. 2007, Outcomes validity and reliability of the modified Rankin scale; implications for stroke clinical trials, Stroke, 38:1091-1096.
Barua et al., 2010, Effects of cigarette smoke exposure on clot dynamics and fibrin structure,: an ex vivo investigation, Arterioscler Thromb Vasc Biol, 30:75-79.
Benjamin et al., Mar. 7, 2017, Heart disease and stroke statistics—2017 update: a report from the American Heart Association, Circulation, 135:e146-e603.
Bio-Techne, Feb. 7, 2018, Human galectin-3 antibody, product description, 1 p.
Bird et al., Oct. 12, 1988, Single-Chain Antigen-Binding Proteins. Science, 242(4877):423-426.
Blanchard et al., 2014, Galectin-3 inhibitors: a patent review (2008-present), Expert Opin. Ther. Patents, 24(10):1053-1065.
Blaney, et al., 2002, Traceless solid-phase organic synthesis, Chem. Rev. 102:2607-2024.
Boza-Serrano et al., Apr. 20, 2019, Galectin-3, a novel endogenous TREM2 ligand, detrimentally regulates inflammatory response in Alzheimer's disease, Acta Neuropathologica, 23 pp.
Brinkmann et al., 2017, The making of bispecific antibodies, MABS, 9(2):182-212.
Brott et al., Jul. 1989, Measurements of acute cerebral infarction: a clinical examination scale, Stroke, 20(7):864-870.
Burguillos et al., Mar. 10, 2015 Microglia-secreted galectin-3 acts as a toll-like receptor 4 ligand and contributes to microglial activation, Cell Reports, 10:1626-1638.
Busby et al., 2016, Systematic comparison of monoclonal versus polyclonal antibodies for mapping histone modifications by ChIP-seq, Epigenetics & Chromatin, 9:49.
Carter et al., Dec. 2007, Heritability of clot formation, morphology, and lysis: the EuroCLOT study, Arterioscler Thromb Vasc Biol, 27:2783-2789.
Carter, May 2006, Potent antibody therapeutics by design. Nat. Rev. Immunol., 6(5):343-357.
Casi et al., 2012, Site-specific traceless coupling of potent cytotoxic drugs to recombinant antibodies for pharmacodelivery, JACS 134(13):5887-5892.
Cedeno-Laurent et al. Dec. 2012, Galectins and their Ligands: Negative Regulators of Anti-Tumor Immunity. Glycoconjugate Journal. 29(8-9):619-625.
Centers for Disease Control and Prevention, 2015, Report to Congress on traumatic braininjury in the United States, epidemiology and rehabilitation, National Center for Injury Prevention and Control; Division of Unintentional Injury Prevention, Atlanta, GA, 72 pp.
Chatal et al., 1985, Clinical prospective study with radioiodinated monoclonal antibodies directed against colorectal cancer, Monoclonal Antibodies for Cancer Detection and Therapy, Baldwin and Byers eds., pp. 159-180, 223-267, Academic Press.
Chistiakov et al., 2017, The role of monocytosis and neutrophilia in atherosclerosis, J. Cell. Mol. Med, XX(X):1-17.
Chothia et al., 1987, Canonical structures for the hypervariable regions of immunoglobulins, J Mol Biol, 196(4):901-917.
Chothia et al., 1989, Conformations of immunoglobulin hypervariable regions, Nature, 342:877-883.
Collet et al., Nov. 2006, Altered fibrin architecture is associated with hypofribinolysis and premature coronary atherothrombosis, Arterioscler Thromb Vasc Biol, 26:2567-2573.
Corrado et al., 2010, An update on the role of markers of inflammation in atherosclerosis, Journal of Atherosclerosis and Thrombosis, 17(1):1-11.
Cortez-Retamozo et al., Apr. 15, 2004, Efficient cancer therapy with a nanobody-based conjugate, Cancer Research, 64:2853-2857.

(56) References Cited

OTHER PUBLICATIONS

Dawson et al., May 14, 1997, Modulation of Reactivity in Native Chemical Ligation through the Use of Thiol Additives, J. Am. Chem. Soc. 119(19):4325-4329.
Dawson et al., Nov. 4, 1994, Synthesis of proteins by native chemical ligation, Science, 266:776-779.
De Pascalis et al., 2002, Grafting of abbreviated complementarity determining regions containing specificity determining residues essential for ligan contact to engineer a less immunogenic humanized monoclonal antibody, Journal of Immunology, 169:3076-3084.
Donkor, 2018, Stroke in the 21st century: a snapshot of the burden, epidemiology, and quality of life, Stroke Research and Treatment, vol. 2018, article ID 3238165, 10 pp.
Dunn et al., 2005, The influence of type 2 diabetes on fibrin structure and function, Diabetologia, 48:1198-1206.
Dunn et al., 2006, Molecular mechanisms involved in the resistance of fibrin to clot lysis by plasmin in subjects with type 2 diabetes mellitus, Diabetologia, 49:1071-1080.
Ebrahim et al., Sep. 2014, Galectins in cancer: carcinogenesis, diagnosis and therapy, Annals of Translational Medicine, 2(9):88.
Edwards et al., 2003, The remarkable flexibility of the human antibody repertoire, isolation of over one thousand different antibodies to a single protein, BLyS, J. Mol Biol., 334:103-118.
Fang et al., Sep. 2010, Trends in thrombolytic use for ischemic stroke in the United States, Journal of Hospital Medicine, 5(7):406-409.
Fatkhullina et al., 2016, The role of cytokines in the development of atherosclerosis, Biochemistry (Moscow), 81(11):1358-1370.
Fredericks et al., 2004, Identification of potent human anti-IUL-IR1, antagonist antibodies, Protein Engineering, Design & Selection, 17(1):95-106.
Freynhofer et al., 2012, The role of platelets in athero-thrombotic events, Current Pharmaceutical Design, 18:5197-5214.
Fugl-Meyer et al., 1975, The post-stroke hemiplegic patient, Scand J. Rehab Med, 7:13-31.
George et al., Aug. 2020, Pulmonary fibrosis and COVID-19: the potential role for antifibrotic therapy, The Lancet, 8:807-815.
Glaser et al., Oct. 15, 1992, Dissection of the combining site in a humanized anti-tax antibody, J. Immunol. 149:2607-2614.
Go et al., Jan. 21, 2014, Heart disease and stroke statistics—2014 update: a report from the American Heart Association, Circulation, 129:e28-e292.
Goel et al., 2004, Plasticity within the antigen-combing in site may manifest as molecular mimicry in the humoral immune response, The Journal of Immunology, pp. 7358-7367.
Goldstein et al., Jun. 1989, Interrater reliability of the NIH stroke scale, Arch Neurol, 46:660-662.
Goplen et al., Apr. 14, 2020, Tissue-resident CD8+ T cells drive age-associated chronic lung sequelae following viral pneumonia, bioRxiv preprint doi: https://doi/org/10.1101/2020.04.13.041096, 46 pp.
Goulay et al., Nov. 28, 2019, From stroke to dementia: a comprehensive review exposing tight interactions between stroke and amyloid-β formation, Translational Stroke Research, 14 pp.
Green et al., 2005, Free radical trapping as a therapeutic approach to neuroprotection in stroke; experimental and clinical studies with NXY-059 and free radical scavengers, Current Drug Targets: CNS & Neurological Disorders, 4(2):109-118.
Green et al., May 1994, Antigen-specific human monoclonal antibodies from mice engineered with human Ig heavy and light chain YACs. Nat. Genet. 7(1):13-21.
Guha et al., Mar. 26, 2013, Cod glycopeptide with picomolar affinity to galectin-3 suppresses t-cell apoptosis and prostate cancer metastatis, PNAS, 110(13):5052-5057.
Gump et al., 2001, An antibody to p16INK4A recognizes a modified form of galectin-3, Hybridoma, 20(3):167-174.
Hachinski et al., Sep. 2006, National Institute of Neurological Disorders and Stroke—Canadian Stroke Network Vascular Cognitive Impairment Harmonization Standards, Stroke, pp. 2220-2241.
Hackeng et al., Aug. 1999, Protein synthesis by native chemical ligation: Expanded scope by using straightforward methodology., Proc. Natl. Acad. Sci. USA, 96:10068-10073.
Halimi et al., Nov. 2014, Glycan dependence of galectin-3 self-association properties, PLOS one, 9(11):e111836, 9 pp.
Hejesen et al., 2013, A traceless aryl-triazene linker for DNA-directed chemistry, Org Biomol Chem, 11(15):2493-2497.
Holliger et al., Jul. 1993, Diabodies: small bivalent and bispecific antibody fragments. PNAS, 90:6444-6448.
Holliger et al., Sep. 2005, Engineered antibody fragments and the rise of single domains. Nat. Biotechnol. 23(9):1126-1136.
Huang et al., Oct. 2014, CEACAM1 regulates TIM-3-mediated tolerance and exhaustion. Nature. 517(7534):386-390.
Hunt, 2010 Mitochondrial and immunoallergic injury increase risk of positive drug rechallenge after drug-induced liver injury: a systematic review, Hepatology, 52(6):2216-2222.
Huston et al. Aug. 1988, Protein engineering of antibody binding sites: Recovery of specific activity in an anti-digoxin single-chain Fv analogue produced in *Escherichia coli*, PNAS, 85:5879-5883.
Inoue et al., 2021, Current management and therapeutic strategies for cerebral amyloid angiopathy, International Journal of Molecular Sciences, 22:3869.
Jin et al., 2013 Spatial and temporal expression, and statin responsiveness of galectin-1 and galectin-3 in murine atherosclerosis, Korean Circulation Journal, pp. 223-230.
Johnson et al., 2000, Kabat database and its applications: 30 years after the first variability plot, Nucleic Acids Res., 28(1):214-218.
Kang et al. , Jun. 2018, Imaging-based tumor treatment response evaluation: Review of conventional, new and emerging concepts. Korean J. Radiol. 13(4):371-390.
Kanyavus et al., Jun. 2019, Breaking the law: unconventional strategies for antibody diversification, Nature Reviews Immunology, 19:355-368.
Khan et al., 2014, Adjustable Locks and Flexible Keys: Plasticity of Epitope-Paratope Interactions in Germline Antibodies, J. Immunol. 192:5398-5405.
Kohler et al., Aug. 7, 1975, Continuous cultures of fused cells secreting antibody of predefined specificity. Nature. 256:495-497.
Korndorfer et al., 2003, Crystallographic analysis of an "anticalin" with tailored specificity for fluorescein reveals high structural plasticity of the lipocalin loop region, Proteins: Structure, Function, and Bioinformatics, 53(1):121-129.
Kunik et al., 2012, Paratome: an online tool for systematic identification of antigen-binding regions in antibodies based on sequence or structure, Nucl Acids Res., 40:W521-W524.
Lam, 1997, Application of combinatorial library methods in cancer research and drug discovery, Anticancer Drug Des. 12:145-167.
Larrick et al., May 15, 1989, Rapid cloning of rearranged immunoglobulin genes from human hybridoma cells using mixed primers and the polymerase chain reactions, Biochem. Biophys. Res. Commun., 160(3):1250-1255.
Leander et al., 2012, Impaired fibrinolytic capacity and increased fibrin formation associate with myocardial infarction, Blood Coagulation, Fibrinolysis and Cellular Haemostasis, Thrombosis and Haemostasis: 107(6):1092-1100.
Lee et al., 2013, Spatial and temporal expression, and statue responsiveness of galectin-1 and galectin-3 in murine atherosclerosis, Korean Circulation Journal, 43:223-230.
Lefranc et al., 2003, IMGT unique numbering for immunoglobulin and T cell receptor variable domains and Ig superfamily V-like domains, Dev Comp Immunol. 27:55-77.
Leitner, J et al. TIM-3 Does Not Act as a Receptor for Galectin-9. PLoS Pathog. Mar. 2013. 9(3):e1003253.
Leung et al., Dec. 1994, Chimerization of LL2, a rapidly internalizing antibody specific for B cell lymphoma. Hybridoma. 13(6):469-476.
Levitt et al., 1983, Molecular dynamics of native protein I. Computer simulation of trajectories, J. Mol. Biol., 168:595-620.
Li, P et al. Design and Synthesis of Paclitaxel Conjugated with an ErbB2-Recognizing Peptide, EC-1. Biopolymers. Nov. 2007; 87(4):225-30.

(56) References Cited

OTHER PUBLICATIONS

Linch et al., Nov. 4, 2015, Galectin-3 inhibition using novel inhibitor GR-MD-02 improves survival and immune function while reducing tumor vasculature, Journal for Immunotherapy of Cancer, 3(Suppl 2):P306.
Liu et al. Feb. 2007, Synthesis of 2'-paclitaxel methyl 2-glucopyranosyl succinate for specific targeted delivery to cancer cells. Bioorg. Med. Chem. Lett., 17(3):617-620.
Liu et al., 1996, Modulation of functional properties of galectin-3 by monoclonal antibodies binding to the non-lectin domains, Biochemistry, 35:6073-6079.
Liu et al., Jul. 21, 2020, Association of the total white blood cell, neutrophils, and monocytes count with the presence, severity, and types of carotid atherosclerotic plaque, Frontiers in Medicine, 7:Article 313, 10 pp.
Liu et al., May 4, 2020, Neutralizing antibodies isolated by a site-directed screening have potent protection on SARS-CoV-2 infection, bioRxiv preprint doi:https//doi.org/10.1101/2020.04.02.074914, 33 pp.
Lloyd et al., 2009, Modelling the human immune response: performance of a $10^{11}$ human antibody repertoire against a broad panel of therapeutically relevant antigens, Protein Engineering, Design & Selection, 22(3):159-168.
Loimaranta et al., 2018, Galectin-3-binding protein: a multitask glycoprotein with innate immunity functions in viral and bacterial infections, Journal of Leukocyte Biology, 104:777-785.
Lonberg et al., Apr. 1994, Antigen-specific human antibodies from mice comprising four distinct genetic modifications. Nature. 368(6474):856-859.
Lu et al., 2017, Modified citrus pectin inhibits galectin-3 function to reduce atherosclerotic lesions in apoE-deficient mice, Molecular Medicine Reports, 16:647-653.
MacCallum et al., 1996, Antibody-antigen interactions; contact analysis and binding site topography, J. Mol. Biol., 5:732-745.
MacKinnon et al., Mar. 1, 2012, Regulation of transforming growth factor-β1-driven lung fibrosis by galectin-3, Am J Respir Crit Care Med, 185(5):537-546.
Madrigal-Matute, 2014, Galectin-3 a biomarker linking oxidative stress and inflammation with the clinical outcomes of patients with atherothrombosis, Journal of the American Heart Association, 114:1-13.
Makabe et al., Jan. 11, 2008, Thermodynamic consequences of mutations in vernier zone residues of a humanized anti-human epidermal growth factor receptor murine antibody, 528, Journal of Biological Chemistry, 283(2):1156-1166.
Mariuzza et al., 1987, The Structural Basis of Antigen-Antibody Recognition Annu. Rev. Biophys. Biphys. Chem., 16:139-159.
Martin et al., Dec. 1989, Modeling antibody hypervariable loops; a combined algorithm, Proc Natl Acad Sci (USA), 86:9268-9272.
Martins et al., 2011, Targeting the insulin-like growth factor pathway in phabdomyosarcomas: rationale and future perspectives, Sarcoma, 2011:1-11.
Mauris et al., 2014, Molecular basis for MMP9 induction and disruption of epithelial cell-cell contacts by galectin-3, Journal of Cell Science, 127:3141-3148.
Mazurek et al., Oct. 1, 2011, A galectin-3 sequence polymorphism confers Trail sensitivity to human breast cancer cells, Cancer, 117(19):4375-4380.
McCafferty et al., Dec. 1990, Phage antibodies: filamentous phage displaying antibody variable domains. Nature, 348(6301):552-554.
McKee, 2014, Military-related traumatic brain injury and neurodegeneration, Alzheimer's & Dementia, 10:S242-S253.
Mehndiratta et al., Apr. 2012, Cerebral amyloid angiopathy-associated intracerebral hemorrhage: pathology and management, Neurosurg Focus, 32(4):E7, 14 pp.
Mills et al., 2002, Altered fibrin clot structure in the healthy relatives of patients with premature coronary artery disease, Circulation, 106:1938-1942.
Murphy et al., Dec. 2009, Plasticity during stroke recovery: from synapse to behavior, Nature Reviews, 10:861-872.
Nachtigal et al., May 1998, Galectin-3 expression in human atherosclerotic lesions, American Journal of Pathology, 152(5):1199-1208.
Nangia-Makker et al., 2010, Cleavage of galectin-3 by matrix metalloproteases induces angiogenesis in breast cancer, Int. J. Cancer, 127:2530-2541.
Nangia-Makker et al., Dec. 15, 2007, Galectin-3 cleavage: a novel surrogate marker for matrix metalloproteinase activity in growing breast cancers, Cancer Res., 67(24):11760-11768.
Nasreddine et al., Apr. 2005, The Montreal cognitive assessment, MoCA: a brief screening tool for mild cognitive impairment, JAGS, 53(4):695-699.
Nishikawa et al., 2018, Possible role of inflammation and galectin-3 in brain injury after subarachnoid hemorrhage, Brain Sci., 8:30, 11 pp.
O'Collins e al., 2006, 1,026 experimental treatments in acute stroke 59:467-477.
Ochieng et al., 1998, Modulation of the biological functions of gelactin-3 by matrix metalloproteinases, Biochimica et Biophysica Acta, 1379:97-106.
Olafsen et al., 2004, Characterization of engineered anti-p185$^{HER-2}$ (scFv-$C_H$3)$_2$ antibody fragments (minibodies) for tumor targeting, Protein Eng Des Sel., 17(4):315-323.
Olsnes et al., 1982, Chimeric Toxins, Pharmac. Ther. 15:355-381.
Orlandi et al., May 1989, Cloning immunoglobulin variable domains for expression by the polymerase chain reaction, Proc. Natl. Acad. Sci. U.S.A., 86: 3833-3837.
Osmancik et al., 2012, High leukocyte count and interleukin-10 predict high on-treatment-platelet-reactivity in patients treated with clopidogrel, J. Thromb Thrombolysis, 33:340-354.
Owens et al., 1994, The genetic engineering of monoclonal antibodies, Journal of Immunological Methods, 168:149-165.
Page et al., Jun. 2012, Clinically important differences for the upper-extremity Fugl-Meyer scale in people with minimal to moderate impairment due to chronic stroke, Physical Therapy, 92(6):791-798.
Papaspyridonos et al., 2008, Galectin-3 is an amplifier of inflammation in atherosclerotic plaque progression through macrophage activation and monocyte chemoattraction, Arterioscler Thromb Vasc Biol., 28:433-440.
Papay et al., 2009, Drug-induced liver injury following positive drug rechallenge, Regulatory Toxicology and Pharmacology, 54:84-90.
Paul et al., Aug. 6, 2007, Fibrin deposition accelerates neurovascular damage and neuroinflammation in mouse models of Alzheimer's disease, Journal of Experimental Medicine, 204(8):1999-2008.
Poosarla et al., 2017, Computational De Novo Design of Antibodies Binding to a Peptide With High Affinity, Biotech. Bioeng. 114(6):1331-1342.
Powers et al., 2001, Expression of single-chain Fv-Fc fusions in pichia pastoris, Journal of Immunological Methods, 251:123-135.
Powers et al., 2018, 2018 guidelines for the early management of patients with acute ischemic stroke, Stroke, 49:e46-e99.
Pulgdellivol et al., Jun. 2020, Sialylation and galectin-3 in microglia-mediated neuroinflammation and neurodegeneration, Frontiers in Cellular Neuroscience, 14:Article 162, 11 pp.
Rasool et al., Nov. 9-12, 2021, Novel therapeutic efficacy of galectin-3 antibody for treating Alzheimer's disease, Conference Poster Brochure, Clinical Trials on Alzheimer's Disease, Boston, MA, p. 30.
Redmond, Feb. 7, 2017, Immunotherapy plus a galectin-3 inhibitor improves anti-tumor immunity: insights from mice in a first-in-human phase I clinical trial, Earle A. Chiles Research Institute, 33 pp.
Reijmer et al., May 6, 2015, Ischemic brain injury in cerebral amyloid angiopathy, Journal of Cerebral Blood Flow & Metabolism, 10 pp.
Rodrigues et al., 2018, The Edinburgh CT and genetic diagnostic criteria for lobar intracerebral haemorrhage associated with cerebral amyloid angiopathy: model development and diagnostic test accuracy study, Lancet Neurol, 17:232-240.

(56) References Cited

OTHER PUBLICATIONS

Roque et al., 2004, Antibodies and genetically engineered related molecules: production and purification, Biotechnol. Prog. 20:639-654.
Samudrala et al., 1999, Ab Initio Protein Structure Prediction Using a Combined Hierarchical Approach, Proteins, Structure, Function and Genetics Suppl., 3:194-198.
Sanford et al., Jul. 1993, Reliability of the Fugl-Meyer assessment for testing motor performance in patients following stroke, Physical Therapy, 73(7):447-454.
Sastry et al., 1989, Cloning of the immunological repertoire in *Escherichia coli* for generation of monoclonal catalytic antibodies: construction of a heavy chain variable region-specific cDNA library, Proc. Natl. Acad. Sci., U.S.A. 86: 5728-5732.
Satoh et al., 2011, Galectin-3 expression in delayed neuronal death of hippocampal CA 1 following transient forebrain ischemia, and its inhibition by hypothermia, Brain Research, 1382:266-274.
Scott et al., 2004, Genetic and environment determinants of fibrin structure and function: relevance to clinical disease, Arterioscler Thromb Vasc Biol, 24:1558-1566.
Shalaby et al., 1992, Development of humanized bispecific antibodies reactive with cytotoxic lymphocytes and tumor cells overexpressing the HER2 protooncogene, J. Exp. Med. 175:217-225.
Shan et al., 2014, A new panel of blood biomarkers for the diagnosis of mild traumatic brain injury/concussion in adults, Journal of Neurotrauma, 30 pp.
Shen et al., 2016, The change of plasma galectin-3 concentrations after traumatic brain injury, Clinica Chimica Acta, 456:75-80.
Strop et al., 2013, Location matters: site of conjugation modulates stability and pharmacokinetics of antibody drug conjugates, Chemistry and Biology, 20(2):161-167.
Sun et al., Apr. 1, 2014, Myosin Va mediates Rab8A-regulated GLUT4 vesicle exocytosis in insulin-stimulated muscle cells, Molecular Biology of the Cell, 25:1159-1170.
Sun et al., Mar. 27, 2020, Macrophage galectin-3 enhances initial translocation of vascular calcification in diabetes mellitus, Am J. Physiol Heart Circ Physiol, 318:H1068-H1079.
Swartz et al., Mar. 2012, Tumor Microenvironment Complexity: Emerging Roles in Cancer Therapy. Cancer Research. 72(10);2473-2480.
Takaya et al., Jan. 1998, Importance of dissolution process on systemic availability of drugs delivered by colon delivery system. J Control Release. 50(1-3):111-122.
Tao et al., 2020, Galectin-3 promotes Aβ oligomerization and AB toxicity in a mouse model of Alzheimer's disease, Cell Death & Differentiation, 27:192-209.
Tempest et al., Mar. 1991, Reshaping a human monoclonal antibody to inhibit human respiratory syncytial virus infection in vivo, Biotechnology 9:266-271.
Thijssen et al., Oct. 15, 2007, Galectins in the tumor endothelium: opportunities for combined cancer therapy, Blood, 119(0):2819-2827.
Thomas et al., Sep. 12, 2018, Galectin-3 mediated glial crosstalk drives oligodendrocyte differention and (re)myelination, Frontiers in Cellular Neuroscience, 12(12):1-16.
Toglia et al., May 2011, The mini-mental state examination and Montreal cognitive assessment in persons with mild subacute stroke: relationship to functional outcome, Arch Phys Med Rehabil, 92:792-798.
Tomlinson et al., 2000, Methods for Generating Multivalent and Bispecific Antibody Fragments. Methods Enzymol. 326:461-479.
Tunduguru et al., Sep. 25, 2017, The actin-related p41ARC subunit contributes to p21-activated kinase-1 (PAK1)-mediated glucose uptake into skeletal muscle cells, J. Biol. Chem., 292(46):19034-19043.
Undas et al., 2007, Altered fibrin clot structure in patients with advanced coronary artery disease: a role of c-reactive protein, lipoprotein(a) and homocysteine, J Thromb Haemost, 5:1988-1990.
Undas et al., 2008, Altered fibrin clot properties in patients on long-term haemodialysis: relation to cardiovascular mortality, 23:2010-2015.
Undas et al., 2008, Reduced clot permeability and susceptibility to lysis in patients with acute coronary syndrome: effects of inflammation and oxidative stress, Atherosclerosis, 196:551-557.
Van Swieten et al., May 1988, Interobserver agreement for the assessment of handicap in stroke patients, Stroke, 19(5):604-697.
Varsateh et al., 2021, Imaging atherosclerotic plaques by targeting galectin-3 and activate macrophages using ($^{89}$Zr)-DFO-Galectin3-F(ab')$_2$ mAb, Theranostics, 11(4):1864-1876.
Veerbeek et al., Feb. 2014, What is the evidence for physical therapy poststroke? A systematic review and meta-analysis, PLOS One, 9(2):e87987.
Virani et al., Mar. 3, 2020, Heart disease and stroke statistics-2020 update: a report from the American Heart Association, Circulation, 141:e139-e596.
Viswanathan et al., 2011, Cerebral amyloid angiopathy in the elderly, Ann Neurol, 70:871-880.
Vuong et al., Apr. 1, 2019, An orally active galectin-3 antagonist inhibits lung adenocarcinoma growth and augments response to PD-L1 blockade, Cancer Research, 79(7):1480-1492.
Wang et al., 2013, Elevated galectin-3 levels in the serum of patients with Alzheimer's disease, American Journal of Alzheimer's Disease & Other Dementias, 4 pp.
Wang et al., Apr. 19, 2021, Galectin-3 mediated inflammatory response contributes to neurological recovery by QiShenYiQi in subacute stroke model, Frontiers in Pharmacology; 12:Article 588587, 16 pp.
Wang et al., Mar. 12, 2020, A human monoclonal antibody blocking SARS-CoV-2 infections, bioRxiv, https://biorxiv.org/content/10.1101/2020.03.11.987958v1, 24 pp.
Ward et al. Oct. 12, 1989, Binding activities of a repertoire of single immunoglobulin variable domains secreted from *Escherichia coli*. Nature. 341:544-546.
Weisel et al., Jan. 10, 2013, Mechanisms of fibrin polymerization and clinical implications, Blood, 31 pp.
Wu et al., Mar. 3, 2009, Site-specific chemical modification of recombinant proteins produced in mammalian cells by using the genetically encoded aldehyde tag, PNAS, 106(9):3000-3005.
Wu, et al. 2006, Building complex glycopeptides: Development of a cysteine-free native chemical ligation protocol, Angew. Chem. Int. Ed. 45:4116-4125.
Xiong et al., 2020, Transcriptomic characteristics of bronchoalveolar lavage fluid and peripheral blood mononuclear cells in COVID-19 patients, Emerging Microbes & Infections, 9:761-770.
Yan et al., 2009, Galectin-3 mediates post-ischemic tissue remodeling, Brain Research, 1288:116-124.
Yip et al., 2017, Galectin-3 released in response to traumatic brain injury acts as an alarmin orchestrating brain immune response and promoting neurodegeneration, Scientific Reports, 7:41689, 13 pp.
Yip et al., Jan. 27, 2017, Galectin-3 released in response to traumatic brain injury acts as an alarmin orchestrating brain immune response and promoting neurodegeneration, Sci. Rep. 27, 13 pp.
Yoo et al., 2008, Undernutrition as a predictor of poor clinical outcomes in acute ischemic stroke patients, Arch Neurol, 61(1):39-43.
Zapata et al., 1995, Engineering linear F(ab')$_2$ fragments for efficient production in *Escherichia coli* and enhanced antiproliferative activity, Protein Eng., 8(10):1057-1062.
Zhu et al., Nov. 13, 2005, The Tim-3 ligand galectin-9 negatively regulates T helper type 1 immunity, Nature Immunology, 6(12):1245-1252.
U.S. Appl. No. 17/775,573, filed May 17, 2022, with acknowledgement receipt, 219 pp.
Office action dated Nov. 26, 2021 in U.S. Appl. No. 16/633,530.
Office action dated Apr. 29, 2022 in U.S. Appl. No. 16/633,530.
International Search Report and Written Opinion dated Oct. 25, 2018 in Application No. PCT/US2018/043513.
International Preliminary Report on Patentability dated Jan. 28, 2020 in Application No. PCT/US2018/043513.
International Search Report and Written Opinion dated Aug. 6, 2020 in Application No. PCT/US20/15692.

(56) References Cited

OTHER PUBLICATIONS

International Search Report and Written Opinion dated Apr. 14, 2021 in Application No. PCT/US20/63134.
International Search Report and Written Opinion dated Jan. 6, 2022 in Application No. PCT/US21/034096.
International Search Report and Written Opinion dated May 19, 2021 in Application No. PCT/US21/13136.
Bio-Techne, 2022, Human galectin-3 antibody, product details, 7 pp.
Supplement to Bio-techne reference submission regarding MAB1154, 2 pp. Supplement submitted with respect to Bio-techne, 2022, Human galectin-3 antibody, product details, 7 pp.
Inufusa et al., 2001, Role of galectin-3 in adenocarcimona liver metastasis, International Journal of Oncology, 19(5):913-991.
Ngiow et al., 2011, Anti-TIM3 antibody promotes T cell IFN-γ-mediated antitumor immunity and suppresses established tumors, Cancer Research, 71(10):35403551.
Notice of Reasons for Refusal dated Sep. 6, 2022 in Japanese patent application No. 2020-527838.
Office action dated Dec. 9, 2021 in U.S. Appl. No. 17/384,542.
International Search Report and Written Opinion dated Sep. 13, 2022 in Application No. PCT/US2022/026005.
International Search Report and Written Opinion dated Nov. 15, 2022 in Application No. PCT/US22/32527.
Abcam, Sep. 27, 2023, Anti-Galectin 3 antibody [A3A12] ab2785, product data sheet, 7 pp.
Al Gwairi et al., 2016, Cellular and molecular pathology of age-related macular degeneration: potential role for proteoglycans, Journal of Ophthalmology, vol. 2016, Aritle ID 2913612, 7 pp.
Almagro et al., Jan. 1, 2008, Humanization of antibodies. Front Biosci., 13:1619-1633.
Boguslawa et al., Dec. 12, 2019, TGF-β and microNRA interpaly in genitourinary cancers, Cells, 8:1619, 40 pp.
Cerel et al., 2019, Inhibition of sialidase activity and galectin binding reduced xenogeneic neutrophil-endothelial adhesion, American Journal of Transplantation, 19(Supplement 3), abstract only, 2 pp.
Chammas, 2013, Cell Adhesion and Cancer Group. Tumors as complex organs: are cancers manageable through the modification of their microenvironment?. BMC Proc, 7(Suppl 2):K16.
Chen et al., Jun. 15, 1995, Enhancement and destruction of antibody function by somatic mutation: unequal occurrence is controlled by V gene combinatorial associations, EMBO J., 14(12)2784-2794.
De Oliveira et al., 2010, Platelet-activating factor receptor (PAF-R)-dependent pathways control tumour growth and tumour response to chemotherapy. BMC Cancer, 10:200.
Fichorova et al., Jan. 8, 2016, Trichomonas vaginalis lipophosphoglycan exploits binding to galectin-1 and -3 to modulate epithelial immunity, J. Biol. Chem, 291(2):998-1013.
GenBank: BAC02420.1, immunoglobulin heavy chain VHDJ region, partial [*Homo sapiens*] NCBI, No. 1, Jul. 26, 2016, 3 pp.
Glinskii et al. Mechanical entrapment is insufficient and intercellular adhesion is essential for metastatic cell arrest in distant organs. Neoplasia. May 2005; 7(5), 522-527.
Greenspan et al., Oct. 1999, Defining epitopes: it's not as easy as it seems, Nature Biotechnology, 17(10):936-937.
Herold et al., Sep. 2017, Determinants of the assembly and function of antibody variable domains, Scientific Reports, 7:12276, 17 pp.
Koenig et al. Jan. 5, 2017, Mutational landscape of antibody variable domains reveals a switch modulating the interdomain conformational dynamics and antigen binding, PNAS, 114(4):E486-E495.
Kranz et al., Sep. 1981, Restricted reassociation of heavy and light chains from hapten-specific monoclonal antibodies, PNAS, 78(9):5807-5811.
Kussie et al., Jan. 1, 1994, A single engineered amino acid substitution changes antibody fine specificity.J Immunol., 152(1):146-152.
Li et al., Nov. 3, 2016, Hematopoietic-derived galectin-3 causes cellular and systemic insulin resistance, Cell, 167(4):973-984.
Linden et al., 2013, The role of galectin-3 in phagocytosis of Candida albicans and Candida parapsilosis by human neutrophils, Cellular Microbiology, 15(7):1127-1142.
Luo et al., May 25, 2018, Expression and clinical significance of galectin 3 in bladder cancer tissues andits effect on malignant biological behavior of T24 cells, Chinese Journal of Cancer Biotherapy, 25(5):503-508.
Priglinger et al., Jul. 29, 2013, Galectin-3 induced clustering of CD147 and integrin-beta 1 transmembrane glycoprotein receptors on the RPE cell surface, Plos One, Article e70011, abstract only.
Razpotnik et al., Sep. 25, 2017, Targeting Malignant Brain Tumors with Antibodies. Front Immunol. 8:1181.
Shi et al., 2019, 032-11-1b is essential for anti-galectin3 antibody induced cutaneous vasculitis in systems lupus erythematosus, Journal of Investigative Dermatology, 2019 Meeting Abstract Supplement, 2 pp.
Shi et al., 2022, Anti-galectin-3 antibodies induce skin vascular inflammation via promoting local production of IL-1β in systemic lupus erythematosus, Int. Immunopharm., 112:109197.
Volarevic et al., 2015, Gal-3 regulates the capacity of dendritic cells to promote NKT-cell-induced liver injury, European Journal of Immunology, 45:531-543.
Xu et al., Recent developments in galectin-3 and its inhibitors. Chinese Journal of Biochemical Pharmaceutics. Dec. 2011; 32(5), 417-420.
Yamamoto-Sugitani et al. 2011, Galectin-3 (Gal-3) induced by leukemia microenvironment promotes drug resistance and bone marrow lodgment in chronic myelogenous leukemia. PNAS 108(42):17468-17473.
Office action dated Aug. 6, 2024, in U.S. Appl. No. 18/354,611.
Examination Report No. 1 dated Jun. 21, 2024 in Australian patent application no. 2018308088.
Examination Report No. 2 dated Nov. 29, 2024 in Australian patent application No. 2018308088.
Dated Oct. 27, 2023 in Canadian patent application No. 3,070,446.
Decision of Rejection dated Mar. 15, 2023 in Japanese patent application No. 2020-527838.
Notice of Reasons for Refusal dated Jun. 25, 2024 in Japanese patent application No. 2023-118382.
First Office Action and Search Report dated Mar. 1, 2023 in Chinese Application No. 2018800616946.6.
Second Office Action and Search Report dated Jul. 31, 2023 in Chinese Application No. 2018800616946.6.
Third Office Action dated Dec. 21, 2023 in Chinese Application No. 2018800616946.6.
Translation of Decision of Rejection received Apr. 12, 2024 in Chinese patent application No. 2018800616946.6.
Dated Oct. 19, 2023 in Canadian patent application No. 3, 127,113.
First Office Action and Search Report dated Jun. 15, 2023 in Chinese Application No. 202080025814.4.
Translation of decision of rejection received Dec. 4, 2023 in Chinese Application No. 202080025814.4.
Translation of second office action received May 23, 2024 in Chinese Application No. 202080025814.4.
Translation of third office action received Sep. 30, 2024 in Chinese Application No. 202080025814.4.
First Office Action dated Jul. 6, 2023 in Chinese Application No. 202211069802.9.
Translation of second office action received Nov. 30, 2023 in Chinese Application No. 202211069802.9.
Translation of decision of rejection received May 21, 2024 in Chinese Application No. 2022113436441.
European Search Report dated Nov. 29, 2022 in patent application No. 20749738.9, 21 pp.
Examination Report dated Dec. 12, 2023 in patent application No. 20749738.9.
Notice of Reasons for Refusal dated Jan. 16, 2024 in Japanese patent application No. 2021-544701.
Decision of Refusal dated Oct. 22, 2024 in Japanese patent application No. 2021-544701.
Requisition by the examiner dated Oct. 18, 2023 in Canadian patent application No. 3,164,060.

(56) References Cited

OTHER PUBLICATIONS

Partial supplemental European search report dated Aug. 17, 2023 in application No. 20896254.8.
Extended supplemental European search report dated Nov. 17, 2023 in application No. 20896254.8.
Office Action dated Jun. 23, 2023 in U.S. Appl. No. 17/303,268.
Office Action dated Oct. 3, 2023 in U.S. Appl. No. 17/303,268.
Office Action dated Apr. 9, 2024 in U.S. Appl. No. 17/303,268.
Partial supplemental European search report dated Jun. 11, 2024 in application No. 21812182.0.
Extended European search report dated Oct. 10, 2024 in application No. 21812182.0.
Office action dated Feb. 1, 2023 in U.S. Appl. No. 17/812,159.
Office action dated Jul. 6, 2023 in U.S. Appl. No. 17/812,159.
Office action dated Jan. 24, 2024 in U.S. Appl. No. 17/812,159.
Office action dated Jun. 20, 2024 in U.S. Appl. No. 17/812,159.
Office action dated Jul. 12, 2024 in U.S. Appl. No. 17/812,159.
Dated Oct. 20, 2023 in Canadian patent application No. 3,166,552.
Translation of First Office Action dated Apr. 28, 2024 in Chinese patent application No. 202180022171.2.
Second Office Action dated Nov. 6, 2024 in Chinese patent application No. 202180022171.2.
Partial supplementary European search report dated Jul. 15, 2024 in patent application No. 21741281.6.
Extended European search report dated Nov. 15, 2024 in patent application No. 21741281.6.
Office action dated Jan. 13, 2023 in U.S. Appl. No. 17/834,703.
Office action dated Feb. 2, 2024 in U.S. Appl. No. 17/834,703.
Office action dated Jul. 29, 2024 in U.S. Appl. No. 17/834,703.
International Search Report and Written Opinion dated Nov. 30, 2022 in Application No. PCT/US22/073694.
International Search Report and Written Opinion dated Mar. 14, 2024 in Application No. PCT/US23/75268.
International Search Report and Written Opinion dated Aug. 12, 2024 in Application No. PCT/US2024/024810.
Li et al., Nov. 30, 2007, Progress in Study on Function of Galectin-3 on Tumor Progression and Metastasis, Letters in Biotechnology, 6:1003-1006.
Dated Jan. 2, 2025 in Canadian patent application No. 3,127,113.
First office action dated Dec. 27, 2024 in Chinese patent application No. 2020800958692, 24 pp.
First office action dated Dec. 31, 2024 in Chinese patent application No. 202180059379.X.
Kang et al., Apr. 12, 2016, Rapid formulation development for monoclonal antibodies, BloProcess International, http://www.bioprocessintl.com/manufacturing/formulation/rapid-formulation-development-for-monoclonal-antibodies/, 6 pp.
Uchiyama, Aug. 13, 2014, Liquid formulation for antibody drugs, Biochimica et Biophysica Acta, 1844(11):2041-2052.
Viola et al., Aug. 2, 2018, Subcutaneous delivery of monoclonal antibodies: How do we get there? Journal of Controlled Release, 286:301-314.
Whitaker et al., Nov. 2017, A formulation development approach to identify and select stable ultra-high-concentration monoclonal antibody formulations with reduced viscosities, Journal of Pharmaceutical Sciences, 106(11):3230-3241.
Examination report dated Jun. 27, 2025, in application No. 20896254.8.
Extended European search report dated Feb. 17, 2025, in patent application No. 22796456.6.
Office action dated May 19, 2025, in U.S. Appl. No. 17/834,703.
Dated Jan. 24, 2025, in Canadian patent application No. 3,070,446.
Second office action dated Jun. 18, 2025, in Chinese patent application No. 2020800958692, 24 pp.

* cited by examiner

A20 hGal3 live/dead stain

| Name | Sequence | SEQ ID NO |
|---|---|---|
| peptide_1 | ADNFSLHDALSGSGNPNPQG | 3 |
| peptide_2 | SGSGNPNPQGWPGAWGNQPA | 4 |
| peptide_3 | WPGAWGNQPAGAGGYPGASY | 5 |
| peptide_4 | GAGGYPGASYPGAYPGQAPP | 6 |
| peptide_5 | PGAYPGQAPPGAYPGQAPPG | 7 |
| peptide_6 | GAYPGQAPPGAYPGAPGAYP | 8 |
| peptide_7 | AYPGAPGAYPGAPAPGVYPG | 9 |
| peptide_8 | GAPAPGVYPGPPSGPGAYPS | 10 |
| peptide_9 | PPSGPGAYPSSGQPSATGAY | 11 |
| peptide_10 | SGQPSATGAYPATGPYGAPA | 12 |
| peptide_11 | PATGPYGAPAGPLIVPYNLP | 13 |
| peptide_12 | GPLIVPYNLPLPGGVVPRML | 14 |
| peptide_13 | LPGGVVPRMLITILGTVKPN | 15 |
| peptide_14 | ITILGTVKPNANRIALDFQR | 16 |
| peptide_15 | ANRIALDFQRGNDVAFHFNP | 17 |
| peptide_16 | GNDVAFHFNPRFNENNRRVI | 18 |
| peptide_17 | RFNENNRRVIVCNTKLDNNW | 19 |
| peptide_18 | VCNTKLDNNWGREERQSVFP | 20 |
| peptide_19 | GREERQSVFPFESGKPFKIQ | 21 |
| peptide_20 | FESGKPFKIQVLVEPDHFKV | 22 |
| peptide_21 | VLVEPDHFKVAVNDAHLLQY | 23 |
| peptide_22 | AVNDAHLLQYNHRVKKLNEI | 24 |
| peptide_23 | NHRVKKLNEISKLGISGDID | 25 |
| peptide_24 | SKLGISGDIDLTSASYTMI | 26 |

Fig. 11A

| Name | Sequence | SEQ ID NO |
|---|---|---|
| peptide_25 | PGAYPGQAPP | 27 |
| peptide_26 | GQAPPGAYPG | 28 |
| peptide_27 | GAYPGQAPPGA | 29 |
| peptide_28 | APPGAYPGAP | 30 |
| peptide_29 | YPGAPGAYP | 31 |
| peptide_30 | APPGAY | 32 |
| peptide_31 | GAYPGQ | 33 |
| peptide_32 | PGQAPP | 34 |

hM2 macrophages mIgG

IMT-001/Gal3

| SEQ ID NO | Trypsin, Chymotrypsin, ASP-N, Elasatse and Thermolysin Interlink between Tim-3 and Gal3 | | | |
|---|---|---|---|---|
| | Sequence | enzyme | Protein1 | Protein2 |
| 305 | GDVSLTIENVTLADSGIYCCR-IALDFQRGNDVAFHFNPRFNENNR-a11-b14 | Trypsin | Tim-3 | Gal3 |
| 306 | IYCCRIQIPGI-FQRGNDVA-a5-b3 | Thermolysin | Tim-3 | Gal3 |
| 307 | YWLNGDFRKGDVSLTIENVTLADSGIYCCR-GNDVAFHFNPRFNENNR-a15-b11 | Trypsin | Tim-3 | Gal3 |
| 308 | TIENVTL-NPRFNENNRRVIVCNTKL-a6-b9 | Chymotrypsin | Tim-3 | Gal3 |
| 309 | KGDVSLTIENVTLADSGIYCCRIQIPGIMNDEK-FNENNRR-a12-b6 | Trypsin | Tim-3 | Gal3 |
| 310 | KGDVSLTIENVTLADSGIYCCRIQIPGIMNDEK-FNENNRR-a22-b6 | Trypsin | Tim-3 | Gal3 |
| 311 | VTLADSG-FNENNRR-a2-b6 | Thermolysin | Tim-3 | Gal3 |
| 312 | VTLADSG-FNENNRRVI-a2-b6 | Thermolysin | Tim-3 | Gal3 |
| 313 | DVSLTIENVTLADSGIYCCRIQIPGIMN-ENNRRVIVCNTKLDNNWGRE-a17-b12 | ASP-N | Tim-3 | Gal3 |

| SEQ ID NO | Trypsin, Chymotrypsin, ASP-N, Elasatse and Thermolysin interlink betwe | | |
|---|---|---|---|
| | Sequence | Sequence Proteine 1 | Sequence Proteine 2 |
| 305 | GDVSLTIENVTLADSGIYCCR-IALDFQRGNDVAFHFNPRFNENNR-a11-b14 | 73-93 | 145-168 |
| 306 | IYCCRIQIPGI-FQRGNDVA-a5-b3 | 89-99 | 149-156 |
| 307 | YWLNGDFRKGDVSLTIENVTLADSGIYCCR-GNDVAFHFNPRFNENNR-a15-b11 | 64-93 | 152-168 |
| 308 | TIENVTL-NPRFNENNRRVIVCNTKL-a6-b9 | 78-84 | 160-177 |
| 309 | KGDVSLTIENVTLADSGIYCCRIQIPGIMNDEK-FNENNRR-a12-b6 | 72-104 | 163-169 |
| 310 | KGDVSLTIENVTLADSGIYCCRIQIPGIMNDEK-FNENNRR-a22-b6 | 72-104 | 163-169 |
| 311 | VTLADSG-FNENNRR-a2-b6 | 82-88 | 163-169 |
| 312 | VTLADSG-FNENNRRVI-a2-b6 | 82-88 | 163-171 |
| 313 | DVSLTIENVTLADSGIYCCRIQIPGIMN-ENNRRVIVCNTKLDNNWGRE-a17-b12 | 74-101 | 165-184 |

| SEQ ID NO | Trypsin, Chymotrypsin, ASP-N, Elasatse and Thermolysin interlink betwe | |
|---|---|---|
| | Sequence | XLType |
| 305 | GDVSLTIENVTLADSGIYCCR-IALDFQRGNDVAFHFNPRFNENNR-a11-b14 | inter-protein xl |
| 306 | IYCCRIQIPGI-FQRGNDVA-a5-b3 | inter-protein xl |
| 307 | YWLNGDFRKGDVSLTIENVTLADSGIYCCR-GNDVAFHFNPRFNENNR-a15-b11 | inter-protein xl |
| 308 | TIENVTL-NPRFNENNRRVIVCNTKL-a6-b9 | inter-protein xl |
| 309 | KGDVSLTIENVTLADSGIYCCRIQIPGIMNDEK-FNENNRR-a12-b6 | inter-protein xl |
| 310 | KGDVSLTIENVTLADSGIYCCRIQIPGIMNDEK-FNENNRR-a22-b6 | inter-protein xl |
| 311 | VTLADSG-FNENNRR-a2-b6 | inter-protein xl |
| 312 | VTLADSG-FNENNRRVI-a2-b6 | inter-protein xl |
| 313 | DVSLTIENVTLADSGIYCCRIQIPGIMN-ENNRRVIVCNTKLDNNWGRE-a17-b12 | inter-protein xl |

| SEQ ID NO | Trypsin, Chymotrypsin, ASP-N, Elasatse and Thermolysin interlink betwe | | | |
|---|---|---|---|---|
| | Sequence | nAA1 | nAA2 | Identified on StavroX |
| 305 | GDVSLTIENVTLADSGIYCCR-IALDFQRGNDVAFHFNPRFNENNR-a11-b14 | 83 | 158 | YES |
| 306 | IYCCRIQIPGI-FQRGNDVA-a5-b3 | 93 | 151 | YES |
| 307 | YWLNGDFRKGDVSLTIENVTLADSGIYCCR-GNDVAFHFNPRFNENNR-a15-b11 | 78 | 162 | YES |
| 308 | TIENVTL-NPRFNENNRRVIVCNTKL-a6-b9 | 83 | 168 | YES |
| 309 | KGDVSLTIENVTLADSGIYCCRIQIPGIMNDEK-FNENNRR-a12-b6 | 83 | 168 | YES |
| 310 | KGDVSLTIENVTLADSGIYCCRIQIPGIMNDEK-FNENNRR-a22-b6 | 93 | 168 | YES |
| 311 | VTLADSG-FNENNRR-a2-b6 | 83 | 168 | YES |
| 312 | VTLADSG-FNENNRRVI-a2-b6 | 83 | 168 | YES |
| 313 | DVSLTIENVTLADSGIYCCRIQIPGIMN-ENNRRVIVCNTKLDNNWGRE-a17-b12 | 90 | 176 | YES |

Fig. 21A

```
peptide_4  ----GAGGYPGASYPGAYPGQAPP--  SEQ ID NO: 6
peptide_5  -----PGAYPGQAPPGAYPGQAPPG-  SEQ ID NO: 7
peptide_6  ------GAYPGQAPPGAYPGAPGAYP  SEQ ID NO: 8
peptide_7  AYPGAPGAYPGAPAPGVYPG------  SEQ ID NO: 9
                 *.***   **.***
```

Fig. 25

| | mIMT001 | 19D9 | 2D10 | 4A11 | 23B10 | 6H6 | 15G7 | 4G2 | 13A12 | 15F10 | 6F7 | 12G5 | 6B3 | 9H2 | 13G4 | Pearson | |
|---|---|---|---|---|---|---|---|---|---|---|---|---|---|---|---|---|---|
| mIMT001 | 10 | 13 | 27 | 30 | 27 | 24 | 45 | 14 | 34 | 43 | 44 | 43 | 44 | 48 | 35 | 1 | Bin1 |
| 19D9.2E5 | 41 | 0 | 7 | 7 | 0 | 6 | 71 | 55 | 72 | 81 | 87 | 85 | 83 | 83 | 88 | 0.69 | Bin2 |
| 2D10.2B2 | 31 | 3 | 0 | 0 | 0 | 5 | 20 | 27 | 67 | 83 | 93 | 91 | 88 | 99 | 87 | 0.7 | Bin3 |
| 4A11.2B5 | 44 | 0 | 0 | 1 | 0 | 1 | 80 | 48 | 79 | 84 | 88 | 85 | 80 | 92 | 86 | 0.7 | Bin3 |
| 23B10.2B12 | 40 | 1 | 5 | 5 | 0 | 7 | 75 | 49 | 73 | 66 | 77 | 71 | 71 | 74 | 81 | 0.67 | Bin3 |
| 6H6.2D6 | 63 | 4 | 7 | 8 | 9 | 2 | 0 | 65 | 91 | 97 | 100 | 102 | 91 | 99 | 93 | 0.48 | Bin4 |
| 15G7.2A7 | 62 | 45 | 34 | 64 | 70 | 11 | 0 | 54 | 60 | 66 | 68 | 66 | 66 | 65 | 59 | 0.12 | Bin5 |
| 4G2.2G6 | 62 | 81 | 79 | 77 | 92 | 66 | 89 | 0 | 8 | 80 | 80 | 83 | 78 | 80 | 85 | 0.38 | Bin6 |
| 13A12.2E5 | 70 | 70 | 78 | 81 | 94 | 63 | 85 | 0 | 0 | 64 | 86 | 76 | 77 | 82 | 76 | 0.34 | Bin7 |
| 15F10.2D6 | 81 | 83 | 85 | 72 | 81 | 73 | 85 | 89 | 84 | 2 | 80 | 80 | 71 | 79 | 89 | -0.28 | Bin8 |
| 6F7.C4 | 97 | 103 | 104 | 96 | 111 | 84 | 110 | 119 | 101 | 99 | 1 | 74 | 70 | 86 | 76 | -0.46 | Bin9 |
| 12G5.D7 | 96 | 107 | 101 | 85 | 103 | 88 | 101 | 100 | 93 | 88 | 74 | 0 | 78 | 1 | 6 | -0.53 | Bin10 |
| 6B3.2D3 | 102 | 109 | 110 | 97 | 109 | 92 | 109 | 114 | 98 | 97 | 91 | 94 | 2 | 2 | 3 | -0.49 | Bin11 |
| 9H2.2H10 | 105 | 104 | 106 | 90 | 94 | 94 | 100 | 105 | 101 | 94 | 79 | 0 | 6 | 0 | 0 | -0.59 | Bin12 |
| 13G4.2F8 | 76 | 78 | 73 | 64 | 68 | 70 | 71 | 71 | 79 | 75 | 44 | 6 | 12 | 8 | 4 | -0.59 | Bin12 |

Fig. 26

| Treatment | Complete Responses |
|---|---|
| IgG | 0/10 |
| mIMT001 | 0/10 |
| anti-PD-L1 | 3/10 |
| mIMT001 + anti-PD-L1 | 5/10 |

Fig. 28A

| Treatment | Response Rate |
|---|---|
| IgG | 0/10 |
| mIMT001 | 0/10 |
| anti-PD1 | 3/10 |
| mIMT001 + anti-PD1 | 6/10 |

Fig. 28C

| ab name | SEQ ID NO: | VH CDR1 | SEQ ID NO: | VH CDR2 | SEQ ID NO: | VH CDR3 |
|---|---|---|---|---|---|---|
| 2D10.2B2 | 37 | GYTFTDY | 65 | IYPGSNDT | 93 | ANYFGCSGWFFDV |
| 3B11.2G2 | 38 | GYKFKTY | 66 | INTYSGVP | 94 | ARDGNYGDPMDY |
| 4A11.2B5 | 39 | GYSFTNY | 67 | IYPGSGNT | 95 | STAPGGFDV |
| 4G2.2G6 | 40 | GYTFTTY | 68 | INTHSGVP | 96 | TRDGNDGDAMDN |
| 6H6.2D6 | 41 | GYTFTTY | 69 | INTYSGVP | 97 | ARGPYAMDY |
| 7D8.2D8 | 42 | GFTFSSY | 70 | ISDGGIYT | 98 | VRDGGY |
| 12G5.D7 | 43 | GYTFTDY | 71 | IYPGTGNT | 99 | ARFAYYYGSGGYFDY |
| 13A12.2E5 | 44 | GYKFKTY | 72 | INTYSGVP | 100 | ARDGNYGDPMDY |
| 13G4.2F8 | 45 | GYTFTSY | 73 | IHPNSGST | 101 | TRWGIYYYARDY |
| 13H12.2F8 | 46 | GYTFTTY | 74 | INTYSGVP | 102 | AVPYEYDGAY |
| 14H10.2C9 | 47 | GYTFTTY | 75 | INTYSGVP | 103 | STPYEYDGAY |
| 15F10.2D6 | 48 | GFAFSSY | 76 | ISDGGVYT | 104 | VRDGGY |
| 15G7.2A7 | 49 | GYTFTDY | 77 | INPNNGGT | 105 | TSGYGFPY |
| 19B5.2E6 | 50 | GYTFTTY | 78 | INTYSGVP | 106 | ARGPYAMDY |
| 19D9.2E5 | 51 | GYTFTTY | 79 | INTYSGVP | 107 | ATPYEYDGAY |
| 20D11.2C6 | 52 | GYTFTDF | 80 | INPKNGGI | 108 | TSGYGFPY |
| 20H5.A3 | 53 | GYAFTTY | 81 | VNTYSGVP | 109 | ARGPYAMDY |
| 23H9.2E4 | 54 | GYTFTTY | 82 | INTYSGVP | 110 | ARGPYAMDY |
| 24D12.2H9 | 55 | GFSLTSY | 83 | IWSGGST | 111 | AKSPDGYDVAWFGY |
| 846.1F5 | 56 | GYTFTNYG | 84 | INTYTGEP | 112 | ARWGGYDGDYYAMDY |
| 846.2H3 | 57 | GYTFTNYG | 85 | INTYTGEP | 113 | ARWGGYDGDYYAMDY |
| 846T.1H2 | 58 | GYTFTNYG | 86 | INTNTGES | 114 | QPGGVTGTLTT |
| 9H2.2H10 | 59 | GYTFTNY | 87 | IDPSDSET | 115 | ARHGYYDY |
| IMT001-4 | 60 | GYTFTNY | 88 | NTNTGE | 116 | APYDNFFAY |
| IMT006-1 | 61 | GYSFTNY | 89 | IYPGSGNT | 117 | STAPGGFDV |
| IMT006-5 | 62 | GYSFTNY | 90 | IYPGSGNT | 118 | STAPGGFDV |
| IMT006-8 | 63 | GYSFTNY | 91 | IYPGSGNT | 119 | STAPGGFDV |
| mIMT001 | 64 | GYTFTNY | 92 | NTNTGE | 120 | APYDNFFAY |

Fig. 35A

| ab name | SEQ ID NO: | VL CDR1 | SEQ ID NO: | VL CDR2 | SEQ ID NO: | VL CDR3 |
|---|---|---|---|---|---|---|
| 2D10.2B2 | 121 | KSLLHSDGITY | 149 | RMS | 177 | AQMIEFPLT |
| 3B11.2G2 | 122 | QSLLYTNGKTY | 150 | LVS | 178 | LQSTHFPLT |
| 4A11.2B5 | 123 | KSLLHSDGITY | 151 | RMS | 179 | AQMLEFPLT |
| 4G2.2G6 | 124 | QSLLYTDGKTY | 152 | LVS | 180 | LQSTHFPLT |
| 6H6.2D6 | 125 | QGISNY | 153 | YTS | 181 | QQYSELPYT |
| 7D8.2D8 | 126 | QSIVHSNGNTY | 154 | KVS | 182 | FQGSHVPLT |
| 12G5.D7 | 127 | QGINSN | 155 | HAT | 183 | VQYAQFPPT |
| 13A12.2E5 | 128 | QSLLYTNGKTY | 156 | LLS | 184 | LQSTHFPLT |
| 13G4.2F8 | 129 | QNVGTN | 157 | GAS | 185 | EQYSNFPLT |
| 13H12.2F8 | 130 | QSLFHSDGKTY | 158 | LVS | 186 | WQGTHFPLT |
| 14H10.2C9 | 131 | QSLFDSDGKTY | 159 | LVS | 187 | WQGTHFPLT |
| 15F10.2D6 | 132 | QSIVHNNGNTY | 160 | KVS | 188 | FQGSHVPLT |
| 15G7.2A7 | 133 | QNINIW | 161 | KAS | 189 | LQGQSYPLT |
| 19B5.2E6 | 134 | QGINNY | 162 | YAS | 190 | QQYSQVPYT |
| 19D9.2E5 | 135 | QSLLHSDGKTY | 163 | LVS | 191 | WQGTHFPLT |
| 20D11.2C6 | 136 | QNIYIW | 164 | KAS | 192 | LQGQSYPLT |
| 20H5.A3 | 137 | QDISNY | 165 | YTS | 193 | QQYSKLPYT |
| 23H9.2E4 | 138 | QGINNY | 166 | YAS | 194 | QQYSQVPYT |
| 24D12.2H9 | 139 | QDVRTA | 167 | WAS | 195 | QQYSSYPWT |
| 846.1F5 | 140 | QSVLYSSNQKNY | 168 | WAS | 196 | HQYLSSLT |
| 846.2H3 | 141 | QSVLYSSNQKNY | 169 | WAS | 197 | HQYLSSLT |
| 846T.1H2 | 142 | QSXKYSXGKTY | 170 | LVC | 198 | VQGPHFXHT |
| 9H2.2H10 | 143 | QDVSTA | 171 | WAS | 199 | QQHYTTPLT |
| IMT001-4 | 144 | RSSKSLLYKDGKTYLN | 172 | LMSTHAS | 200 | QQLVDYPLT |
| IMT006-1 | 145 | KSLLHSDGITY | 173 | RMS | 201 | AQMLEFPLT |
| IMT006-5 | 146 | KSLLHSDGITY | 174 | RMS | 202 | AQMLEFPLT |
| IMT006-8 | 147 | KSLLHSDGITY | 175 | RMS | 203 | AQMLEFPLT |
| mIMT001 | 148 | RSSKSLLYKDGKTYLN | 176 | LMSTHAS | 204 | QQLVDYPLT |

Fig. 35B

| SEQ ID NO | ab name | VH Variable |
|---|---|---|
| 205 | 2D10.2B2 | QVQLQQSGPELVKPGASVKISCKASGYTFTDYYINWVKQRPGQGLEWIGWIYPGSNDTKYN EKFKGKATLTVDTSSSTAYMQLGSLTSEDSAVYFCANYFGCSGWFFDVWGTGTTVTVSS |
| 206 | 3B11.2G2 | QIQLVQSGPELKKPGETVKISCKTSGYKFKTYVMSWVKQAPGKALKWMGWINTYSGVPTYA DDFKGRFAFSLETSASTAYLEIINLKNEDTATYFCARDGNYGDPMDYWGQGTSVTVSS |
| 207 | 4A11.2B5 | QVQLQQSGPELVKPGASVKISCKASGYSFTNYYIHWVKQRPGQGLEWIGWIYPGSGNTNYN EKFKGKATLTADTSSSTTNMQLSSLTSEDSAVYYCSTAPGGFDVWGSGTTVTVSS |
| 208 | 4G2.2G6 | QIQLVQSGPDLKKPGETVKISCKASGYTFTTYVMSWVKQAPGKDLKWMGWINTHSGVPTY ADDFKGRFDFSLETSANTAFLQINNLKNEDTATYFCTRDGNDGDAMDNWGQGTSVTVSS |
| 209 | 6H6.2D6 | QIQLVQSGPELKKPGETVKISCKASGYTFTTYGMSWVKQAPGKGLKWMAWINTYSGVPTYA DDFKGRFAFSLETSASTAYLQINNLTNEDTATYFCARGPYAMDYWGQGTSVTVSS |
| 210 | 7D8.2D8 | EVQLVESGGGLVKPGGSLKLSCAASGFTFSSYAMSWVRQTPEKRLEWVATISDGGIYTYYPD NVKGRFTISRDNAKNNLFLQMSHLKSEDTAMYYCVRDGGYWGQGTTLTVSS |
| 211 | 12G5.D7 | QVQLKQSGAELVRPGASVKLSCKASGYTFTDYYINWVKQRPGQGLEWIARIYPGTGNTDYN EKFKGRATLTAEKSSSTAYMQLSSLTSEDSAVYFCARFAYYYGSGGYFDYWGHGTTLTVSS |
| 212 | 13A12.2E5 | QIQLVQSGPELKKPGETVKISCKTSGYKFKTYVMSWVKQAPGKALKWMGWINTYSGVPTYA DDFKGRFAFSLETSASTAYLEIINLKNEDTATYFCARDGNYGDPMDYWGQGTSVTVSS |
| 213 | 13G4.2F8 | QVQLQQPGAELVKPGASVKLSCKASGYTFTSYWMHWVKQRPGQGLEWIGMIHPNSGSTD YNEKFKNKATLNVDKSSSTAYIQLSSLTSEDSAVYYCTRWGIYYYARDYWGQGTTLTVSS |
| 214 | 13H12.2F8 | QIQLVQSGPELKKPGETVKISCKASGYTFTTYGMSWVKQAPGKGLKWMGWINTYSGVPTYA DDFKGRFAFSLETSASTAYLQINNLKNEDTATYFCAVPYEYDGAYWGQGTLVTVSA |
| 215 | 14H10.2C9 | QIQLVQSGPELKKPGETVKISCKASGYTFTTYGMGWVKQAPGKDLKWMGWINTYSGVPTY ADDFKGRFAFSLETSASTAYLQISNLKNEDTATYFCSTPYEYDGAYWGQGTLVTVSA |
| 216 | 15F10.2D6 | EVQLVESGGGLVKPGGSLKLSCAASGFAFSSYAMSWVRQTPEKRLEWVATISDGGVYTYYTD HVKGRFTISRDNAEDNLYLQMSHLKSEDTAMYYCVRDGGYWGQGTTLTVSS |
| 217 | 15G7.2A7 | EVQLQQSGPELVKPGASVKISCKASGYTFTDYYMNWVKQSHGKSLEWIGDINPNNGGTNY NQKFKGKATLTVDKSSSTAYMELRSLTSEDSAVYYCTSGYGFPYWGQGTLVTVSA |
| 218 | 19B5.2E6 | QIQLVQSGPELKKPGETVKISCKASGYTFTTYAMSWVKQAPGKGLKWMGWINTYSGVPTYA DDLKGRFAFSLETSASTAYLQINNLKNEDTATYFCARGPYAMDYWGQGTSVTVSS |
| 219 | 19D9.2E5 | QIQLVQSGPELKKPGETVKISCKASGYTFTTYGMGWVKQAPGKGLKWMGWINTYSGVPTY ADDFKGRFAFSLETSTSTAYLQINNLKNEDMATYFCATPYEYDGAYWGQGTLVTVSA |
| 220 | 20D11.2C6 | EVQLQQSGPELVKPGASVKISCKASGYTFTDFYINWVKQSHGKSLEWIGDINPKNGGINYNP KFKIKATLTVDKSSSTSYMDLRGLTSEDSAVYYCTSGYGFPYWGQGTLVTVSA |

Fig. 36A

| | | |
|---|---|---|
| **221** | 20H5.A3 | QIQLVQSGPELKKPGESVKISCKASGYAFTTYGMSWVQQAPGKGLKWMGWVNTYSGVPTCADDFKGRFAFSLETSASTAYLQINNLRNEDTATYFCARGPYAMDYWGQGTSVTVSS |
| **222** | 23H9.2E4 | QIQLVQSGPELKKPGETVKISCKASGYTFTTYAMSWVKQAPGKGLKWMGWINTYSGVPTYADDLKGRFAFSLETSASTAYLQINNLKNEDTATYFCARGPYAMDYWGQGTSVTVSS |
| **223** | 24D12.2H9 | QVQLKQSGPGLVQPSQSLSITCTVSGFSLTSYGVHWVRQAPGKGLEWLGVIWSGGSTDYNAAFMSRLSISKDNSKSQVFFKMNSLQADDTAIYYCAKSPDGYDVAWFGYWGQGTLVTVSA |
| **224** | 846.1F5 | QIQLVQSGPELKKPGETVKISCKASGYTFTNYGMNWVKQAPGKGLKWMGWINTYTGEPSYADDFKGRFAFSLETSASTAYLQINNLKNEDMATYFCARWGGYDGDYYAMDYWGQGTSVTVSS |
| **225** | 846.2H3 | QIQLVQSGPELKKPGETVKISCKASGYTFTNYGMNWVKQAPGKGLKWMGWINTYTGEPSYADDFKGRFAFSLETSASTAYLQINNLKNEDMATYFCARWGGYDGDYYAMDYWGQGTSVTVSS |
| **226** | 846T.1H2 | QIQLVQSGPELKKPGETVKISCKASGYTFTNYGMNWVKQAPGKGLKWMGWINTNTGEPTYAEEFKGRFAFSLETSASTAYLQINNLKNEDTATYFCATGGGNWDFDYWGQGTTLTVSS |
| **227** | 9H2.2H10 | QVQLQQPGAELVGPGSSVKLSCKASGYTFTNYWIHWVKQRPLQGLEWIGNIDPSDSETHYNQKFKDKATLTVDKSSSTAYMQLSSLTSEDSAVYYCARHGYYDYWGQGTTLTVSS |
| **228** | IMT001-4 | QVQLVQSGSELKKPGASVKVSCKASGYTFTNYGMNWVRQAPGQGLKWMGWINTNTGEPTYVEEFTGRFVFSLETSVSTAYLQISSLKAEDTAVYFCAPYDNFFAYWGQGTTVTVSS |
| **229** | IMT006-1 | QVQLVQSGAEVKKPGASVKVSCKASGYSFTNYYMHWVRQAPGQGLEWMGWIYPGSGNTNYNEKFQGRVTMTADTSISTAYMELSRLRSDDTAVYYCSTAPGGFDVWGQGTTVTVSS |
| **230** | IMT006-5 | QVQLVQSGAEVKKPGASVKVSCKASGYSFTNYYMHWVRQAPGQRLEWMGWIYPGSGNTNYNEKFQGRVTITADTSASTAYMELSSLRSEDTAVYYCSTAPGGFDVWGQGTTVTVSS |
| **231** | IMT006-8 | QVQLVQSGAEVKKPGASVKVSCKASGYSFTNYYIHWVRQAPGQRLEWMGWIYPGSGNTNYNEKFQGRVTLTADTSASTTYMELSSLRSEDTAVYYCSTAPGGFDVWGQGTTVTVSS |
| **232** | mIMT001 | QIQLVQSGPELKKPGETVKISCKASGYTFTNYGMNWVKQAPGKGLKWMGWINTNTGEPTYVEEFKGRFAFSLETSASTAYLQINNLKNEDTATYFCAPYDNFFAYWGQGTLVTVSA |

Fig. 36A cont.

| SEQ ID NO | ab name | VL Variable |
|---|---|---|
| 233 | 2D10.2B2 | DIVMTQAAFSNPVTLGTSASISCRSSKSLLHSDGITYLYWYLQRPGQSPQLLIYRMSNLASG VPDRFSGSGSGTDFTLRISRVEAEDVGVYYCAQMIEFPLTFGAGTILELK |
| 234 | 3B11.2G2 | DVVMTQTPLTLSVAIGQPASISCKSSQSLLYTNGKTYLNWLLQRPGQSPKRLIYLVSKLDSG VPDRFSGSGSGTDFTLKISRVEAEDLGVYYCLQSTHFPLTFGAGTKLELK |
| 235 | 4A11.2B5 | DIVMTQAAFSNPVTLGTSASISCRSSKSLLHSDGITYLYWYLQRPGQSPQLLIYRMSNLASG VPDRFSGSGSGTDFTLRISRVEAEDVGVYYCAQMLEFPLTFGAGTKLELK |
| 236 | 4G2.2G6 | DVVMTQTPLTLSVTIGQPASISCKSSQSLLYTDGKTYLSWFLQRPGQSPKRLIYLVSKLDSGV PDRFSGSGSGTDFTLKISRVEAEDLGVYYCLQSTHFPLTFGAGTKLEVK |
| 237 | 6H6.2D6 | DIQMTQTTSSLSASLGDRVTISCSASQGISNYLNWYQQKPDGTVKLLIYYTSSLHSGVPSRFS GSGSGTDYSLTISNLEPEDIATYYCQQYSELPYTFGSGTKLEIK |
| 238 | 7D8.2D8 | DVLMTQTPLSLPVSLGDQASISCRSSQSIVHSNGNTYLEWYLQKPGQSPKLLIYKVSNRFSG VPDRFSGSGSGTDFTLKISRVEAEDLGVYYCFQGSHVPLTFGAGTKLELK |
| 239 | 12G5.D7 | DILMTQSPSSMSVSLGDTVSITCHASQGINSNMGWLQQKPGKSFKGLIYHATNLEDGVPS RFSGSGSGADYSLTISSLESEDFADYYCVQYAQFPPTFGSGTKLEIK |
| 240 | 13A12.2E5 | DVVMTQTPLTLSVAIGQPASISCKSSQSLLYTNGKTYLNWLLQRPGQSPKRLIYLLSKLDSGV PDRFSASGSGTDFTLKISRVEAEDLGVYYCLQSTHFPLTFGAGTKLEMK |
| 241 | 13G4.2F8 | DIVMTQSQKFMSTSVGERVSITCKASQNVGTNVAWYQQKAGQSLELLIYGASNRHTGVP DRFTGSGSGTDFTLTITNVQSEDMTNYFCEQYSNFPLTFGAGTKLELK |
| 242 | 13H12.2F8 | DVVMTQTPLTLSVTIGQPASISCKSSQSLFHSDGKTYLNWLLQRPGQSPKRLIYLVSKLDSG VPDRFTGSGSGTDFTLKISRVEAEDLGVYYCWQGTHFPLTFGAGTKLEMK |
| 243 | 14H10.2C9 | DVVMTQTPLTLSVTIGQPASISCKSSQSLFDSDGKTYLNWLLQRPGQSPKRLIYLVSKLDSG VPDRFTGSGSGTDFTLKISRVEAEDLGVYYCWQGTHFPLTFGAGTKLEMK |
| 244 | 15F10.2D6 | DVLMTQTPLSLPVSLGDQASISCRSSQSIVHNNGNTYLEWYLQKPGQSPKLLIYKVSNRFSG VPDRFSGSGSGTDFTLKISRVEAEDLGVYYCFQGSHVPLTFGGGTKLELK |
| 245 | 15G7.2A7 | DIQMNQSPSSLSASLGDTISITCRASQNINIWLSWYQQKPGNIPQLLIYKASNLHTGVPSRF SGSGSGTDFTLTISSLQPEDIATYYCLQGQSYPLTFGAGTKLVMK |
| 246 | 19B5.2E6 | DIQMTQTTSSLSASLGDRVTISCSASQGINNYLNWYQQKPDGTVKLLIYYASSLHSGVPSRF SGSGSGTDYSLTISNLEPEDIATYYCQQYSQVPYTFGSGTKLEIK |
| 247 | 19D9.2E5 | DVVMTQTPLTLSVTIGQPASISCKSSQSLLHSDGKTYLNWLLQRPGQPPKRLMYLVSTLDS GVPDRFTGSGSGTDFTLKISRVEAEDLGVYYCWQGTHFPLTFGAGTKPELK |

Fig. 36B

| | | |
|---|---|---|
| **248** | 20D11.2C6 | DIQMNQSPSSLSASLGDTITITCRASQNIYIWLSWYQQKPGNIPKLLIYKASNLHTGVPSRFSGSGSGTDFTLTISTLQPEDIATYFCLQGQSYPLTFGAGTKLEMK |
| **249** | 20H5.A3 | DIQMTQTTSSLSASLGDRVTINCSASQDISNYLNWYQQKPDGTVKLLIYYTSSLLSGVPSRFSGSGSGTDYSLTISNLEPEDIATYFCQQYSKLPYTFGSGTHLEIK |
| **250** | 23H9.2E4 | DIQMTQTTSSLSASLGDRVTISCSASQGINNYLNWYQQKPDGTVKLLIYYASSLHSGVPSRFSGSGSGTDYSLTISNLEPEDIATYYCQQYSQVPYTFGSGTKLEIK |
| **251** | 24D12.2H9 | DIVMTQSHKFMSTSVGDRVSITCKASQDVRTAVAWYQQKPGQSPKLLIYWASTRHTGVPDRFTGSGSGTDFTLTLSNVQSEDLADYFCQQYSSYPWTFGGGTKLEIK |
| **252** | 846.1F5 | NIMMTQSPSSLAVSAGEKVTMSCKSSQSVLYSSNQKNYLAWYQQKPGQSPKLLIYWASTRESGVPDRFTGSGSGTDFTLTISSVQPEDLAVYYCHQYLSSLTFGAGTKLELK |
| **253** | 846.2H3 | NIMMTQSPSSLAVSAGEKVTMSCKSSQSVLYSSNQKNYLAWYQQKPGQSPKLLIYWASTRESGVPDRFTGSGSGTDFTLTISSVQPEDLAVYYCHQYLSSLTFGAGTKLELK |
| **254** | 846T.1H2 | DVVMTQTPLTLSVTIGQPASISCKSSQSLLYSNGKTYLNWLLQRPGQSPKRLIYLVSKLDSGVPDRFTGSGSGTDFTLKISRVEAEDLGVYYCVQGTHFPQTFGGGTKLEIK |
| **255** | 9H2.2H10 | DIVMTQSHKFMSTSVGDRVSITCKASQDVSTAVAWYQQKPGQSPKLLIYWASTRHTGVPDRFTGSGSGTDYTLTISSVQAEDLALYYCQQHYTTPLTFGAGTKLELK |
| **256** | IMT001-4 | DIVLTQSPLSLPVTPGEPASISCRSSKSLLYKDGKTYLNWFLQKPGQSPQLLIYLMSTHASGVPDRFSGSGSGTDFTLKISRVEAEDVGVYYCQQLVDYPLTFGGGTKLEIK |
| **257** | IMT006-1 | DIVMTQTPLSLSVTPGQPASISCKSSKSLLHSDGITYLYWYLQKPGQSPQLLIYRMSNLASGVPDRFSGSGSGTDFTLKISRVEAEDVGVYYCAQMLEFPLTFGQGTKLEIK |
| **258** | IMT006-5 | DIVMTQTPLSLSVTPGQPASISCKSSKSLLHSDGITYLYWYLQKPGQSPQLLIYRMSNLASGVPDRFSGSGSGTDFTLKISRVEAEDVGVYYCAQMLEFPLTFGQGTKLEIK |
| **259** | IMT006-8 | DIVMTQSPLSLPVTPGEPASISCRSSKSLLHSDGITYLYWYLQKPGQSPQLLIYRMSNLASGVPDRFSGSGSGTDFTLKISRVEAEDVGVYYCAQMLEFPLTFGQGTKLEIK |
| **260** | mIMT001 | DIVITQDELSNPVTSGESVSISCRSSKSLLYKDGKTYLNWFLQRPGQSPQLLIYLMSTHASGVSDRFSGSGSGTDFTLEISRVKAEDVGVYYCQQLVDYPLTFGAGTKLELK |

Fig. 36B cont.

| SEQ ID NO: | Antibody | constant | Amino acid Seq |
|---|---|---|---|
| **261** | IMT001-4 | hIgG4 (S228P) | MGSTAILGLLLAVLQGVCAQVQLVQSGSELKKPGASVKVSCKASGYTF TNYGMNWVRQAPGQGLKWMGWINTNTGEPTYVEEFTGRFVFSLET SVSTAYLQISSLKAEDTAVYFCAPYDNFFAYWGQGTTVTVSSASTKGPS VFPLAPCSRSTSESTAALGCLVKDYFPEPVTVSWNSGALTSGVHTFPAV LQSSGLYSLSSVVTVPSSSLGTKTYTCNVDHKPSNTKVDKRVESKYGPPC PPCPAPEFLGGPSVFLFPPKPKDTLMISRTPEVTCVVVDVSQEDPEVQF NWYVDGVEVHNAKTKPREEQFNSTYRVVSVLTVLHQDWLNGKEYKC KVSNKGLPSSIEKTISKAKGQPREPQVYTLPPSQEEMTKNQVSLTCLVK GFYPSDIAVEWESNGQPENNYKTTPPVLDSDGSFFLYSRLTVDKSRWQ EGNVFSCSVMHEALHNHYTQKSLSLSLG |
| **262** | IMT001-4 | hKappa | MDMRVPAQLLGLLLLWLRGARCDIVLTQSPLSLPVTPGEPASISCRSSK SLLYKDGKTYLNWFLQKPGQSPQLLIYLMSTHASGVPDRFSGSGSGTD FTLKISRVEAEDVGVYYCQQLVDYPLTFGGGTKLEIKRTVAAPSVFIFPPS DEQLKSGTASVVCLLNNFYPREAKVQWKVDNALQSGNSQESVTEQDS KDSTYSLSSTLTLSKADYEKHKVYACEVTHQGLSSPVTKSFNRGEC |
| **263** | IMT006-1 | hIgG4 (S228P) | MDPKGSLSWRILLFLSLAFELSYGQVQLVQSGAEVKKPGASVKVSCKAS GYSFTNYYMHWVRQAPGQGLEWMGWIYPGSGNTNYNEKFQGRVT MTADTSISTAYMELSRLRSDDTAVYYCSTAPGGFDVWGQGTTVTVSS ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKRV ESKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDW LNGKEYKCKVSNKGLPSSIEKTISKAKGQPREPQVYTLPPSQEEMTKNQ VSLTCLVKGFYPSDIAVEWESNGQPENNYKTTPPVLDSDGSFFLYSRLT VDKSRWQEGNVFSCSVMHEALHNHYTQKSLSLSLG |
| **264** | IMT006-1 | hKappa | METDTLLLWVLLLWVPGSTGDIVMTQTPLSLSVTPGQPASISCKSSKSL LHSDGITYLYWYLQKPGQSPQLLIYRMSNLASGVPDRFSGSGSGTDFTL KISRVEAEDVGVYYCAQMLEFPLTFGQGTKLEIKRTVAAPSVFIFPPSDE QLKSGTASVVCLLNNFYPREAKVQWKVDNALQSGNSQESVTEQDSKD STYSLSSTLTLSKADYEKHKVYACEVTHQGLSSPVTKSFNRGEC |

Fig. 37

| | | | |
|---|---|---|---|
| **265** | IMT006-5 | hIgG4 (S228P) | MDPKGSLSWRILLFLSLAFELSYGQVQLVQSGAEVKKPGASVKVSCKASGYSFTNYYMHWVRQAPGQRLEWMGWIYPGSGNTNYNEKFQGRVTITADTSASTAYMELSSLRSEDTAVYYCSTAPGGFDVWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| **266** | IMT006-5 | hKappa | METDTLLLWVLLLWVPGSTGDIVMTQTPLSLSVTPGQPASISCKSSKSLLHSDGITYLYWYLQKPGQSPQLLIYRMSNLASGVPDRFSGSGSGTDFTLKISRVEAEDVGVYYCAQMLEFPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| **267** | IMT006-8 | hIgG4 (S228P) | MDPKGSLSWRILLFLSLAFELSYGQVQLVQSGAEVKKPGASVKVSCKASGYSFTNYYIHWVRQAPGQRLEWMGWIYPGSGNTNYNEKFQGRVTLTADTSASTTYMELSSLRSEDTAVYYCSTAPGGFDVWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG |
| **268** | IMT006-8 | hKappa | METDTLLLWVLLLWVPGSTGDIVMTQSPLSLPVTPGEPASISCRSSKSLLHSDGITYLYWYLQKPGQSPQLLIYRMSNLASGVPDRFSGSGSGTDFTLKISRVEAEDVGVYYCAQMLEFPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

Fig. 37 cont.

| bin | ab name | VH CDR1 | VH CDR2 | VH CDR3 | VL CDR1 | VL CDR2 | VL CDR3 |
|---|---|---|---|---|---|---|---|
| 1 | 846T.1H2 | GYTFTNYG | INTNTGES | QPGGVTGTLTT | ---QSLLYSNGKTY- | LVS | VQGTHFPQT |
| 1 | mIMT001 | GYTFTNY- | -NTNTGE- | APYDNFFAY | RSSKSLLYKDGKTYLN | LMSTHAS | QQLVDYPLT |
| | alignment | ******<br>*- | -*******- | QPGGVTGTLTT-----<br>----------APYDNFFAY<br>-------. .---- | ----QSLLYSNGKTY--<br>RSSKSLLYKDGKTYLN<br>---:****.:****-- | LVS-----<br>LMSTHAS<br>*:*----- | -* ..:* * |
| | | SEQ ID NO: 269<br><br>GYTFTNYXn1<br><br>wherein Xn1 = G or absent | SEQ ID NO: 270<br><br>Xn1NTNTGEXn2<br><br>wherein Xn1 = I or absent, Xn2 = S or absent | SEQ ID NO: 271<br><br>Xn1Xn2Xn3Xn4Xn5Xn6Xn7Xn8Xn9Xn10Xn11Xn12Xn13Xn14Xn15<br><br>wherein Xn1 = Q or absent, Xn2 = P or absent, Xn3 = G or absent, Xn4 = G or absent, Xn5 = V or absent, Xn6 = T or absent, Xn7 = G or A, Xn8 = T or F, Xn9 = L or Y, Xn10 = T or D, Xn11 = T or N, Xn12 = F or absent, Xn13 = F or absent, Xn14 = A or absent, Xn15 = Y or absent | SEQ ID NO: 272<br><br>Xn1Xn2Xn3Xn4SLLYXn5Xn6GKTYXn7Xn8<br><br>wherein Xn1 = R or absent, Xn2 = S or absent, Xn3 = S or absent, Xn4 = K or Q, Xn5 = S or K, Xn6 = N or D, Xn7 = L or absent, Xn8 = N or absent | SEQ ID NO: 273<br><br>LXn1SXn2Xn3Xn4Xn5<br><br>wherein Xn1 = V or M, Xn2 = T or absent, Xn3 = H or absent, Xn4 = A or absent, Xn5 = S or absent | SEQ ID NO: 274<br><br>Xn1QXn2Xn3Xn4Xn5PXn6T<br><br>wherein Xn1 = V, Q or absent, Xn2 = G or L, Xn3 = T or V, Xn4 = H or D, Xn5 = F or Y, Xn6 = Q or L |

Fig. 38

| bin | ab name | VH CDR1 | VH CDR2 | VH CDR3 | VL CDR1 | VL CDR2 | VL CDR3 |
|---|---|---|---|---|---|---|---|
| 2 | 13H12.2F8 | GYTFTTY | INTYSGVP | AVPYEYDGAY | QSLFHSDGKTY | LVS | WQGTHFPLT |
| 2 | 14H10.2C9 | GYTFTTY | INTYSGVP | STPYEYDGAY | QSLFDSDGKTY | LVS | WQGTHFPLT |
| 2 | 19D9.2E5 | GYTFTTY | INTYSGVP | ATPYEYDGAY | QSLLHSDGKTY | LVS | WQGTHFPLT |
| 2 | alignment | ******** | ******** | :.******** | ***:.****** | *** | ******** |
| | | SEQ ID NO: 275<br><br>GYTFTTY | SEQ ID NO: 276<br><br>INTYSGVP | SEQ ID NO: 277<br><br>Xn1Xn2PYEYDGAY wherein Xn1 = A or S, Xn2 = V or T | SEQ ID NO: 278<br><br>QSLXn1Xn2SDGKTY wherein Xn1 = L or F, Xn2 = D or H | SEQ ID NO: 279<br><br>LVS | SEQ ID NO: 280<br><br>WQGTHFPLT |

| bin | ab name | VH CDR1 | VH CDR2 | VH CDR3 | VL CDR1 | VL CDR2 | VL CDR3 |
|---|---|---|---|---|---|---|---|
| 3 | 2D10.2B2 | GYTFTDY | IYPGSNDT | ANYFGCSGWFFDV | KSLLHSDGITY | RMS | AQMIEFPLT |
| 3 | 4A11.2B5 | GYSFTNY | IYPGSGNT | STAPGGFDV | KSLLHSDGITY | RMS | AQMLEFPLT |
| 3 | 846.1F5 | GYTFTNYG | INTYTGEP | ARWGGYDGDYYAMDY | QSVLYSSNQKNY | WAS | HQYLSSLT |
| 3 | 846.2H3 | GYTFTNYG | INTYTGEP | ARWGGYDGDYYAMDY | QSVLYSSNQKNY | WAS | HQYLSSLT |
| 3 | alignment | **:**:* | --IYPGSNDT<br>--IYPGSGNT<br>INTYTGEP--<br>INTYTGEP--<br>---* *.--- | ARWGGYDGDYYAMDY<br>ARWGGYDGDYYAMDY<br>ANYFGCSGWFFDV--<br>----STAPGGFDV--<br>--. : :---- | -KSLLHSDGITY<br>-KSLLHSDGITY<br>QSVLYSSNQKNY<br>QSVLYSSNQKNY<br>-. * *: .* | --* | AQMIEFPLT<br>AQMLEFPLT<br>HQYLS-SLT<br>-* :. ** |

Fig. 38 Cont.

| | | | | | | | |
|---|---|---|---|---|---|---|---|
| | | SEQ ID NO: 281<br><br>GYXn1FTXn2YXn3<br><br>wherein Xn1 = S or T, Xn2 = D or N, Xn3 = G or absent | SEQ ID NO: 282<br><br>Xn1Xn2Xn3YXn4GXn5Xn6Xn7Xn8<br><br>wherein Xn1 = I or absent, Xn2 = N or absent, Xn3 = I or T, Xn4 = P or T, Xn5 = S or E, Xn6 = N, G, P or absent, Xn7 = N, D or absent, Xn8 = T or absent | SEQ ID NO: 283<br><br>Xn1Xn2Xn3Xn4Xn5Xn6Xn7Xn8Xn9Xn10Xn11Xn12Xn13Xn14Xn15<br><br>wherein Xn1 = A or absent, Xn2 = R, N or absent, Xn3 = W, Y or absent, Xn4 = G, F or absent, Xn5 = G or S, Xn6 = Y, C or T, Xn7 = D, S or A, Xn8 = G or P, Xn9 = D, w or G, Xn10 = Y, F or G, Xn11 = Y or F, Xn12 = A, D or absent, Xn13 = M, V or absent, Xn14 = D or absent, Xn15 = Y or absent | SEQ ID NO: 284<br><br>Xn1Xn2Xn3LXn4Xn5SXn6Xn7Xn8Xn9Y<br><br>wherein Xn1 = Q or absent, Xn2 = K or S, Xn3 = S or V, Xn4 = L or Y, Xn5 = H or S, Xn6 = D or N, Xn7 = G or Q, Xn8 = I or K, Xn9 = T or N | SEQ ID NO: 285<br><br>Xn1Xn2S<br><br>wherein Xn1 = W, R or absent, Xn2 = A, M or absent | SEQ ID NO: 286<br><br>Xn1QXn2Xn3Xn4Xn5Xn6LT<br><br>wherein Xn1 = A, H or absent, Xn2 = M or Y, Xn3 = I or L, Xn4 = E or S, Xn5 = F or absent, Xn6 = P or S |

Fig. 38 Cont.

| bin | ab name | VH CDR1 | VH CDR2 | VH CDR3 | VL CDR1 | VL CDR2 | VL CDR3 |
|---|---|---|---|---|---|---|---|
| 4 | 6H6.2D6 | GYTFTTY | INTYSGVP | ARGPYAMDY | QGISNY | YTS | QQYSELPYT |
| 4 | 19B5.2E6 | GYTFTTY | INTYSGVP | ARGPYAMDY | QGINNY | YAS | QQYSQVPYT |
| 4 | 20H5.A3 | GYAFTTY | VNTYSGVP | ARGPYAMDY | QDISNY | YTS | QQYSKLPYT |
| 4 | 23H9.2E4 | GYTFTTY | INTYSGVP | ARGPYAMDY | QGINNY | YAS | QQYSQVPYT |
| 4 | alignment | **:**** | :******* | ********* | *.*.** | *:* | ****::*** |
| | | SEQ ID NO: 287<br><br>GYXn1FTTY<br><br>wherein Xn1 = A or T | SEQ ID NO: 288<br><br>Xn1NTYSGVP<br><br>wherein Xn1 = I or V | SEQ ID NO: 289<br><br>ARGPYAMDY | SEQ ID NO: 290<br><br>QXn1IXn2NY<br><br>wherein Xn1 = G or D, Xn2 = S or N | SEQ ID NO: 291<br><br>YXn1S<br><br>wherein Xn1 = A or T | SEQ ID NO: 292<br><br>QQYSXn1Xn2PYT<br><br>wherein Xn1 = E, Q or K, Xn2 = L or V |

Fig. 38 Cont.

| bin | ab name | VH CDR1 | VH CDR2 | VH CDR3 | VL CDR1 | VL CDR2 | VL CDR3 |
|---|---|---|---|---|---|---|---|
| 5 | 15G7.2A7 | GYTFTDY | INPNNGGT | TSGYGFPY | QNINIW | KAS | LQGQSYPLT |
| 5 | 20D11.2C6 | GYTFTDF | INPKNGGI | TSGYGFPY | QNIYIW | KAS | LQGQSYPLT |
| 5 | alignment | ******: | ***:*** | ******** | *** ** | *** | ********* |
| | | SEQ ID NO: 293<br><br>GYTFTDXn1<br><br>wherein Xn1 = F or Y | SEQ ID NO: 294<br><br>INPXn1NGGI<br><br>wherein Xn1 = N or K | SEQ ID NO: 295<br><br>TSGYGFPY | SEQ ID NO: 296<br><br>QNIXn1IW<br><br>wherein Xn1 = N or Y | SEQ ID NO: 279<br><br>KAS | SEQ ID NO: 298<br><br>LQGQSYPLT |

| bin | ab name | VH CDR1 | VH CDR2 | VH CDR3 | VL CDR1 | VL CDR2 | VL CDR3 |
|---|---|---|---|---|---|---|---|
| 7 | 3B11.2G2 | GYKFKTY | INTYSGVP | ARDGNYGDPMDY | QSLLYTNGKTY | LVS | LQSTHFPLT |
| 7 | 13A12.2E5 | GYKFKTY | INTYSGVP | ARDGNYGDPMDY | QSLLYTNGKTY | LLS | LQSTHFPLT |
| 7 | alignment | ******* | ******** | ************ | *********** | *:* | ********* |
| | | SEQ ID NO: 299<br><br>GYKFKTY | SEQ ID NO: 300<br><br>INTYSGVP | SEQ ID NO: 301<br><br>ARDGNYGDPMDY | SEQ ID NO: 302<br><br>QSLLYTNGKTY | SEQ ID NO: 303<br><br>LXn1S<br><br>wherein Xn1 = L or V | SEQ ID NO: 304<br><br>LQSTHFPLT |

Fig. 38 cont.

ANTI-GAL3 ANTIBODIES AND USES THEREOF

RELATED APPLICATIONS

This application is a Continuation Application under 35 U.S.C. § 111 (a) of U.S. Continuation application Ser. No. 17/384,542, filed on Jul. 23, 2021, which is a continuation of International Application No. PCT/US2020/015692, filed on Jan. 29, 2020, designating the United States and published in the English language, which claims the benefit of U.S. Provisional Application Ser. No. 62/798,945, filed Jan. 30, 2019, and U.S. Provisional Application Ser. No. 62/798,949, filed Jan. 30, 2019, each of which are hereby incorporated by reference in its entirety.

REFERENCE TO SEQUENCE LISTING

The present application is being filed along with a Sequence Listing in electronic format. The Sequence Listing is provided as a file entitled IMMUT003C2SubstituteeqListing, created and last saved on Mar. 20, 2024, which is 377,440 bytes in size. The information in the electronic format of the Sequence Listing is hereby incorporated by reference in its entirety.

FIELD OF THE INVENTION

Disclosed herein, in some embodiments, are antibodies that specifically bind to Gal3 (or "anti-Gal3 antibody") and disrupt an interaction between Gal3 and TIM-3 and promote T cell or Natural Killer (NK) cell proliferation. Also disclosed herein are methods of utilizing the antibody to elicit an immune response and methods of treatment. Also disclosed herein are methods of reducing fibrosis or propensity thereof in a tissue by contacting the tissue with an antibody that specifically binds to Gal3. Also described herein are methods of disrupting a Gal3-TIM-3 interaction by an antibody that specifically binds to Gal3, under conditions to reduce expression of one or more fibrosis biomarkers in the tissue.

BACKGROUND OF THE INVENTION

Galectin-3 (Gal3) is a lectin, or a carbohydrate-binding protein, with specificity towards beta-galactosides. In human cells, Gal3 is expressed and can be found in the nucleus, cytoplasm, cell surface, and in the extracellular space. T-cell immunoglobulin and mucin-domain containing-3 (TIM-3) is a protein expressed on immune cells such as T cells, dendritic cells, NK cells, and monocytes.

SUMMARY OF THE INVENTION

Disclosed herein, in some embodiments, are antibodies that specifically bind to Gal3 (or "anti-Gal3 antibody") and disrupt an interaction between Gal3 and TIM-3. Disclosed herein, in some embodiments, are antibodies that specifically bind to Gal3 and promote T cell or Natural Killer cell proliferation. In some embodiments, also disclosed herein are methods of utilizing the antibody to elicit an immune response and methods of treatment.

Embodiments of the present invention provided herein are described by way of the following numbered alternatives:

1. A method of inducing immune activation, comprising: contacting a plurality of cells comprising a Gal3-expressing cell and a TIM-3-expressing cell with an antibody under conditions to disrupt an interaction between Gal3 and TIM-3, wherein the antibody specifically binds to Gal3, wherein the Gal3-expressing cell upon binding to the antibody expresses a cytokine which induces immune activation, and wherein the antibody is not IMT001.

2. The method of alternative 1, wherein the cytokine is an interferon.

3. The method of alternative 2, wherein the interferon is IFNγ.

4. The method of alternative 3, wherein the IFNγ production is 150%, 160%, 170%, 180%, 190%, 200%, or more of IFNγ production by an isotype antibody.

5. The method of alternative 1, wherein the cytokine is an interleukin.

6. The method of alternative 5, wherein the interleukin is IL-2.

7. The method of any one of the alternatives 1-6, wherein the immune activation comprises a proliferation of CD3+ T lymphocytes, CD4+ T helper cells, CD8+ cytotoxic T cells, Natural Killer cells, or a combination thereof.

8. The method of any one of the alternatives 1-7, wherein the immune activation comprises an increase in M1 macrophage population within the plurality of cells.

9. The method of any one of the alternatives 1-8, wherein the immune activation comprises a decrease in M2 macrophage population within the plurality of cells.

10. A method of promoting T cell or Natural Killer (NK) cell proliferation, comprising:

contacting a plurality of cells comprising T cells, NK cells, and a Gal3-expressing cell with an antibody under conditions to effect proliferation of T cells and/or NK cells in the plurality of cells, wherein the antibody specifically binds to Gal3, and wherein the antibody is not IMT001.

11. The method of alternative 10, wherein the plurality of cells further comprises a TIM-3 expressing cell.

12. The method of alternative 11, wherein the antibody further disrupts an interaction of Gal3 and TIM-3.

13. A method of inducing immune activation, comprising: contacting a plurality of cells comprising a Gal3-expressing cell and a TIM-3-expressing cell with an antibody under conditions to disrupt an interaction between Gal3 and TIM-3, wherein the antibody specifically binds to Gal3, and wherein the Gal3-TIM-3 interaction is reduced to less than 70%, less than 60%, less than 59%, less than 50%, less than 40%, less than 34%, less than 30%, less than 20%, less than 14%, less than 10%, less than 7%, less than 5%, less than 4%, or less than 1%.

14. The method of alternative 13, wherein the interaction occurs at one or more residues of Gal3 selected from region 145-168, 160-177, or 165-184, wherein the residue positions correspond to positions 145-168, 160-177, or 165-184 of SEQ ID NO: 1.

15. The method of alternative 13, wherein the interaction occurs at one or more residues of Gal3 selected from region 149-156, 152-168, 163-169, 163-177, or 163-171, wherein the residue positions correspond to positions 149-156, 152-168, 163-169, 163-177, or 163-171 of SEQ ID NO: 1.

16. The method of any one of alternatives 13-15, wherein the interaction occurs at one or more residues of TIM-3 selected from region 91-111 or 82-111, wherein the residue positions correspond to positions 91-111 or 82-111 of SEQ ID NO: 2.

17. The method of any one of alternatives 13-15, wherein the interaction occurs at one or more residues of TIM-3 selected from region 91-111, 107-117, 96-102, 100-106, or 92-119, herein the residue positions correspond to positions 91-111, 107-117, 96-102, 100-106, or 92-119 of SEQ ID NO: 2.

18. The method of any one of the alternatives 13-17, wherein the TIM-3 is human TIM-3.

19. The method of any one of the alternatives 1-18, wherein the Gal3-expressing cell is a tumor cell.

20. The method of any one of the alternatives 1-19, wherein the plurality of cells is located within a tumor microenvironment (TME).

21. The method of any one of the alternatives 1-20, wherein the antibody induces a decrease of tumor cells within the TME.

22. The method of any one of the alternatives 1-21, wherein the plurality of cells further comprises tumor-infiltrating lymphocytes (TILs).

23. The method of any one of the alternatives 1-22, wherein the plurality of cells further comprises CD3+ T lymphocytes, CD4+ T helper cells, CD8+ cytotoxic T cells, or a combination thereof.

24. The method of any one of the alternatives 1, 10, 13, or 22, wherein the contacting further induces TIL proliferation.

25. The method of any one of the alternatives 1, 10, 13, or 23, wherein the contacting further induces proliferation of CD3+ T lymphocytes, CD4+ T helper cells, CD8+ cytotoxic T cells, or a combination thereof.

26. The method of any one of the alternatives 1, 10, 13, or 22-25, wherein the contacting further comprises an increase in proliferation of M1 macrophages.

27. The method of any one of the alternatives 1, 10, 13, or 22-26, wherein the contacting further comprises a decrease in M2 macrophage population within the TME.

28. The method of any one of the alternatives 1-27, wherein the antibody binds to at least one amino acid residue within a Gal3 region that corresponds to residues 1-20 of SEQ ID NO: 1.

29. The method of any one of the alternatives 1-27, wherein the antibody binds to at least one amino acid residue within a Gal3 region that corresponds to residues 41-91 of SEQ ID NO: 1.

30. The method of any one of the alternatives 1-27 or 29, wherein the antibody binds to at least one amino acid residue within a Gal3 region that corresponds to residues 41-71 of SEQ ID NO: 1.

31. The method of any one of the alternatives 1-27 or 29, wherein the antibody binds to at least one amino acid residue within a Gal3 region that corresponds to residues 71-91 of SEQ ID NO: 1.

32. The method of any one of the alternatives 1-31, wherein the antibody binds to at least one amino acid residue within peptide_1, peptide_4, peptide_5, peptide_6, peptide_7, or peptide_8.

33. The method of any one of the alternatives 1-32, wherein the antibody comprises a $K_D$ of less than 1 nM, 1.2 nM, 2 nM, 5 nM, 10 nM, 13.5 nM, 15 nM, 20 nM, 25 nM, or 30 nM.

34. The method of any one of the alternatives 1-33, wherein the antibody comprises a humanized antibody.

35. The method of any one of the alternatives 1-34, wherein the antibody comprises a full-length antibody or a binding fragment thereof.

36. The method of any one of the alternatives 1-35, wherein the antibody comprises a bispecific antibody or a binding fragment thereof.

37. The method of any one of the alternatives 1-36, wherein the antibody comprises a monovalent Fab', a divalent Fab2, a single-chain variable fragment (scFv), a diabody, a minibody, a nanobody, a single-domain antibody (sdAb), or a camelid antibody or binding fragment thereof.

38. The method of any one of the alternatives 1-37, wherein the antibody comprises an IgG framework.

39. The method of any one of the alternatives 1-38, wherein the antibody comprises an IgG1, IgG2, or IgG4 framework.

40. The method of any one of the alternatives 1-39, wherein the antibody further comprises a Fc mutation.

41. The method of any one of the alternatives 1-33 or 35-40, wherein the antibody comprises a chimeric antibody.

42. The method of any one of the alternatives 1, 10, or 13, further comprising administering to a subject the antibody prior to the contacting step.

43. The method of alternative 42, wherein the subject is diagnosed with a cancer.

44. The method of alternative 43, wherein the cancer is a solid tumor.

45. The method of alternative 44, wherein the cancer is breast cancer, colorectal cancer, kidney cancer, liver cancer, or lung cancer.

46. The method of alternative 43, wherein the cancer is a hematologic malignancy.

47. The method of any one of the alternatives 43-46, wherein the cancer is a metastatic cancer.

48. The method of any one of the alternatives 43-46, wherein the cancer is a relapsed or refractory cancer.

49. The method of any one of the alternatives 42-48, wherein the antibody is formulated for systemic administration.

50. The method of any one of the alternatives 42-49, wherein the antibody is formulated for parenteral administration.

51. The method of any one of the alternatives 42-50, wherein the antibody is administered in combination with an additional therapeutic agent.

52. The method of alternative 51, wherein the antibody and the additional therapeutic agent are administered simultaneously.

53. The method of alternative 51, wherein the antibody and the additional therapeutic agent are administered sequentially.

54. The method of alternative 53, wherein the antibody is administered prior to administering the additional therapeutic agent.

55. The method of alternative 53, wherein the antibody is administered after administering the additional therapeutic agent.

56. The method of any one of the alternatives 51-55, wherein the additional therapeutic agent comprises an immune checkpoint modulator.

57. The method of any one of the alternatives 51-55, wherein the additional therapeutic agent comprises a chemotherapeutic agent, targeted therapeutic agent, hormonal therapeutic agent, or a stem cell-based therapeutic agent.

58. The method of any of the preceding alternatives, wherein the subject is a human.

59. The method of alternative 58, wherein the antibody is administered either prior to or after surgery.

60. The method of alternative 58, wherein the antibody is administered in conjunction with, before, or after radiation therapy.

61. The method of any of the preceding alternatives, wherein the antibody has a $K_D$ that is higher than the $K_D$ of antibody IMT001.

62. A method of reducing fibrosis or propensity thereof in a tissue, comprising: contacting the tissue with an antibody that specifically binds Gal3 antibody under conditions such that expression level of a fibrosis biomarker is reduced in the tissue.

63. The method of alternative 62, wherein the tissue further comprises a TIM-3 expressing cell.

64. The method of alternative 63, wherein the antibody further disrupts interaction of Gal3 and TIM-3.

65. The method of alternative 63, wherein the antibody does not disrupt interaction of Gal3 and TIM-3.

66. The method of any one of the alternatives 62-65, wherein the at least one fibrosis biomarker comprises α-smooth muscle actin (α-SMA).

67. The method of any one of the alternatives 62-65, wherein the at least one fibrosis biomarker comprises fibronectin.

68. The method of any one of the alternatives 62-65, wherein the at least one fibrosis biomarker comprises α-smooth muscle actin (α-SMA) and fibronectin.

69. The method of any one of the alternatives 62-68, wherein the tissue is a kidney tissue or liver tissue.

70. The method of any one of the alternatives 62-68, wherein the tissue is selected from a group consisting of a liver tissue, a kidney tissue, a skin tissue, a lung tissue, a heart tissue, a brain tissue, an intestine tissue, a bone marrow tissue, and a soft tissue.

71. The method of any one of the alternatives 62-70, wherein expression of the at least one fibrosis biomarker in the tissue treated with the antibody is less than expression of the at least one fibrosis biomarker in a control tissue treated with a mIgG2b antibody.

72. The method of any one of the alternatives 62-71, wherein the antibody results in reduced accumulation of extracellular matrix proteins in the tissue.

73. The method of alternative 72, wherein the extracellular matrix proteins comprises collagen.

74. The method of alternative 73, wherein the tissue comprises a collagen-producing cell.

75. The method of alternative 74, wherein the collagen-producing cell is a fibroblast cell.

76. The method of alternative 75, wherein the fibroblast cell is activated by a fibrogenic cytokine.

77. The method of alternative 76, wherein the fibrogenic cytokine is TGF-β1.

78. The method of any one of alternatives 62-77, wherein the tissue has an elevated TGF-β1 expression.

79. The method of any one of the alternatives 62-78, wherein the antibody comprises a humanized antibody.

80. The method of any one of the alternatives 62-79, wherein the antibody comprises a full-length antibody or a binding fragment thereof.

81. The method of any one of the alternatives 62-79, wherein the antibody comprises a bispecific antibody or a binding fragment thereof.

82. The method of any one of the alternatives 62-79, wherein the antibody comprises a chimeric antibody.

83. The method of any one of the alternatives 62-82, wherein the antibody binds to at least one amino acid residue within a Gal3 region that corresponds to residues 1-20 of SEQ ID NO: 1.

84. The method of any one of the alternatives 62-82, wherein the antibody binds to at least one amino acid residue within a Gal3 region that corresponds to residues 41-91 of SEQ ID NO: 1.

85. The method of any one of the alternatives 62-82 or 84, wherein the antibody binds to at least one amino acid residue within a Gal3 region that corresponds to residues 41-71 of SEQ ID NO: 1.

86. The method of any one of the alternatives 62-82 or 84, wherein the antibody binds to at least one amino acid residue within a Gal3 region that corresponds to residues 71-91 of SEQ ID NO: 1.

87. The method of any one of the alternatives 62-86, wherein the antibody binds to at least one amino acid residue within peptide_1, peptide_4, peptide_5, peptide_6, peptide_7 or peptide 8.

88. The method of any one of the alternatives 62-87, wherein the antibody comprises a $K_D$ of less than 1 nM, 1.2 nM, 2 nM, 5 nM, 10 nM, 13.5 nM, 15 nM, 20 nM, 25 nM, or 30 nM.

89. The method of any one of the alternatives 62-88, wherein the antibody comprises a monovalent Fab', a divalent Fab2, a single-chain variable fragment (scFv), a diabody, a minibody, a nanobody, a single-domain antibody (sdAb), or a camelid antibody or binding fragment thereof.

90. The method of any one of the alternatives 62-89, wherein the antibody comprises an IgG framework.

91. The method of any one of the alternatives 62-90, wherein the antibody comprises an IgG1, IgG2, or IgG4 framework.

92. The method of any one of the alternatives 62-91, wherein the antibody further comprises a Fc mutation.

93. The method of any one of alternatives 62-92, further comprising administering to a subject the antibody prior to the contacting step.

94. The method of alternative 93, wherein the subject is diagnosed with a fibrotic disease.

95. The method of alternative 94, wherein the fibrotic disease is renal fibrosis.

96. The method of alternative 94, wherein the fibrotic disease is liver fibrosis.

97. The method of any one of the alternatives 93-96, wherein the antibody is formulated for systemic administration.

98. The method of any one of the alternatives 93-96, wherein the antibody is formulated for parenteral administration.

99. The method of any one of the alternatives 93-98, wherein the subject is a mammal.

100. The method of any one of alternatives 64 and 66-99, wherein the Gal3-TIM-3 interaction is reduced to less than 70%, less than 60%, less than 59%, less than 50%, less than 40%, less than 34%, less than 30%, less than 20%, less than 14%, less than 10%, less than 7%, less than 5%, less than 4%, or less than 1%.

101. The method of alternative 100, wherein the interaction occurs at one or more residues of Gal3 selected from region 145-168, 160-177, or 165-184, wherein the residue positions correspond to positions 145-168, 160-177, or 165-184 of SEQ ID NO: 1.

102. The method of alternative 100, wherein the interaction occurs at one or more residues of Gal3 selected from region 149-156, 152-168, 163-169, or 163-171, wherein the residue positions correspond to positions 149-156, 152-168, 163-169, or 163-171 of SEQ ID NO: 1.

103. The method of any one of alternatives 100-102, wherein the interaction occurs at one or more residues of TIM-3 selected from region 90-122 or 82-111, wherein the residue positions correspond to positions 90-122 or 82-111 of SEQ ID NO: 2.

104. The method of any one of alternatives 100-102, wherein the interaction occurs at one or more residues of TIM-3 selected from region 91-111, 107-117, 96-102, 100-106, or 92-119, herein the residue positions correspond to positions 91-111, 107-117, 96-102, 100-106, or 92-119 of SEQ ID NO: 2.

105. An anti-Gal3 antibody for use in the treatment of an immune related disease in a subject, wherein the anti-Gal3 antibody induces activation of the immune system. 106. The anti-Gal3 antibody for use in the treatment of an immune related disease of alternative 105, wherein the anti-Gal3 antibody inhibits the interaction between Gal3 and TIM-3.

107. The anti-Gal3 antibody for use in the treatment of an immune related disease of alternative 105 or 106, wherein the activation of the immune system comprises proliferation of CD3+ T lymphocytes, CD4+ T helper cells, CD8+ cytotoxic T cells, NK cells, M1 macrophages, or a combination thereof.

108. The anti-Gal3 antibody for use in the treatment of an immune related disease according to any one of alternatives 105-107, wherein the activation of the immune system comprises a reduction in M2 macrophages.

109. The anti-Gal3 antibody for use in the treatment of an immune related disease according to any one of alternatives 105-108, wherein the immune related disease is cancer.

110. The anti-Gal3 antibody for use in the treatment of an immune related disease of alternative 109, wherein the cancer is breast cancer, colorectal cancer, kidney cancer, liver cancer, lung cancer, or a hematological malignancy.

111. The anti-Gal3 antibody for use in the treatment of an immune related disease of alternative 109 or 110, wherein the cancer is a metastatic cancer, a relapsed cancer, or a refractory cancer.

112. The anti-Gal3 antibody for use in the treatment of an immune related disease according to any one of alternatives 109-111, wherein the anti-Gal3 antibody is administered in combination with an additional therapeutic agent, such as an immune checkpoint modulator, chemotherapeutic agent, targeted therapeutic agent, hormonal therapeutic agent, stem cell-based therapeutic agent, surgery, or radiation therapy.

113. The anti-Gal3 antibody for use in the treatment of an immune related disease according to any one of alternatives 105-108, wherein the immune related disease is fibrosis, and the anti-Gal3 antibody results in reduced accumulation of extracellular matrix proteins in a tissue.

114. The anti-Gal3 antibody for use in the treatment of an immune related disease of alternative 113, wherein the extracellular matrix proteins comprises collagen.

115. The anti-Gal3 antibody for use in the treatment of an immune related disease of alternative 113 or 114, wherein the expression level of at least one fibrosis biomarker in a subject is reduced, and wherein the at least one fibrosis biomarker comprises α-SMA, fibronectin, or both.

116. The anti-Gal3 antibody for use in the treatment of an immune related disease according to any one of alternatives 113-115, wherein the tissue is selected from a group consisting of a liver tissue, a kidney tissue, a skin tissue, a lung tissue, a heart tissue, a brain tissue, an intestine tissue, a bone marrow tissue, and a soft tissue.

117. The anti-Gal3 antibody for use in the treatment of an immune related disease according to any one of alternatives 113-116, wherein the fibrosis is renal fibrosis, liver fibrosis, lung fibrosis, cardiac fibrosis, or vascular fibrosis. In some embodiments, this can be IV or subcutaneous administration.

118. The anti-Gal3 antibody for use in the treatment of an immune related disease according to any one of alternatives 105-117, wherein the anti-Gal3 antibody is formulated for systemic administration, parenteral administration, intravenous administration, or subcutaneous administration.

119. The anti-Gal3 antibody for use in the treatment of an immune related disease according to any one of alternatives 105-118, wherein the subject is a human.

120. The method of any one of alternatives 1-104, wherein the anti-Gal3 antibody is selected from the group consisting of one or more of 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, and mIMT001.

121. The method of any one of alternatives 1-104, wherein the anti-Gal3 antibody is an antibody having 1, 2, 3, 4, 5, or 6 CDRs from the CDRs within one or more of 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, and mIMT001.

121. The method of any one of alternatives 1-104, wherein the anti-Gal3 antibody is IMT001-4, IMT006-1, IMT006-5, or IMT006-8.

122. The anti-Gal3 antibody for use in the treatment of an immune related disease according to any one of alternatives 105-119, wherein the anti-Gal3 antibody is selected from the group consisting of 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, and mIMT001.

123. The anti-Gal3 antibody for use in the treatment of an immune related disease according to any one of alternatives 105-119, wherein the anti-Gal3 antibody is IMT001-4, IMT006-1, IMT006-5, or IMT006-8.

124. An anti-GAL3 antibody comprising at least the HCDR3 within any one of the antibodies of FIGS. 35A-36B.

125. The anti-GAL3 antibody of alternative 124, further comprising all 3 HCDRs within any one of the antibodies of FIGS. 35A-36B.

126. The anti-GAL3 antibody of alternative 125, further comprising all 3 LCDRs within any one of the antibodies of FIGS. 35A-36B.

127. An anti-GAL3 antibody that comprises any one of the heavy chain sequences within FIG. 36A, or a sequence that is at least 80% identical thereto.

128. An anti-GAL3 antibody that comprises any one of the light chain sequences within FIG. 36B or a sequence that is at least 80% identical thereto.

129. The anti-GAL3 antibody of alternative 128 that further comprises any one of the heavy chain sequences within FIG. 36A, or a sequence that is at least 80% identical thereto.

130. The anti-GAL3 antibody that comprises 6 CDRs, wherein the 6 CDRs are, across their combined sequences, at least 80% identical to any set of 6 CDRs within FIGS. 35A and 35B.

131. An anti-GAL3 antibody that comprises at least one of the CDRs from FIG. 38.

132. An anti-GAL3 antibody that comprises at least two of the CDRs from FIG. 38.

133. An anti-GAL3 antibody that comprises at least three of the CDRs from FIG. 38.

134. An anti-GAL3 antibody that comprises at least four of the CDRs from FIG. 38.

135. An anti-GAL3 antibody that comprises at least five of the CDRs from FIG. 38.

136. An anti-GAL3 antibody that comprises six of the CDRs from FIG. 38.

137. An anti-GAL3 antibody that comprises six of the CDRs from FIG. 38, and wherein all six are from a single bin.

138. An anti-GAL3 antibody that comprises six of the CDRs from FIG. 38, or a set of 6 CDRs which, across their entire sequence, is at least 80% identical thereto.

BRIEF DESCRIPTION OF THE DRAWINGS

In addition to the features described above, additional features and variations will be readily apparent from the following descriptions of the drawings and exemplary embodiments. It is to be understood that these drawings depict typical embodiments and are not intended to be limiting in scope.

FIG. 1A shows TIM-3 expression in the 293T cells co-transfected with a plasmid encoding a HA-tagged hTIM-3 and a plasmid encoding hGal3, hGal9, or hCEACAM1. FIG. 1B shows expression of hGal9, hGal3, or hCEACAM1. FIG. 1C shows that hGal3, but not CEACAM1, pulled down the-HA-tagged hTIM-3 in the co-transfected 293T cells. The results also show that human Gal9 (hGal9) pulled down hTIM-3, but the pull down was accompanied with protein aggregation (FIG. 1B), indicating the binding between hGal9 and hTIM-3 might be non-specific.

In FIG. 5A, plates were coated with mGal3 at 10 μg/ml, mGal3 polyclonal antibody (mGal3 pAb) and monoclonal antibody IMT001, but not monoclonal antibody M3/38, were shown to block the interaction between Gal3 and Tim3. FIG. 5B shows that lactose blocked Gal9, but not Gal3 from binding to TIM-3, indicating that the binding between Gal3 and Tim3 is sugar-independent binding. FIG. 5C shows that antibody RMT3-23 blocked phosphatidylserine (PS), but not Gal3 from binding to TIM-3, indicating the epitopes on TIM-3 that bind to Gal3 is different from those that bind to PS.

FIG. 6A shows that mouse A20 cell clones #41, #31, and #15 overexpress Gal3. FIG. 6B shows that when these cells were mixed with mouse DO11.10 T cells, much less IL-2 was produced as compared to parental A20 cells.

FIG. 7A shows high expression of Gal3 on B16F10 tumor cells. FIG. 7B shows representative images of the whole lung from three treated groups. FIG. 7C shows numbers of metastatic colonies on surface of the left lung lobe (Mean±SEM). FIG. 7D and FIG. 7E show lung weight and body weight of different treatment groups (Mean±SEM). As compared to animals that were treated with the isotype control, animals treated with the monoclonal anti-human Gal3 antibody showed significant reduction of tumor number ($p<0.01$) (FIG. 7B) and much less tumor burden as indicated by lung weight ($p<0.05$) (FIG. 7D). However, animals treated with PD1 antibody did not show significant reduction of tumor number or burden in this lung metastasis model ($p>0.05$). FIG. 7E shows that animals treated with either the PD1 antibody or the Gal3 antibody had similar body weight as the control group, indicating that there were no adverse effects associated with administration of either antibody.

FIG. 8A shows the images of metastasized tumor colonies on the lung of mice that have been implanted with 4T1 cells and then treated with either control antibody ("isotype") or IMT001. The antibodies were administered intraperitoneally on day 0, 3, 7, 10 and 14 during a period of 30 days. The images were taken at the day 30 when the mice were sacrificed. FIG. 8B shows the body weight measurements of these mice during the same period. FIG. 8C shows the number of metastasized tumor colonies on the surface of the left lobe of these mice at day 30.

FIGS. 11A-D show the results of epitope mapping. A peptide array derived from hGal3 protein sequence was synthesized (FIG. 11A) and dot blotted with anti Gal3 antibody IMT001 (FIG. 11B). Peptides 5 and 6 showed good signal, indicating that the anti Gal3 monoclonal antibody, IMT001, can bind to these peptides. To further map the binding epitopes of IMT001 on these peptides, several shorter peptides derived from these peptide sequences were synthesized (FIG. 11C) and their binding to IMT001 was measured by ELISA (FIG. 11D). Peptide with sequence GQAPPGAYPG (SEQ ID NO: 28) produced the highest signal.

FIG. 13A shows the results from staining squamous cell carcinoma and FIG. 13B shows the results from staining of adenocarcinoma.

FIG. 15B shows detection of expression of Gal3 by IHC on mouse macrophage cell line RAW264.7, as compared to control (FIG. 15A). FIG. 15C shows the expression of Gal 3 on mouse macrophage cell line by flow cytometry using cells stained with IMT001. The anti Gal3 antibody IMT001, but not anti mouse PD-1 antibody 29F, enhanced IL-2 production in RAW macrophages/DO11.10 T cell mixed reaction (FIG. 15D).

FIG. 17A: antibodies mab1, mab3, mab4, and mab5; FIG. 17B: antibodies mab2, mab3, mab6, and mab7. Results illustrate Gal3-targeted antibodies exhibit differential blockade of Gal3-TIM3 binding.

FIG. 19A: mab1; kD=13.5 nM. FIG. 19B: mab4; kD=1.2 nM. FIG. 19C: mab5; kD=32 nM.

FIGS. 21A-C illustrate MALDI-MS identification of GAL3 and TIM3 regions mediating the interaction between TIM3 and GAL3. Note that amino acid numeration is based on the mature protein after processing of the signal peptide. Also see Table 2. FIG. 21A illustrates potential sequences involved in the binding interface. FIG. 21B illustrates potential residues involved in the interaction. FIG. 21C illustrates the sequence locations mapped on the respective TIM-3 and Gal3. Note that amino acid numeration is based on the mature protein after processing of the signal peptide.

FIG. 25. Alignment of GAL3 peptides with ability to bind GAL3-TIM3 blocking GAL3-targeted antibodies.

FIG. 26. Identification of Galectin-3 binding antibody bins by antibody competition. Values represent inhibition as assessed by biolayer interferometry.

FIGS. 28A-D. Tumor volumes of mice engrafted with subcutaneous MBT2 tumors and treated with control, IMT001, anti-PD-L1 antibody, or combinations thereof (FIG. 28A), or with control, IMT001, anti-PD-1 antibody, or combinations thereof (FIG. 28C). Plots of tumor volume for anti-PD-L1 (FIG. 28B) or anti-PD-1 (FIG. 28D) represent daily measurements of individual animals.

FIG. 35A depicts some embodiments of the VH CDR regions of various embodiments of anti-GAL3 antibodies. In some embodiments, any of the method or compositions provided herein can include one or more of the CDRs provided herein, including 1, 2, or 3 of them.

FIG. 35B depicts some embodiments of the VL CDR regions of various embodiments of anti-GAL3 antibodies. In some embodiments, any of the method or compositions provided herein can include one or more of the CDRs provided herein, including 1, 2, or 3 of them.

FIG. 36A depicts some embodiments of the full VH regions of various embodiments of anti-GAL3 antibodies. In some embodiments, any of the methods or compositions provided herein can include any one of these VH regions.

FIG. 36B depicts some embodiments of the full VL regions of various embodiments of anti-GAL3 antibodies. In some embodiments, any of the methods or compositions provided herein can include any one of these VL regions.

FIG. 37 depicts some embodiments of various GAL3 antibodies (including full heavy chain or kappa chain sequences). In some embodiments, any one or more of the VH/VL and/or CDRs provided in the other figures can be paired with any one or more of the relevant sequences in FIG. 37 (e.g., IgG4 section or kappa sequence).

FIG. 38 depicts alignments of some embodiments of the VH CDR or VL CDR regions of various embodiments of anti-Gal3 antibodies. In some embodiments, any of the methods or compositions provided herein can use any 1, 2, 3, 4, 5, or 6 of the consensus CDRs provided in FIG. 38.

DETAILED DESCRIPTION

Figure 1A:
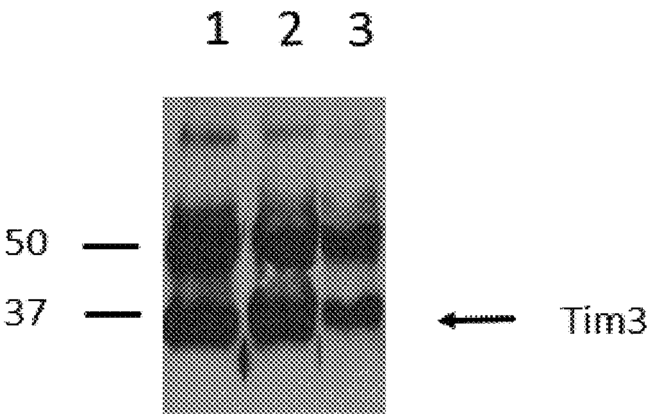
FIGS. 1A-C illustrate the results of co-immunoprecipitation assay indicating that human Gal3 (hGal3) specifically pulled down human TIM-3 (hTIM-3).

Galectin-3 (Gal3, GAL3, or Gal-3) is expressed in several cell types and involved in a broad range of physiological and pathological processes, which include cell adhesion, cell activation and chemoattraction, cell cycle, apoptosis, cell growth and differentiation, and tumor progression and metastasis. Gal3 expresses on tumors cells and cells in the tumor microenvironment, e.g., tumor-associated macrophages, especially M2 macrophages. Further, it is implicated in the activation of a variety of profibrotic factors that promote fibroblast proliferation and transformation, and mediate collagen production. Furthermore, Gal3 is thought to play a key role in fibrogenesis of various tissues, including liver, kidney, lung, and myocardia.

TIM-3 is a molecule expressed on immune cells, especially on T cells and can suppress an immune response, e.g., T cell signaling, through the interaction with Gal3. The anti-Gal3 antibodies interfere with the interaction between Gal3 and TIM-3 and activate an immune response.

Tumors are often associated with an immune infiltrate as part of the reactive stroma that is enriched for macrophages. Tumor-associated macrophages (TAMs) play an important role in facilitating tumor growth by promoting neovascularization and matrix degradation. When associated with tumors, macrophages demonstrate functional polarization towards one of two phenotypically different subsets of macrophages: M1 macrophages or M2 macrophages. M1 macrophages are known to produce pro-inflammatory cytokines and play an active role in cell destruction, while M2 macrophages primarily scavenge debris and promote angiogenesis and wound repair. Consequently, many tumors with a high number of TAMs have an increased tumor growth rate, local proliferation, and distant metastasis. The M2 macrophage population is phenotypically similar to the TAM population that promotes tumor growth and development. In addition to expressing Gal3, M2 macrophages, in some cases, also express one or more cell surface markers selected from the group consisting of CD206, IL-4r, IL-1ra, decoy IL-1rll, IL-10r, CD23, macrophage scavenging receptors A and B, Ym-1, Ym-2, Low density receptor-related protein 1 (LRP1), IL-6r, CXCR1/2, CD136, CD14, CD1a, CD1b, CD93, CD226, (FcγR) and PD-L1.

Tissue fibrosis is a progressive debilitating disease characterized by an abundant accumulation of extracellular matrix (ECM) proteins such as collagens and fibronectin, leading to tissue scarring, organ injury, organ function decline, and subsequent organ failure. Tissue fibrosis can be located in the kidney, liver, lung, heart, skin, pancreas, intestine, eye, nervous system, joint, tendon, mediastinum, or retroperitoneum. Features of tissue fibroses comprise epithelial and endothelial injury and dysfunction, abnormal proliferation of myofibroblasts (MFb), smooth muscle cells and stellate cells, and ECM deposition. The presence of cytokines, chemokines, growth factors, and angiogenic factors further regulate the activation of the ECM-producing cells during profibrotic process.

Galectin-3 (Gal3) is known to play an important role in cell proliferation, adhesion, differentiation, angiogenesis, and apoptosis. Further, it is implicated in the activation of a variety of profibrotic factors that promote fibroblast proliferation and transformation, and mediate collagen production. Furthermore, Gal3 is thought to play a key role in fibrogenesis of various tissues, including liver, kidney, lung, and myocardia.

Disclosed herein, in some embodiments, are methods of reducing fibrosis or propensity thereof in a tissue with an anti-Gal3 antibody. In some embodiments, reducing fibrosis or propensity thereof in a tissue includes preventing fibrosis from occurring in a normal tissue. In some embodiments, reducing fibrosis or propensity thereof in a tissue includes slowing down or arresting progression of fibrosis in a fibrotic tissue. In some embodiments, reducing fibrosis or propensity thereof in a tissue includes reducing the amount of degree of fibrosis in a fibrotic tissue. In some embodiments, reducing fibrosis or propensity thereof in a tissue includes eliminating fibrosis in a fibrotic tissue.

In some embodiments, also described herein are methods of monitoring the progression of a tissue fibrosis by monitoring one or more fibrosis biomarkers. In additional instances, disclosed herein are methods of treating a tissue fibrosis with an anti-Gal3 antibody, in which the anti-Gal3 antibody disrupts an interaction between Gal3 and TIM-3.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Unless defined otherwise, technical and scientific terms used herein have the same meaning as commonly understood by one of ordinary skill in the art to which the present disclosure belongs. For purposes of the present disclosure, the following terms are defined below.

The articles "a" and "an" are used herein to refer to one or to more than one (for example, at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

In some embodiments, anti-Gal3 antibodies or binding fragments thereof or compositions comprising anti-Gal3 antibodies or binding fragments thereof are provided. In some embodiments, methods of using the anti-Gal3 antibodies or binding fragments thereof or compositions comprising anti-Gal3 antibodies or binding fragments thereof to block or disrupt an interaction between Gal3 and a TGF-beta receptor either in vitro or in vivo are provided. In some embodiments, the methods of using the anti-Gal3 antibodies or binding fragments thereof or compositions comprising anti-Gal3 antibodies or binding fragments thereof to block or disrupt an interaction between Gal3 and TIM-3 are used to treat, cure, or prevent a disease or disorder in a subject. In some embodiments, the disease or disorder is cancer, breast cancer, colorectal cancer, kidney cancer, liver cancer, lung cancer, or a hematologic malignancy. In some embodiments, the cancer is a metastatic cancer, a relapsed cancer, or a refractory cancer. In some embodiments, the antibody is administered in combination with an additional therapeutic agent, such as an immune checkpoint inhibitor, a chemotherapeutic agent, targeted therapeutic agent, hormonal therapeutic agent, or stem cell-based therapeutic agent. In some embodiments, the disease or disorder is fibrosis in a tissue such as a liver tissue, kidney tissue, skin tissue, lung tissue, heart tissue, brain tissue, intestine tissue, bone marrow tissue, or soft tissue.

As used herein, the terms "individual(s)", "subject(s)" and "patient(s)" mean any mammal or bird. In some embodiments, the mammal is a human. In some embodiments, the mammal is a non-human, including but not limited to farm animals (e.g. cows, pigs, horses, chickens, etc.), sport animals, pets, primates, dogs, cats, mice and rats. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the terms "polypeptide", "peptide", and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfation, glycosylation, lipidation, acetylation, phosphorylation, iodination, methylation, oxidation, proteolytic processing, phosphorylation, prenylation, racemization, selenylation, transfer-RNA mediated addition of amino acids to proteins such as arginylation, ubiquitination, or any other manipulation, such as conjugation with a labeling component.

As used herein, the term "amino acid" refers to either natural and/or unnatural or synthetic amino acids, including glycine and both the D or L optical isomers, and amino acid analogs and peptidomimetics.

A polypeptide or amino acid sequence "derived from" a designated protein refers to the origin of the polypeptide. Preferably, the polypeptide has an amino acid sequence that is essentially identical to that of a polypeptide encoded in the sequence, or a portion thereof wherein the portion consists of at least 10-20 amino acids, or at least 20-30 amino acids, or at least 30-50 amino acids, or which is immunologically identifiable with a polypeptide encoded in the sequence. This terminology also includes a polypeptide expressed from a designated nucleic acid sequence.

As used herein, the term "antibody" is intended to include any polypeptide chain-containing molecular structure with a specific shape that fits to and recognizes an epitope, where one or more non-covalent binding interactions stabilize the complex between the molecular structure and the epitope. Antibodies utilized in the present invention may be polyclonal antibodies, although monoclonal antibodies are preferred because they may be reproduced by cell culture or recombinantly and can be modified to reduce their antigenicity.

In addition to entire immunoglobulins (or their recombinant counterparts), immunoglobulin fragments or "binding fragments" comprising the epitope binding site (e.g., Fab', F(ab')2, single-chain variable fragment (scFv), diabody, minibody, nanobody, single-domain antibody (sdAb), or other fragments) are useful as antibody moieties in the present invention. Such antibody fragments may be generated from whole immunoglobulins by ricin, pepsin, papain, or other protease cleavage. Minimal immunoglobulins may be designed utilizing recombinant immunoglobulin techniques. For instance "Fv" immunoglobulins for use in the present invention may be produced by linking a variable light chain region to a variable heavy chain region via a peptide linker (e.g., poly-glycine or another sequence which does not form an alpha helix or beta sheet motif). Nanobodies or single-domain antibodies can also be derived from alternative organisms, such as dromedaries, camels, llamas, alpacas, or sharks. In some embodiments, antibodies can be conjugates, e.g. pegylated antibodies, drug, radioisotope, or toxin conjugates. Monoclonal antibodies directed against a specific epitope, or combination of epitopes, will allow for the targeting and/or depletion of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (e.g. U.S. Pat. No. 5,985,660, hereby expressly incorporated by reference in its entirety).

As used herein, the term "humanized" as applies to a non-human (e.g. rodent or primate) antibodies are hybrid immunoglobulins, immunoglobulin chains or fragments thereof which contain minimal sequence derived from non-human immunoglobulin.

A "variable region" of an antibody refers to the variable region of the antibody light chain or the variable region of the antibody heavy chain, either alone or in combination. As known in the art, the variable regions of the heavy and light chains each consist of four framework regions (FRs) connected by three complementarity determining regions (CDRs) also known as hypervariable regions, and contribute to the formation of the antigen binding site of antibodies. If variants of a subject variable region are desired, particularly with substitution in amino acid residues outside of a CDR region (i.e., in the framework region), appropriate amino acid substitution, preferably, conservative amino acid substitution, can be identified by comparing the subject variable region to the variable regions of other antibodies which contain CDR1 and CDR2 sequences in the same canonical class as the subject variable region (Chothia and Lesk, J Mol Biol 196 (4): 901-917, 1987).

In some embodiments, definitive delineation of a CDR and identification of residues comprising the binding site of an antibody is accomplished by solving the structure of the antibody and/or solving the structure of the antibody-ligand complex. In some embodiments, that can be accomplished by any of a variety of techniques known to those skilled in the art, such as X-ray crystallography. In some embodiments, various methods of analysis can be employed to identify or approximate the CDR regions. In some embodiments, various methods of analysis can be employed to identify or approximate the CDR regions. Examples of such methods include, but are not limited to, the Kabat definition, the Chothia definition, the IMGT approach (Lefranc et al., 2003) Dev Comp Immunol. 27:55-77), computational programs such as Paratome (Kunik et al., 2012, Nucl Acids Res. W521-4), the AbM definition, and the conformational definition.

The Kabat definition is a standard for numbering the residues in an antibody and is typically used to identify CDR regions. See, e.g., Johnson & Wu, 2000, Nucleic Acids Res., 28:214-8. The Chothia definition is similar to the Kabat definition, but the Chothia definition takes into account positions of certain structural loop regions. See, e.g., Chothia et al., 1986, J. Mol. Biol., 196:901-17; Chothia et al., 1989, Nature, 342:877-83. The AbM definition uses an integrated suite of computer programs produced by Oxford Molecular Group that model antibody structure. See, e.g., Martin et al., 1989, Proc Natl Acad Sci (USA), 86:9268-9272; "AbM.TM., A Computer Program for Modeling Variable Regions of Antibodies," Oxford, UK; Oxford Molecular, Ltd. The AbM definition models the tertiary structure of an antibody from primary sequence using a combination of knowledge databases and ab initio methods, such as those described by Samudrala et al., 1999, "Ab Initio Protein Structure Prediction Using a Combined Hierarchical Approach," in PROTEINS, Structure, Function and Genetics Suppl., 3:194-198. The contact definition is based on an analysis of the available complex crystal structures. See, e.g., MacCallum et al., 1996, J. Mol. Biol., 5:732-45. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches but will nonetheless overlap with at least a portion of the Kabat CDRs, although they may be shortened or lengthened in light of prediction or experimental findings that particular residues or groups of residues do not significantly impact antigen binding. As used herein, a CDR may refer to CDRs defined by any approach known in the art, including combinations of approaches. The methods used herein may utilize CDRs defined according to any of these approaches. In some embodiments containing more than one CDR, the CDRs may be defined in accordance with any of Kabat, Chothia, extended, IMGT, Paratome, AbM, and/or conformational definitions, or a combination of any of the foregoing. In some embodiments, the residue number of a variable region is numbered using the IMGT numbering system. In the sequences provided herein, the CDRs are mapped according to IMGT (https://world wide web. Ebi-.ac.uk/ipd/imgt/hla/align.html).

As known in the art, a "constant region" of an antibody refers to the constant region of the antibody light chain or the constant region of the antibody heavy chain, either alone or in combination.

The term "compete," as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

An antibody that "preferentially binds" or "specifically binds" (used interchangeably herein) to an epitope is a term well understood in the art, and methods to determine such specific or preferential binding are also well known in the art. A molecule is said to exhibit "specific binding" or "preferential binding" if it reacts or associates more frequently, and/or more rapidly, and/or with greater duration and/or with greater affinity with a particular cell or substance than it does with alternative cells or substances. An antibody "specifically binds" or "preferentially binds" to a target if it binds with greater affinity, and/or avidity, and/or more readily, and/or with greater duration than it binds to other substances. For example, an antibody that specifically or preferentially binds to a CFD epitope is an antibody that binds this epitope with greater affinity, and/or avidity, and/or more readily, and/or with greater duration than it binds to other CFD epitopes or non-CFD epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably, at least 90% pure, more preferably, at least 95% pure, yet more preferably, at least 98% pure, and most preferably, at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3. As is known in the art, an Fc region can be present in dimer or monomeric form.

As used herein, "vector" means a construct, which is capable of delivering, and, preferably, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, various types of wetting agents, detergents such as polysorbate 20 to prevent aggregation, and sugars such as sucrose as cryoprotectant. Preferred diluents for aerosol or parenteral administration are phosphate buffered saline (PBS) or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, refers to the rate constant for association of an antibody (or bioconjugate) to an antigen. Specifically, the rate constants ($k_{on}$ and $k_{off}$) and equilibrium dissociation constants are measured using full-length antibodies and/or Fab antibody fragments (i.e. univalent) and CFD.

The term "$k_{off}$", as used herein, refers to the rate constant for dissociation of an antibody (or bioconjugate) from the antibody/antigen complex.

The term "$K_D$", as used herein, refers to the equilibrium dissociation constant of an antibody-antigen (or bioconjugate-antigen) interaction.

As used herein, the terms "treating" or "treatment" (and as well understood in the art) means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable. "Treating" and "treatment" as used herein also include prophylactic treatment. Treatment methods comprise administering to a subject a therapeutically effective amount of an active agent. The administering step may consist of a single administration or may comprise a series of administrations. The compositions are administered to the subject in an amount and for a duration sufficient to treat the patient. The length of the treatment period depends on a variety of factors, such as the severity of the condition, the age and genetic profile of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some embodiments, chronic administration may be required.

The term "administering" includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a first compound described herein is administered at the same time, just prior to, or just after the administration of a second compound described herein.

As used herein, the term "therapeutic target" refers to a gene or gene product that, upon modulation of its activity (e.g., by modulation of expression, biological activity, and the like), can provide for modulation of the disease phenotype (e.g., fibrosis or cancer). As used throughout, "modulation" is meant to refer to an increase or a decrease in the indicated phenomenon (e.g., modulation of a biological activity refers to an increase in a biological activity or a decrease in a biological activity).

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. Detection of cancerous cells is of particular interest. The term "normal" as used in the context of "normal cell," is meant to refer to a cell of an untransformed phenotype or exhibiting a morphology of a non-transformed cell of the tissue type being examined. "Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

The term "tumor microenvironment" refers to a cellular environment in which the tumor exists, including tumor cells and surrounding blood vessels, immune cells, fibroblasts, bone marrow-derived inflammatory cells, lymphocytes, signaling molecules and the extracellular matrix.

The term "immune cells" refers to cells of hematopoietic origin that are involved in the specific recognition of antigens. Immune cells include antigen presenting cells (APCs), such as dendritic cells or macrophages, B cells, T cells, natural killer cells, and myeloid cells, such as monocytes, macrophages, eosinophils, mast cells, basophils, and granulocytes.

The term "immune response" refers to T cell-mediated, NK cell-mediated, macrophage-mediated, and/or B cell-mediated immune responses. Exemplary immune responses include B cell responses (e.g., antibody production), NK cell responses or T cell responses (e.g., cytokine production, and cellular cytotoxicity) and activation of cytokine responsive cells, e.g., macrophages. The term "activating immune response" refers to enhancing the level of T-cell-mediated and/or B cell-mediated immune response, using methods known to one of skilled in the art. In some embodiments, the level of enhancement is at least 20-50%, alternatively at least 60%, at least 70%, at least 80%, at least 90%, at least 100%, at least 120%, at least 150%, or at least 200%.

As used herein, the term "transforming growth factor beta receptor" (TGF-b receptor) refers to a family of serine/threonine kinase receptors expressed on cell surfaces that are specific for the protein transforming growth factor beta (TGF-b). The interaction between TGF-b and the receptor triggers a signaling pathway that is responsible for many functions, including but not limited to cell growth, differentiation (e.g. stem cells, immune cells), apoptosis, homeostasis, chemotaxis, inflammation, and immune cell activation.

As used herein, the term "fibrosis" refers to the medical condition wherein tissues or organs harden or scar as a result of unregulated production of extracellular matrix, such as collagen proteins. Fibrosis has been associated with chronic inflammation, where immune cells such as macrophages signal fibroblasts to express extracellular matrix proteins in response. This signaling is achieved through pathways such as the TGF-b pathway, although there are other pro-fibrotic pathways as well. Fibrosis includes but is not limited to liver fibrosis, bridging fibrosis, cirrhosis, kidney fibrosis, pulmonary fibrosis, idiopathic pulmonary fibrosis, cystic fibrosis, cardiovascular fibrosis, arterial fibrosis, venous thrombosis, cardiac fibrosis, pulmonary arterial fibrosis, arthrofibrosis, Crohn's disease, Dupuytren's contracture, keloids, mediastinal fibrosis, myelofibrosis, Peyronie's disease, nephrogenic systemic fibrosis, progressive massive fibrosis, retroperitoneal fibrosis, or systemic sclerosis.

The term "% w/w" or "% wt/wt" means a percentage expressed in terms of the weight of the ingredient or agent over the total weight of the composition multiplied by 100.

In some embodiments, disclosed herein are methods of inducing immune activation, comprising contacting an anti-Gal3 antibody to a plurality of cells comprising a Gal3-expressing cell and a TIM-3 expressing cell. In some embodiments, disclosed herein, are methods of reducing fibrosis, comprising contacting a tissue comprising a Gal3-expressing cell and at least one fibrosis biomarker with an anti-Gal3 antibody for a time sufficient to reduce expression of the at least one fibrosis biomarker in the tissue. In some embodiments, the anti-Gal3 antibody results in reduced accumulation of one or more extracellular matrix proteins in the tissue, including, but not limited to, collagen.

In some cases, upon binding to the anti-Gal3 antibody, the Gal3-expressing cell expresses a cytokine which induces immune activation. In some cases, the cytokine is an interferon. In some cases, the interferon is IFNγ. In some cases, the IFNγ production is 110%, 120%, 130%, 140%, 150%, 160%, 170%, 180%, 190%, 200%, 300%, 400%, 500%, 600%, or more of IFNγ production by an isotype antibody. In some cases, the IFNγ production is 150% of IFNγ production by an isotype antibody. In some cases, the IFNγ production is 160% of IFNγ production by an isotype antibody. In some cases, the IFNγ production is 170% of IFNγ production by an isotype antibody. In some cases, the IFNγ production is 180% of IFNγ production by an isotype antibody. In some cases, the IFNγ production is 190% of IFNγ production by an isotype antibody. In some cases, the IFNγ production is 200% of IFNγ production by an isotype antibody. In some cases, the IFNγ production is more than 200% of IFNγ production by an isotype antibody. In some cases, the IFNγ production is more than 300% of IFNγ production by an isotype antibody. In some cases, the IFNγ production is more than 400% of IFNγ production by an isotype antibody. In some cases, the IFNγ production is more than 500% of IFNγ production by an isotype antibody. In some cases, the cytokine is an interleukin. In some cases, the interleukin is IL-2.

In some cases, the immune activation comprises a proliferation of CD3+ T lymphocytes, CD4+ T helper cells, CD8+ cytotoxic T cells, Natural Killer (NK) cells, or a combination thereof. In some cases, the immune activation comprises a proliferation of CD3+ T lymphocytes. In some cases, the immune activation comprises a proliferation of CD4+ T helper cells. In some cases, the immune activation comprises a proliferation of CD8+ cytotoxic T cells. In some cases, the immune activation comprises a proliferation of NK cells. In some cases, the immune activation comprises a proliferation of T cells and NK cells.

In some cases, the immune activation comprises an increase in M1 macrophage population within the plurality of cells. In some cases, the immune activation comprises a decrease in M2 macrophage population within the plurality of cells. In some cases, the immune activation comprises an increase in M1 macrophage population within the plurality of cells and a decrease in M2 macrophage population within the plurality of cells.

In some cases, anti-Gal3 antibody binds to Gal3 and disrupts an interaction between Gal3 and TIM-3. In some cases, disruption of an interaction between Gal3 and TIM-3 includes partial inhibition of interaction between Gal3 and TIM-3. In some cases, disruption of an interaction between Gal3 and TIM-3 includes complete inhibition of interaction between Gal3 and TIM-3. In some cases, the Gal3-TIM-3 interaction is reduced to less than 99%, less than 95%, less than 90%, less than 85%, less than 80%, less than 75%, less than 70%, less than 65%, less than 60%, less than 59%, less than 55%, less than 50%, less than 45%, less than 40%, less than 34%, less than 30%, less than 25%, less than 20%, less than 14%, less than 10%, less than 7%, less than 5%, less than 4%, less than 3%, less than 2%, or less than 1%. In some cases, the Gal3-TIM-3 interaction is reduced to less than 70%. In some cases, the Gal3-TIM-3 interaction is reduced to less than 60%. In some cases, the Gal3-TIM-3 interaction is reduced to less than 59%. In some cases, the Gal3-TIM-3 interaction is reduced to less than 50%. In some cases, the Gal3-TIM-3 interaction is reduced to less than 40%. In some cases, the Gal3-TIM-3 interaction is reduced to less than 34%. In some cases, the Gal3-TIM-3 interaction is reduced to less than 30%. In some cases, the Gal3-TIM-3 interaction is reduced to less than 20%. In some cases, the Gal3-TIM-3 interaction is reduced to less than 14%. In some cases, the Gal3-TIM-3 interaction is reduced to less than 10%. In some cases, the Gal3-TIM-3 interaction is reduced to less than 7%. In some cases, the Gal3-TIM-3 interaction is reduced to less than 5%. In some cases, the Gal3-TIM-3 interaction is reduced to less than 4%. In some cases, the Gal3-TIM-3 interaction is reduced to less than 1%.

In some cases, the interaction between Gal3 and TIM-3 occurs at one or more residues of Gal3 selected from region 145-168, 160-177, or 165-184, wherein the residue positions correspond to positions 145-168, 160-177, or 165-184 of SEQ ID NO: 1. In some cases, the interaction between Gal3 and TIM-3 occurs at one or more residues of Gal3 from region 145-168, wherein the residue positions correspond to positions 145-168 of SEQ ID NO: 1. In some cases, the interaction between Gal3 and TIM-3 occurs at one or more residues of Gal3 from region 160-177, wherein the residue positions correspond to positions 160-177 of SEQ ID NO: 1. In some cases, the interaction between Gal3 and TIM-3 occurs at one or more residues of Gal3 from region 165-184, wherein the residue positions correspond to positions 165-184 of SEQ ID NO: 1. In some cases, the interaction between Gal3 and TIM-3 occurs at one or more residues of Gal3 selected from region 149-156, 152-168, 163-169, or 163-171, wherein the residue positions correspond to positions 149-156, 152-168, 163-169, or 163-171 of SEQ ID NO: 1. In some cases, the interaction between Gal3 and TIM-3 occurs at one or more residues of Gal3 from region 149-156, wherein the residue positions correspond to positions 149-156 of SEQ ID NO: 1. In some cases, the interaction between Gal3 and TIM-3 occurs at one or more residues of Gal3 from region 152-168, wherein the residue positions correspond to positions 152-168 of SEQ ID NO: 1. In some cases, the interaction between Gal3 and TIM-3 occurs at one or more residues of Gal3 from region 163-169, wherein the residue positions correspond to positions 163-169 of SEQ ID NO: 1. In some cases, the interaction between Gal3 and TIM-3 occurs at one or more residues of Gal3 from region 163-171, wherein the residue positions correspond to positions 163-171 of SEQ ID NO: 1.

In some cases, the interaction between Gal3 and TIM-3 occurs at one or more residues of TIM-3 selected from region 91-111 or 82-111, wherein the residue positions correspond to positions 91-111 or 82-111 of SEQ ID NO: 2. In some cases, the interaction between Gal3 and TIM-3 occurs at one or more residues of TIM-3 from region 91-111, wherein the residue positions correspond to positions 91-111 of SEQ ID NO: 2. In some cases, the interaction between Gal3 and TIM-3 occurs at one or more residues of TIM-3 from region 82-111, wherein the residue positions correspond to positions 82-111 of SEQ ID NO: 2. In some cases, the interaction between Gal3 and TIM-3 occurs at one or more residues of TIM-3 selected from region 91-111, 107-117, 96-102, 100-106, or 92-119, herein the residue positions correspond to positions 91-111, 107-117, 96-102, 100-106, or 92-119 of SEQ ID NO: 2. In some cases, the interaction between Gal3 and TIM-3 occurs at one or more residues of TIM-3 from region 91-111, wherein the residue positions correspond to positions 91-111 of SEQ ID NO: 2. In some cases, the interaction between Gal3 and TIM-3 occurs at one or more residues of TIM-3 from region 107-117, wherein the residue positions correspond to positions 107-117 of SEQ ID NO: 2. In some cases, the interaction between Gal3 and TIM-3 occurs at one or more residues of TIM-3 from region 96-102, wherein the residue positions correspond to positions 96-102 of SEQ ID NO: 2. In some cases, the interaction between Gal3 and TIM-3 occurs at one or more residues of TIM-3 from region 100-106, wherein the residue positions correspond to positions 100-106 of SEQ ID NO: 2. In some cases, the interaction between Gal3 and TIM-3 occurs at one or more residues of TIM-3 from region 92-119, wherein the residue positions correspond to positions 92-119 of SEQ ID NO: 2. In some cases, TIM-3 is human TIM-3

In some embodiments, disclosed herein, are methods of promoting T cell or Natural Killer (NK) cell proliferation, comprising contacting a plurality of cells comprising T cells, NK cells, and Gal3-expressing cells with an anti-Gal3 antibody for a time sufficient to promote proliferation of T cells or NK cells in the plurality of cells. In some embodiments, disclosed herein, are methods of promoting T cell and Natural Killer (NK) cell proliferation, comprising contacting a plurality of cells comprising T cells, NK cells, and Gal3-expressing cells with an anti-Gal3 antibody for a time sufficient to promote proliferation of T cells and NK cells in the plurality of cells. In some embodiments, the plurality of cells further comprises a TIM-3 expressing cell. In some embodiments, anti-Gal3 antibody binds to Gal3 and disrupts an interaction between Gal3 and TIM-3. In some embodiments, anti-Gal3 antibody binds to Gal3 and disrupts an interaction between Gal3 and TIM-3. In some embodiments, the anti-Gal3 antibody binds to Gal3 and disrupts an interaction between Gal3 and TIM-3 greater than 25%, greater than 50%, greater than 100%, or greater than 200%.

In some embodiments, the plurality of cells further comprises tumor-infiltrating lymphocytes (TILs). In some cases, the plurality of cells further comprises CD3+ T lymphocytes, CD4+ T helper cells, CD8+ cytotoxic T cells, or a combination thereof. In some cases, the plurality of cells further comprises CD3+ T lymphocytes. In some cases, the plurality of cells further comprises CD4+ T helper cells. In some cases, the plurality of cells further comprises CD8+ cytotoxic T cells. In some cases, the plurality of cells further comprises CD3+ T lymphocytes and CD4+ T helper cells. In some cases, the plurality of cells further comprises CD3+ T lymphocytes and CD8+ cytotoxic T cells. In some cases, the plurality of cells further comprises CD4+ T helper cells, CD8+ cytotoxic T cells. In some cases, the plurality of cells further comprises CD3+ T lymphocytes, CD4+ T helper cells, and CD8+ cytotoxic T cells.

In some embodiments, the contacting further induces TIL proliferation. In some cases, the contacting further induces proliferation of CD3+ T lymphocytes, CD4+ T helper cells, CD8+ cytotoxic T cells, or a combination thereof. In some cases, the contacting further induces proliferation of CD3+ T lymphocytes. In some cases, the contacting further induces proliferation of CD4+ T helper cells. In some cases, the contacting further induces proliferation of CD8+ cytotoxic T cells. In some cases, the contacting further induces proliferation of CD3+ T lymphocytes and CD4+ T helper cells. In some cases, the contacting further induces proliferation of CD3+ T lymphocytes and CD8+ cytotoxic T cells. In some cases, the contacting further induces proliferation of CD4+ T helper cells and CD8+ cytotoxic T cells. In some cases, the contacting further induces proliferation of CD3+ T lymphocytes, CD4+ T helper cells, and CD8+ cytotoxic T cells.

In some embodiments, the contacting further comprises an increase in proliferation of M1 macrophages. In some embodiments, the contacting further comprises a decrease in M2 macrophage population within the TME. In some embodiments, the contacting further comprises an increase in proliferation of M1 macrophages and a decrease in M2 macrophage population within the TME.

In some embodiments, the anti-Gal3 antibody binds to at least one amino acid residue within a Gal3 region that corresponds to residues 1-20 of SEQ ID NO: 1. In some cases, the anti-Gal3 antibody binds to at least one amino acid residue within a Gal3 region that corresponds to residues 41-91 of SEQ ID NO: 1. In some cases, the anti-Gal3 antibody binds to at least one amino acid residue within a Gal3 region that corresponds to residues 41-71 of SEQ ID NO: 1. In some cases, the anti-Gal3 antibody binds to at least one amino acid residue within a Gal3 region that corresponds to residues 71-91 of SEQ ID NO: 1. In some cases, the anti-Gal3 antibody binds to at least one amino acid residue within peptide_1, peptide_4, peptide_5, peptide_6, peptide_7, or peptide_8. In some cases, the anti-Gal3 antibody binds to at least one amino acid residue within peptide_1. In some cases, the anti-Gal3 antibody binds to at least one amino acid residue within peptide_4. In some cases, the anti-Gal3 antibody binds to at least one amino acid residue within peptide_5. In some cases, the anti-Gal3 antibody binds to at least one amino acid residue within peptide_6. In some cases, the anti-Gal3 antibody binds to at least one amino acid residue within peptide_7. In some cases, the anti-Gal3 antibody binds to at least one amino acid residue within peptide_8.

In some embodiments, the anti-Gal3 antibody comprises a binding affinity ($K_D$) of less than 1 nM, less than 1.2 nM, less than 2 nM, less than 5 nM, less than 10 nM, less than 13.5 nM, less than 15 nM, less than 20 nM, less than 25 nM, or less than 30 nM. In some embodiments, the anti-Gal3 antibody comprises a $K_D$ of less than 1 nM. In some embodiments, the anti-Gal3 antibody comprises a $K_D$ of less than 1.2 nM. In some embodiments, the anti-Gal3 antibody comprises a $K_D$ of less than 2 nM. In some embodiments, the anti-Gal3 antibody comprises a $K_D$ of less than 5 nM. In some embodiments, the anti-Gal3 antibody comprises a $K_D$ of less than 10 nM. In some embodiments, the anti-Gal3 antibody comprises a $K_D$ of less than 13.5 nM. In some embodiments, the anti-Gal3 antibody comprises a $K_D$ of less than 15 nM. In some embodiments, the anti-Gal3 antibody comprises a $K_D$ of less than 20 nM. In some embodiments, the anti-Gal3 antibody comprises a $K_D$ of less than 25 nM. In some embodiments, the anti-Gal3 antibody comprises a $K_D$ of less than 30 nM.

In some embodiments, the anti-Gal3 antibody comprises a humanized antibody. In other embodiments, the anti-Gal3 antibody comprises a chimeric antibody. In some cases, the anti-Gal3 antibody comprises a full-length antibody or a binding fragment thereof. In some cases, the anti-Gal3 antibody comprises a bispecific antibody or a binding fragment thereof. In some cases, the anti-Gal3 antibody comprises a monovalent Fab', a divalent Fab2, a single-chain variable fragment (scFv), a diabody, a minibody, a nanobody, a single-domain antibody (sdAb), or a camelid antibody or binding fragment thereof.

In some embodiments, the anti-Gal3 antibody is a bispecific antibody or binding fragment thereof. Exemplary bispecific antibody formats include, but are not limited to, Knobs-into-Holes (KiH), Asymmetric Re-engineering Technology-immunoglobulin (ART-Ig), Triomab quadroma, bispecific monoclonal antibody (BiMAb, BsmAb, BsAb, bsMab, BS-Mab, or Bi-MAb), Azymetric, Bispecific Engagement by Antibodies based on the T-cell receptor (BEAT), Bispecific T-cell Engager (BiTE), Biclonics, Fab-scFv-Fc, Two-in-one/Dual Action Fab (DAF), FinomAb, scFv-Fc-(Fab)-fusion, Dock-aNd-Lock (DNL), Adaptir (previously SCORPION), Tandem diAbody (TandAb), Dual-affinity-ReTargeting (DART), nanobody, triplebody, tandems scFv (taFv), triple heads, tandem dAb/VHH, triple dAb/VHH, or tetravalent dAb/VHH. In some cases, the anti-Gal3 antibody is a bispecific antibody or binding fragment thereof comprising a bispecific antibody format illustrated in FIG. 2 of Brinkmann and Kontermann, "The making of bispecific antibodies," *MABS* 9 (2): 182-212 (2017).

In some embodiments, an anti-Gal3 antibody comprises a framework region selected from IgM, IgG (e.g., IgG1, IgG2, IgG3, or IgG4), IgA, or IgE. In some cases, the anti-Gal3 antibody comprises an IgM framework. In some cases, the anti-Gal3 antibody comprises an IgG (e.g., IgG1, IgG2, IgG3, or IgG4) framework. In some cases, the anti-Gal3 antibody comprises an IgG1 framework. In some cases, the anti-Gal3 antibody comprises an IgG2 framework. In some cases, the anti-Gal3 antibody comprises an IgG4 framework. In some embodiments, the anti-Gal3 antibody can further comprise a Fc mutation. In some embodiments, any one or more of the Fc region or kappa regions in FIG. 37 can be paired with any of the CDR, VH/VL sequences herein, including FIGS. 35A-36B.

In some embodiments, the anti-Gal3 antibody comprises one or more mutations in the framework region, e.g., in the CH1 domain, CH2 domain, CH3 domain, hinge region, or a combination thereof. In some cases, the one or more mutations modulate Fc receptor interactions, e.g., to increase Fc effector functions such as ADCC and/or complement-dependent cytotoxicity (CDC). In some cases, the one or more mutations stabilize the antibody and/or increase the half-life of the antibody. In additional cases, the one or more mutations modulate glycosylation.

In some embodiments, the Fc region comprises one or more mutations that modulate Fc receptor interactions, e.g., to enhance effector functions such as ADCC and/or CDC. In such embodiments, exemplary residues when mutated modulate effector functions include S228, S239, K326, A330, I332, or E333, in which the residue position correspond to IgG1 and the residue numbering is in accordance to Kabat numbering (EU index of Kabat et al 1991 Sequences of Proteins of Immunological Interest). In some embodiments, the one or more mutations comprise S228P, S239D, K326W, A330L, I332E, E333A, E333S, or a combination thereof. In some cases, the one or more mutations comprise S228P, S239D, I332E, or a combination thereof. In some cases, the one or more mutations comprise S228P, S239D, A330L, I332E, or a combination thereof. In some cases, the one or more mutations comprise K326W, E333S, or a combination thereof. In some cases, the mutation comprises E333A. In some embodiments, the Fc region is an IgG4 Fc region. In some embodiments the S228P mutation is in the hinge region of IgG4. In some embodiments, the S228P mutation enhances the stability of IgG4 by preventing Fab arm exchange.

In some embodiments, an anti-Gal3 antibody comprises a humanization score quantified as the overall sequence similarity of the humanized antibody compared to an IMGT curated human germline antibody. In some embodiments, an anti-Gal3 antibody comprises a humanization score of above 70, above 80, above 81, above 82, above 83, above 84, above 85, above 86, above 87, above 88, above 89, above 90, or above 95. In some embodiments, the anti-Gal3 antibody comprises a humanization score of above 80. In some embodiments, the anti-Gal3 antibody comprises a humanization score of above 83. In some embodiments, the anti-Gal3 antibody comprises a humanization score of above 85. In some embodiments, the anti-Gal3 antibody comprises a humanization score of above 87. In some embodiments, the anti-Gal3 antibody comprises a humanization score of above 90. In some case, the anti-Gal3 antibody comprises a humanization score of the heavy chain of above 70, above 80, above 81, above 82, above 83, above 84, above 85, above 86, above 87, above 88, above 89, above 90, or above 95, optionally above 80, above 85, or above 87. In some case, the anti-Gal3 antibody comprises a humanization score of the light chain of above 70, above 80, above 81, above 82, above 83, above 84, above 85, above 86, above 87, above 88, above 89, above 90, or above 95, optionally above 80, above 83, or above 85.

In some embodiments, the anti-Gal3 antibody comprises complementarity determining regions (CDRs) as provided herein. In some embodiments, the CDRs are part of the heavy chain (VH) of the antibody. In some embodiments, the CDRs are part of the light chain (VL). In some embodiments, the VH comprises a VH CDR1, a VH CDR2, and/or a VH CDR3. In some embodiments, the VH CDR1 comprises one of the sequences of SEQ ID NOS: 37-64. In some embodiments, the VH CDR2 comprises one of the sequences of SEQ ID NOs: 65-92. In some embodiments, the VH CDR3 comprises one of the sequences of SEQ ID NOs: 93-120. In some embodiments, the VL comprises a VL CDR1, a VL CDR2, and/or a VL CDR3. In some embodiments, the VL CDR1 comprises one of the sequences of SEQ ID NOs: 121-148. In some embodiments, the VL CDR2 comprises one of RMS, LVS, RMS, LVS, YTS, KVS, HAT, LLS, GAS, LVS, LVS, KVS, KAS, YAS, LVS, KAS, YTS, YAS, WAS, WAS, WAS, LVC, WAS, LMSTHAS, RMS, RMS, RMS, and LMSTHAS. In some embodiments, the VL CDR3 comprises one of the sequences of SEQ ID NOs: 177-204. In some embodiments, the VH comprises one of the sequences of SEQ ID NOs: 205-232. In some embodiments, the VL comprises one of the sequences of SEQ ID NOs: 233-260. In some embodiments, the anti-Gal3 antibody comprises an hIgG4 constant region. In some embodiments, the hIgG4 constant region comprises the hIgG4 constant region sequence within SEQ ID NOs: 261, 263, 265, or 267. In some embodiments, the anti-Gal3 antibody comprises a hKappa constant region. In some embodiments, the hKappa constant region comprises the hKappa constant region sequence within SEQ ID NOs: 262, 264, 266, or 268.

In some embodiments, the anti-Gal3 comprises a sequence depicted in FIG. 35A-B, 36A-B, or 37. In some embodiments, the anti-Gal3 antibody is selected from the group consisting of 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, and mIMT001 (IMT001). In some embodiments, the anti-Gal3 antibody is 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, or mIMT001, or any combination thereof. In some embodiments, the anti-Gal3 antibody is mIMT001 (IMT001). In some embodiments, the anti-Gal3 antibody is not mIMT001 (IMT001). In some embodiments, the anti-Gal3 antibody is 4A11.2B5. In some embodiments, the anti-Gal3 antibody is mIMT001 and/or 4A11.2B5. In some embodiments, the anti-Gal3 antibody includes 1, 2, or 3 HCDRs from mIMT001 and/or 4A11.2B5. In some embodiments, the anti-Gal3 antibody includes 1, 2, or 3 LCDRs from mIMT001 and/or 4A11.2B5. In some embodiments, the anti-Gal3 antibody includes 1, 2, or 3 HCDRs from mIMT001 and/or 4A11.2B5 and 1, 2, or 3 LCDRs from mIMT001 and/or 4A11.2B5. In some embodiments, the anti-Gal3 antibody includes 1, 2, or 3 HCDRs from mIMT001 and/or 4A11.2B5 and 1, 2, or 3 LCDRs from mIMT001 and/or 4A11.2B5, alternatively having 1, 2, 3, 4, 5, 6, 7, or 8 amino acid substitutions thereto. In some embodiments, the anti-Gal3 antibody includes 1, 2, or 3 HCDRs from mIMT001 and/or 4A11.2B5 and 1, 2, or 3 LCDRs from mIMT001 and/or 4A11.2B5, and further comprises the mIMT001 and/or 4A11.2B5 VH and VL sequences (as shown within FIGS. 36A and 36B) or a sequence that is at least 80, 85, 90, 91, 92, 93, 94, 95, 96, 97, 98, 99 or 100% identical to the VH and VL sequences.

In some embodiments, the anti-Gal3 antibody is any one of IMT001-4, IMT006-1, IMT006-5, or IMT006-8. In some embodiments, the anti-Gal3 antibody is any one of IMT001-4, IMT006-1, IMT006-5, and/or IMT006-8. In some embodiments, the anti-Gal3 antibody includes 1, 2, or 3 HCDRs from any one of IMT001-4, IMT006-1, IMT006-5, and/or IMT006-8. In some embodiments, the anti-Gal3 antibody includes 1, 2, or 3 LCDRs from any one of IMT001-4, IMT006-1, IMT006-5, and/or IMT006-8. In some embodiments, the anti-Gal3 antibody includes 1, 2, or 3 HCDRs from any one of IMT001-4, IMT006-1, IMT006-5, and/or IMT006-8 and 1, 2, or 3 LCDRs from any one of IMT001-4, IMT006-1, IMT006-5, and/or IMT006-8. In some embodiments, the anti-Gal3 antibody includes 1, 2, or 3 HCDRs from any one of IMT001-4, IMT006-1, IMT006-5, and/or IMT006-8 and 1, 2, or 3 LCDRs from any one of IMT001-4, IMT006-1, IMT006-5, and/or IMT006-8, alternatively having 1, 2, 3, 4, 5, 6, 7, or 8 amino acid substitutions thereto. In some embodiments, the anti-Gal3 antibody includes 1, 2, or 3 HCDRs from any one of IMT001-4, IMT006-1, IMT006-5, and/or IMT006-8 and 1, 2, or 3 LCDRs from any one of IMT001-4, IMT006-1, IMT006-5, and/or IMT006-8, and further comprises the any one of IMT001-4, IMT006-1, IMT006-5, and/or IMT006-8 VH and VL sequences (as shown within FIGS. 36A and 36B) or a sequence that is at least 80, 85, 90, 91, 92, 93, 94, 95, 96, 97, 98, 99 or 100% identical to the VH and VL sequences.

In some embodiments, the anti-GAL3 antibody competes for binding with one or more of: 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, and mIMT001 (IMT001).

In some embodiments, the anti-GAL3 antibody comprises at least the HCDR3 within any one of the antibodies of FIGS. 35A-36B. In some embodiments, the anti-GAL3 antibody further comprises all 3 HCDRs within any one of the antibodies of FIGS. 35A-36B. In some embodiments, the anti-GAL3 antibody further comprises all 3 LCDRs within any one of the antibodies of FIGS. 35A-36B.

In some embodiments, the anti-GAL3 antibody comprises any one of the heavy chain sequences within FIG. 36A, or a sequence that is at least 80% identical thereto, such as 85, 90, 91, 92, 93, 94, 95, 96, 97, 98, 99, or 100% identical.

In some embodiments, the anti-GAL3 antibody comprises any one of the light chain sequences within FIG. 36B or a sequence that is at least 80% identical thereto, such as 85, 90, 91, 92, 93, 94, 95, 96, 97, 98, 99, or 100% identical. In some embodiments, the anti-GAL3 antibody further comprises any one of the heavy chain sequences within FIG. 36A, or a sequence that is at least 80% identical thereto such as 85, 90, 91, 92, 93, 94, 95, 96, 97, 98, 99, or 100% identical.

In some embodiments, the anti-GAL3 antibody comprises 6 CDRs, wherein the 6 CDRs are, across their combined sequences, at least 80% identical to any set of 6 CDRs within FIGS. 35A and 35B, such as 85, 90, 91, 92, 93, 94, 95, 96, 97, 98, 99, or 100% identical.

In some embodiments, the anti-GAL3 antibody comprises at least one of the CDRs from FIG. 38 (with 1, 2, or 3 amino acid conservative substitutions). An anti-GAL3 antibody that comprises at least two of the CDRs from FIG. 38 (with 1, 2, or 3 amino acid conservative substitutions). An anti-GAL3 antibody that comprises at least three of the CDRs from FIG. 38 (with 1, 2, or 3 amino acid conservative substitutions) (with 1, 2, or 3 amino acid conservative substitutions). An anti-GAL3 antibody that comprises at least four of the CDRs from FIG. 38 (with 1, 2, or 3 amino acid conservative substitutions). An anti-GAL3 antibody that comprises at least five of the CDRs from FIG. 38 (with 1, 2, or 3 amino acid conservative substitutions). An anti-GAL3 antibody that comprises six of the CDRs from FIG. 38 (with 1, 2, or 3 amino acid conservative substitutions). In some embodiments, the anti-GAL3 antibody comprises six of the CDRs from FIG. 38, and wherein all six are from a single bin. In some embodiments, the anti-GAL3 antibody comprises six of the CDRs from FIG. 38, or a set of 6 CDRs which, across their entire sequence, is at least 80% identical thereto.

In some embodiments is a method of inducing immune activation comprising, consisting essentially of, or consisting of contacting a plurality of cells comprising a Gal3-expressing cell and a TIM-3-expressing cell with an antibody under conditions to disrupt an interaction between Gal3 and TIM-3, wherein the antibody specifically binds to Gal3, wherein the Gal3-expressing cell upon binding to the antibody expresses a cytokine which induces immune activation. In some embodiments, the cytokine is an interferon or an interleukin. In some embodiments, the cytokine is IFNγ or IL-2. In some embodiments, the immune activation comprises a proliferation of CD3+ T lymphocytes, CD4+ T helper cells, CD8+ cytotoxic T cells, Natural Killer cells, or a combination thereof. In some embodiments is a method of promoting T cell or NK cell proliferation comprising, consisting essentially of, or consisting of contacting a plurality of cells comprising T cells, NK cells, and a Gal3-expressing cell with an antibody under conditions to effect proliferation of T cells and/or NK cells in the plurality of cells, wherein the antibody specifically binds to Gal3. In some embodiments is a method of inducing immune activation comprising, consisting essentially of, or consisting of contacting a plurality of cells comprising a Gal3-expressing cell and a TIM-3-expressing cell with an antibody under conditions to disrupt an interaction between Gal3 and TIM-3, wherein the antibody specifically binds to Gal3, and wherein the Gal3-TIM-3 interaction is reduced to less than 70%, less than 60%, less than 59%, less than 50%, less than 40%, less than 34%, less than 30%, less than 20%, less than 14%, less than 10%, less than 7%, less than 5%, less than 4%, or less than 1%. In some embodiments is a method of reducing fibrosis or propensity thereof in a tissue comprising, consisting essentially of, or consisting of contacting the tissue with an antibody that specifically binds anti-Gal3 antibody under conditions such that expression level of a fibrosis biomarker is reduced in the tissue. In some embodiments is an anti-Gal3 antibody for use in the treatment of an immune related disease in a subject, wherein the anti-Gal3 antibody induces activation of the immune system. In some embodiments or any of the preceding embodiments, the anti-Gal3 antibody is selected from the group consisting of 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, and mIMT001 (IMT001). In some embodiments, the anti-Gal3 antibody is 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, or mIMT001, or any combination thereof. In some embodiments or any of the preceding embodiments, the anti-Gal3 antibody is mIMT001 (IMT001). In some embodiments or any of the preceding embodiments, the anti-Gal3 antibody is not mIMT001 (IMT001). In some embodiments or any of the preceding embodiments, the anti-Gal3 antibody is 4A11.2B5, IMT001-4, IMT006-1, IMT006-5, and/or IMT006-8. In some embodiments or any of the preceding embodiments, the anti-Gal3 antibody is mIMT001, 4A11.2B5, IMT001-4, IMT006-1, IMT006-5, and/or IMT006-8. In some embodiments or any of the preceding embodiments, the anti-Gal3 antibody is one or more of IMT001-4, IMT006-1, IMT006-5, or IMT006-8. In some embodiments or any of the preceding embodiments, the anti-Gal3 antibody is not mIMT001 (IMT001). In some embodiments or any of the preceding embodiments, the anti-Gal3 antibody is IMT001-4, IMT006-1, IMT006-5, and/or IMT006-8.

With regard to the nature of the various antibodies, it is noted that IMT001-4, IMT006-1, and IMT006-5 are humanized antibodies. mIMT001 is a murine antibody from which IMT001 was derived. 4A11.2B5 is the original murine antibody from which IMT006-1 and IMT006-5 were derived. mIMT001, 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10 are all murine antibodies. IMT001-4, IMT006-1, IMT006-5, and IMT006-8 are all humanized antibodies.

Method of Treatment

Disclosed herein, in some embodiments, is a method of inducing immune activation, comprising, consisting essentially of, or consisting of: contacting a plurality of cells comprising, consisting essentially of, or consisting of a Gal3-expressing cell and a TIM-3-expressing cell with an antibody under conditions to disrupt an interaction between Gal3 and TIM-3. In some embodiments, the antibody is an anti-Gal3 antibody.

In some embodiments, disclosed herein, are methods of reducing fibrosis, comprising contacting a tissue comprising a Gal3-expressing cell and at least one fibrosis biomarker with an anti-Gal3 antibody for a time sufficient to reduce expression of the at least one fibrosis biomarker in the tissue. In some instances, the anti-Gal3 antibody results in reduced accumulation of one or more extracellular matrix proteins in the tissue, including, but not limited to, collagen.

In some embodiments, the anti-Gal3 antibody is not IMT001. In some embodiments, the antibody is IMT001. In some embodiments, the anti-Gal3 antibody is 4A11.2B5. In some embodiments, the anti-Gal3 antibody is IMT001-4, IMT006-1, IMT006-5, or IMT006-8.

In some embodiments, the anti-Gal3 antibody inhibits or disrupts an interaction of Gal3 and TIM-3. In some embodiments, the Gal3-TIM-3 interaction is reduced to 99%, 95%, 90%, 80%, 78%, 70%, 66%, 60%, 56%, 52%, 50%, 40%, 30%, 29%, 27%, 20%, 19%, 17%, 10%, 5%, 4%, 3%, 2%, 1%, 0%, about 99%, about 95%, about 90%, about 80%, about 78%, about 70%, about 66%, about 60%, about 56%, about 52%, about 50%, about 40%, about 30%, about 29%, about 27%, about 20%, about 19%, about 17%, about 10%, about 5%, about 4%, about 3%, about 2%, about 1%, about 0%, less than 99%, less than 95%, less than 90%, less than 80%, less than 78%, less than 70%, less than 66%, less than 60%, less than 56%, less than 52%, less than 50%, less than 40%, less than 30%, less than 29%, less than 27%, less than 20%, less than 19%, less than 17%, less than 10%, less than 5%, less than 4%, less than 3%, less than 2%, or less than 1%.

In some embodiments, the anti-Gal3 antibody does not inhibit or disrupt an interaction between Gal3 and TIM-3.

In some embodiments, the interaction occurs at one or more residues of GAL3 selected from region 145-168, 160-177, or 165-184, wherein the residue positions correspond to positions 145-168, 160-177, or 165-184 of SEQ ID NO: 1. In some embodiments, the interaction occurs at one or more residues of GAL3 selected from region 149-156, 152-168, 163-169, or 163-171, wherein the residue positions correspond to positions 149-156, 152-168, 163-169, or 163-171 of SEQ ID NO: 1. In some embodiments, the interaction occurs at one or more residues of TIM-3 selected from region 90-122 or 82-111, wherein the residue positions correspond to positions 90-122 or 82-111 of SEQ ID NO: 2. In some embodiments, the interaction occurs at one or more residues of TIM-3 selected from region 91-111, 107-117, 96-102, 100-106, or 92-119, herein the residue positions correspond to positions 91-111, 107-117, 96-102, 100-106, or 92-119 of SEQ ID NO: 2.

In some embodiments, the Gal3-expressing cell upon binding to the antibody expresses a cytokine which induces immune activation. As used herein, the term "cytokine" refers to small proteins, polypeptides, or peptides that are involved in cell signaling. Cytokines include but are not limited to chemokines, interferons, interleukins, lymphokines, tumor necrosis factors, CCL1, CC12, CCL3, CCL4, CCL5, CCL6, CCL7, CCL8, CCL9, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, CX3CL1, XCL1, XCL2, INFα, INFβ, INFγ, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, IL-37, IL-38, GM-CSF, TNFα, TNFβ, TNFγ, TNFSF4, TNFSF5, TNFSF6, TNFSF7, TNFSF8, TNFSF9, TNFSF10, TNFSF11, TNFSF12, TNFSF13, TNFSF13B, TNFSF14, TNFSF15, TNFSF18, or TNFSF19, or any combination thereof.

In some embodiments, the cytokine is an interferon. In some embodiments, the interferon is IFNγ. In some embodiments, the antibody results in IFNγ production that is 100%, 150%, 160%, 170%, 180%, 190%, 200%, 300%, 400%, 500%, 600%, 700%, 800%, 900%, 1000% or more of IFNγ production from an isotype antibody. In some embodiments, the cytokine is an interleukin. In some embodiments, the interleukin is IL-2.

In some embodiments, the immune activation or activation of the immune system comprises, consists essentially of, or consists of a proliferation of CD3+ T lymphocytes, CD4+ T helper cells, CD8+ cytotoxic T cells, TFH cells, Th3 cells, Th17 cells, Natural Killer T (NKT) cells, or Natural Killer (NK) cells, or a combination thereof. In some embodiments, immune activation or activation of the immune system comprises, consists essentially of, or consists of promoting T cell or NK cell proliferation. In some embodiments, the immune activation or activation of the immune system comprises, consists essentially of, or consists of an increase in M1 macrophage, neutrophil, mast cell, eosinophil, basophil, or dendritic cell populations within the plurality of cells. In some embodiments, the immune activation or activation of the immune system comprises, consists essentially of, or consists of a decrease in M2 macrophage population within the plurality of cells.

In some embodiments, the TIM-3 is human TIM-3.

In some embodiments, the plurality of cells comprises, consists essentially of, or consists of a tumor cell. In some embodiments, the plurality of cells is located within a tumor microenvironment (TME) and comprises, consists essentially of, or consists of tumor cells and immune cells. In some embodiments, the TME comprises tumor cells, immune cells, carcinoma associated fibroblasts, myeloid-derived suppressor cells, neutrophils, tumor infiltrating lymphocytes (TILs), or any combination thereof. In some embodiments, the plurality of cells comprises, consists essentially of, or consists of CD3+ T lymphocytes, CD4+ T helper cells, CD8+ cytotoxic T cells, TFH cells, Th3 cells, Th17 cells, Natural Killer T (NKT) cells, Natural Killer (NK) cells, M1 macrophages, neutrophils, mast cells, eosinophils, basophils, or dendritic cells. In some embodiments, the anti-TIM-3 antibody induces a decrease of tumor cells within the TME.

In some embodiments, the antibody binds to at least one amino acid residue within a Gal3 region that corresponds to residues 1-20 of SEQ ID NO: 1. In some embodiments, the antibody binds to at least one amino acid residue within a Gal3 region that corresponds to residues 41-91 of SEQ ID NO: 1. In some embodiments, the antibody binds to at least one amino acid residue within a Gal3 region that corresponds to residues 41-71 of SEQ ID NO: 1. In some embodiments, the antibody binds to at least one amino acid residue within a Gal3 region that corresponds to residues 71-91 of SEQ ID NO: 1.

In some embodiments, the antibody binds to at least one amino acid residue within peptide_1, peptide_2, peptide_3, peptide_4, peptide_5, peptide_6, peptide_7, peptide_8, peptide_9, peptide_10, peptide_11, peptide_12, peptide_13, peptide_14, peptide_15, peptide_16, peptide_17, peptide_18, peptide_19, peptide_20, peptide_21, peptide_22, peptide_23, or peptide_24, or any combination thereof.

In some embodiments, the antibody comprises a $K_D$ of 1 fM, 10 fM, 100 fM, 1 pM, 10 pM, 100 pM, 1 nM, 1.2 nM, 2 nM, 5 nM, 10 nM, 13.5 nM, 15 nM, 20 nM, 25 nM, 30 nM, 100 nM, 200 nM, 300 nM, 400 nM, 500 nM, 1 uM, 10 uM, 100 μM, about 1 fM, about 10 fM, about 100 fM, about 1 pM, about 10 pM, about 100 pM, about 1 nM, about 1.2 nM, about 2 nM, about 5 nM, about 10 nM, about 13.5 nM, about 15 nM, about 20 nM, about 25 nM, about 30 nM, about 100 nM, about 200 nM, about 300 nM, about 400 nM, about 500 nM, about 1 uM, about 10 pM, about 100 uM, less than 1 fM, less than 10 fM, less than 100 fM, less than 1 pM, less than 10 pM, less than 100 pM, less than 1 nM, less than 1.2 nM, less than 2 nM, less than 5 nM, less than 10 nM, less than 13.5 nM, less than 15 nM, less than 20 nM, less than 25 nM, less than 30 nM, less than 100 nM, less than 200 nM, less than 300 nM, less than 400 nM, less than 500 nM, less than 1 μM, less than 10 μM, or less than 100 uM.

In some embodiments, the antibody comprises a humanized antibody. In some embodiments, the antibody comprises a full-length antibody or a binding fragment thereof. In some embodiments, the antibody comprises a bispecific antibody or a binding fragment thereof. In some embodiments, the antibody comprises a monovalent Fab', a divalent Fab2, a single-chain variable fragment (scFv), a diabody, a minibody, a nanobody, a single-domain antibody (sdAb), or a camelid antibody or binding fragment thereof. In some embodiments, the antibody comprises an IgG framework. In some embodiments, the antibody comprises an IgG1, IgG2, or IgG4 framework. In some embodiments, the antibody further comprises a Fc mutation. In some embodiments, the antibody comprises a chimeric antibody.

In some embodiments, the anti-Gal3 antibody is selected from the group consisting of 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, and mIMT001 (IMT001). In some embodiments, the anti-Gal3 antibody is mIMT001 (IMT001). In some embodiments, the anti-Gal3 antibody is not mIMT001 (IMT001). In some embodiments, the anti-Gal3 antibody is 4A11.2B5. In some embodiments, the anti-Gal3 antibody is mIMT001 and/or 4A11.2B5. In some embodiments, the antibody competes for binding to Gal3 with one or more of these antibodies (including any one of IMT001-4, IMT006-1, IMT006-5, and/or IMT006-8). In some embodiments, the antibody is one or more of: IMT001-4, IMT006-1, IMT006-5, or IMT006-8. In some embodiments, the antibody for the method includes one or more of the CDRs from one or more of: IMT001-4, IMT006-1, IMT006-5, or IMT006-8. In some embodiments, the antibody for the method includes one or more of the VH, VL, or VH and VL from one or more of: IMT001-4, IMT006-1, IMT006-5, or IMT006-8.

In some embodiments, the method further comprises administering to a subject the anti-Gal3 antibody prior to the contacting step.

In some embodiments, the subject is diagnosed with a cancer.

In some embodiments, the cancer is a solid tumor. In some embodiments, the cancer is breast cancer, colorectal cancer, kidney cancer, liver cancer, lung cancer, prostate cancer, melanoma, bladder cancer, uterine cancer, pancreatic cancer, thyroid cancer, brain cancer, bone cancer, sarcoma, or stomach cancer. In some embodiments, the lung cancer is a non-small cell lung cancer (NSCLC), lung adenocarcinoma, squamous cell carcinoma, large cell carcinoma, or small cell lung cancer (SCLC).

In some embodiments, the cancer is a hematologic malignancy, including but not limited to leukemias, Non-Hodgkin's lymphomas, Hodgkin's lymphomas, multiple myeloma, acute lymphoblastic leukemia, acute myelogenous leukemia, chronic lymphocytic leukemia, chronic myelogenous leukemia, acute monocytic leukemia, or any combination thereof.

In some embodiments, the cancer is a metastatic cancer. In some embodiments, the cancer is a relapsed or refractory cancer. Staging of a cancer or tumor is used to determine the progression of spread of the cancer or tumor within a patient. A commonly recognized standard for the classification of solid tumors is the TNM classification standard, which distinguishes a tumor based on the size of the tumor (T), extent of spread to lymph nodes (N), and metastasis (M). These classifications are further grouped into stages, wherein stage 0 growths are non-malignant neoplasms, stage I and II tumors are locally contained, stage III tumors have spread to nearby lymph nodes, and stage IV tumors have metastasized. While the TNM standard is a widely used method of classification, alternative or modified standards which may represent the behavior of a particular cancer type may also be employed. Accordingly, while these standards are useful for determining progression, prognosis of early or late stages of a cancer or tumor are independent from a specific classification.

Disclosed herein, in some embodiments, are methods of reducing fibrosis or propensity thereof in a tissue of a subject by contacting the tissue with an antibody. In some embodiments, the antibody specifically binds Gal3 or is an anti-Gal3 antibody. In some embodiments, the contacting induces the expression level of at least one fibrosis biomarker to be reduced in the tissue. In some embodiments, the tissue comprises at least one TIM-3 expressing cell. In some embodiments, the anti-Gal3 antibody disrupts interaction of Gal3 and TIM-3. In some embodiments, the anti-Gal3 antibody does not disrupt interaction of Gal3 and TIM-3.

In some embodiments, reducing fibrosis or propensity thereof in a tissue includes preventing fibrosis from occurring in a normal tissue. In some embodiments, reducing fibrosis or propensity thereof in a tissue includes slowing down or arresting progression of fibrosis in a fibrotic tissue.

In some embodiments, reducing fibrosis or propensity thereof in a tissue includes reducing the amount of degree of fibrosis in a fibrotic tissue. In some embodiments, reducing fibrosis or propensity thereof in a tissue includes eliminating fibrosis in a fibrotic tissue.

In some embodiments, also described herein are methods of monitoring the progression of a tissue fibrosis by monitoring one or more fibrosis biomarkers. In some embodiments disclosed herein are methods of treating a tissue fibrosis with an anti-Gal3 antibody, in which the anti-Gal3 antibody disrupts an interaction between Gal3 and TIM-3.

In some embodiments, the at least one fibrosis biomarker comprises, consists essentially of, or consists of α-smooth muscle actin (α-SMA), fibronectin, collagen, collagen I, collagen III, collagen IV, elastin, laminin, hyaluronic acid, or proteoglycans, or any combination thereof. In some embodiments, the at least one fibrosis biomarker comprises, consists essentially of, or consists of α-smooth muscle actin (α-SMA). In some embodiments, the at least one fibrosis biomarker comprises, consists essentially of, or consists of fibronectin. In some embodiments, the at least one fibrosis biomarker comprises, consists essentially of, or consists of α-smooth muscle actin (α-SMA) and fibronectin.

In some embodiments, the tissue is selected from a group consisting of a liver tissue, a kidney tissue, a skin tissue, a lung tissue, a heart tissue, a brain tissue, a colorectal tissue, an intestine tissue, a bone marrow tissue, a breast tissue, a prostate tissue, a bladder tissue, a uterine tissue, a pancreatic tissue, a thyroid tissue, a muscle tissue, a stomach tissue, and a soft tissue. In some embodiments, the tissue is a kidney tissue or liver tissue.

In some embodiments, expression of the at least one fibrosis biomarker in the tissue treated with the anti-Gal3 antibody is less than expression of the at least one fibrosis biomarker in a control tissue treated with a mIgG2b antibody.

In some embodiments, the anti-Gal3 antibody results in reduced accumulation of extracellular matrix (ECM) proteins in the tissue. In some embodiments, the extracellular matrix is comprised of, consists essentially of, or consists of agrin, nidogen, cadherins, clathrin, collagen, defensin, elastin, entactin, fibrillin, fibronectin, keratin, laminin, microtubule-actin cross-linking factor 1, SPARC-like protein, nesprin (nesprin-1, nesprin-2, nesprin-3), fibrous sheath-interacting protein, myomesin, nebulin, plakophilin, integrin, talins, exportins, transportin, tenascin, perlecan, sortilin-related receptor, tensin, or titin or any combination thereof. In some embodiments, the extracellular matrix proteins comprises, consists essentially of, or consists of collagen. In some embodiments, the tissue comprises, consists essentially of, or consists of a collagen-producing cell. In some embodiments, the collagen-producing cell is a fibroblast cell. In some embodiments, the fibroblast cell is activated by a fibrogenic cytokine. In some embodiments, the fibrogenic cytokine is TGF-β, TGF-β1, IL-1β, TNF-α, or GM-CSF. In some embodiments, the tissue has an elevated fibrogenic cytokine expression.

In some embodiments, the antibody binds to at least one amino acid residue within a Gal3 region that corresponds to residues 1-20 of SEQ ID NO: 1. In some embodiments, the antibody binds to at least one amino acid residue within a Gal3 region that corresponds to residues 41-91 of SEQ ID NO: 1. In some embodiments, the antibody binds to at least one amino acid residue within a Gal3 region that corresponds to residues 41-71 of SEQ ID NO: 1. In some embodiments, the antibody binds to at least one amino acid residue within a Gal3 region that corresponds to residues 71-91 of SEQ ID NO: 1.

In some embodiments, the subject is diagnosed with a fibrotic disease or fibrosis. In some embodiments, the subject is diagnosed with a fibrotic disease. In some embodiments, the fibrotic disease is renal fibrosis. In some embodiments, the fibrotic disease is liver fibrosis. In some embodiments, the antibody is formulated for systemic administration. In some embodiments, the antibody is formulated for parenteral administration. In some embodiments, the subject is a mammal.

In some embodiments, the fibrotic disease or fibrosis is liver fibrosis, bridging fibrosis, cirrhosis, renal (kidney) fibrosis, pulmonary fibrosis, idiopathic pulmonary fibrosis, cystic fibrosis, cardiovascular fibrosis, arterial fibrosis, venous thrombosis, arthrofibrosis, Crohn's disease, Dupuytren's contracture, keloids, mediastinal fibrosis, myelofibrosis, Peyronie's disease, nephrogenic systemic fibrosis, progressive massive fibrosis, retroperitoneal fibrosis, or systemic sclerosis. In some embodiments, the fibrotic disease is renal (kidney) fibrosis. In some embodiments, the fibrotic disease is liver fibrosis.

In some embodiments, the method involves an antibody that binds to Gal3, but disrupts an interaction between Gal3 and TIM-3. This can be a direct obstruction of the interaction zone between Gal3 and TIM-3, or an indirect alteration, such as a binding that results in a conformational change of Gal3, so that it no longer binds or is active with TIM-3. It can also result by binding to a first section of Gal3, where some other part of the antibody obstructs or alters the interaction of Gal3 with TIM-3.

In some embodiments is disclosed the use of an anti-Gal3 antibody in the manufacture of a medicament or composition. In some embodiments, the medicament or composition is used for the treatment of an immune related disease. In some embodiments, the medicament or composition is used for the treatment of cancer. In some embodiments, the medicament or composition is used for the treatment of a fibrotic disease or fibrosis.

In some embodiments is an anti-Gal3 antibody for use in the treatment of a disease in a subject. In some embodiments, the anti-Gal3 antibody inhibits the interaction between Gal3 and TIM-3. In some embodiments, the anti-Gal3 antibody does not inhibit the interaction between Gal3 and TIM-3.

In some embodiments, the anti-Gal3 antibody is for use in the treatment of a disease, wherein the disease is immune related, and wherein the anti-Gal3 antibody induces activation of the immune system of the subject. In some embodiments, the immune related disease is an autoimmune disease. In some embodiments, the immune related disease is an immunodeficiency. In some embodiments, the immunodeficiency is immunosenescence, humoral immunodeficiency, B cell deficiency, T cell deficiency, neutropenia, asplenia, or complement deficiency. In some embodiments, the activation of the immune system comprises proliferation of CD3+ T lymphocytes, CD4+ T helper cells, CD8+ cytotoxic T cells, TFH cells, Th3 cells, Th17 cells, Natural Killer T (NKT) cells, NK cells, or M1 macrophages, or a combination thereof. In some embodiments, the activation of the immune system comprises a reduction in M2 macrophages.

In some embodiments, the anti-Gal3 antibody is for use in the treatment of a disease, wherein the disease is cancer and the anti-TIM-3 antibody is for use in the treatment of cancer.

In some embodiments, the anti-Gal3 antibody is for use in the treatment of a disease, wherein the disease is a fibrotic disease or fibrosis. In some embodiments, the anti-Gal3 antibody for use in the treatment of a disease results in reduced accumulation of extracellular matrix proteins in a tissue.

In some embodiments, the anti-Gal3 antibody for use in the treatment of a disease is administered in combination with an additional therapeutic agent, such as an immune checkpoint modulator, chemotherapeutic agent, targeted therapeutic agent, hormonal therapeutic agent, stem cell-based therapeutic agent, surgery, or radiation therapy.

In some embodiments, the antibody is formulated for systemic administration. In some embodiments, the antibody is formulated for parenteral, subcutaneous, intramuscular, intradermal, or intravenous administration, or any combination thereof.

In some embodiments, the anti-Gal3 antibody is administered to the subject in combination with an additional therapeutic agent. In some embodiments, the additional therapeutic agent comprises an immunotherapeutic agent. In some embodiments, the additional therapeutic agent comprises an immune checkpoint modulator. In some embodiments, the additional therapeutic agent comprises a chemotherapeutic agent, targeted therapeutic agent, hormonal therapeutic agent, or a stem cell-based therapeutic agent.

In some embodiments, the additional therapeutic agent comprises an immunotherapeutic agent. In some embodiments, the immunotherapy is an adoptive cell therapy. Exemplary adoptive cell therapies include AFP TCR, MAGE-A10 TCR, or NY-ESO-TCR from Adaptimmune; ACTR087/rituximab from Unum Therapeutics; anti-BCMA CAR-T cell therapy, anti-CD19 "armored" CAR-T cell therapy, JCAR014, JCAR018, JCAR020, JCAR023, JCAR024, or JTCR016 from Juno Therapeutics; JCAR017 from Celgene/Juno Therapeutics; anti-CD19 CAR-T cell therapy from Intrexon; anti-CD19 CAR-T cell therapy, axicabtagene ciloleucel, KITE-718, KITE-439, or NY-ESO-1 T-cell receptor therapy from Kite Pharma; anti-CEA CAR-T therapy from Sorrento Therapeutics; anti-PSMA CAR-T cell therapy from TNK Therapeutics/Sorrento Therapeutics; ATA520 from Atara Biotherapeutics; AU101 and AU105 from Aurora BioPharma; baltaleucel-T (CMD-003) from Cell Medica; bb2121 from bluebird bio; BPX-501, BPX-601, or BPX-701 from Bellicum Pharmaceuticals; BSK01 from Kiromic; IMCgp100 from Immunocore; JTX-2011 from Jounce Therapeutics; LN-144 or LN-145 from Lion Biotechnologies; MB-101 or MB-102 from Mustang Bio; NKR-2 from Celyad; PNK-007 from Celgene; tisagenlecleucel-T from Novartis Pharmaceuticals; or TT12 from Tessa Therapeutics.

In some embodiments, the immunotherapy is a dendritic cell-based therapy.

In some embodiments, the immunotherapy comprises a cytokine-based therapy, comprising e.g., an interleukin (IL) such as IL-2, IL-15, or IL-21, interferon (IFN)-α, or granulocyte macrophage colony-stimulating factor (GM-CSF).

In some embodiments, the immunotherapy comprises an immune checkpoint modulator. Exemplary immune checkpoint modulators include PD-1 modulators such as nivolumab (Opdivo) from Bristol-Myers Squibb, pembrolizumab (Keytruda) from Merck, AGEN 2034 from Agenus, BGB-A317 from BeiGene, B1-754091 from Boehringer-Ingelheim Pharmaceuticals, CBT-501 (genolimzumab) from CBT Pharmaceuticals, INCSHR1210 from Incyte, JNJ-63723283 from Janssen Research & Development, MEDI0680 from MedImmune, MGA 012 from MacroGenics, PDR001 from Novartis Pharmaceuticals, PF-06801591 from Pfizer, REGN2810 (SAR439684) from Regeneron Pharmaceuticals/Sanofi, or TSR-042 from TESARO; CTLA-4 modulators such as ipilimumab (Yervoy), or AGEN 1884 from Agenus; PD-L1 modulators such as durvalumab (Imfinzi) from AstraZeneca, atezolizumab (MPDL3280A) from Genentech, avelumab from EMD Serono/Pfizer, CX-072 from CytomX Therapeutics, FAZ053 from Novartis Pharmaceuticals, KN035 from 3D Medicine/Alphamab, LY3300054 from Eli Lilly, or M7824 (anti-PD-L1/TGFbeta trap) from EMD Serono; LAG3 modulators such as BMS-986016 from Bristol-Myers Squibb, IMP701 from Novartis Pharmaceuticals, LAG525 from Novartis Pharmaceuticals, or REGN3767 from Regeneron Pharmaceuticals; OX40 modulators such as BMS-986178 from Bristol-Myers Squibb, GSK3174998 from GlaxoSmithKline, INCAGN1949 from Agenus/Incyte, MEDI0562 from MedImmune, PF-04518600 from Pfizer, or RG7888 from Genentechp; GITR modulators such as GWN323 from Novartis Pharmaceuticals, INCAGN1876 from Agenus/Incyte, MEDI1873 from MedImmune, MK-4166 from Merck, or TRX518 from Leap Therapeutics; KIR modulators such as lirilumab from Bristol-Myers Squibb; or TIM modulators such as MBG453 from Novartis Pharmaceuticals or TSR-022 from Tesaro.

In some embodiments, the additional therapeutic agent comprises a chemotherapeutic agent. Exemplary chemotherapeutic agents include, but are not limited to, alkylating agents such as cyclophosphamide, mechlorethamine, chlorambucil, melphalan, dacarbazine, or nitrosoureas; anthracyclines such as daunorubicin, doxorubicin, epirubicin, idarubicin, mitoxantrone, or valrubicin; cytoskeletal disruptors such as paclitaxel, docetaxel, abraxane, or taxotere; epothilones; histone deacetylase inhibitors such as vorinostat or romidepsin; topoisomerase I inhibitors such as irinotecan or topotecan; topoisomerase II inhibitors such as etoposide, teniposide, or tafluposide; kinase inhibitors such as bortezomib, erlotinib, gefitinib, imatinib, vemurafenib, or vismodegib; nucleotide analogs and precursor analogs such as azacitidine, azathioprine, capecitabine, cytarabine, doxifluridine, fluorouracil, gemcitabine, hydrozyurea, mercaptopurine, methotrexate, or tioguanine; platinum-based agents such as carboplatin, cisplatin, or oxaliplatin; retinoids such as tretinoin, alitretinoin, or bexarotene; or vinca alkaloids and derivatives such as vinblastine, vincristine, vindesine, or vinorelbine.

In some embodiments, the additional therapeutic agent comprises a hormone-based therapeutic agent. Exemplary hormone-based therapeutic agents include, but are not limited to, aromatase inhibitors such as letrozole, anastrozole, exemestane, or aminoglutethimide; gonadotropin-releasing hormone (GnRH) analogues such as leuprorelin or goserelin; selective estrogen receptor modulators (SERMs) such as tamoxifen, raloxifene, toremifene, or fulvestrant; antiandrogens such as flutamide or bicalutamide; progestogens such as megestrol acetate or medroxyprogesterone acetate; androgens such as fluoxymesterone; estrogens such as estrogen diethylstilbestrol (DES), Estrace, or polyestradiol phosphate; or somatostatin analogs such as octreotide.

In some embodiments, the additional therapeutic agent is a first-line therapeutic agent.

In some embodiments, the anti-Gal3 antibody and the additional therapeutic agent are administered simultaneously. In some embodiments, the anti-Gal3 antibody and the additional therapeutic agent are administered sequentially. In some embodiments, the anti-Gal3 antibody is administered to the subject prior to administering the additional therapeutic agent. In some embodiments, the anti-Gal3 antibody is administered to the subject after the additional therapeutic agent is administered.

In some embodiments, the additional therapeutic agent and the anti-Gal3 antibody are formulated as separate dosage.

In some embodiments, the subject has undergone surgery. In some cases, the anti-Gal3 antibody and optionally the additional therapeutic agent are administered to the subject prior to surgery. In some embodiments, the anti-Gal3 antibody and optionally the additional therapeutic agent are administered to the subject after surgery.

In some embodiments, the subject has undergone radiation. In some embodiments, the anti-Gal3 antibody and optionally the additional therapeutic agent are administered to the subject during or after radiation treatment. In some cases, the anti-Gal3 antibody and optionally the additional therapeutic agent are administered to the subject prior to undergoing radiation.

In some embodiments, the subject is a mammal. In some embodiments, the subject is a human.

Disclosed herein, in some embodiments, are methods of reducing fibrosis or propensity thereof in a tissue by contacting the tissue with an antibody that specifically binds to Gal3. In some embodiments, also described herein are methods of disrupting a Gal3-TIM-3 interaction by an antibody that specifically binds to Gal3, under conditions to reduce expression of one or more fibrosis biomarkers in the tissue.

Disclosed herein, in certain embodiments, is a method of reducing fibrosis or propensity thereof in a tissue, comprising: contacting the tissue with an antibody that specifically binds Gal3 antibody under conditions such that expression level of a fibrosis biomarker is reduced in the tissue. In some embodiments, the tissue further comprises a TIM-3 expressing cell. In some embodiments, the antibody further disrupts interaction of Gal3 and TIM-3. In some embodiments, the antibody does not disrupt interaction of Gal3 and TIM-3. In some embodiments, the at least one fibrosis biomarker comprises α-smooth muscle actin (α-SMA). In some embodiments, the at least one fibrosis biomarker comprises fibronectin. In some embodiments, the at least one fibrosis biomarker comprises α-smooth muscle actin (α-SMA) and fibronectin. In some embodiments, the tissue is a kidney tissue or liver tissue. In some embodiments, the tissue is selected from a group consisting of a liver tissue, a kidney tissue, a skin tissue, a lung tissue, a heart tissue, a brain tissue, an intestine tissue, a bone marrow tissue, and a soft tissue. In some embodiments, expression of the at least one fibrosis biomarker in the tissue treated with the antibody is less than expression of the at least one fibrosis biomarker in a control tissue treated with a mIgG2b antibody. In some embodiments, the antibody results in reduced accumulation of extracellular matrix proteins in the tissue. In some embodiments, the extracellular matrix proteins comprises collagen. In some embodiments, the tissue comprises a collagen-producing cell. In some embodiments, the collagen-producing cell is a fibroblast cell. In some embodiments, the fibroblast cell is activated by a fibrogenic cytokine. In some embodiments, the fibrogenic cytokine is TGF-β1. In some embodiments, the tissue has an elevated TGF-β1 expression.

Antibody Production

In some embodiments, anti-Gal3 antibodies are raised by standard protocol by injecting a production animal with an antigenic composition. See, e.g., Harlow and Lane, Antibodies: A Laboratory Manual, Cold Spring Harbor Laboratory, 1988. When utilizing an entire protein, or a larger section of the protein, antibodies may be raised by immunizing the production animal with the protein and a suitable adjuvant (e.g., Freund's, Freund's complete, oil-in-water emulsions, etc.). When a smaller peptide is utilized, it is advantageous to conjugate the peptide with a larger molecule to make an immunostimulatory conjugate. Commonly utilized conjugate proteins that are commercially available for such use include bovine serum albumin (BSA) and keyhole limpet hemocyanin (KLH). In order to raise antibodies to particular epitopes, peptides derived from the full sequence may be utilized. Alternatively, in order to generate antibodies to relatively short peptide portions of the protein target, a superior immune response may be elicited if the polypeptide is joined to a carrier protein, such as ovalbumin, BSA or KLH.

Polyclonal or monoclonal anti-Gal3 antibodies can be produced from animals which have been genetically altered to produce human immunoglobulins. A transgenic animal can be produced by initially producing a "knock-out" animal which does not produce the animal's natural antibodies, and stably transforming the animal with a human antibody locus (e.g., by the use of a human artificial chromosome). In such cases, only human antibodies are then made by the animal. Techniques for generating such animals, and deriving antibodies therefrom, are described in U.S. Pat. Nos. 6,162,963 and 6,150,584, incorporated fully herein by reference. Such antibodies can be referred to as human xenogenic antibodies.

Alternatively, anti-Gal3 antibodies can be produced from phage libraries containing human variable regions. See U.S. Pat. No. 6,174,708, incorporated fully herein by reference.

In some aspects of some embodiments disclosed herein, an anti-Gal3 antibody is produced by a hybridoma.

For monoclonal anti-Gal3 antibodies, hybridomas may be formed by isolating the stimulated immune cells, such as those from the spleen of the inoculated animal. These cells can then be fused to immortalized cells, such as myeloma cells or transformed cells, which are capable of replicating indefinitely in cell culture, thereby producing an immortal, immunoglobulin-secreting cell line. The immortal cell line utilized can be selected to be deficient in enzymes necessary for the utilization of certain nutrients. Many such cell lines (such as myelomas) are known to those skilled in the art, and include, for example: thymidine kinase (TK) or hypoxanthine-guanine phosphoriboxyl transferase (HGPRT). These deficiencies allow selection for fused cells according to their ability to grow on, for example, hypoxanthine aminopterin-thymidine medium (HAT).

In addition, the anti-Gal3 antibody may be produced by genetic engineering.

Anti-Gal3 antibodies disclosed herein can have a reduced propensity to induce an undesired immune response in humans, for example, anaphylactic shock, and can also exhibit a reduced propensity for priming an immune response which would prevent repeated dosage with an antibody therapeutic or imaging agent (e.g., the human-anti-murine-antibody "HAMA" response). Such anti-Gal3 antibodies include, but are not limited to, humanized, chimeric, or xenogenic human anti-Gal3 antibodies.

Chimeric anti-Gal3 antibodies can be made, for example, by recombinant means by combining the murine variable light and heavy chain regions (VK and VH), obtained from a murine (or other animal-derived) hybridoma clone, with the human constant light and heavy chain regions, in order to produce an antibody with predominantly human domains. The production of such chimeric antibodies is well known in the art, and may be achieved by standard means (as described, e.g., in U.S. Pat. No. 5,624,659, incorporated fully herein by reference).

The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some embodiments, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In some examples, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

Humanized antibodies can be engineered to contain human-like immunoglobulin domains, and incorporate only the complementarity-determining regions of the animal-derived antibody. This can be accomplished by carefully examining the sequence of the hyper-variable loops of the variable regions of a monoclonal antigen binding unit or monoclonal antibody, and fitting them to the structure of a human antigen binding unit or human antibody chains. See, e.g., U.S. Pat. No. 6,187,287, incorporated fully herein by reference.

Methods for humanizing non-human antibodies are well known in the art. "Humanized" antibodies are antibodies in which at least part of the sequence has been altered from its initial form to render it more like human immunoglobulins. In some versions, the heavy (H) chain and light (L) chain constant (C) regions are replaced with human sequence. This can be a fusion polypeptide comprising a variable (V) region and a heterologous immunoglobulin C region. In some versions, the complementarity determining regions (CDRs) comprise non-human antibody sequences, while the V framework regions have also been converted to human sequences. See, for example, EP 0329400. In some versions, V regions are humanized by designing consensus sequences of human and mouse V regions, and converting residues outside the CDRs that are different between the consensus sequences.

In principle, a framework sequence from a humanized antibody can serve as the template for CDR grafting; however, it has been demonstrated that straight CDR replacement into such a framework can lead to significant loss of binding affinity to the antigen. Glaser et al. (1992) *J. Immunol.* 149:2606; Tempest et al. (1992) *Biotechnology* 9:266; and Shalaby et al. (1992) *J. Exp. Med.* 17:217. The more homologous a human antibody (HuAb) is to the original murine antibody (muAb), the less likely that the human framework will introduce distortions into the murine CDRs that could reduce affinity. Based on a sequence homology search against an antibody sequence database, the HuAb IC4 provides good framework homology to muM4TS.22, although other highly homologous HuAbs would be suitable as well, especially kappa L chains from human subgroup I or H chains from human subgroup III. Kabat et al. (1987). Various computer programs such as ENCAD (Levitt et al. (1983) *J. Mol. Biol.* 168:595) are available to predict the ideal sequence for the V region. The invention thus encompasses HuAbs with different variable (V) regions. It is within the skill of one in the art to determine suitable V region sequences and to optimize these sequences. Methods for obtaining antibodies with reduced immunogenicity are also described in U.S. Pat. No. 5,270,202 and EP 699,755.

Humanized antibodies can be prepared by a process of analysis of the parental sequences and various conceptual humanized products using three dimensional models of the parental and humanized sequences. Three dimensional immunoglobulin models are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved.

A process for humanization of subject antigen binding units can be as follows. The best-fit germline acceptor heavy and light chain variable regions are selected based on homology, canonical structure and physical properties of the human antibody germlines for grafting. Computer modeling of mVH/VL versus grafted hVH/VL is performed and prototype humanized antibody sequence is generated. If modeling indicated a need for framework back-mutations, second variant with indicated FW changes is generated. DNA fragments encoding the selected germline frameworks and murine CDRs are synthesized. The synthesized DNA fragments are subcloned into IgG expression vectors and sequences are confirmed by DNA sequencing. The humanized antibodies are expressed in cells, such as 293F and the proteins are tested, for example in MDM phagocytosis assays and antigen binding assays. The humanized antigen binding units are compared with parental antigen binding units in antigen binding affinity, for example, by FACS on cells expressing the target antigen. If the affinity is greater than 2-fold lower than parental antigen binding unit, a second round of humanized variants can be generated and tested as described above.

As noted above, an anti-Gal3 antibody can be either "monovalent" or "multivalent." Whereas the former has one binding site per antigen-binding unit, the latter contains multiple binding sites capable of binding to more than one antigen of the same or different kind. Depending on the number of binding sites, antigen binding units may be bivalent (having two antigen-binding sites), trivalent (having three antigen-binding sites), tetravalent (having four antigen-binding sites), and so on.

Multivalent anti-Gal3 antibodies can be further classified on the basis of their binding specificities. A "monospecific" anti-Gal3 antibody is a molecule capable of binding to one or more antigens of the same kind. A "multispecific" anti-Gal3 antibody is a molecule having binding specificities for at least two different antigens. While such molecules normally will only bind two distinct antigens (i.e. bispecific anti-Gal3 antibodies), antibodies with additional specificities such as trispecific antibodies are encompassed by this expression when used herein. This disclosure further provides multispecific anti-Gal3 antibodies. Multispecific anti-Gal3 antibodies are multivalent molecules capable of binding to at least two distinct antigens, e.g., bispecific and trispecific molecules exhibiting binding specificities to two and three distinct antigens, respectively.

Monoclonal antibodies can be obtained by injecting mice with a composition comprising an antigen, e.g. a Gal3 or an epitope of thereof, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

Monoclonal antibodies produced can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992). After the initial raising of antibodies to the target protein, the antibodies can be sequenced and subsequently prepared by recombinant techniques. Humanization and chimerization of murine antibodies and antibody fragments are well known to those skilled in the art. See, for example, Leung et al. Hybridoma 13:469 (1994); US20140099254 A1, each of which are hereby expressly incorporated by reference in its entirety.

Human antibodies can be produced using transgenic mice that have been genetically engineered to produce specific human antibodies in response to antigenic challenge using the target protein. See Green et al., Nature Genet. 7:13 (1994), Lonberg et al., Nature 368:856 (1994). Human antibodies against the target protein can also be constructed by genetic or chromosomal transfection methods, phage display technology, or by in vitro activated B cells. See e.g., McCafferty et al., 1990, *Nature* 348:552-553; U.S. Pat. Nos. 5,567,610 and 5,229,275, each of which are hereby expressly incorporated by reference in its entirety.

In some embodiments, the Gal3-TIM-3 interaction can be reduced to less than 70%, less than 60%, less than 59%, less than 50%, less than 40%, less than 34%, less than 30%, less than 20%, less than 14%, less than 10%, less than 7%, less than 5%, less than 4%, or less than 1%.

Polynucleotides and Vectors

In some embodiments, the present disclosure provides isolated nucleic acids encoding any of the anti-Gal3 antibodies disclosed herein. In some embodiments, the present disclosure provides vectors comprising a nucleic acid sequence encoding any anti-Gal3 antibody disclosed herein. In some embodiments, this invention provides isolated nucleic acids that encode a light-chain CDR and a heavy-chain CDR of an anti-Gal3 antibody disclosed herein.

The subject anti-Gal3 antibodies can be prepared by recombinant DNA technology, synthetic chemistry techniques, or a combination thereof. For instance, sequences encoding the desired components of the anti-Gal3 antibodies, including light chain CDRs and heavy chain CDRs are typically assembled cloned into an expression vector using standard molecular techniques know in the art. These sequences may be assembled from other vectors encoding the desired protein sequence, from PCR-generated fragments using respective template nucleic acids, or by assembly of synthetic oligonucleotides encoding the desired sequences. Expression systems can be created by transfecting a suitable cell with an expressing vector which comprises an anti-Gal3 antibody of interest.

Nucleotide sequences corresponding to various regions of light or heavy chains of an existing antibody can be readily obtained and sequenced using convention techniques including but not limited to hybridization, PCR, and DNA sequencing. Hybridoma cells that produce monoclonal antibodies serve as a preferred source of antibody nucleotide sequences. A vast number of hybridoma cells producing an array of monoclonal antibodies may be obtained from public or private repositories. The largest depository agent is American Type Culture Collection (atcc.org), which offers a diverse collection of well-characterized hybridoma cell lines. Alternatively, antibody nucleotides can be obtained from immunized or non-immunized rodents or humans, and form organs such as spleen and peripheral blood lymphocytes. Specific techniques applicable for extracting and synthesizing antibody nucleotides are described in Orlandi et al. (1989) *Proc. Natl. Acad. Sci. U.S.A* 86:3833-3837; Larrick et al. (1989) *Biochem. Biophys. Res. Commun.* 160:1250-1255; Sastry et al. (1989) *Proc. Natl. Acad. Sci., U.S.A.* 86:5728-5732; and U.S. Pat. No. 5,969,108.

Polynucleotides encoding anti-Gal3 antibodies can also be modified, for example, by substituting the coding sequence for human heavy and light chain constant regions in place of the homologous non-human sequences. In that manner, chimeric antibodies are prepared that retain the binding specificity of the original anti-Gal3 antibody.

Host Cells For Antibody Production

In some embodiments, the present disclosure provides host cells expressing any one of the anti-Gal3 antibodies disclosed herein. A subject host cell typically comprises a nucleic acid encoding any one of the anti-Gal3 antibodies disclosed herein. In some embodiments, the host cell is a Chinese hamster ovary (CHO) cell. In some embodiments, the host cell is an NS0 cell.

The invention provides host cells transfected with the polynucleotides, vectors, or a library of the vectors described above. The vectors can be introduced into a suitable prokaryotic or eukaryotic cell by any of a number of appropriate means, including electroporation, microprojectile bombardment; lipofection, infection (where the vector is coupled to an infectious agent), transfection employing calcium chloride, rubidium chloride, calcium phosphate, DEAE-dextran, or other substances. The choice of the means for introducing vectors will often depend on features of the host cell.

For most animal cells, any of the above-mentioned methods is suitable for vector delivery. Preferred animal cells are vertebrate cells, preferably mammalian cells, capable of expressing exogenously introduced gene products in large quantity, e.g. at the milligram level. Non-limiting examples of preferred cells are NIH3T3 cells, COS, HeLa, and CHO cells.

Once introduced into a suitable host cell, expression of the anti-Gal3 antibodies can be determined using any nucleic acid or protein assay known in the art. For example, the presence of transcribed mRNA of light chain CDRs or heavy chain CDRs, or the anti-Gal3 antibody can be detected and/or quantified by conventional hybridization assays (e.g. Northern blot analysis), amplification procedures (e.g. RT-PCR), SAGE (U.S. Pat. No. 5,695,937), and array-based technologies (see e.g. U.S. Pat. Nos. 5,405,783, 5,412,087 and 5,445,934), using probes complementary to any region of a polynucleotide that encodes the anti-Gal3 antibody.

Expression of the vector can also be determined by examining the expressed anti-Gal3 antibody. A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunoflourescent assays, and SDS-PAGE.

Payload

In some embodiments, an anti-Gal3 antibody further comprises a payload. In some cases, the payload comprises a small molecule, a protein or functional fragment thereof, a peptide, or a nucleic acid polymer.

In some cases, the number of payloads conjugated to the anti-Gal3 antibody (e.g., the drug-to-antibody ratio or DAR) is about 1:1, one payload to one anti-Gal3 antibody. In some cases, the ratio of the payloads to the anti-Gal3 antibody is about 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1. In some cases, the ratio of the payloads to the anti-Gal3 antibody is about 2:1. In some cases, the ratio of the payloads to the anti-Gal3 antibody is about 3:1. In some cases, the ratio of the payloads to the anti-Gal3 antibody is about 4:1. In some cases, the ratio of the payloads to the anti-Gal3 antibody is about 6:1. In some cases, the ratio of the payloads to the anti-Gal3 antibody is about 8:1. In some cases, the ratio of the payloads to the anti-Gal3 antibody is about 12:1.

In some embodiment, the payload is a small molecule. In some embodiments, the small molecule is a cytotoxic payload. Exemplary cytotoxic payloads include, but are not limited to, microtubule disrupting agents, DNA modifying agents, or Akt inhibitors.

In some embodiments, the payload comprises a microtubule disrupting agent. Exemplary microtubule disrupting agents include, but are not limited to, 2-methoxyestradiol, auristatin, chalcones, colchicine, combretastatin, cryptophycin, dictyostatin, discodermolide, dolastain, eleutherobin, epothilone, halichondrin, laulimalide, maytansine, noscapinoid, paclitaxel, peloruside, phomopsin, podophyllotoxin, rhizoxin, spongistatin, taxane, tubulysin, vinca alkaloid, vinorelbine, or derivatives or analogs thereof.

In some embodiments, the maytansine is a maytansinoid. In some embodiments, the maytansinoid is DM1, DM4, or ansamitocin. In some embodiments, the maytansinoid is DM1. In some embodiments, the maytansinoid is DM4. In some embodiments, the maytansinoid is ansamitocin. In some embodiments, the maytansinoid is a maytansionid derivative or analog such as described in U.S. Pat. Nos. 5,208,020, 5,416,064, 7,276,497, and 6,716,821 or U.S. Publication Nos. 2013029900 and US20130323268.

In some embodiments, the payload is a dolastatin, or a derivative or analog thereof. In some embodiments, the dolastatin is dolastatin 10 or dolastatin 15, or derivatives or analogs thereof. In some embodiments, the dolastatin 10 analog is auristatin, soblidotin, symplostatin 1, or symplostatin 3. In some embodiments, the dolastatin 15 analog is cemadotin or tasidotin.

In some embodiments, the dolastatin 10 analog is auristatin or an auristatin derivative. In some embodiments, the auristatin or auristatin derivative is auristatin E (AE), auristatin F (AF), auristatin E5-benzoylvaleric acid ester (AEVB), monomethyl auristatin E (MMAE), monomethyl auristatin F (MMAF), or monomethyl auristatin D (MMAD), auristatin PE, or auristatin PYE. In some embodiments, the auristatin derivative is monomethyl auristatin E (MMAE). In some embodiments, the auristatin derivative is monomethyl auristatin F (MMAF). In some embodiments, the auristatin is an auristatin derivative or analog such as described in U.S. Pat. Nos. 6,884,869, 7,659,241, 7,498,298, 7,964,566, 7,750,116, 8,288,352, 8,703,714, and 8,871,720.

In some embodiments, the payload comprises a DNA modifying agent. In some embodiments, the DNA modifying agent comprises DNA cleavers, DNA intercalators, DNA transcription inhibitors, or DNA cross-linkers. In some embodiments, the DNA cleaver comprises bleomycine A2, calicheamicin, or derivatives or analogs thereof. In some embodiments, the DNA intercalator comprises doxorubicin, epirubicin, PNU-159682, duocarmycin, pyrrolobenzodiazepine, oligomycin C, daunorubicin, valrubicin, topotecan, or derivatives or analogs thereof. In some embodiments, the DNA transcription inhibitor comprises dactinomycin. In some embodiments, the DNA cross-linker comprises mitomycin C.

In some embodiments, the DNA modifying agent comprises amsacrine, anthracycline, camptothecin, doxorubicin, duocarmycin, enediyne, etoposide, indolinobenzodiazepine, netropsin, teniposide, or derivatives or analogs thereof.

In some embodiments, the anthracycline is doxorubicin, daunorubicin, epirubicin, idarubicin, mitomycin-C, dactinomycin, mithramycin, nemorubicin, pixantrone, sabarubicin, or valrubicin.

In some embodiments, the analog of camptothecin is topotecan, irinotecan, silatecan, cositecan, exatecan, lurtotecan, gimatecan, belotecan, rubitecan, or SN-38.

In some embodiments, the duocarmycin is duocarmycin A, duocarmycin B1, duocarmycin B2, duocarmycin C1, duocarmycin C2, duocarmycin D, duocarmycin SA, or CC-1065. In some embodiments, the enediyne is a calicheamicin, esperamicin, or dynemicin A.

In some embodiments, the pyrrolobenzodiazepine is anthramycin, abbeymycin, chicamycin, DC-81, mazethramycin, neothramycins A, neothramycin B, porothramycin, prothracarcin, sibanomicin (DC-102), sibiromycin, or tomaymycin. In some embodiments, the pyrrolobenzodiazepine is a tomaymycin derivative, such as described in U.S. Pat. Nos. 8,404,678 and 8,163,736. In some embodiments, the pyrrolobenzodiazepine is such as described in U.S. Pat. Nos. 8,426,402, 8,802,667, 8,809,320, 6,562,806, 6,608,192, 7,704,924, 7,067,511, 7,612,062, 7,244,724, 7,528,126, 7,049,311, 8,633,185, 8,501,934, and 8,697,688 and U.S. Publication No. US20140294868.

In some embodiments, the pyrrolobenzodiazepine is a pyrrolobenzodiazepine dimer. In some embodiments, the PBD dimer is a symmetric dimer. Examples of symmetric PBD dimers include, but are not limited to, SJG-136 (SG-2000), ZC-423 (SG2285), SJG-720, SJG-738, ZC-207 (SG2202), and DSB-120. In some embodiments, the PBD dimer is an unsymmetrical dimer. Examples of unsymmetrical PBD dimers include, but are not limited to, SJG-136 derivatives such as described in U.S. Pat. Nos. 8,697,688 and 9,242,013 and U.S. Publication No. 20140286970.

In some embodiments, the payload comprises an Akt inhibitor. In some cases, the Akt inhibitor comprises ipatasertib (GDC-0068) or derivatives thereof.

In some embodiments, the payload comprises a polymerase inhibitor, including, but not limited to polymerase II inhibitors such as a-amanitin, and poly(ADP-ribose) polymerase (PARP) inhibitors. Exemplary PARP inhibitors include, but are not limited to Iniparib (BSI 201), Talazoparib (BMN-673), Olaparib (AZD-2281), Olaparib, Rucaparib (AG014699, PF-01367338), Veliparib (ABT-888), CEP 9722, MK 4827, BGB-290, or 3-aminobenzamide.

In some embodiments, the payload comprises a detectable moiety. Exemplary detectable moieties include fluorescent dyes; enzymes; substrates; chemiluminescent moieties; specific binding moieties such as streptavidin, avidin, or biotin; or radioisotopes.

In some embodiments, the payload comprises an immunomodulatory agent. Useful immunomodulatory agents include anti-hormones that block hormone action on tumors and immunosuppressive agents that suppress cytokine production, down-regulate self-antigen expression, or mask MHC antigens. Representative anti-hormones include anti-estrogens including, for example, tamoxifen, raloxifene, aromatase inhibiting 4 (5)-imidazoles, 4-hydroxytamoxifen, trioxifene, keoxifene, LY 117018, onapnstone, and toremifene; and anti-androgens such as flutamide, nilutamide, bicalutamide, leuprolide, and goserelin; and anti-adrenal agents. Illustrative immunosuppressive agents include, but are not limited to 2-amino-6-aryl-5-substituted pyrimidines, azathioprine, cyclophosphamide, bromocryptine, danazol, dapsone, glutaraldehyde, anti-idiotypic antibodies for MHC antigens and MHC fragments, cyclosporin A, steroids such as glucocorticosteroids, streptokinase, or rapamycin.

In some embodiments, the payload comprises an immune modulator. Exemplary immune modulators include, but are not limited to, gancyclovier, etanercept, tacrolimus, sirolimus, voclosporin, cyclosporine, rapamycin, cyclophosphamide, azathioprine, mycophenolgate mofetil, methotrextrate, glucocorticoid and its analogs, xanthines, stem cell growth factors, lymphotoxins, hematopoietic factors, tumor necrosis factor (TNF) (e.g., TNFα), interleukins (e.g., interleukin-1 (IL-1), IL-2, IL-3, IL-6, IL-10, IL-12, IL-18, and IL-21), colony stimulating factors (e.g., granulocyte-colony stimulating factor (G-CSF) and granulocyte macrophage-colony stimulating factor (GM-CSF)), interferons (e.g., interferons-alpha, interferon-beta, interferon-gamma), the stem cell growth factor designated "S1 factor," erythropoietin and thrombopoietin, or a combination thereof.

In some embodiments, the payload comprises an immunotoxin. Immunotoxins include, but are not limited to, ricin, radionuclides, pokeweed antiviral protein, *Pseudomonas* exotoxin A, diphtheria toxin, ricin A chain, fungal toxins such as restrictocin and phospholipase enzymes. See, generally, "Chimeric Toxins," Olsnes and Pihl, *Pharmac. Ther.* 15:355-381 (1981); and "Monoclonal Antibodies for Cancer Detection and Therapy," eds. Baldwin and Byers, pp. 159-179, 224-266, Academic Press (1985).

In some embodiments, the payload comprises a nucleic acid polymer. In some embodiments, the nucleic acid polymer comprises short interfering nucleic acid (siNA), short interfering RNA (siRNA), double-stranded RNA (dsRNA), micro-RNA (miRNA), short hairpin RNA (shRNA), an antisense oligonucleotide. In some embodiments, the nucleic acid polymer comprises an mRNA, encoding, e.g., a cytotoxic protein or peptide or an apoptotic triggering protein or peptide. Exemplary cytotoxic proteins or peptides include a bacterial cytotoxin such as an alpha-pore forming toxin (e.g., cytolysin A from *E. coli*), a beta-pore-forming toxin (e.g., α-Hemolysin, PVL-panton Valentine leukocidin, aerolysin, clostridial Epsilon-toxin, *Clostridium perfringens* enterotoxin), binary toxins (anthrax toxin, edema toxin, *C. botulinum* C2 toxin, C spirofome toxin, *C. perfringens* iota toxin, *C. difficile* cyto-lethal toxins (A and B)), prion, parasporin, a cholesterol-dependent cytolysins (e.g., pneumolysin), a small pore-forming toxin (e.g., Gramicidin A), a cyanotoxin (e.g., microcystins, nodularins), a hemotoxin, a neurotoxin (e.g., botulinum neurotoxin), a cytotoxin, cholera toxin, diphtheria toxin, *Pseudomonas* exotoxin A, tetanus toxin, or an immunotoxin (idarubicin, ricin A, CRM9, Pokeweed antiviral protein, DT). Exemplary apoptotic triggering proteins or peptides include apoptotic protease activating factor-1 (Apaf-1), cytochrome-c, caspase initiator proteins (CASP2, CASP8, CASP9, CASP10), apoptosis inducing factor (AIF), p53, p73, p63, Bcl-2, Bax, granzyme B, poly-ADP ribose polymerase (PARP), and P 21-activated kinase 2 (PAK2). In some embodiments, the nucleic acid polymer comprises a nucleic acid decoy. In some embodiments, the nucleic acid decoy is a mimic of protein-binding nucleic acids such as RNA-based protein-binding mimics. Exemplary nucleic acid decoys include transactivating region (TAR) decoy and Rev response element (RRE) decoy.

In some cases, the payload is an aptamer. Aptamers are small oligonucleotide or peptide molecules that bind to specific target molecules. Exemplary nucleic acid aptamers include DNA aptamers, RNA aptamers, or XNA aptamers which are RNA and/or DNA aptamers comprising one or more unnatural nucleotides. Exemplary nucleic acid aptamers include ARC19499 (Archemix Corp.), REG1 (Regado Biosciences), and ARC1905 (Ophthotech).

Nucleic acids in accordance with some embodiments described herein optionally include naturally occurring nucleic acids, or one or more nucleotide analogs or have a structure that otherwise differs from that of a naturally occurring nucleic acid. For example, 2'-modifications include halo, alkoxy, and allyloxy groups. In some embodiments, the 2'-OH group is replaced by a group selected from H, OR, R, halo, SH, SR, $NH_2$, NHR, NR2 or CN, wherein R is $C_1$-$C_6$ alkyl, alkenyl, or alkynyl, and halo is F, Cl, Br, or I. Examples of modified linkages include phosphorothioate and 5'-N-phosphoramidite linkages.

Nucleic acids having a variety of different nucleotide analogs, modified backbones, or non-naturally occurring internucleoside linkages are utilized in accordance with some embodiments described herein. In some cases, nucleic acids include natural nucleosides (i.e., adenosine, thymidine, guanosine, cytidine, uridine, deoxyadenosine, deoxythymidine, deoxyguanosine, and deoxycytidine) or modified nucleosides. Examples of modified nucleotides include base modified nucleoside (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, M1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, O(6)-methylguanine, and 2-thiocytidine), chemically or biologically modified bases (e.g., methylated bases), modified sugars (e.g., 2'-fluororibose, 2'-aminoribose, 2'-azidoribose, 2'-O-methylribose, L-enantiomeric nucleosides arabinose, and hexose), modified phosphate groups (e.g., phosphorothioates and 5'-N-phosphoramidite linkages), and combinations thereof. Natural and modified nucleotide monomers for the chemical synthesis of nucleic acids are readily available. In some cases, nucleic acids comprising such modifications display improved properties relative to nucleic acids consisting only of naturally occurring nucleotides. In some embodiments, nucleic acid modifications described herein are utilized to reduce and/or prevent digestion by nucleases (e.g. exonucleases, endonucleases, etc.). For example, the structure of a nucleic acid may be stabilized by including nucleotide analogs at the 3' end of one or both strands order to reduce digestion.

Different nucleotide modifications and/or backbone structures may exist at various positions in the nucleic acid. Such modification include morpholinos, peptide nucleic acids (PNAs), methylphosphonate nucleotides, thiolphosphonate nucleotides, 2'-fluoro N3-P5'-phosphoramidites, 1', 5'-anhydrohexitol nucleic acids (HNAs), or a combination thereof.

Conjugation Chemistry

In some embodiments, the payload is conjugated to an anti-Gal3 antibody described herein by a native ligation. In some embodiments, the conjugation is as described in: Dawson, et al. "Synthesis of proteins by native chemical ligation," *Science* 1994, 266, 776-779; Dawson, et al. "Modulation of Reactivity in Native Chemical Ligation through the Use of Thiol Additives," *J. Am. Chem. Soc.* 1997, 119, 4325-4329; Hackeng, et al. "Protein synthesis by native chemical ligation: Expanded scope by using straightforward methodology," *Proc. Natl. Acad. Sci. USA* 1999, 96, 10068-10073; or Wu, et al. "Building complex glycopeptides: Development of a cysteine-free native chemical ligation protocol," *Angew. Chem. Int. Ed.* 2006, 45, 4116-4125. In some embodiments, the conjugation is as described in U.S. Pat. No. 8,936,910.

In some embodiments, the payload is conjugated to an anti-Gal3 antibody described herein by a site-directed method utilizing a "traceless" coupling technology (Philochem). In some embodiments, the "traceless" coupling technology utilizes an N-terminal 1,2-aminothiol group on the binding moiety which is then conjugate with a polynucleic acid molecule containing an aldehyde group. (see Casi et al., "Site-specific traceless coupling of potent cytotoxic drugs to recombinant antibodies for pharmacodelivery," *JACS* 134 (13): 5887-5892 (2012))

In some embodiments, the payload is conjugated to an anti-Gal3 antibody described herein by a site-directed method utilizing an unnatural amino acid incorporated into the binding moiety. In some embodiments, the unnatural amino acid comprises p-acetylphenylalanine (pAcPhe). In some embodiments, the keto group of pAcPhe is selectively coupled to an alkoxy-amine derivatived conjugating moiety to form an oxime bond. (see Axup et al., "Synthesis of site-specific antibody-drug conjugates using unnatural amino acids," *PNAS* 109 (40): 16101-16106 (2012)).

In some embodiments, the payload is conjugated to an anti-Gal3 antibody described herein by a site-directed method utilizing an enzyme-catalyzed process. In some embodiments, the site-directed method utilizes SMARTag™ technology (Redwood). In some embodiments, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized polynucleic acid molecule via hydrazino-Pictet-Spengler (HIPS) ligation. (see Wu et al., "Site-specific chemical modification of recombinant proteins produced in mammalian cells by using the genetically encoded aldehyde tag," *PNAS* 106 (9): 3000-3005 (2009); Agarwal, et al., "A Pictet-Spengler ligation for protein chemical modification," *PNAS* 110 (1): 46-51 (2013)).

In some embodiments, the enzyme-catalyzed process comprises microbial transglutaminase (mTG). In some cases, the payload is conjugated to the anti-Gal3 antibody utilizing a microbial transglutaminze catalyzed process. In some embodiments, mTG catalyzes the formation of a covalent bond between the amide side chain of a glutamine within the recognition sequence and a primary amine of a functionalized polynucleic acid molecule. In some embodiments, mTG is produced from *Streptomyces mobarensis*. (see Strop et al., "Location matters: site of conjugation modulates stability and pharmacokinetics of antibody drug conjugates," *Chemistry and Biology* 20 (2) 161-167 (2013)).

In some embodiments, the payload is conjugated to an anti-Gal3 antibody by a method as described in PCT Publication No. WO2014/140317, which utilizes a sequence-specific transpeptidase.

In some embodiments, the payload is conjugated to an anti-Gal3 antibody described herein by a method as described in U.S. Patent Publication Nos. 2015/0105539 and 2015/0105540.

Linker

In some embodiments, a linker described above comprises a natural or synthetic polymer, consisting of long chains of branched or unbranched monomers, and/or cross-linked network of monomers in two or three dimensions. In some embodiments, the linker includes a polysaccharide, lignin, rubber, or polyalkylen oxide (e.g., polyethylene glycol).

In some embodiments, the linker includes, but is not limited to, alpha-, omega-dihydroxylpolyethyleneglycol, biodegradable lactone-based polymer, e.g. polyacrylic acid, polylactide acid (PLA), poly(glycolic acid) (PGA), polypropylene, polystyrene, polyolefin, polyamide, polycyanoacrylate, polyimide, polyethylenterephthalat (PET, PETG), polyethylene terephthalate (PETE), polytetramethylene glycol (PTG), or polyurethane as well as mixtures thereof. As used herein, a mixture refers to the use of different polymers within the same compound as well as in reference to block copolymers. In some cases, block copolymers are polymers wherein at least one section of a polymer is build up from monomers of another polymer. In some embodiments, the linker comprises polyalkylene oxide. In some embodiments, the linker comprises PEG. In some embodiments, the linker comprises polyethylene imide (PEI) or hydroxy ethyl starch (HES).

In some cases, the polyalkylene oxide (e.g., PEG) is a polydispers or monodispers compound. In some embodiments, polydispers material comprises disperse distribution of different molecular weight of the material, characterized by mean weight (weight average) size and dispersity. In some embodiments, the monodisperse PEG comprises one size of molecules. In some embodiments, the linker is poly- or monodispersed polyalkylene oxide (e.g., PEG) and the indicated molecular weight represents an average of the molecular weight of the polyalkylene oxide, e.g., PEG, molecules.

In some embodiments, the linker comprises a polyalkylene oxide (e.g., PEG) and the molecular weight of the polyalkylene oxide (e.g., PEG) is about 200, 300, 400, 500, 600, 700, 800, 900, 1000, 1100, 1200, 1300, 1400, 1450, 1500, 1600, 1700, 1800, 1900, 2000, 2100, 2200, 2300, 2400, 2500, 2600, 2700, 2800, 2900, 3000, 3250, 3350, 3500, 3750, 4000, 4250, 4500, 4600, 4750, 5000, 5500, 6000, 6500, 7000, 7500, 8000, 10,000, 12,000, 20,000, 35,000, 40,000, 50,000, 60,000, or 100,000 Da.

In some embodiments, the polyalkylene oxide (e.g., PEG) is a discrete PEG, in which the discrete PEG is a polymeric PEG comprising more than one repeating ethylene oxide units. In some embodiments, a discrete PEG (dPEG) comprises from 2 to 60, from 2 to 50, or from 2 to 48 repeating ethylene oxide units. In some embodiments, a dPEG comprises about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some embodiments, a dPEG comprises about 2 or more repeating ethylene oxide units. In some cases, a dPEG is synthesized as a single molecular weight compound from pure (e.g., about 95%, 98%, 99%, or 99.5%) staring material in a step-wise fashion. In some cases, a dPEG has a specific molecular weight, rather than an average molecular weight. In some cases, a dPEG described herein is a dPEG from Quanta Biodesign, LMD.

In some embodiments, the linker is a discrete PEG, optionally comprising from 2 to 60, from 2 to 50, or from 2 to 48 repeating ethylene oxide units. In some cases, the linker comprises a dPEG comprising about 2, 3, 4, 5, 6, 7, 8, 9, 10, 11, 12, 13, 14, 15, 16, 17, 18, 19, 20, 22, 24, 26, 28, 30, 35, 40, 42, 48, 50 or more repeating ethylene oxide units. In some cases, the linker is a dPEG from Quanta Biodesign, LMD.

In some embodiments, the linker is a polypeptide linker. In some embodiments, the polypeptide linker comprises at least 2, 3, 4, 5, 6, 7, 8, 10, 15, 20, 25, 30, 35, 40, 45, 50, 60, 70, 80, 90, 100, or more amino acid residues. In some embodiments, the polypeptide linker comprises at least 2, 3, 4, 5, 6, 7, 8, or more amino acid residues. In some embodiments, the polypeptide linker comprises at most 2, 3, 4, 5, 6, 7, 8, or less amino acid residues. In some cases, the polypeptide linker is a cleavable polypeptide linker (e.g., either enzymatically or chemically). In some cases, the polypeptide linker is a non-cleavable polypeptide linker. In some embodiments, the polypeptide linker comprises Val-Cit (valine-citrulline), Gly-Gly-Phe-Gly, Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu, or Gly-Phe-Leu-Gly. In some embodiments, the polypeptide linker comprises a peptide such as: Val-Cit (valine-citrulline), Gly-Gly-Phe-Gly, Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu, or Gly-Phe-Leu-Gly. In some cases, the polypeptide linker comprises L-amino acids, D-amino acids, or a mixture of both L- and D-amino acids.

In some embodiments, the linker comprises a homobifuctional linker. Exemplary homobifuctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis (sulfosuccinimidyl) suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio) propionamido) butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the linker comprises a heterobifunctional linker. Exemplary heterobifunctional linker include, but are not limited to, amine-reactive and sulfhydryl cross-linkers such as N-succinimidyl 3-(2-pyridyldithio) propionate (sPDP), long-chain N-succinimidyl 3-(2-pyridyldithio) propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio) toluene (SMPT), sulfosuccinimidyl-6-[α-methyl-α-(2-pyridyldithio)toluamido]hexanoate (sulfo-LC-sMPT), succinimidyl-4-(N-maleimidomethyl) cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl) butyrate (SMPB), sulfosuccinimidyl-4-(p-maleimidophenyl) butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl) amino)hexanoate (SIAX), succinimidyl 6-[6-(((iodoacetyl) amino)hexanoyl)amino]hexanoate (SIAXX), succinimidyl 4-(((iodoacetyl)amino)methyl)cyclohexane-1-carboxylate (SIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2-pyridyldithio) propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4 (4-azidophenyl) 1,3'-dithiopropionate (sADP), N-sulfosuccinimidyl(4-azidophenyl)-1,3'-dithiopropionate (sulfo-sADP), sulfosuccinimidyl 4-(ρ-azidophenyl) butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), ρ-nitrophenyl diazopyruvate (ρNPDP), ρ-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido) butane (AsIB), N-[4-(ρ-azidosalicylamido)butyl]-3'-(2'-pyridyldithio) propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido)butylamine (AsBA), and arginine-reactive and photoreactive cross-linkers such as ρ-azidophenyl glyoxal (APG).

In some embodiments, the linker comprises a benzoic acid group, or its derivatives thereof. In some embodiments, the benzoic acid group or its derivatives thereof comprise paraaminobenzoic acid (PABA). In some embodiments, the benzoic acid group or its derivatives thereof comprise gamma-aminobutyric acid (GABA).

In some embodiments, the linker comprises one or more of a maleimide group, a peptide moiety, and/or a benzoic acid group, in any combination. In some embodiments, the linker comprises a combination of a maleimide group, a peptide moiety, and/or a benzoic acid group. In some embodiments, the maleimide group is maleimidocaproyl (mc). In some embodiments, the peptide group is val-cit. In some embodiments, the benzoic acid group is PABA. In some embodiments, the linker comprises a mc-val-cit group. In some cases, the linker comprises a val-cit-PABA group. In additional cases, the linker comprises a mc-val-cit-PABA group.

In some embodiments, the linker is a self-immolative linker or a self-elimination linker. In some cases, the linker is a self-immolative linker. In other cases, the linker is a self-elimination linker (e.g., a cyclization self-elimination linker). In some embodiments, the linker comprises a linker described in U.S. Pat. No. 9,089,614 or PCT Publication No. WO2015038426.

In some embodiments, the linker is a dendritic type linker. In some embodiments, the dendritic type linker comprises a branching, multifunctional linker moiety. In some embodiments, the dendritic type linker comprises PAMAM dendrimers.

In some embodiments, the linker is a traceless linker or a linker in which after cleavage does not leave behind a linker moiety (e.g., an atom or a linker group) to the antibody or payload. Exemplary traceless linkers include, but are not limited to, germanium linkers, silicium linkers, sulfur linkers, selenium linkers, nitrogen linkers, phosphorus linkers, boron linkers, chromium linkers, or phenylhydrazide linker. In some cases, the linker is a traceless aryl-triazene linker as described in Hejesen, et al., "A traceless aryl-triazene linker for DNA-directed chemistry," *Org Biomol Chem* 11 (15): 2493-2497 (2013). In some embodiments, the linker is a traceless linker described in Blaney, et al., "Traceless solid-phase organic synthesis," *Chem. Rev.* 102:2607-2024 (2002). In some embodiments, a linker is a traceless linker as described in U.S. Pat. No. 6,821,783.

Pharmaceutical Compositions

In some embodiments, a pharmaceutical formulation for reducing tissue fibrosis can comprise an anti-Gal3 antibody described supra. The anti-Gal3 antibody can be formulated for systemic administration. Alternatively, the anti-Gal3 antibody can be formulated for parenteral administration.

In some embodiments, an anti-Gal3 antibody is further formulated as a pharmaceutical composition. In some embodiments, the pharmaceutical composition is formulated for administration to a subject by multiple administration routes, including but not limited to, parenteral (e.g., intravenous, subcutaneous, intramuscular, intraarterial, intradermal, intraperitoneal, intravitreal, intracerebral, or intracerebroventricular), oral, intranasal, buccal, rectal, or transdermal administration routes. In some embodiments, the pharmaceutical composition describe herein is formulated for parenteral (e.g., intravenous, subcutaneous, intramuscular, intraarterial, intradermal, intraperitoneal, intravitreal, intracerebral, or intracerebroventricular) administration. In some embodiments, the pharmaceutical composition describe herein is formulated for oral administration. In still other embodiments, the pharmaceutical composition describe herein is formulated for intranasal administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical compositions further include pH adjusting agents or buffering agents which include acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some embodiments, the pharmaceutical compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the pharmaceutical compositions further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as I Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In some embodiments, the pharmaceutical formulation can further comprise an additional therapeutic agent. The additional therapeutic agent can have anti-fibrotic effect. The additional therapeutic agent can be inhibitor of ligands such as growth factors, cytokines and matrix metalloproteinases (MMPs). The additional therapeutic agent can be inhibitor of TGF-β, ALK5, BMP-7, PDGF, platelet-derived growth factor, VEGF, TNF, HGF, IL-13, chemokine (C-C motif) ligand 2; CCR5, MMP, and TIMP. The additional therapeutic agent can be SHP-627 (FT011), Hydronidone (F351), PXS-25, Disitertide (P-144), Fresolimumab (GC-1008), LY2382770, STX-100, CWHM-12, SB-431542, THR-184, PF-06473871, RXI-109, FG-3019, Imatinib, BOT-191, Nilotinib (AMN-107), Dasatinib, Nintedanib (BIBF-1120), Sorafenib (BAY 43-9006), Thalidomide, Pomalidomide, Etanercept, Belimumab, Refanalin (BB-3), Dectrekumab (QAX-576), Tralokinumab, Anakinra, Rilonacept, SAR156597, Carlumab (CNTO-888), Bindarit, Maraviroc, RS-504393, Actimmune, Interferon, alpha oral lozenge, Batimastat (BB-49), Marimastat, Macitentan, Bosentan, Ambrisentan, Sparsentan (RE-021), Atrasentan, Losartan, BMS-986020, SAR-100842, PAR1 antagonism, Curcumin, Silymarin, β-caryophyllene, Beraprost, Iloprost, Treprostinil, Aviptadil, Sivelestat, UK-396082, Serelaxin, PRM-151, or Dioscin, NTU281.

Therapeutic Regimens

In some embodiments, the anti-Gal3 antibodies disclosed herein are administered for therapeutic applications. In some embodiments, the anti-Gal3 antibody is administered once per day, twice per day, three times per day or more. The anti-Gal3 antibody is administered daily, every day, every alternate day, five days a week, once a week, every other week, two weeks per month, three weeks per month, once a month, twice a month, three times per month, or more. The anti-Gal3 antibody is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the anti-Gal3 antibody is given continuously; alternatively, the dose of the anti-Gal3 antibody being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, can be reduced, as a function of the symptoms, to a level at which the improved disease, disorder, or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some embodiments, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in some embodiments, are kits and articles of manufacture for use with one or more of the compositions and methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In some embodiments, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include an anti-Gal3 antibody as disclosed herein, host cells for producing one or more antibodies described herein, and/or vectors comprising nucleic acid molecules that encode the antibodies described herein. Such kits optionally include an identifying description or label or instructions relating to its use in the methods described herein.

A kit typically includes labels listing contents and/or instructions for use, and package inserts with instructions for use. A set of instructions will also typically be included.

In some embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In some embodiments, a label is used to indicate that the contents are to be used for a specific therapeutic application. The label also indicates directions for use of the contents, such as in the methods described herein.

In some embodiments, the pharmaceutical compositions are presented in a pack or dispenser device which contains one or more unit dosage forms containing a compound provided herein. The pack, for example, contains metal or plastic foil, such as a blister pack. In some embodiments, the pack or dispenser device is accompanied by instructions for administration. In some embodiments, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are also prepared, placed in an appropriate container, and labeled for treatment of an indicated condition.

Fibrosis Biomarkers

In some embodiments, fibrosis is characterized with one or more biomarkers such as collagen, extracellular matrix (ECM) molecules and enzymes, cytokines, proteomic markers, or genetic markers. In some cases, the fibrosis biomarkers include, but are not limited to, collagens (I, III and IV), Procollagen N-terminal peptide, fibronectin, elastin, laminin, alpha-smooth muscle actin (α-SMA), hyaluronic acid (HA), proteoglycans, YKL-40, TIMP-1, TIMP-2, MMP-2, MMP-9, TGFβ, TNFα, angiotensin-II, microfibril-associated protein 4 (MFAP-4), tropomyosin, SNP of AZIN1, TLR4, TRPM5, AQP2, or STXBP5L. The expression or absence of certain biomarkers is associated with one or more fibrotic diseases. The increase or reduction of such biomarkers when treated with anti-Gal3 antibodies can indicate the reduction of tissue fibrosis.

In some embodiments, the fibrosis biomarker is alpha-smooth muscle actin (α-SMA). α-SMA is a 42 kDa actin isoform that predominates within vascular smooth-muscle cells and are involved in fibrogenesis. Myofibroblasts are a form of fibroblast cells that has differentiated partially towards a smooth muscle phenotype. In particular, myofibroblasts can contract by using cytoskeletal proteins including α-SMA. In several fibrotic diseases, it has been observed that there is an accumulation of myofibroblasts, leading to expansion of the extracellular matrix. Thus, altered expression (e.g., elevated expression) of α-SMA correlates with the activation of myofibroblasts and in further cases, serve as a fibrosis biomarker.

In some embodiments, the fibrosis biomarker is fibronectin. Fibronectin is a high molecular weight (~440 kDa) glycoprotein within the extracellular matrix and further binds to integrins, collagens, fibrins, and heparan sulfate proteoglycans. Fibronectin plays a major role in cell adhesion, growth, migration, and differentiation, and is further involved in wound healing among a plethora of functions. Fibronectin can be soluble plasma fibronectin or insoluble cellular fibronectin, and can be Type I, II, or III. Altered expression (e.g., decreased expression) of fibronectin is associated with fibrosis.

In some embodiments, the fibrosis biomarker is transforming growth factor (TGF)-beta 1. TGF-β1 is a polypeptide member of the TGF-beta superfamily of cytokines and TGF-β1 is involved in cell growth, cell proliferation, cell differentiation, and apoptosis. Further, a collagen-producing cell, e.g., a fibroblast cell, is activated by a fibrogenic cytokine such as TGF-β1. Within a fibrosis context, TGF-β1 is proposed to be a master regulator and a potent inducer of ECM synthesis. Moreover, TGF-β1 is produced by a variety of cells such as macrophages, neutrophils, activated alveolar epithelial cells, endothelial cells, fibroblasts, and myofibroblasts. Activation of TGF-β1 leads to enhanced expression of proinflammatory and fibrogenic cytokines such as TNF-α, PDGF, IL-1B, and/or IL-13, further enhancing and perpetuating the fibrotic response.

In some embodiments, administration of an anti-Gal3 antibody to a tissue site of interest modulates the presence and/or expression of one or more fibrosis biomarkers. In some embodiments, the anti-Gal3 antibody alters the presence or absence or the expression of one or more fibrosis biomarkers selected from collagens (I, III and IV), Procollagen N-terminal peptide, fibronectin, elastin, laminin, alpha-smooth muscle actin (α-SMA), hyaluronic acid (HA), proteoglycans, YKL-40, TIMP-1, TIMP-2, MMP-2, MMP-9, TGFβ, TNFα, angiotensin-II, microfibril-associated protein 4 (MFAP-4), tropomyosin, SNP of AZIN1, TLR4, TRPM5, AQP2, and STXBP5L. In some embodiments, the anti-Gal3 antibody alters the presence or absence or the expression of α-SMA, fibronectin, TGF-β1, or a combination thereof. In some embodiments, administration of an anti-Gal3 antibody at a tissue site of interest leads to a decrease in the expression of α-SMA. In some embodiments, administration of an anti-Gal3 antibody at a tissue site of interest leads to an increase in the expression of fibronectin. In some embodiments, administration of an anti-Gal3 antibody at a tissue site of interest leads to a decrease in the expression of TGF-β1.

In some embodiments, one or more of the fibrosis biomarkers are utilized for monitoring the presence or absence of fibrosis, or the progression of fibrosis.

In some cases, the reduced expression of the fibrosis biomarkers disclosed herein can indicate reduction of tissue fibrosis.

In some cases, the expression of the at least one fibrosis biomarker in the tissue treated with the anti-Gal3 antibody is different than expression of the at least one fibrosis biomarker in a control tissue treated with a control antibody. In some cases, the control antibody is an anti-Gal3 antibody that does not bind to one or more epitopes described above and/or does not disrupt the interaction between Gal3 and TIM-3. In some cases, the control antibody is an IgG2b antibody, e.g., a murine IgG2b (mIgG2b) antibody. In some cases, the expression of the at least one fibrosis biomarker in the tissue treated with the anti-Gal3 antibody is less than expression of the at least one fibrosis biomarker in a control tissue treated with a mIgG2b antibody.

Fibrotic Diseases

In some embodiments, the anti-Gal3 antibody can be administered to treat one or more fibrotic diseases. The fibrotic diseases can be liver fibrosis. The fibrotic disease can be pulmonary fibrosis. The fibrotic disease can be cystic fibrosis, idiopathic pulmonary fibrosis, myelofibrosis, interstitial lung disease, hepatic fibrosis, progressive massive fibrosis, cirrhosis, renal fibrosis, cardiac fibrosis, pneumonitis, pulmonary fibrosis, pancreatic fibrosis, myelofibrosis, intestinal fibrosis, arthrofibrosis, retinal fibrosis, hepatitis C-associated fibrosis, or nephrogenic systemic fibrosis.

In some cases, the anti-Gal3 antibody can be administered to fibrotic diseases associated with expression of α-SMA or fibronectin. The fibrotic diseases associated with increased α-SMA can be renal fibrosis, hepatic fibrosis, cirrhosis, hepatitis C-associated fibrosis, cardiac fibrosis, pulmonary fibrosis, interstitial lung disease, idiopathic pulmonary fibrosis, pneumonitis, myelofibrosis, arthrofibrosis, retinal fibrosis, or nephrogenic systemic fibrosis. The fibrotic diseases associated with fibronectin expression can be cystic fibrosis, pulmonary fibrosis, idiopathic pulmonary fibrosis, myelofibrosis, interstitial lung disease, hepatic fibrosis, progressive massive fibrosis, cirrhosis, renal fibrosis, cardiac fibrosis, pneumonitis, pulmonary fibrosis, pancreatic fibrosis, myelofibrosis, intestinal fibrosis, arthrofibrosis, retinal fibronectin, hepatitis C-associated fibrosis, or nephrogenic systemic fibrosis.

The subject of the treatment can be diagnosed with a fibrotic disease. In some embodiments, the treatment subject can be human, rat, mouse, or other animal. In some embodiments, the treatment subject can be mammal. In some embodiments, the mammal can be human. The mammal can be primate. The primates can be chimpanzees or gorillas.

In some embodiments, the anti-Gal3 antibody binds to specific epitopes within a Gal3 protein. In some cases, anti-Gal3 antibody can bind to at least 1, 2, 3, 4, 5, 6, 10, 15, or 20 amino acid residues within a Gal3 region that corresponds to residues 2-21 of SEQ ID NO: 1 (hGal3). In some embodiments, the anti-Gal3 can bind to at least 1, 2, 3, 4, 5, 6, 10, 15, or 20 amino acid residues corresponding to residues 42-71 of SEQ ID NO: 1. In other embodiments, the anti-Gal3 can bind to at least 1, 2, 3, 4, 5, 6, 10, 15, 20, 30, 40, or 50 amino acid residues corresponding to residues 42-91 of SEQ ID NO: 1. Alternatively, the anti-Gal3 antibody can bind to at least 1, 2, 3, 4, 5, 6, 10, 15, or 20 amino acid residues corresponding to residues 72-91 of SEQ ID NO: 1. In some cases, the anti-Gal3 antibody can bind to Gal3 at one or more residues that correspond to residues 2-21 and 42-71; 42-91; 2-21 and 72-91; or 2-21 and 42-91. Gal3 and TIM-3 sequences are listed in Table 1.

TABLE 1

| | SEQ ID NO | SEQUENCE |
|---|---|---|
| Galectin-3 (Gal3) peptide sequence Isoform 1 (*homo sapiens*) NCBI Ref. No.: NP_002297.2 | 1 | MADNFSLHDALSGSGNPNPQGWPGAWGNQPAGAGGYPGAS<br>YPGAYPGQAPPGAYPGQAPPGAYPGAPGAYPGAPAPGVYPG<br>PPSGPGAYPSSGQPSATGAYPATGPYGAPAGPLIVPYNLPLPG<br>GVVPRMLITILGTVKPNANRIALDFQRGNDVAFHFNPRFNEN<br>NRRVIVCNTKLDNNWGREERQSVFPFESGKPFKIQVLVEPDH<br>FKVAVNDAHLLQYNHRVKKLNEISKLGISGDIDLTSASYTMI |
| GAL3 nucleotide sequence Isoform 1 (*homo sapiens*) NCBI Ref. No.: NM_002306.4 | 35 | gcccgcagcacctcctcgccagcagccgtccggagccagccaacgagcggaaaatg<br>gcagacaatttttcgctccatgatgcgttatctgggtctggaaacccaaaccctcaaggat<br>ggcctggcgcatggggaaccagcctgctggggcaggggctacccaggggcttcct<br>atcctggggcctaccccgggcaggcacccccaggggcttatcctggacaggcacctcc<br>aggcgcctaccctggagcacctggagcttatcccggagcacctgcacctggagtctacc<br>cagggccacccagcggccctggggcctacccatcttctggacagccaagtgccaccg<br>gagcctaccctgccactggcccctatggcgcccctgctgggccactgattgtgccttata<br>acctgcctttgcctgggggagtggtgcctcgcatgctgataacaattctgggcacggtga<br>agcccaatgcaaacagaattgctttagatttccaaagagggaatgatgttgccttccacttt<br>aacccacgcttcaatgagaacaacaggagagtcattgtttgcaatacaaagctggataat<br>aactggggaagggaagaaagacagtcggttttcccatttgaaagtgggaaaccattcaa<br>aatacaagtactggttgaacctgaccacttcaaggttgcagtgaatgatgctcacttgttgc<br>agtacaatcatcgggttaaaaaactcaatgaaatcagcaaactgggaatttctggtgacat<br>agacctcaccagtgcttcatataccatgatataatctgaaaggggcagattaaaaaaaaaa<br>aaagaatctaaaccttacatgtgtaaaggtttcatgttcactgtgagtgaaaatttttacattc<br>atcaatatccctcttgtaagtcatctacttaataaatattacagtgaattacctgtctcaa |
| TIM-3 peptide sequence (*homo sapiens*) NCBI Ref No.: NP_116171.3 | 2 | MFSHLPFDCVLLLLLLLLLTRSSEVEYRAEVGQNAYLPCFYTP<br>AAPGNLVPVCWGKGACPVFECGNVVLRTDERDVNYWTSRY<br>WLNGDFRKGDVSLTIENVTLADSGIYCCRIQIPGIMNDEKFNL<br>KLVIKPAKVTPAPTRQRDFTAAFPRMLTTRGHGPAETQTLGS<br>LPDINLTQISTLANELRDSRLANDLRDSGATIRIGIYIGAGICAG<br>LALALIFGALIFKWYSHSKEKIQNLSLISLANLPPSGLANAVAE<br>GIRSEENIYTIEENVYEVEEPNEYYCYVSSRQQPSQPLGCRFA<br>MP |
| TIM-3 nucleotide sequence (*homo sapiens*) NCBI Ref No.: NM_032782.5 | 36 | atttggagagttaaaactgtgcctaacagaggtgtcctctgacttttcttctgcaagctccat<br>gttttcacatcttccctttgactgtgtcctgctgctgctgctgctactacttacaaggtcctca<br>gaagtggaatacagagcggaggtcggtcagaatgcctatctgccctgcttctacacccc<br>agccgccccagggaacctcgtgcccgtctgctggggcaaaggagcctgtcctgtgtttg<br>aatgtggcaacgtggtgctcaggactgatgaaagggatgtgaattattggacatccagat<br>actggctaaatggggatttccgcaaaggagatgtgtccctgaccatagagaatgtgactc<br>tagcagacagtgggatctactgctgccggatccaaatcccaggcataatgaatgatgaaa<br>aatttaacctgaagttggtcatcaaaccagccaaggtcacccctgcaccgactcggcaga<br>gagacttcactgcagcctttccaaggatgcttaccaccaggggacatggcccagcagag<br>acacagacactggggagcctccctgatataaatctaacacaaatatccacattggccaat<br>gagttacgggactctagattggccaatgacttacgggactctggagcaaccatcagaata<br>ggcatctacatcggagcagggatctgtgctgggctggctctggctcttatcttcggcgcttt<br>aattttcaaatggtattctcatagcaaagagaagatacagaatttaagcctcatctctttggc<br>caacctccctccctcaggattggcaaatgcagtagcagagggaattcgctcagaagaaa<br>acatctataccattgaagagaacgtatatgaagtggaggagcccaatgagtattattgctat<br>gtcagcagcaggcagcaaccctcacaacctttgggttgtcgctttgcaatgccatagatc<br>caaccaccttatttttgagcttggtgttttgtctttttcagaaactatgagctgtgtcacctgact<br>ggttttggaggttctgtccactgctatggagcagagttttcccattttcagaagataatgact<br>cacatgggaattgaactgggacctgcactgaacttaaacaggcatgtcattgcctctgtatt<br>taagccaacagagttacccaacccagagactgttaatcatggatgttagagctcaaacgg<br>gcttttatatacactaggaattcttgacgtggggtctctggagctccaggaaattcgggcac<br>atcatatgtccatgaaacttcagataaactagggaaaactgggtgctgaggtgaaagcat<br>aactttttggcacagaaagtctaaaggggccactgattttcaaagagatctgtgatcccttt<br>ttgtttttgtttttgagatggagtcttgctctgttgcccaggctggagtgcaatggcacaatc<br>tcggctcactgcaagctccgcctcctgggttcaagcgattctcctgcctcagcctcctgag<br>tggctgggattacaggcatgcaccaccatgcccagctaatttgttgtatttttagtagagac<br>agggtttcaccatgttggccagtgtggtctcaaactcctgacctcatgatttgcctgcctcg<br>gcctcccaaagcactgggattacaggcgtgagccaccacatccagccagtgatccttaa<br>aagattaagagatgactggaccaggtctaccttgatcttgaagattcccttggaatgttgag<br>atttaggcttatttgagcactgcctgcccaactgtcagtgccagtgcatagcccttcttttgtc |

TABLE 1-continued

| SEQ ID NO | SEQUENCE |
| --- | --- |
| | tcccttatgaagactgccctgcagggctgagatgtggcaggagctcccagggaaaaac<br>gaagtgcatttgattggtgtgtattggccaagttttgcttgttgtgtgcttgaaagaaaatatc<br>tctgaccaacttctgtattcgtggaccaaactgaagctatatttttcacagaagaagaagca<br>gtgacggggacacaaattctgttgcctggtggaaagaaggcaaaggccttcagcaatct<br>atattaccagcgctggatcctttgacagagagtggtccctaaacttaaatttcaagacggta<br>taggcttgatctgtcttgcttattgttgccccctgcgcctagcacaattctgacacacaattg<br>gaacttactaaaaatttttttttactgtt |

In some embodiments, the anti-Gal3 antibody may bind to at least 1, 2, 3, 4, 5, 6, 10, 15, or 20 amino acid residues within a peptide illustrated in Table 2 (and shown in FIG. 11A).

TABLE 2

| hGal3 PEPTIDE NO | SEQ ID NO | SEQUENCE |
| --- | --- | --- |
| 1 | 3 | ADNFSLHDALSGSGNPNPQG |
| 2 | 4 | SGSGNPNPQGWPGAWGNQPA |
| 3 | 5 | WPGAWGNQPAGAGGYPGASY |
| 4 | 6 | GAGGYPGASYPGAYPGQAPP |
| 5 | 7 | PGAYPGQAPPGAYPGQAPPG |
| 6 | 8 | GAYPGQAPPGAYPGAPGAYP |
| 7 | 9 | AYPGAPGAYPGAPAPGVYPG |
| 8 | 10 | GAPAPGVYPGPPSGPGAYPS |
| 9 | 11 | PPSGPGAYPSSGQPSATGAY |
| 10 | 12 | SGQPSATGAYPATGPYGAPA |
| 11 | 13 | PATGPYGAPAGPLIVPYNLP |
| 12 | 14 | GPLIVPYNLPLPGGVVPRML |
| 13 | 15 | LPGGVVPRMLITILGTVKPN |
| 14 | 16 | ITILGTVKPNANRIALDFQR |
| 15 | 17 | ANRIALDFQRGNDVAFHFNP |
| 16 | 18 | GNDVAFHFNPRFNENNRRVI |
| 17 | 19 | RFNENNRRVIVCNTKLDNNW |
| 18 | 20 | VCNTKLDNNWGREERQSVFP |
| 19 | 21 | GREERQSVFPFESGKPFKIQ |
| 20 | 22 | FESGKPFKIQVLVEPDHFKV |
| 21 | 23 | VLVEPDHFKVAVNDAHLLQY |
| 22 | 24 | AVNDAHLLQYNHRVKKLNEI |
| 23 | 25 | NHRVKKLNEISKLGISGDID |
| 24 | 26 | SKLGISGDIDLTSASYTMI |

In some embodiments, the anti-Gal3 antibody may bind to at least 1, 2, 3, 4, 5, 6, 10, 15, or 20 amino acid residues within peptide_1 (SEQ ID NO: 3), peptide_5 (SEQ ID NO: 4), peptide_6 (SEQ ID NO: 5), or peptide_8 (SEQ ID NO: 6). In some embodiments, the anti-Gal3 antibody may bind to at least 1, 2, 3, 4, 5, 6, 10, 15, or 20 amino acid residues within peptide_1 (SEQ ID NO: 3). In some embodiments, the anti-Gal3 antibody may bind to at least 1, 2, 3, 4, 5, 6, 10, 15, or 20 amino acid residues within peptide_5 (SEQ ID NO: 4). In some embodiments, the anti-Gal3 antibody may bind to at least 1, 2, 3, 4, 5, 6, 10, 15, or 20 amino acid residues within peptide_6 (SEQ ID NO: 5). In some embodiments, the anti-Gal3 antibody may bind to at least 1, 2, 3, 4, 5, 6, 10, 15, or 20 amino acid residues within peptide_8 (SEQ ID NO: 6).

In some embodiments, the anti-Gal3 antibody further disrupts an interaction between Gal3 and TIM-3. TIM-3 is a molecule expressed on immune cells, especially on T cells and can suppress immune response, e.g., T cell signaling, through the interaction with Gal3.

In some embodiments, the Gal3-TIM-3 antibody is designed based on the interface where Gal3 and TIM-3 interaction occurs. The interaction on Gal3 can occur at one or more residues selected from region 145-168, 149-168, 160-177, and/or 165-184, wherein the regions correspond to position 145-168, 149-168, 160-177, and 165-184 of SEQ ID NO: 1. In some embodiments, the interaction on Gal3 can occur at one or more residues within region 145-177, wherein the region 145-177 correspond to position 145-177 of SEQ ID NO: 1. The interaction may occur at one or more residues within region 160-184, wherein region 160-184 correspond to position 160-184 of SEQ ID NO: 1. In some embodiments, the interaction may occur at one or more residues within region 145-184, wherein region 145-184 correspond to position 145-168 of SEQ ID NO: 1.

In some embodiments, the Gal3-TIM-3 antibody disrupts an interaction between Gal3 and TIM-3, in which the interaction on Gal3 involves one or more residues selected from region 145-168, 149-168, 160-177, and/or 165-184 of SEQ ID NO: 1. The interaction on Gal3 can occur at one or more residues within region 145-177 of SEQ ID NO: 1. The interaction may occur at one or more residues within region 160-184 of SEQ ID NO: 1. The interaction may occur at one or more residues within region 145-184 of SEQ ID NO: 1.

In some embodiments, the interaction can occur at one or more residues of Gal3 selected from region 149-156, 152-171, 152-169, 152-168, 163-169, or 163-171, in which the regions correspond to positions 149-156, 152-171, 152-169, 152-168, 163-169, and 163-171 of SEQ ID NO: 1. In some embodiments, the Gal3-TIM-3 antibody disrupts an interaction between Gal3 and TIM-3, in which the interaction on Gal3 involves one or more residues selected from region 149-156, 152-171, 152-169, 152-168, 163-169, or 163-171, in which the regions correspond to positions 149-156, 152-171, 152-169, 152-168, 163-169, and 163-171 of SEQ ID NO: 1. The interaction can occur at one or more residues of Gal3 selected from region 149-156, in which the region corresponds to position 149-156 of SEQ ID NO: 1. The interaction can occur at one or more residues of Gal3 within region 163-169, in which the region corresponds to position 163-169 of SEQ ID NO: 1. The interaction can occur at one or more residues of Gal3 within region 163-171, in which the region corresponds to 163-171 of SEQ ID NO: 1. The interaction can occur at one or more residues of Gal3 within region 152-169, in which the region corresponds to position 152-169 of SEQ ID NO: 1. The interaction can occur at one or more residues of Gal3 within region 152-171, in which the region corresponds to position 152-171 of SEQ ID NO: 1. The interaction can occur at one or more residues of Gal3 within region 163-171, in which the region corresponds to position 163-171 of SEQ ID NO: 1.

In some embodiments, the Gal3-TIM-3 antibody disrupts an interaction between Gal3 and TIM-3, in which the interaction on Gal3 involves one or more residues selected from region 149-156, 152-171, 152-169, 152-168, 163-169, or 163-171 of SEQ ID NO: 1. The interaction can occur at one or more residues of Gal3 within region 149-156 of SEQ ID NO: 1. The interaction can occur at one or more residues of Gal3 within region 163-169 of SEQ ID NO: 1. The interaction can occur at one or more residues of Gal3 within region 163-171 of SEQ ID NO: 1. The interaction can occur at one or more residues of Gal3 within region 152-169 of SEQ ID NO: 1. The interaction can occur at one or more residues of Gal3 within region 152-171 of SEQ ID NO: 1. The interaction can occur at one or more residues of Gal3 within region 163-171 of SEQ ID NO: 1.

The Gal3-TIM-3 antibody can interact with at least 1, 2, 3, 4, 5, 6, 10, 15, 20, 30, or 40 amino acid residues within a Gal3 region that interfaces with TIM-3 at the positions described herein.

The interaction on TIM-3 can occur at one or more residues corresponding to positions 72-104 and/or 64-93, in which the residues correspond to position 90-122 and 82-111 of SEQ ID NO: 2. Alternatively, the interaction on TIM-3 can occur at one or more residues at positions 91-111, 107-117, 96-102, 100-106, and/or 92-119, in which the residues correspond to positions 91-111, 107-117, 96-102, 100-106, and 92-119 of SEQ ID NO: 2. The interaction on TIM-3 can occur at one or more residues at positions 91-117, 91-119, 96-117, 100-117, or 96-106. The Gal3-TIM-3 disrupting antibody can be designed interact with at least 1, 2, 3, 4, 5, 6, 10, 15, 20, 30, or 40 amino acid residues within TIM-3 region that interfaces with Gal3 at the positions described herein.

In some cases, the interaction can occur at one or more residues of Gal3 selected from region 149-156, 152-168, 163-169, and/or 163-171 of SEQ ID NO: 1; and at one or more residues corresponding to positions 90-122 and/or 82-111 of SEQ ID NO: 2. the interaction can occur at one or more residues of Gal3 selected from region 149-156, 152-168, 163-169, and/or 163-171 of SEQ ID NO: 1; and at one or more residues at positions 91-111, 107-117, 96-102, 100-106, and/or 92-119 of SEQ ID NO: 2. The interaction on Gal3 can occur at one or more residues selected from region 145-168, 160-177, and/or 165-184 of SEQ ID NO: 1; and at one or more residues corresponding to positions 90-122 and/or 82-111 of SEQ ID NO: 2. The interaction on Gal3 can occur at one or more residues selected from region 145-168, 160-177, and/or 165-184 of SEQ ID NO: 1; and at one or more residues at positions 91-111, 107-117, 96-102, 100-106, and/or 92-119 of SEQ ID NO: 2. The Gal3-TIM-3 disrupting antibody can be designed interact with at least 1, 2, 3, 4, 5, 6, 10, 15, 20, 30, or 40 amino acid residues on Gal3 region and on TIM-3 that interface with each other at the positions described herein.

For any of the embodiments provided herein, the anti-Gal3 antibody used can be substituted with another anti-Gal3 antibody. This anti-Gal3 antibody may be selected from the group consisting of 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, and mIMT001 (IMT001). This anti-Gal3 antibody may be 2D10.2B2, 3B11.2G2, 4A11.2B5, 4G2.2G6, 6H6.2D6, 7D8.2D8, 12G5.D7, 13A12.2E5, 13G4.2F8, 13H12.2F8, 14H10.2C9, 15F10.2D6, 15G7.2A7, 19B5.2E6, 19D9.2E5, 20D11.2C6, 20H5.A3, 23H9.2E4, 24D12.2H9, 846.1F5, 846.2H3, 846T.1H2, 9H2.2H10, IMT001-4, IMT006-1, IMT006-5, IMT006-8, or mIMT001, or any combination thereof. This anti-Gal3 antibody may be mIMT001. This anti-Gal3 antibody may be an antibody other than mIMT001. This anti-Gal3 antibody may be 4A11.2B5. This anti-Gal3 antibody may be one or more of IMT001-4, IMT006-1, IMT006-5, or IMT006-8. This anti-Gal3 antibody may be 4A11.2B5. This anti-Gal3 antibody may be one IMT001-4. This anti-Gal3 antibody may be IMT006-1. This anti-Gal3 antibody may be IMT006-5. This anti-Gal3 antibody may be IMT006-8. In some embodiments, the antibody comprises one or more of the CDRS, VH, and/or VL of any one or more of these antibodies.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Example 1: Generation of Gal3-Overexpressing Cell Lines

A20, a mouse B lymphoma cell line, obtained from American Tissue and cell culture Collection (ATCC, Manassas, VA), was transfected with nucleic acid construct encoding a Flag-tagged human Gal3 protein or a Flag-tagged human PDL1 protein. The constructs additionally contain an antibiotics-resistant marker. The transformed cells were selected based on the antibiotics resistance to create A20 cells stably expressing the Flag-tagged human Gal3 protein (A20 Gal3 cells) or A20 cells stably expressing the Flag-tagged human PDL1 protein (A20 hPDL1 cells).

Example 2. Gal3 Specifically Binds to TIM-3

This example describes various assays that have been conducted to evaluate the interaction between Gal3 and TIM-3.

Binding Assays-Co-Immunoprecipitation

Co-immunoprecipitation experiments were performed to test whether TIM-3 specifically interacts with Gal3. 293T cells were co-transfected with a plasmid encoding HA-tagged TIM-3 and a plasmid encoding Flag-tagged Gal3, Flag-tagged Gal9, or Flag-tagged CEACAM1. The transfection was performed using lipofectamine 3000 (Waltham, MA) following manufacturer's protocols. The transfected cells were grown over night and then washed and lysed in 1 ml lysis buffer. The lysed cells were centrifuged and supernatant (the lysate) was collected. The lysates were prepared and separated on SDS PAGE and probed with anti-HA (FIG. 1A) and anti-Flag antibodies (FIG. 1B), respectively. Both the anti-Flag and the anti-HA antibodies were purchased from Sigma. The arrows in FIG. 1A and FIG. 1B indicate the presence of the various proteins.

Figure 1B:
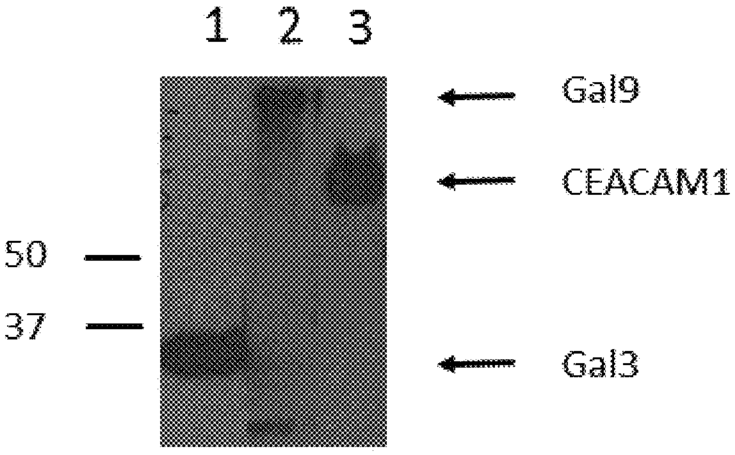
Figure 1C:
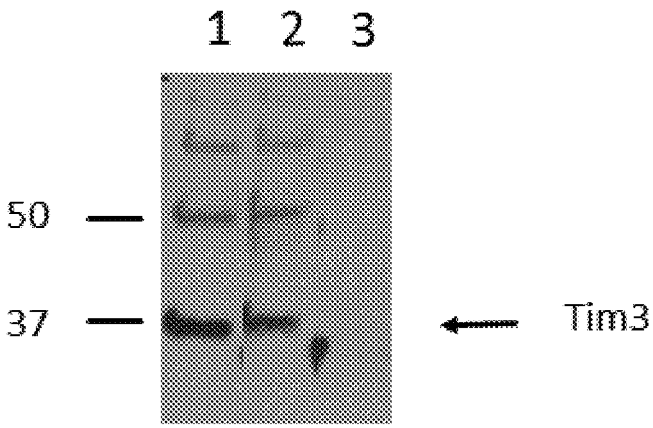

For immunoprecipitation, anti-Flag agarose beads (Abcam, Cambridge, MA) were added to the supernatant (the lysate) produced above. The beads and the lysates were incubated by rotating at 4° C. overnight to allow the Flag-tagged proteins to attach. The beads were then washed 3× with lysis buffer and mixed with 1×SDS PAGE sample buffer, boiled and separated on SDS-PAGE. The SDS-PAGE gel was transferred onto a membrane which was probed with ant-HA antibody (FIG. 1C). In FIG. 1A-C, lanes 1-3 represents the results from lysate produced from the cells co-transfected with a plasmid encoding HA-tagged TIM-3 and a plasmid encoding Flag-tagged Gal3; cells co-transfected with a plasmid encoding HA-tagged TIM-3 and a plasmid encoding Flag-tagged Gal9, or cells co-transfected with a plasmid encoding HA-tagged TIM-3 and a plasmid encoding Flag-tagged CEACAM1, respectively.

The results, as shown in FIG. 1A-C, indicate that human Gal3 specifically pulled down human TIM-3, while human CEACAM1 was not able to pull down the HA-tagged human TIM-3. Although it appeared that human Gal9 also pulled down human TIM-3 (lane 2 of FIG. 1C), this appeared to be non-specific due to Gal9 protein aggregation—the molecular weight of Gal9 appears to be much larger than its actual size of 40 kDa. The conclusion that the interaction between Gal9 and TIM-3 is non-specific in nature is also supported by the evidence shown in FIG. 5B, below.

Figure 2:
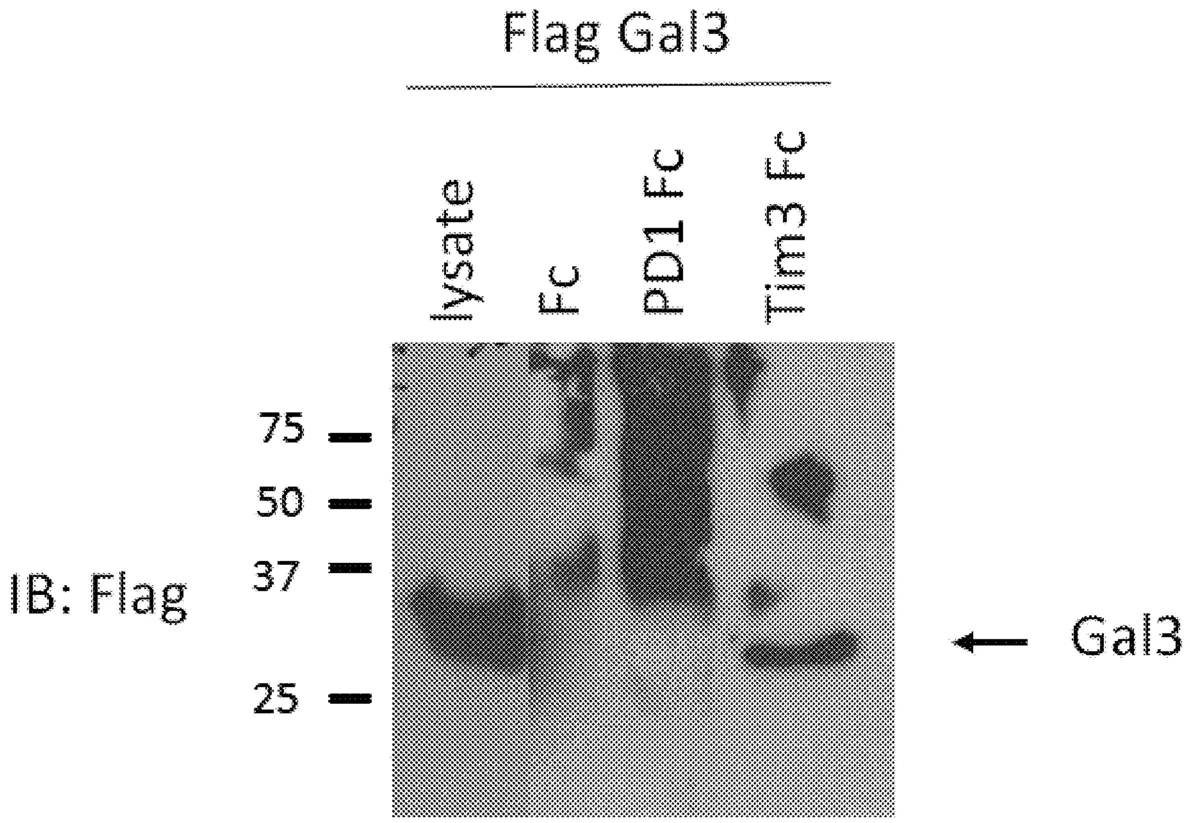
FIG. 2 shows the results of pull-down assays using a fusion protein composed of a hTIM-3 extracellular domain fused with the Fc portion of hIgG (hTIM-3 Fc). The results show that the binding between Gal3 and TIM-3 was specific. As shown in this figure, hTIM-3 Fc, but not hFc or hPD1 Fc, pulled down the over-expressed, Flag-tagged hGal3 protein from 293T cells.

Additional co-immunoprecipitation experiments were performed to test if Gal3 specifically interacts with TIM-3. Flag-human Gal3 plasmid (OriGene, Rockville, MD) was transfected into 293T cells, which were at 80% confluency. The transfections were performed in 10 cm plates using lipofectamine 3000 as described above. After overnight transfection, the cells were replaced on 10 cm plates that had been coated with human Fc, human PD1-Fc, or human TIM-3 Fc for 3 hours. The cells were washed once in 1×PBS, and then lysed in 1 ml lysis buffer. Cell lysates were collected and centrifuged. Protein G beads was added to the supernatant formed after the centrifugation and incubated by rotating at 4° C. for 4 hours. The beads were then washed 3× with lysis buffer, followed by addition of 1×SDS PAGE sample buffer. The samples containing the beads were boiled and separated on SDS-PAGE, transferred onto membrane. The membrane was then probed with ant-Flag antibodies. As shown in FIG. 2, human TIM-3 specifically pulled down Flag-tagged Gal3. In contrast, neither human Fc nor human PD1 Fc was able to pull down TIM-3. This shows that Gal3 does not bind to Fc or PD1 Fc and that the binding between Gal3 and TIM-3 is specific.

Binding Assays—Cell Adhesion Assay

Next, cell adhesion assays were performed to confirm the binding of Gal3 and TIM-3. In this experiment, 96-well plates were coated with human Fc, human PD1-Fc, human VISTA-Fc, human TIM-3-Fc at 4° C. overnight, then blocked with 2% BSA in PBS at 37° C. for 2 hours. A20, A20 cells overexpressing human Gal3 (A20 Gal3), or A20 cells overexpressing human PDL1 (A20 PDL1) cells were seeded into the wells that were coated with the various Fc proteins as described above. The plates were then centrifuged at 720 rpm and then were stopped. The plates were incubated at 37° C. for 30 minutes and then submerged into PBS. The plates were slowly flipped 180 degrees and kept at the flipped position for 30 min. After plates were flipped back and removed from PBS, 200 μl solution from each well was removed and discarded and the remaining solution, about 100 μl in volume, was transfer into a 96-well plate. The cells were counted by flow cytometry analysis.

Figure 3:
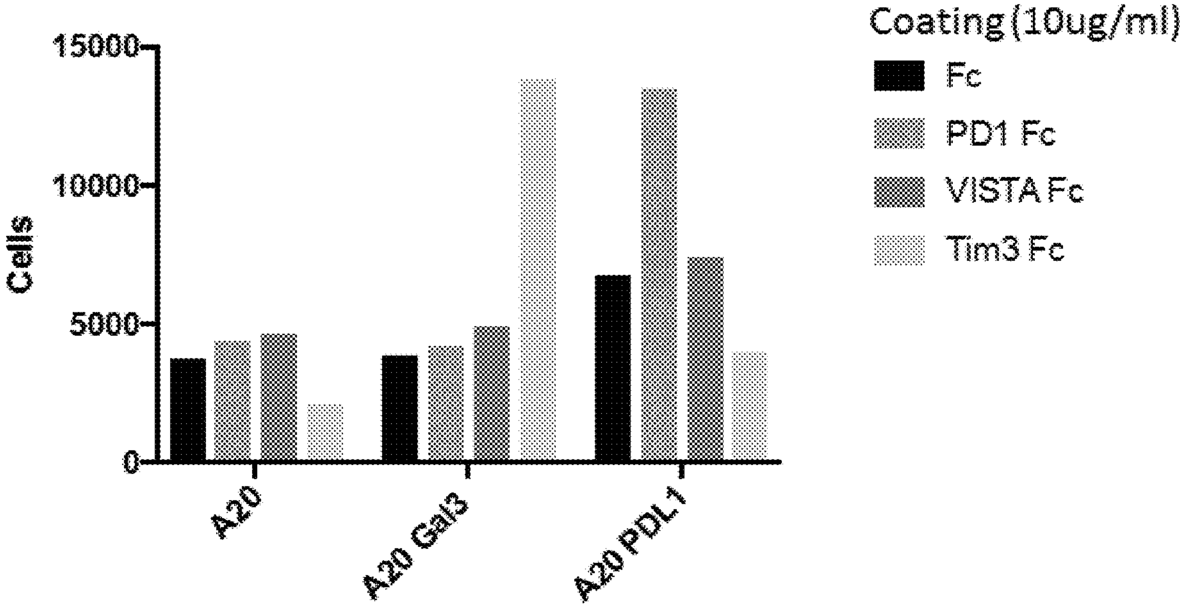
FIG. 3 shows the results of cell adhesion assay indicating the specific interaction between hGal3 and hTIM-3. As shown in the figure, a significantly higher number of A20 cells expressing hGal3 (A20 Gal3 cells) were able to adhere to plates coated with hTIM-3 Fc than to plates coated with hVISTA Fc or hPD1 Fc. The results also indicate that a higher number of A20 PDL1 cells were able to adhere to plates coated with hPD1 Fc than to plates coated with human VISTA Fc (hVISTA Fc) or plates coated with hTIM-3 Fc.

The results (FIG. 3) show that the number of A20 expressing human Gal3 (A20 Gal3) cells that were adhered to human TIM-3 Fc coated plates were significantly greater than that of the cells adhered to plates coated with human VISTA Fc or human PD1 Fc. As expected, since PDL1 is a known ligand for PD1, the number of A20 PDL1 cells that were shown to be adhered to hPD1 Fc was significantly greater than those adhered to plates coated with human VISTA Fc or human TIM-3 Fc. These results further confirmed the interaction between Gal3 and TIM-3 is specific.

Blocking Assays—Flow Cytometry

Flow cytometry analysis was performed to evaluate the binding between TIM-3 and Gal3 using A20 cells. A20 Gal3 cells were incubated with 10% FBS HBSS solution that contains with or without mouse TIM-3 Fc on ice for 20 minutes. There are five experimental groups: in group 1, A20 Gal3 cells were incubated without mTIM-3 Fc protein as control; in group 2, A20 Gal3 cells were incubated with mTIM-3 Fc protein; in groups 3, 4, 5, in addition to mTIM-3 Fc protein, anti-mouse TIM-3 polyclonal antibody (R&D System, Minneapolis, MN) (group 3), monoclonal antibody RMT3-23 (Bio X cell, West Lebanon, NH) (group 4), monoclonal antibody 215015 (R&D Systems) (group 5), were also added to test if these antibodies could block Gal3 and TIM-3 binding. For blocking, cells were incubated with 10% FBS HBSS containing mentioned antibodies, then were added with 10% FBS HBSS containing mTIM-3 Fc for 20 min. Samples were centrifuged and pellet were added 10% FBS HBSS containing APC conjugated anti-hFc antibodies (Jackson ImmunoResearch, West Grove, PA) for 20 min. After spinning, live/dead cells were stained with Violet dead cell stain kit (Life Technologies). Stained cells were subjected to flow analysis.

Figure 4A:
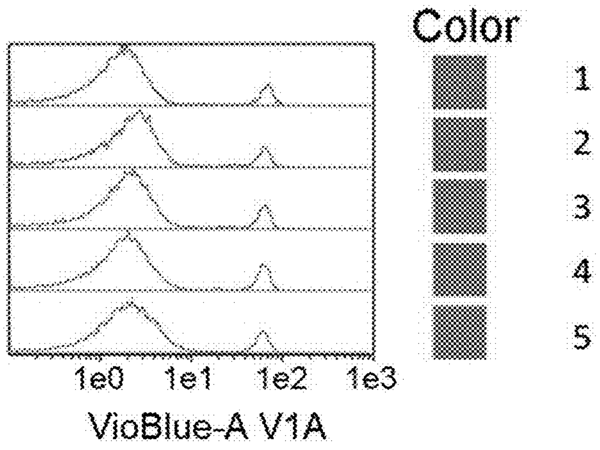
FIG. 4A shows live A20 cells (the peak on the left) and dead A20 cells (the peak on the right) by flow cytometry analysis.
Figure 4B:
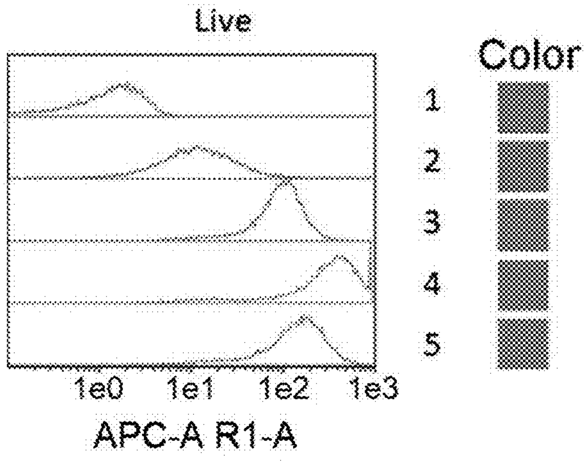
FIGS. 4B-C show the results of flow cytometry analysis of the live cells (FIG. 4B) and dead cells (FIG. 4C) that are stained with anti hFc APC antibody. In group 1, A20 Gal3 cells were incubated without mTIM-3 Fc protein as control; in group 2, A20 Gal3 cells were incubated with mTIM-3 Fc protein; in groups 3, 4, 5, in addition to mTIM-3 Fc protein, anti-mouse TIM-3 polyclonal antibody (R&D System, Minneapolis, MN) (group 3), monoclonal antibody RMT3-23 (Bio X cell, West Lebanon, NH) (group 4), monoclonal antibody 215015 (R&D Systems) (group 5), were also added to test if these antibodies could block Gal3 and Tim3 binding.
Figure 4C:
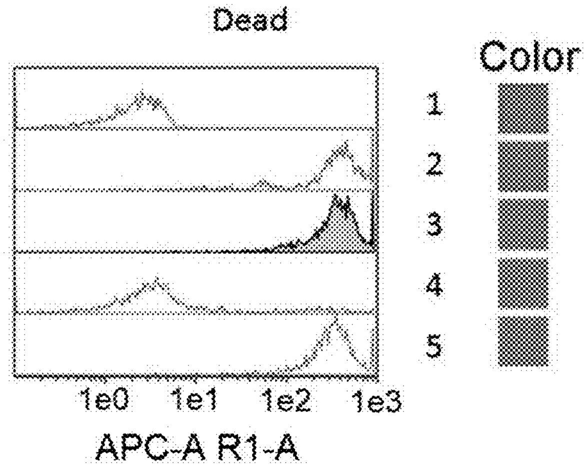

FIG. 4 shows that mTIM-3 was able to bind to dead cells and the Gal 3 protein on live cells and that Gal3 and dead cells bind different epitopes on TIM-3. FIG. 4A shows live A20 cells (the peak on the left) and dead A20 cells (the peak on the right) by flow cytometry analysis. In this assay, TIM-3 Fc binds both dead cells (FIG. 4C, row 2) and Gal3 expressed on live cells (FIG. 4B, row 2). However, mTIM-3 monoclonal antibody RMT3-23 blocked the binding of TIM-3 to dead cells (FIG. 4C, row 4), but not to Gal3 expressed on live cells (FIG. 4B, row 4). This shows that the Gal3 and dead cells bind to different epitopes on TIM-3. As controls, neither mTIM-3 polyclonal antibody nor monoclonal antibody 215015 (R&D System, Minneapolis, MN) has any effect on TIM-3 binding to Gal3 (FIG. 4B, rows 3 and 5) or to dead cells (FIG. 4C, row 3 and 5), respectively.

Blocking Assays—ELISA

Figure 5A:
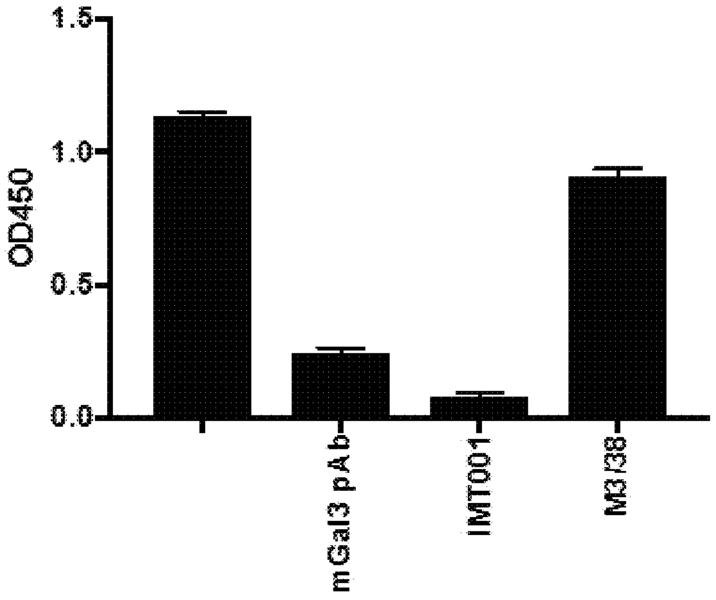
FIGS. 5A-C show the ELISA results indicating the specific binding of Gal3 on TIM-3.

ELISA assays were also performed to test the interaction between Gal3 and TIM-3. 96 well ELISA plates (ThermoFisher Scientific) were coated with mouse Gal3 protein (BioLegend, San Diego, CA) in PBS or human Gal9 protein (R&D systems) in PBS or phosphatidylserine (PS) (Sigma) in ethanol and incubated at 4° C. for overnight. The plate was washed three times with TBST and then blocked with PBS buffer containing 2% BSA at room temperature for 1 hour. In FIG. 5A, different anti Gal3 antibodies, i.e. mGal3 polyclonal antibody (R&D systems), mAb IMT001 (also described in WO 2019/023247, hereby expressly incorporated by reference in its entirety), mAb M3/38 (Thermofisher Scientific) (FIG. 5A), were added to well that has been coated with Gal3. The antibodies were incubated for 10 minutes and mouse TIM-3 Fc were then added to the plates and incubated for an additional one-hour incubation. Plates were then washed for three times and followed by incubation with anti-human-IgG-HRP (Jackson ImmunoResearch) for 1 h at room temperature. The color was developed with TMB subtract (GeneTex, Irvine, CA) after three time washes with TBST and the reaction was terminated with 1N HCl. The optical density (OD) was read at 450 nm. The results were expressed as the average OD of duplicates±SD. The results in FIG. 5A showed that among all antibodies tested, mouse Gal3 polyclonal antibody and monoclonal antibody IMT001 blocked the interaction between Gal3 and TIM-3 (FIG. 5A).

Figure 5B:
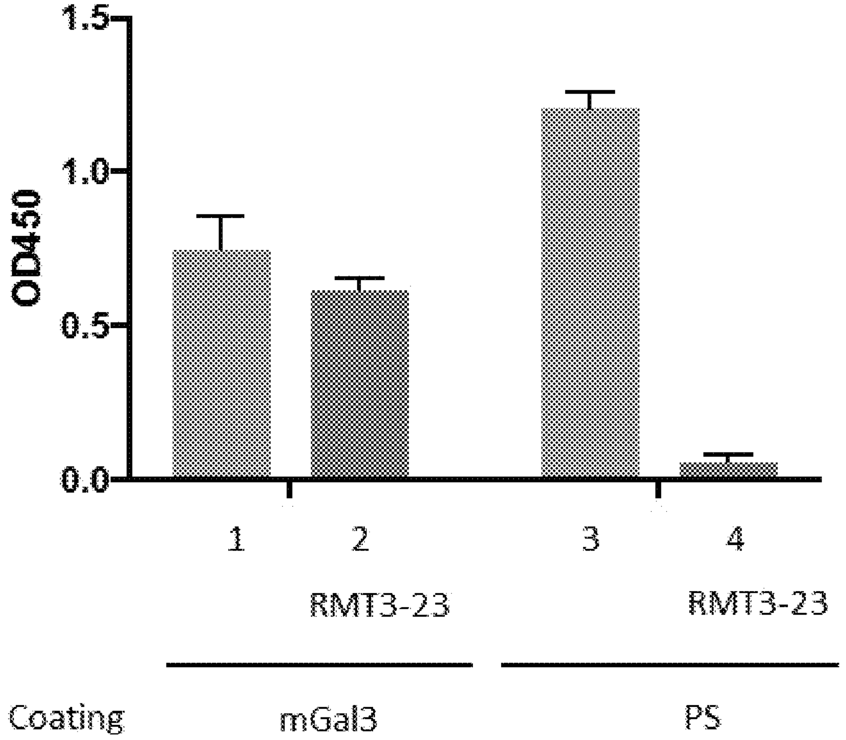

In FIG. 5B, mouse Gal3 protein (BioLegend) in PBS (groups 1 and 2) or PS (Sigma-Aldrich, St. Louis, MO) in ethanol (groups 3 and 4) were coated on the plates and incubated at 4° C. overnight. Anti mTIM-3 mouse antibodies, mAb RMT3-23 (Bio X cell), was added to the coated plates for groups 2 and 4 only. Secondary anti human-IgG-HRP antibody and substrates were added as described above to detect the binding of the mTIM-3 to mGal3 or PS. The results showed a dramatic reduction in signal in group 4 as compared to group 3, indicating that RMT3-23 blocked PS from binding to TIM-3; meanwhile the results showed no significant reduction in signal in group 2 as compared to group 1, indicating that RMT3-23 did not block Gal3 from binding to TIM-3. Since TIM-3 binds to dead cells through its interaction with PS externalized and exposed on dead cell surface, these experiments corroborated the observations in FIG. 4A-FIG. 4C that Gal3 and PS bind to different epitopes on TIM-3.

Figure 5C:
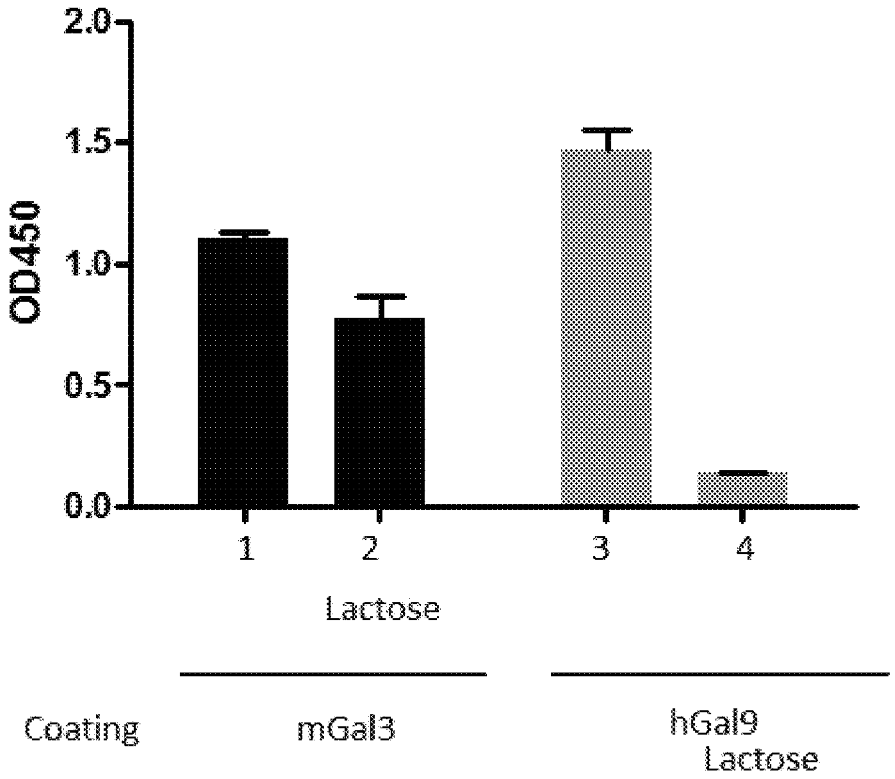

For sugar-dependence assay, ELISA plates were coated with either mGal3 (groups 1 and 2, or hGal9 (groups 3 and 4). Mouse TIM-3 Fc protein (R&D systems) was added to the coated ELISA plates with (groups 2 and 4) or without (groups 1 and 3) 25 mM of α-Lactose (Sigma-Aldrich) at room temperature for 1 h. Secondary anti human-IgG-HRP antibody and substrates were added as described above to detect the binding of mTIM-3-Fc to mGal3 or hGal9. FIG. 5C showed that lactose blocked Gal9 from binding to TIM-3, as shown by a dramatic, more than 10 fold reduction in signal in group 4 (lactose is present) as compared to group 3 (lactose is absent), indicating sugar dependent binding between Gal9 and TIM-3. In contrast, while lactose's blocking effect on Gal3 from binding to TIM-3 was minimal—there was no significant difference in signal produced from the binding of TIM-3 and Gal3 between group 2 (lactose was present) and group 1 (lactose was absent). This shows that the interaction between Gal3 and TIM-3 was not affected by the presence of sugar, i.e., the interaction was sugar-independent.

Example 3. Overexpressed Gal3 Suppresses T Cell Activation

This example describes experiments that were conducted to evaluate the functional properties of overexpression of Gal3 in A20 cells.

Figure 6A:
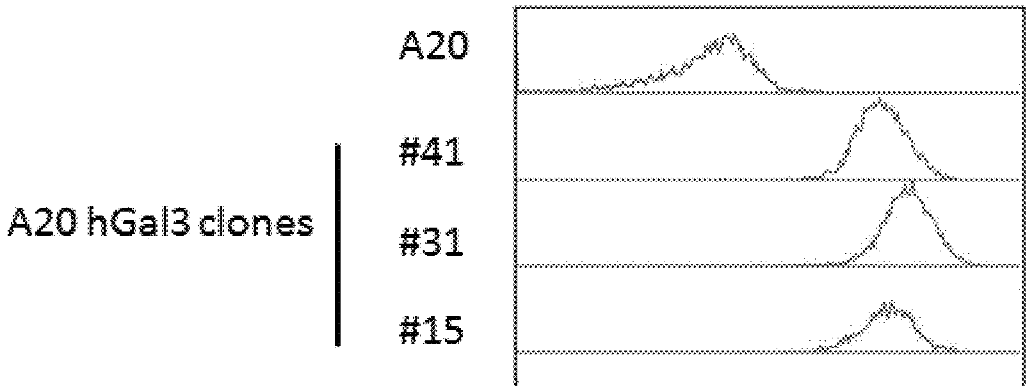
FIGS. 6A-B show that over-expressed Gal3 suppressed T cell activation.
Figure 6B:
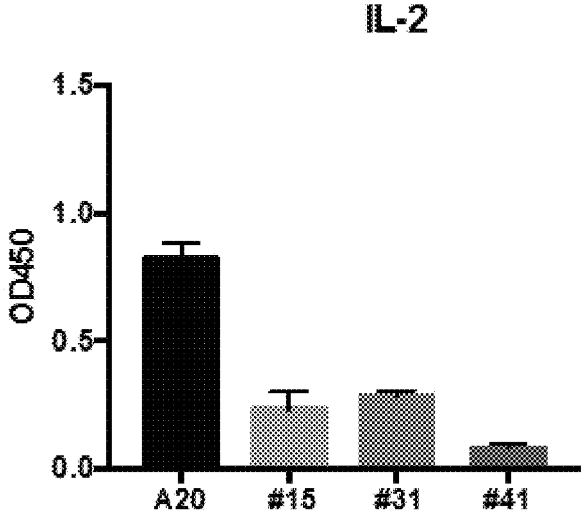

A20 clones, #41, #31, and #15, stably overexpressing hGal3 were generated as described above. FIG. 6A shows results of flow cytometry analysis that shows hGal3 expression level in these clones. Cells of A20 or the A20 Gal3 clones were mixed with mouse DO11.10 T cells. The mixture was placed to each well of flat 96-well plates and OVA323-339 peptide (Invivogen, San Diego, CA) was then added to the plates. After overnight incubation, supernatant was used for measuring IL-2 production of the T cells by ELISA (Thermo Fisher Scientific). As shown in FIG. 6B, the IL-2 production by the mouse DO11.10 T cells were significantly reduced when mixed with any of the three mouse A20 cell clones as compared to when the T cells were mixed with parental A20 cells (FIG. 6B).

Example 4. An Anti-Gal3 Antibody Shows Anti-Tumor Activity in Mouse Lung Metastasis Model The experiments in this example were conducted to evaluate the anti-tumor efficacy of Gal3: TIM-3 inhibitor in vivo. The animal experiments were conducted according to a protocol approved by the Molecular Medicine Research Institute Institutional Animal Care and Use Committee. C57BL/6 mice were placed in a facility accredited by the Association for Assessment and Accreditation of Laboratory Animal Care upon arrival. Thirty six of 7-week old female mice were randomly assigned into three groups (n=12). On day 0, B16F10 cells ($2\times10^5$ in 0.1 mL PBS) were washed and resuspended in PBS before injection into the tail veins of mice using a syringe with a 27-ga needle. Following injection of the B16F10 cells, the animals were administrated intraperitoneally with 10 mg/Kg of mouse IgG2b (Bio X Cell, West Lebanon, NH) on day 0, 3, 7 and 10, mPD1 antibody (Bio X Cell, West Lebanon, NH) on day 0, 3 and 7 or Gal3 antibody IMT001 on day 0, 3, 7, 10 and 15. The Gal3 antibody clone IMT001 used in this experiment recognizes an epitope corresponding to peptide_5 (PGAYPGQAPPGAYPGQAPPG, SEQ ID NO: 7) on Gal3. On day 21, the animals were humanely sacrificed and lung tissues were removed and fixed in a 10% buffered formaldehyde solution. The number of black metastatic colonies on one surface of the left lobes in the lungs were counted (FIG. 7B). Results were expressed as mean±SEM. The statistical analysis was performed in comparison with IgG control group using one-way ANOVA.

Figure 7A:
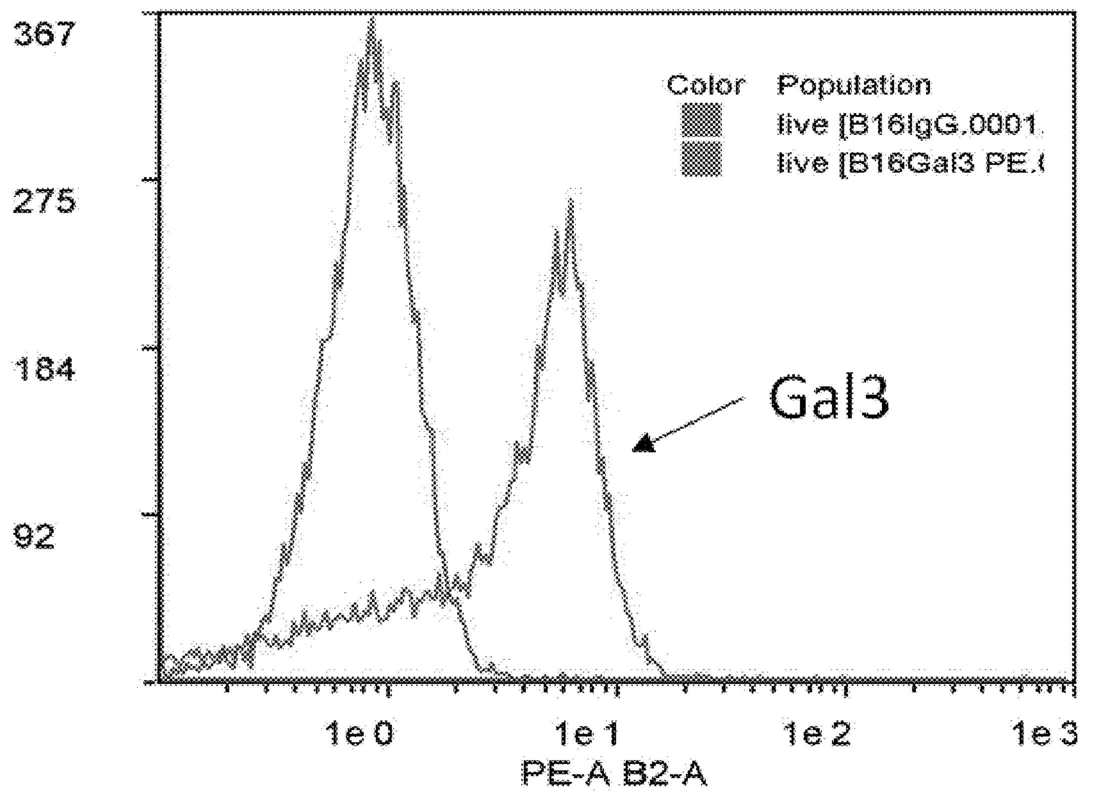
FIGS. 7A-E show that Gal3 antibody has anti-tumor activity in a lung metastasis model.
Figure 7B:
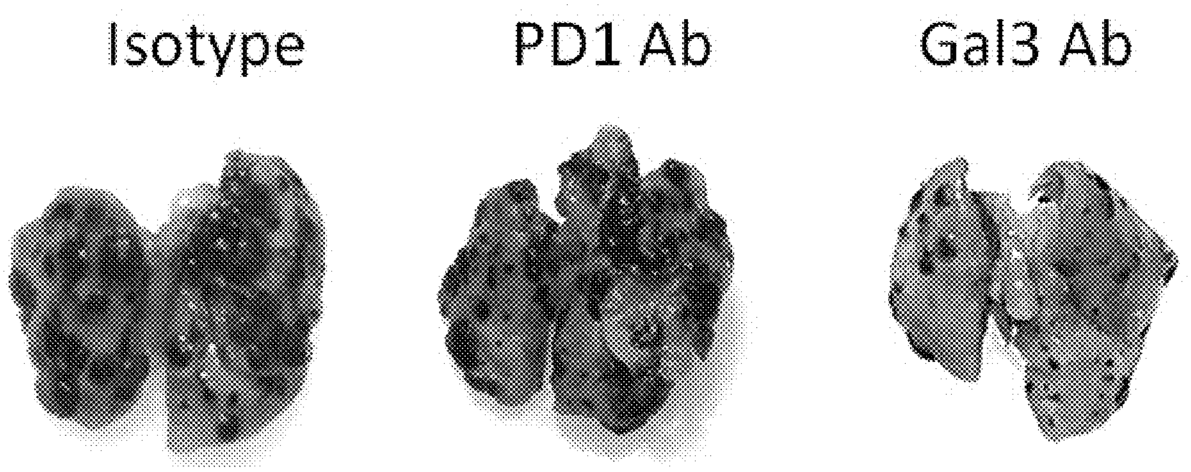
Figure 7C:
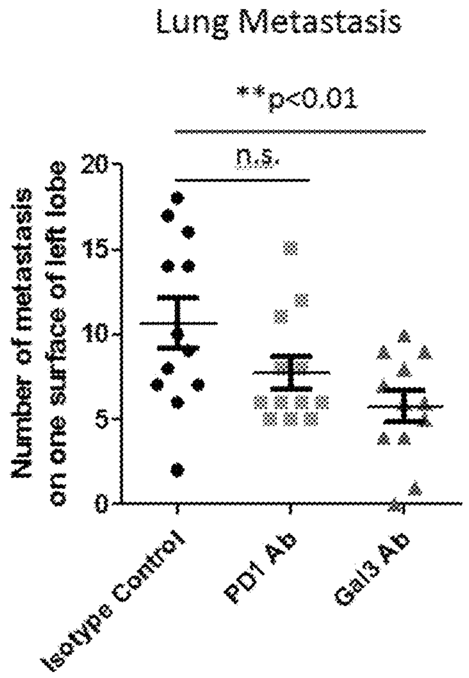
Figure 7D:
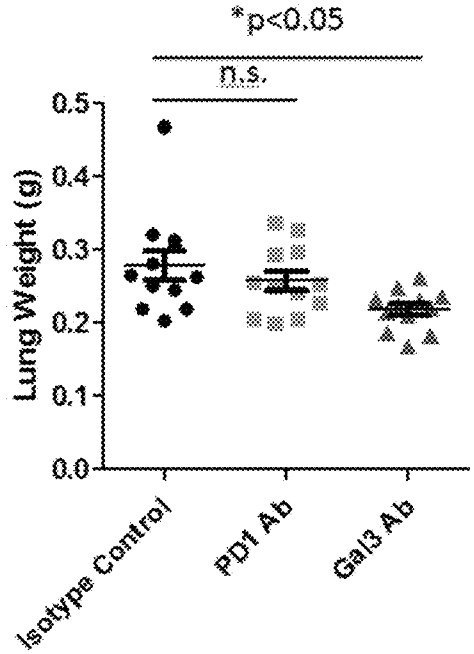
Figure 7E:
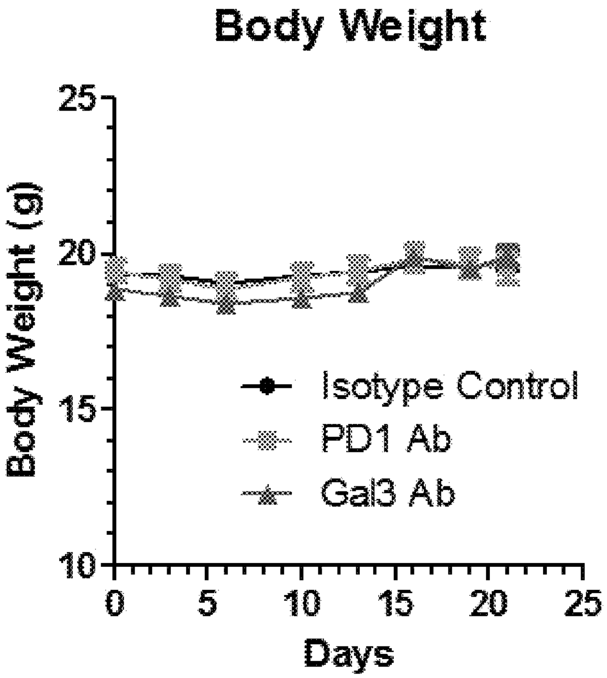

FIG. 7A shows that the mean fluorescence intensity (MFI) of B16F10 cells stained with anti-mGal3 antibody is nearly ten-fold higher than that of cells stained with isotype control antibody. In details, B16F10 cells were incubated with 10% FBS HBSS solution that contains control rat IgG PE or rat anti mouse Gal3 PE antibody (Thermo Fisher Scientific, Waltham, MA) on ice for 20 minutes. After spinning, live/dead cells were stained with Violet dead cell stain kit (Thermo Fisher Scientific, Waltham, MA). Stained cells were subjected to flow analysis. FIG. 7B shows representative images of the whole lung from three treated groups. FIG. 7C shows numbers of metastatic colonies on surface of the left lung lobe (Mean±SEM). FIG. 7D and FIG. 7E shows lung weight and body weight of different treatment groups (Mean±SEM). As compared to isotype control group, the Gal3 antibody treated group showed significant (about 46%) reduction of tumor number ($p<0.01$) as indicated by the number of black metastatic colonies. However, in comparison with isotype control group, anti-mouse PD1 antibody 29F did not show significant anti-tumor effect in this lung metastasis model ($p>0.05$).

Example 5. An Anti-Gal3 Antibody Shows Anti-Tumor Activity in 4T1 Orthotopic Tumor Induced Lung Metastasis Model The animal experiment followed a protocol approved by the Molecular Medicine Research Institute Institutional Animal Care and Use Committee. 7-week old female Balb/c mice were placed in a facility accredited by the Association for Assessment and Accreditation of Laboratory Animal Care upon arrival. On the day of tumor implantation, 4T1 cells were collected, washed and resuspended in PBS. Mice were anesthetized by inhalation anesthetic (3 to 5% Isoflurane in medical grade air). $2\times10^5$ cells in 0.1 mL PBS were subcutaneously injected into the mammary gland by using a syringe with a 25-ga needle. Mice were randomly assigned into two groups (n=10). Following injection of the 4T1 cells, the mice were administrated intraperitoneally with 10 mg/Kg of mouse IgG2b (Bio X Cell) on day 0, 3 and 7 or Gal3 antibody IMT001 on day 0, 3, 7, 10 and 14. The tumor volumes and body weights were monitored twice per week. On day 30, the mice were humanely sacrificed and lung tissues were inflated with 30% sucrose, removed and fixed in Bouin's solution (Sigma-Aldrich). The number of metastatic colonies on one surface of the left lobes in the lungs was counted. Results were expressed as mean±SEM. The statistical analysis was performed in comparison with IgG control group using unpaired T test.

Figure 8A:
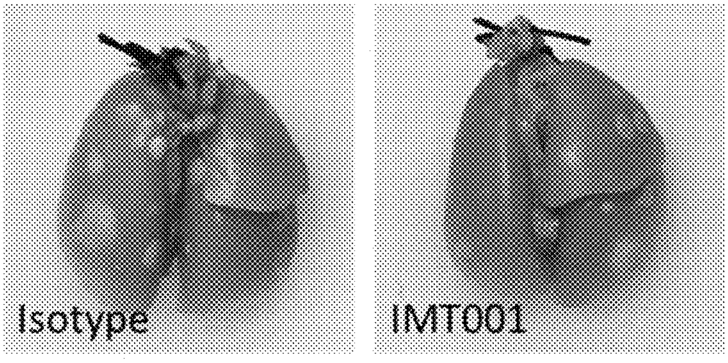
FIGS. 8A-C show the anti-tumor activity of Gal3 antibody in 4T1 orthotopic tumor induced lung metastasis.
Figure 8B:
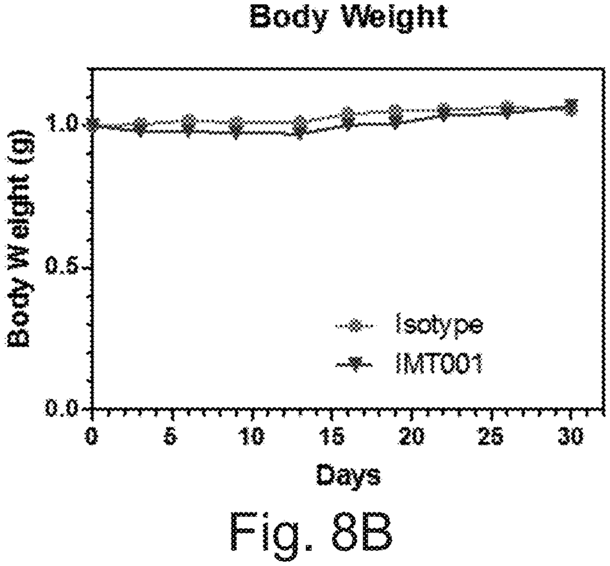
Figure 8C:
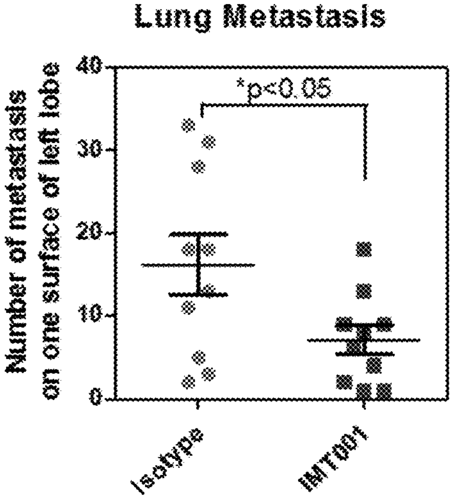

FIG. 8A shows representative images of the whole lung from the treated groups. FIG. 8B shows body weight of different treatment groups (Mean±SEM). FIG. 8C shows numbers of metastatic colonies on one surface of the left lung lobe (Mean±SEM). As compared to mice treated with the isotype control antibody, animals treated with the monoclonal anti-human Gal3 antibody showed significant reduction of lung metastatic number ($p<0.05$).

Figure 9:
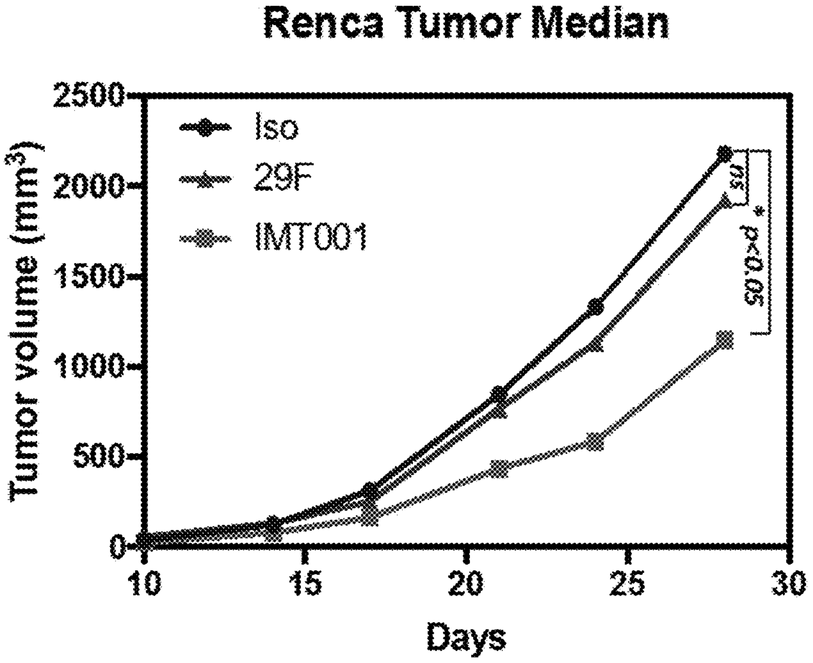
FIG. 9 shows the tumor growth in mice implanted with Renca tumor cells and treated with Gal3 antibody. As compared to mice implanted with Renca tumor cells and treated with the isotype control antibody ("iso"), mice treated with Gal3 antibody ("IMT001") showed much reduced tumor size ($p<0.05$), while anti mouse PD-1 antibody 29F had no effects ($p>0.05$).

Example 6. An Anti-Gal3 Antibody Shows Anti-Tumor Activity in Primary Mouse RENCA Renal Tumor Model The experiments were conducted to evaluate the anti-tumor efficacy of Gal3: TIM-3 inhibitor in primary tumor model (FIG. 9). The animal experiments were conducted according to a protocol approved by the Molecular Medicine Research Institute Institutional Animal Care and Use Committee. Balb/c mice were placed in a facility accredited by the Association for Assessment and Accreditation of Laboratory Animal Care upon arrival. Seven-week old female mice were randomly assigned into three groups (n=15). On the day of tumor implantation, mice were anesthetized by inhalation anesthetic (3 to 5% Isoflurane in medical grade air), Renca cells were washed and resuspended in PBS before subcutaneously injecting $2\times10^5$ cells in 0.1 mL PBS using a syringe with a 25-ga needle. Following injection of the Renca cells, mice were i.p. administrated with either 10 mg/Kg of mouse IgG2b (Bio X Cell) or mPD1 antibody (BioXCell) on day 0, 3 and 7 or Gal3 antibody IMT001 antibody on day 0, 3, 7, 10 and 14. The animals were humanely sacrificed when tumor volume in the control group reached between 2000-2500 mm3. Results were expressed as mean #SEM. The statistical analysis was performed in comparison with IgG2b control group using unpaired t test.

The results show the anti-tumor activity of Gal3 antibody (IMT001) in a renal carcinoma model. As compared to isotype control group, the anti-Gal3 antibody treated group showed significant (about 35%) reduction of tumor growth ($p<0.05$), while anti-PD-1 antibody had no effect (FIG. 9).

Example 7. An Anti-Gal3 Antibody Shows Anti-Tumor Activity in Primary Mouse MC38 COLON Tumor Model The animal experiment followed a protocol approved by the Molecular Medicine Research Institute Institutional Animal Care and Use Committee. 7-week old female C57BL/6 mice were placed in a facility accredited by the Association for Assessment and Accreditation of Laboratory Animal Care upon arrival. On the day of tumor implantation, MC38 murine colon adenocarcinoma cells were collected, washed and resuspended in PBS. Mice were anesthetized by inhalation anesthetic (3 to 5% Isoflurane in medical grade air). $5\times10^5$ cells in 0.1 mL PBS were subcutaneously injected into the right flank of mice by using a syringe with a 25-ga needle. On day 7, the tumor volumes were measured and mice were randomly assigned into two groups (n=8). The mice were administrated intraperitoneally with 10 mg/Kg of mouse IgG2b (BioXCell) or Gal3 antibody IMT001 on day 7, 10, 14, 17 and 22. The tumor volumes and body weights were monitored twice per week. The animals were humanely sacrificed when tumor volume reached 3000 $mm^3$. Results were expressed as mean±SEM. The statistical analysis was performed in comparison with IgG control group using unpaired T test.

Figure 10:
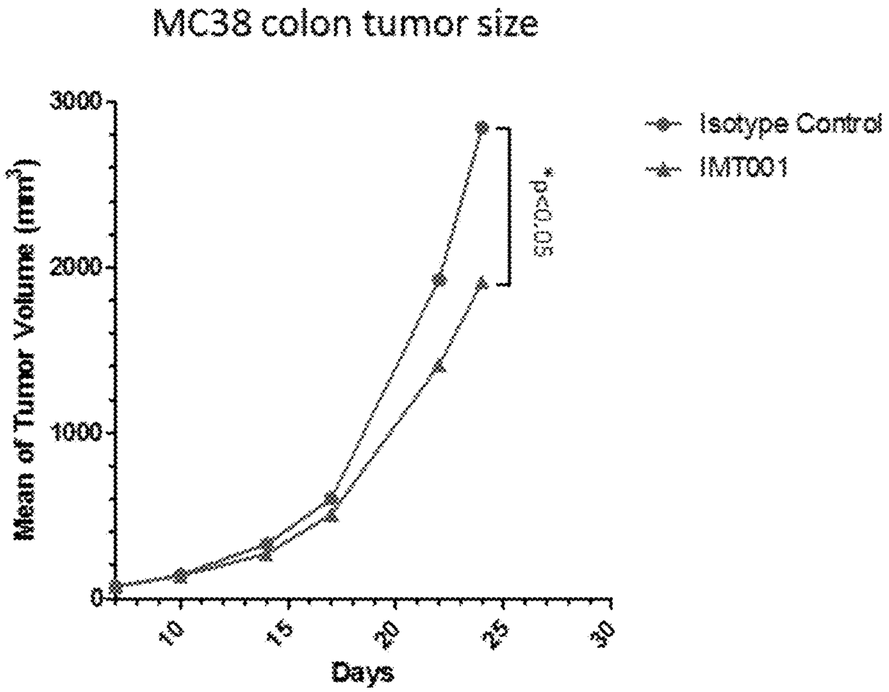
FIG. 10 shows the tumor growth in mice implanted with MC38 colon cancer cells and treated with the anti Gal3 antibody. As compared to mice implanted with MC38 tumor cells and treated with the isotype control antibody ("iso"), mice treated with Gal3 antibody ("IMT001") showed much reduced tumor size ($p<0.05$).

The results in FIG. 10 show that IMT001 antibody has anti-tumor activity in the MC38 colon cancer model. As compared to mice that were treated with the isotype control antibody, IMT001 antibody treated mice showed significant reduction (about 33%) of tumor burden on day 24 ($p<0.05$).

Example 8. Epitope Binding of Gal3 Antibody Clone IMT001

Figures 11B, 11C:
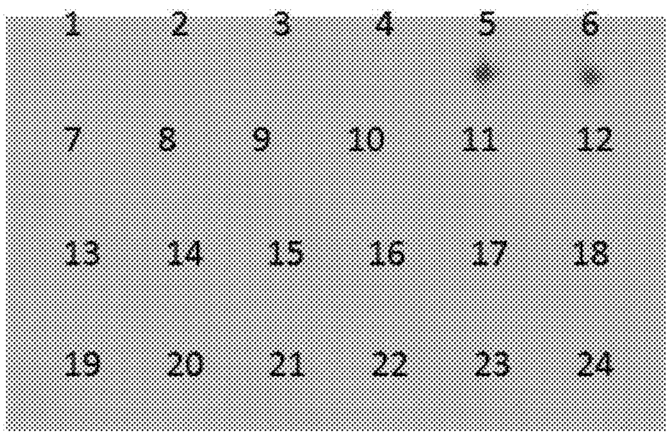

A peptide array containing 24 20 amino acid peptides overlapping by 10 amino acid and covering the whole human Gal3 protein sequence was synthesized (Genscript, Piscataway, NJ) (FIG. 11A). 20 μg of each peptide was dot blotted onto a membrane. After blocking with 5% milk in PBS, the membrane was incubated with 1 ug/ml IMT001 antibody at 4C for overnight. After three times of washes, the membrane was incubated with 1:8000 diluted anti mIgG HRP antibody (Southern Biotech, Birmingham, AL) for one hour. After three times of washes, the membrane was incubated with Western ECL blotting substrates (Bio-Rad, Hercules, CA) and developed (FIG. 11B). Peptides 5 (SEQ ID NO: 7) and 6 (SEQ ID NO: 8) showed good signal, indicating the epitope on hGal3 to which IMT001 binds is PGAYPGQAPPGAYPGQAPPGAYPGAPGAYP.

Figure 11D:
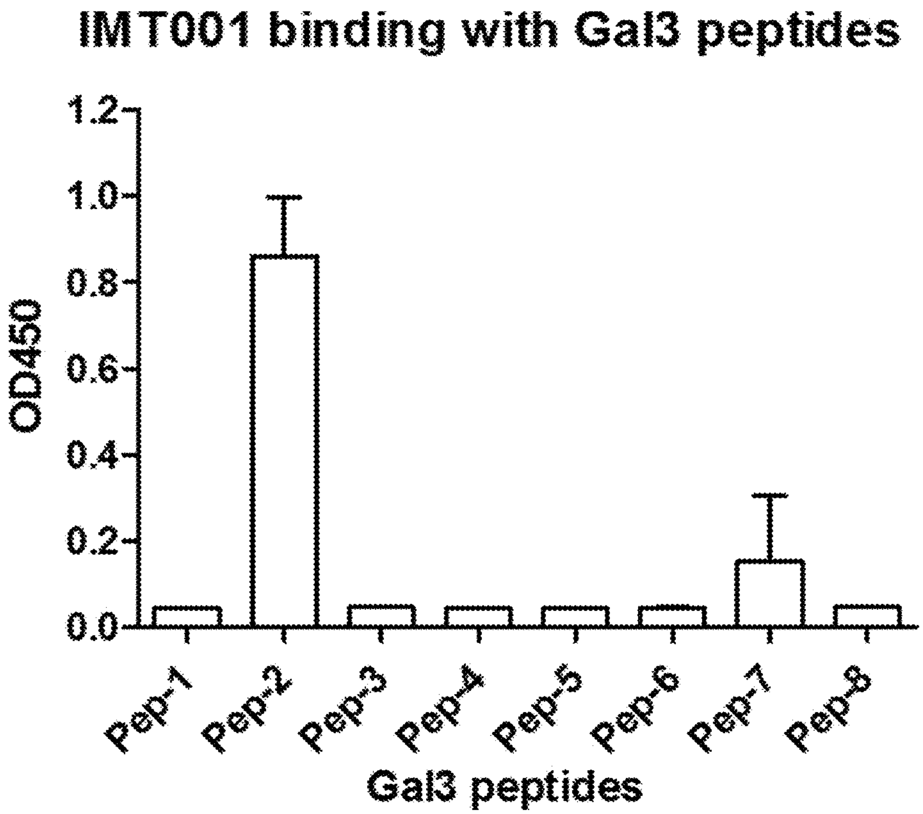

To further define binding epitope of IMT001 on the above peptide, 8 shorter peptides derived from it were synthesized (Genscript, Piscataway, NJ) (FIG. 11C) and their binding by IMT001 was determined by ELISA (FIG. 11D). 96 well Elisa plate (Thermo Scientific) was coated with these peptides in PBS buffer and incubated at 4° C. for overnight. The plate was washed three times with TBST and then blocked with PBST buffer containing 2% BSA at room temperature for 1 h. IMT001 at 10 μg/mL was incubated in the coated Elisa plate at room temperature for 1 h. The plate was washed for three times and followed by incubation with 1:8000 dilution of anti-mouse-IgG-HRP for 1 h at room temperature. The color was developed with 100 μL of TMB subtract (GeneTex) after three time washes with TBST and stopped by 50 μL of 1 N HCl. The optical density (OD) was read at 450 nm. The results were expressed as the average OD of duplicates±SD. Pep-2 showed good signal, indicating the binding epitope of IMT001 on human Gal3 is GQAPPGAYPG.

Example 9. Immune Profiling in B16F10 Lung Metastasis Mice Tumor

Figure 12:
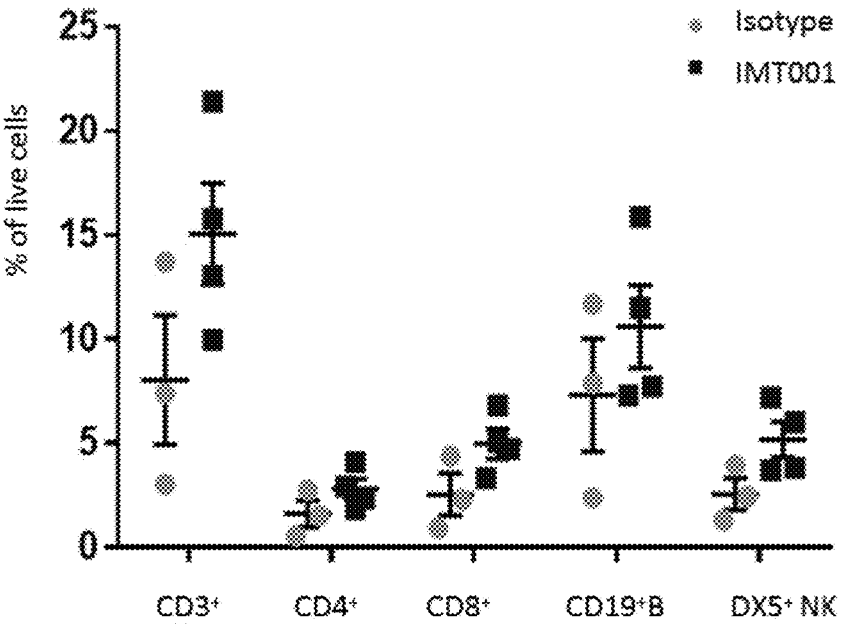
FIG. 12 summarizes the number of immune cells from mice implanted with B16F10 cells that express various lymphocyte markers: CD3, CD4, CD8, CD19, or DX5. These mice have been treated with the isotype control antibody or IMT001.

Mice were implanted with 1 million B16F10 cells I.V. Mice were then treated with IMT001 or isotype control (10 mg/kg I.P.) on Day 0, 1, 3 and 7 and sacrificed on day 8 for lung immune cell isolation and phenotyping. Cells were isolated from the lungs, and then stained with fluorescently labeled antibodies against lymphocyte markers CD3, CD4, CD8, CD19, DX5 and analyzed by flow cytometry. The results in FIG. 12 show that the anti-Gal3 antibody IMT001 treatment, as compared to isotype control antibody treatment, increased the number of various immune effector cell, including CD3 T lymphocytes, CD4 T helpers, CD8 cytotoxic T cells, CD19 B cells and DX5 Natural Killer cells in lungs that host the tumors. This indicates that the anti-Gal3 antibody was able to activate immune cells.

Example 10. Gal3 Expression Detected on Human Ling Cancer Associated Macrophages Immunohistochemistry (IHC) experiment was conducted to detect Gal3 expression in human lung cancers. The frozen tissue slides of human lung cancers (US Biomax Inc.) were fixed in 10% neutral buffered formalin (Fisher Scientific) at room temperature for 10 min and washed twice for 5 min in PBS. Endogenous peroxidase was blocked by immersing slides in 3% $H_2O_2$ at room temperature for 10 min. After washing twice in PBS for 5 min, the slides were incubated in streptavidin reagent (Molecular Probes) for 15 min at room temperature, followed by rinse thoroughly with PBS, incubation in biotin reagent (Molecular Probes) for 15 min and another rinse in PBS to block the endogenous biotin background. The slides were blocked with 10% FBS, 200 μg/mL mIgG and 200 μg/mL hIgG for 1 h, incubated with $1^{st}$ antibody IMT001-biotin (5 μg/mL) at 4° C. for overnight, washed three times, then followed by incubation with $2^{nd}$ antibody HRP avidin (BioLegend) at 1:100 for 1 h and washes for three time. The staining was developed by incubating with DAB substrate (Vector Laboratories) and stopped by immersing slides in distilled water. Human lung cancer slides were finally counterstained in Hematoxylin QS (Vector Laboratories), washed in distilled water, dehydrated in a graded series of ethanol and xylenes solutions, and mounted in VectaMount™ Mounting Medium (Vector Laboratories).

Figure 13A:
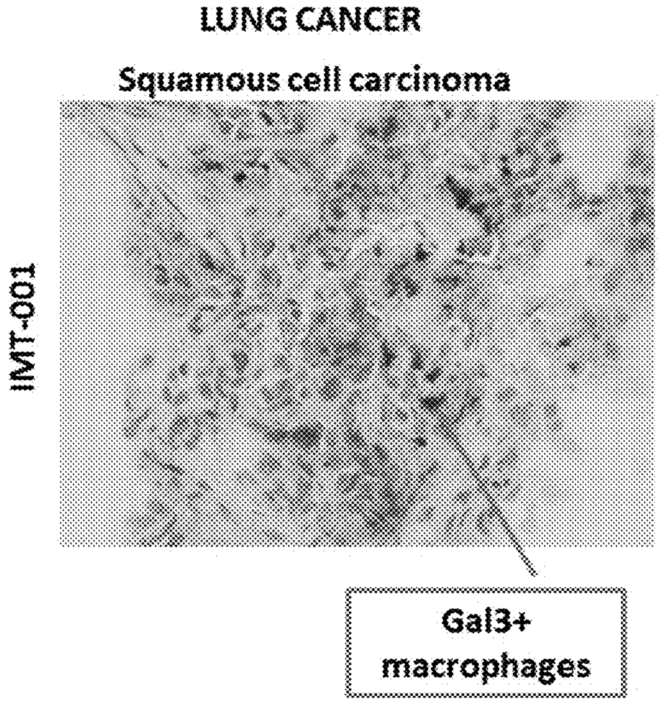
FIGS. 13A-B show Gal3 expression on tumor associated macrophages in human lung cancer in immunohistochemistry (IHC) assays. IMT001 was used to stain human lung cancer frozen slides to detect Gal3 expression on tumor associated macrophages.
Figure 13B:
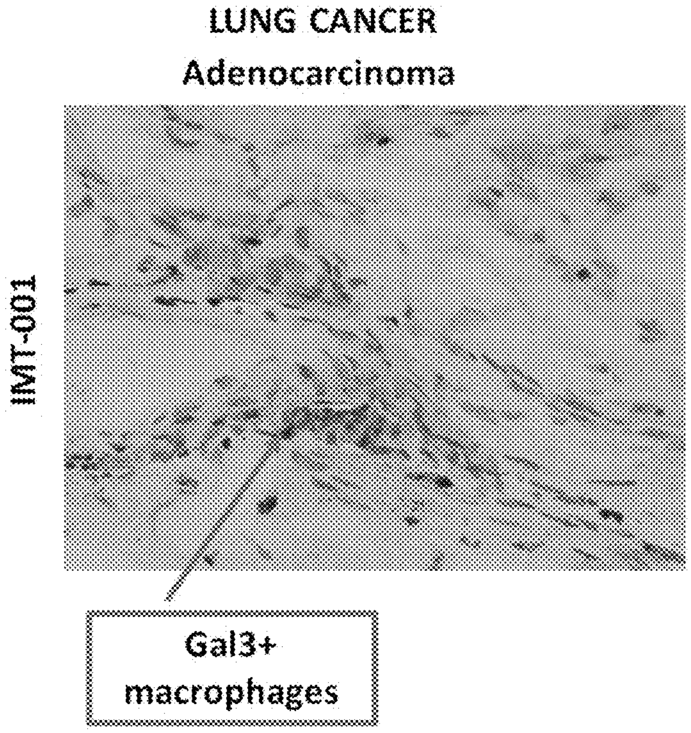

Results in FIG. 13A-B show that the canopy shaped tumor associated macrophages in those human lung cancer slides (squamous cell carcinoma and adenocarcinoma) express Gal3, as evidenced by their positive staining by IMT001.

Example 11. Gal3 Expression on Human M2 Macrophages

Figure 14A:
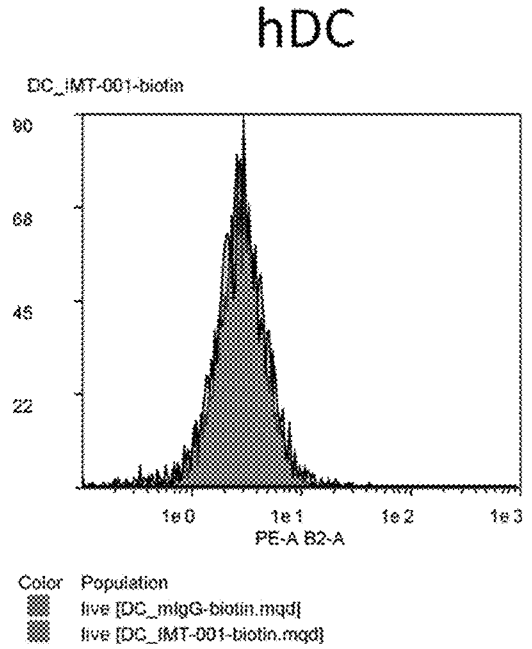
FIGS. 14A-C show that expression of Gal3 was detected on human M2 macrophages (FIG. 14C), but not on Dendritic cells (DC) (FIG. 14A) or M1 macrophages (FIG. 14B).
Figure 14B:
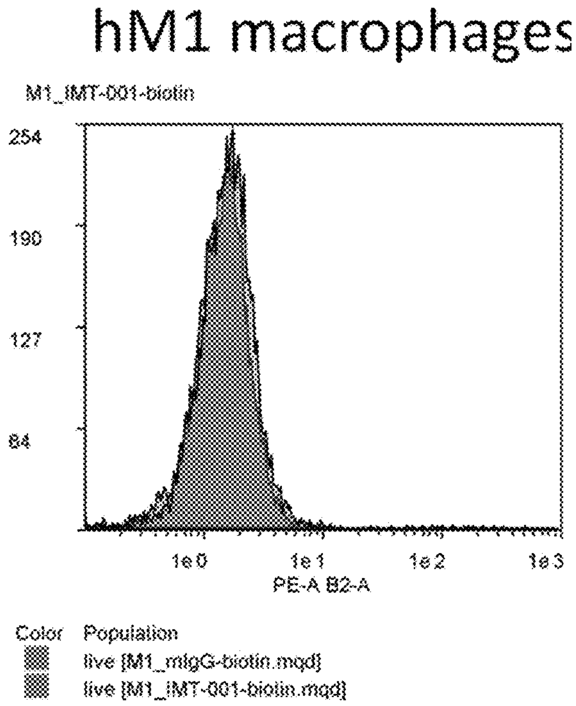
Figure 14C:
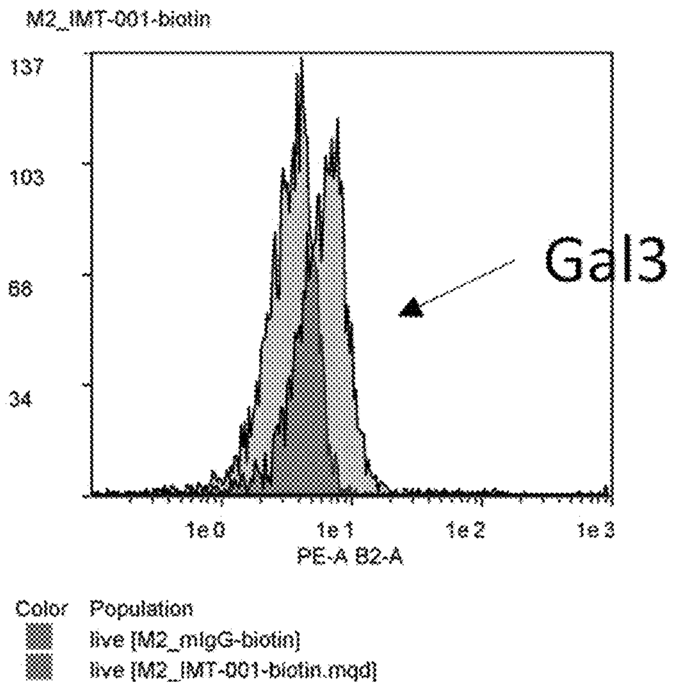

First Human CD14 monocytes were isolated from peripheral blood mononuclear cells (PBMC) with a CD14 cell positive selection kit (Miltenyi, Auburn, CA) and differentiated into dendritic cells (DC), or into M1 macrophages, or into M2 macrophages in the presence of GM-CSF plus IL-4, or GM-CSF, or M-CSF (Rocky Hill, NJ), respectively. Then flow cytometry analysis was performed to detect Gal3 expression on human dendritic cells (DC), M1 and M2 macrophage cells. In details, 100,000 DC, M1 or M2 cells were incubated with 100 μl 10% FBS HBSS solution that contains with control mIgG-biotin (BioLegend) or IMT001-biotin at 10 μg/ml on ice for 20 minutes. Then cells were washed and incubated with PE-streptavidin (BioLegend) at 1:1000 on ice for 20 min. After spinning, live/dead cells were stained with Violet dead cell stain kit (Life Technologies). Stained cells were subjected to flow analysis. Results in FIG. 14C. show that the mean fluorescence intensity (MFI) of M2 cells stained with IMT001 is much higher than that of cells stained with isotype control antibody, indicating the specific binding of IMT001 with M2 cells, while dendritic cells (FIG. 14A) and M1 macrophages (FIG. 14B) could not be stained.

Figure 15A:
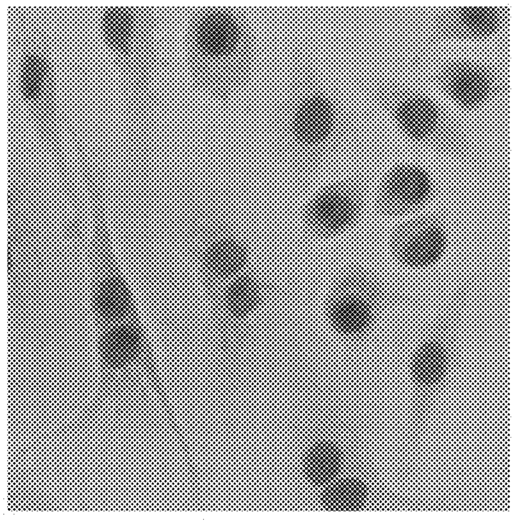
FIGS. 15A-D show the immune activity of Gal3 antibody ("IMT001") in mouse macrophage/T cell reaction.
Figure 15B:
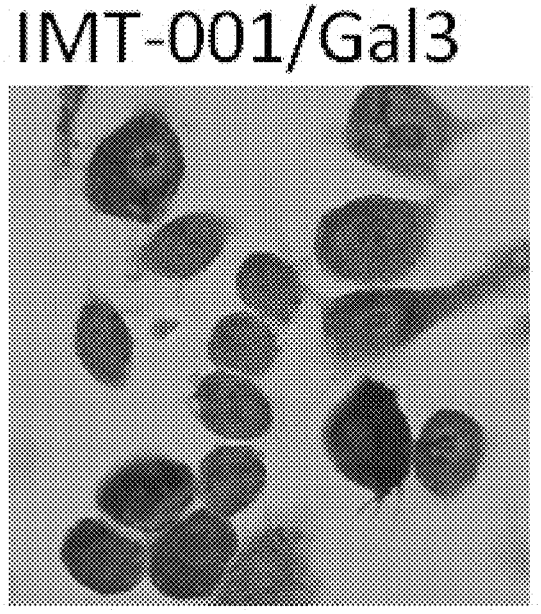

Example 12. Anti-Gal3 Antibody Enhances Mouse T Cell Activity in Macrophage/T Cell Reaction The expression of Gal3 on mouse macrophages was detected by both IHC and Flow cytometry analysis. In the details of IHC, 100,000 cells per well were seeded overnight. On the second day, cells were washed once with PBS, fixed with 3% formaldehyde at room temperature for 10 min, then washed twice with PBS and blocked in PBS containing 10% FBS and 200 μg/mL for 1 h at room temperature. After blocking, cells were incubated with 10 μg/mL of $1^{st}$ antibody mIgG-biotin (BioLegend) or IMT001-biotin at 4° C. overnight, washed three times with PBST, stained with avidin-HRP (1:1000) at room temperature for 1 h and then washed three times again with PBST. The staining was developed using peroxidase substrate and counterstained with Hematoxylin QS (Vector Laboratories). Results shows that, as compared to mIgG control (FIG. 15A), IMT001 clearly detected Gal3 expression on macrophages (FIG. 15B).

Figure 15C:
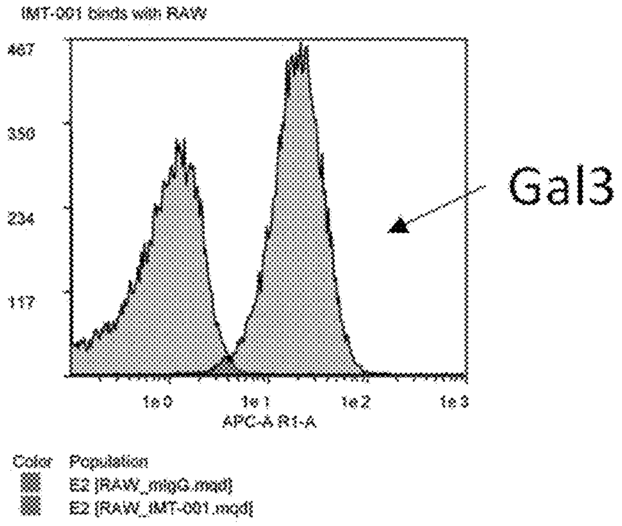

In the experiment of flow cytometry, 100,000 RAW cells were blocked with 10% FBS plus 200 μg/mL hIgG on ice for 20 min, and then incubated with 100 μl 10% FBS HBSS solution that contains control mIgG (BD Biosciences) or IMT001 at 10 μg/ml on ice for 20 minutes. Then cells were washed and incubated with APC conjugated anti-mFc antibodies (Jackson ImmunoResearch) at 1:100 on ice for 20 min. After spinning, live/dead cells were stained with Violet dead cell stain kit (Life Technologies). Stained cells were subjected to flow analysis. FIG. 15C shows that, as compared to that of cells stained with isotype control antibody, the mean fluorescence intensity (MFI) of RAW cells stained with IMT001 is more than 10-folds higher.

The ability of IMT001 to activate T cell was demonstrated by Mixed Lymphocyte Reaction (MLR) assay. RAW mouse macrophage cells were mixed with DO11 mouse T cells at 1:1 ratio, treated with OVA peptide, and cultured in the presence of mIgG (BD Biosciences), anti mPD1 antibody 29F (BioXCell) or IMT001 at 10 μg/ml for overnight 37° C. 50 μl of the culture medium was taken for mIL-2 measurement. The mIL-2 production was measured according to the commercial kit mouse IL-2 Elisa Ready-SET-Go from eBioscience.

Figure 15D:
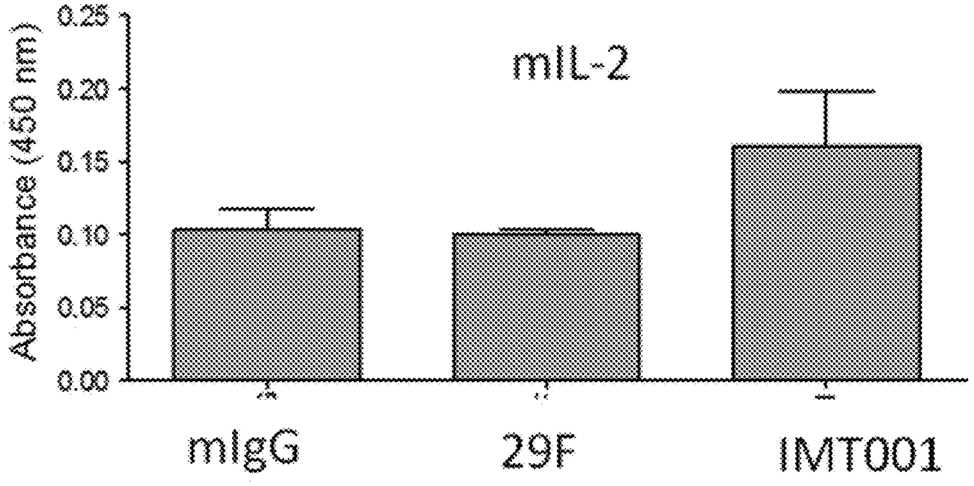

FIG. 15D shows that in comparison of mIgG or mPD1 antibody treated cells, IMT001 antibody, but not mouse PD-1 antibody 29F, enhanced the production of IL-2, indicating the reversion of macrophage induced T-cell inactivation.

Example 13: Identifying Antibodies Blocking Gal3-TIM-3 Interaction

To identify Gal3-targeted antibodies with the ability to block the interaction of Gal3 and TIM-3, purified Gal3 and TIM-3 proteins were incubated in the presence (or absence) of various Gal3-targeted or control antibodies, or without antibody, and protein interaction was evaluated by ELISA.

Human Gal3 protein (Acro Biosystems, GA3-H5129) was diluted in phosphate buffered saline (PBS) (Corning) to a concentration of 0.5 ug/ml and 100 ul of the diluted hGal3 was added to each well of a 96-well ELISA plate (Thermo Fisher, 44-2404-21). After incubating the plate at 4° C.

overnight, the plate was washed three times with 300 ul of PBS with 0.05% TWEEN (VWR) (PBST) per well. The plate was then blocked for an hour with 200 μl of 2% bovine serum albumin (BSA) (Sigma) in PBST per well at room temperature with gentle rocking. Thereafter, the 2% BSA in PBST was removed and 50 ul of an anti-Gal3 antibody at 20 ug/ml in 2% BSA in PBST was added to the wells to incubate for 10 minutes at room temperature with gentle rocking. Antibodies mab1, mab2, mab3, mab4, mab5, mab6, and mab7 were used in the experiment. The antibodies used are listed in Table 3.

Afterwards, 50 ul of 1 ug/ml of human TIM-3 extracellular domain protein (Acro Biosystems, TM3-H5229) in 2% BSA in PBST was added to the wells. The plate was incubated for an hour at room temperature with gentle rocking. The plate was then washed three times with 300 μl of PBST per well, and 100 ul of 0.3 ug/ml of anti-human TIM-3 biotinylated Antibody (R&D Systems, BAF2365) in 2% BSA in PBST was added to each well. The plate was incubated for an hour with gentle rocking and then washed three times with 300 μl of PBST per well. 100 ul of avidin-HRP (1:1000) (Jackson ImmunoResearch) was then added to each well and the plate was incubated at room temperature for 30 minutes with gentle rocking. The plate was subsequently washed three times with 300 μl of PBST per well and 100 ul of TMB substrate (Fisher Scientific, 34029) was added to each well. The reaction was stopped with 50 ul of 1 M HCl (VWR) per well. The plate was read using a plate reader (Molecular Devices) at absorbance of 450 nm. Percent blockade of Gal3-TIM-3 interaction was calculated as the fraction of signal obtained in the absence of antibody with the background signal subtracted.

Figure 16:
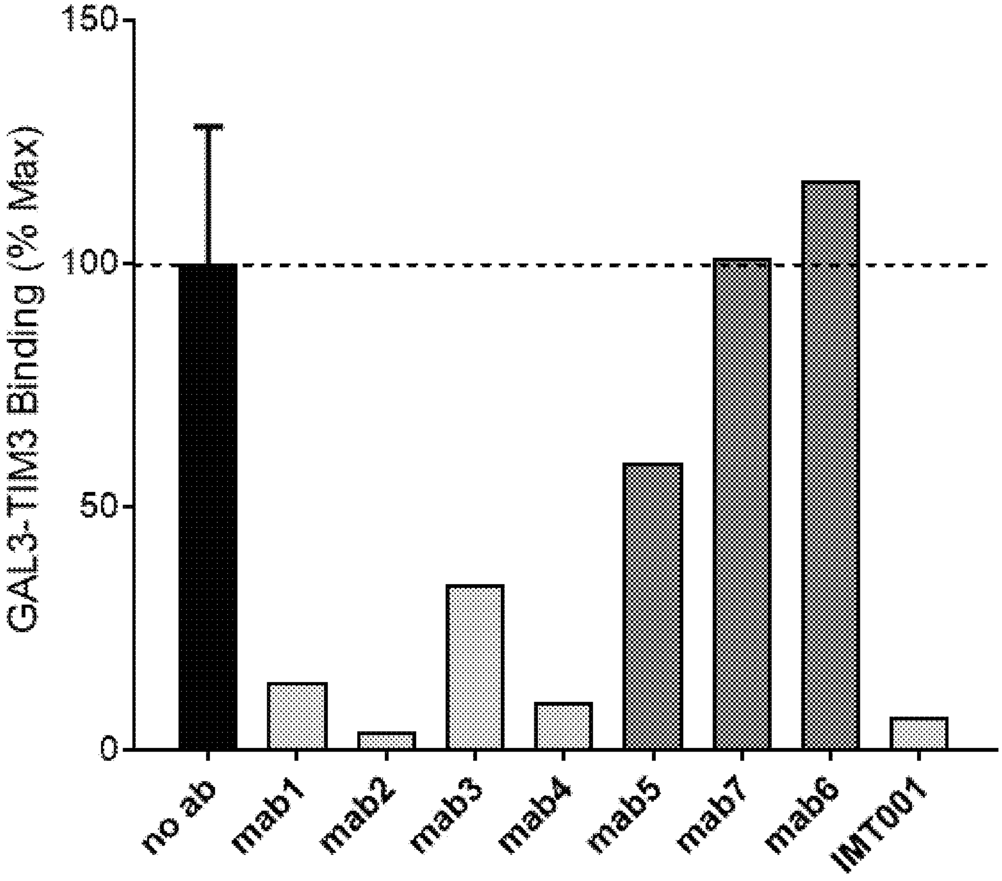
FIG. 16 illustrates ELISA assessment of GAL3-TIM3 interaction blockade by GAL3 binding antibodies. Results illustrate Gal3-targeted antibodies exhibit differential blockade of Gal3-TIM3 binding. Percent of TIM3-GAL3 binding in the absence of antibody is shown.

As shown in FIG. 16, anti-Gal3 antibodies exhibited differential ability to block the interaction of Gal3 and TIM-3. Each of the antibodies mab1, mab2, mab4, and IMT001 disrupted Gal3-TIM-3 binding, resulting a reduction in Gal3-TIM-3 binding to 14%, 4%, 10%, and 7% of unblocked control (no antibody), respectively. Antibodies mab3 and mab5 moderately disrupted the Gal3-TIM-3 binding, reducing the interaction to 34% and 59% of unblocked controls, respectively. Finally, mab6 and mab7 did not impact Gal3-TIM-3 binding. The results showed that antibodies mab1, mab2, mab3, mab4, mab5, and IMT001 all blocked the interaction of Gal3-TIM-3 to some degree. It also demonstrated that Gal3 binding alone was not sufficient to disrupt the interaction of Gal3 and TIM-3, and specific properties were required for this disrupting activity.

TABLE 3

| Antibody | Manufacturer | Catalog number |
|---|---|---|
| mab1 | R&D Systems | MAB11542 |
| mab2 | Santa Cruz Biotechnology | sc-32790 |
| mab3 | R&D Systems | MAB1197 |
| mab4 | R&D Systems | MAB1154 |
| mab5 | R&D Systems | MAB11541 |
| mab6 | BioLegend | 677301 |
| mab7 | BioLegend | 126702 |
| IMT001 | Immutics | IMT001 |

Example 14: Identifying Antibodies Binding to Distinct Epitopes of Gal3

To determine the epitopes on Gal3 that are associated with Gal3-TIM-3 antibody blocking site, an ELISA assay performed by applying anti-Gal3 antibodies with and without the Gal3-TIM-3 blocking activity to Gal3 peptides.

Figure 17A:
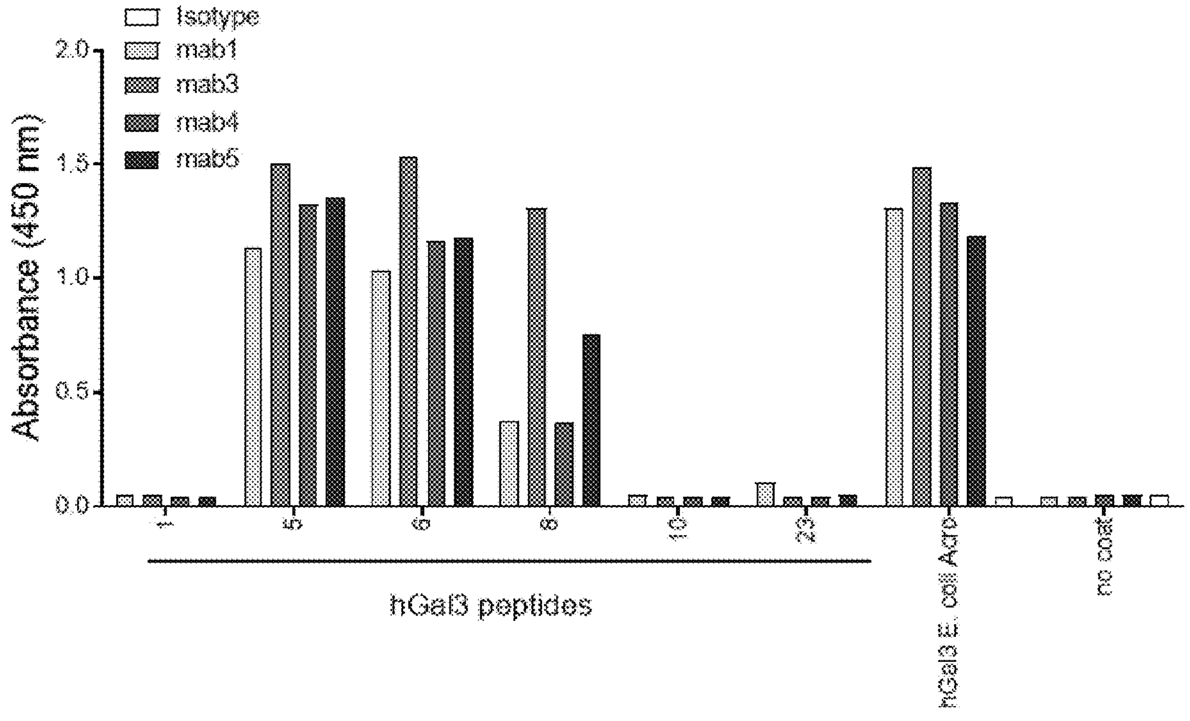
FIGS. 17A-17B illustrate ELISA assessment of anti-GAL3 antibody binding to peptide fragments of GAL3.
Figure 17B:
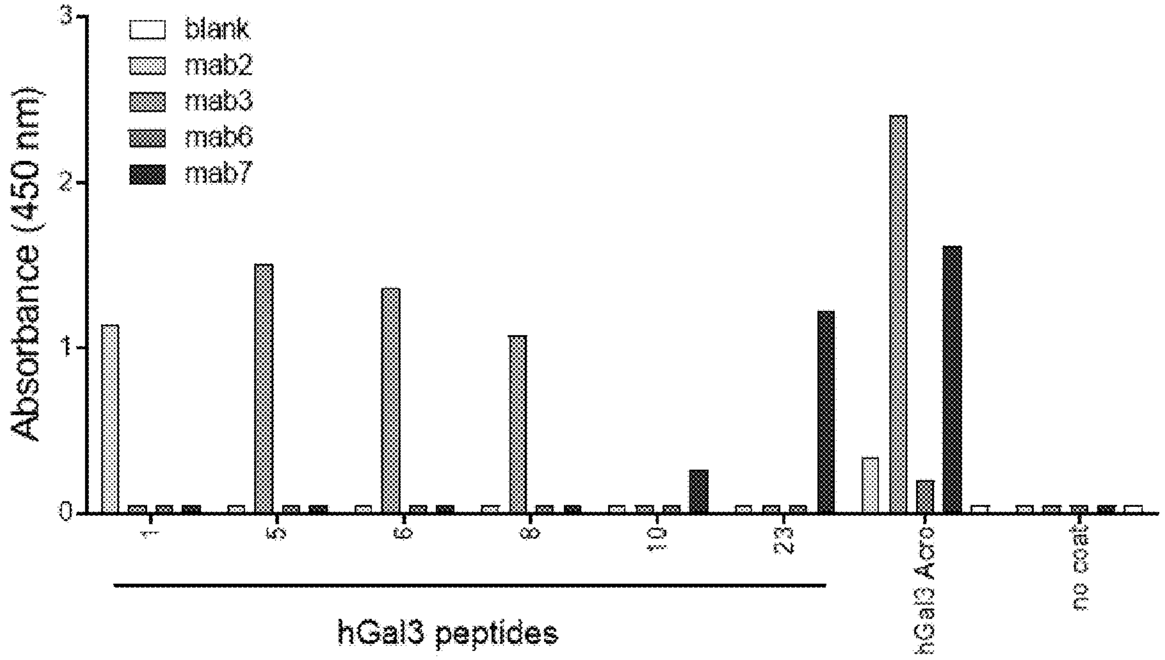

A library of 20 amino acid peptides each representing a certain regions of hGal3 (SEQ ID NO: 1) was produced. At least 2 ug/ml of the produced hGal3 peptide: peptide 1 (SEQ ID NO: 3), 5 (SEQ ID NO: 7), 6 (SEQ ID NO: 8), 8 (SEQ ID NO: 10), or 23 (SEQ ID NO: 25) in 50 ul of PBS was added to the wells of a 96-well ELISA plate (Thermo Fisher, 44-2404-21). As a positive control, 0.1 ug/ml of full-length human Galectin-3 protein (Acro Biosystems, GA3-H5129) in 100 ul of PBS was added to the wells of the ELISA plate. After incubating the plate at 4° C. overnight, the plate was washed three times with 300 ul of PBST per well. The plate was then blocked for an hour with 200 ul of 2% BSA in PBST per well at room temperature with gentle rocking. Thereafter, the 2% BSA in PBST was removed and 100 ul of 0.1 ug/ml of antibody in 2% BSA in PBST was added to the wells (FIG. 17A-B). As for negative control group, the antibodies were applied without the hGal3 peptides or the hGal3 protein.

The plate was incubated for an hour at room temperature with gentle rocking and then washed three times with 300 μl of PBST per well. Subsequently, HRP conjugated secondary antibodies were added to the wells and incubated for 30 minutes at room temperature with gentle rocking. After washing the plate three times with 300 μl of PBST per well, 100 ul of TMB substrate (Fisher Scientific, 34029) was then added to each well. The reaction was stopped with 50 ul of 1M HCl (VWR) per well and the plate was read using a plate reader (Molecular Devices) at absorbance of 450 nm.

The anti-Gal3 antibodies with known Gal3-TIM-3 blocking activity, mab1, mab3, mab4, and IMT001 were bound to hGal3 peptides 5 (SEQ ID NO: 7), 6 (SEQ ID NO: 8), and 8 (SEQ ID NO: 10) with varying degrees (FIG. 17A), suggesting that these Gal3-TIM-3 blocking antibodies share some common epitopes on Gal3. Antibody mab5, an antibody with partial Gal3-TIM-3 blocking activity also bound this region. Antibody mab2, an antibody with strong Gal3-TIM-3 blocking activity was bound to a distinct Gal3 peptide, peptide 1 (SEQ ID NO: 3) (FIG. 17B). In contrast, anti-Gal3 antibodies without Gal3-TIM-3 blocking activity mab7 exhibited binding activity to peptides 10 (SEQ ID NO: 12) and 23 (SEQ ID NO: 25) whereas mab6 failed to show substantial binding to any of the peptides, but did show binding to hGal3 protein, suggesting a non-linear binding epitope for this antibody. Peptides which failed to bind to any Gal3 antibodies are not shown for the purpose of clarity. Overall, these observations identified the sequences represented by peptides 1 (SEQ ID NO: 3), 5 (SEQ ID NO: 7), 6 (SEQ ID NO: 8), and 8 (SEQ ID NO: 10), as the features which are predictive of Gal3-TIM-3 blocking activity. These peptides corresponded to the first 2-21 N-terminal amino acids of Gal3 and residues 52-71 and 72-91 of hGal3 (SEQ ID NO: 1).

Example 15: Binding Domains of Anti-Gal3 Antibodies

To evaluate whether anti-Gal3 antibodies with Gal3-TIM-3 blocking activity bind to the same or overlapping regions of the Gal3 molecule, an epitope binning assay were performed to assess the ability of the antibodies to bind simultaneously to Gal3.

100 ul of 0.1 ug/ml of hGal3 (Acro Biosystems, GA3-H5129) was added to each well of a 96-well ELISA plate (Thermo Fisher, 44-2404-21) except for those of a control group, "no coat." After incubating the plate at 4° C. overnight, the plate was washed three times with 300 ul of PBST per well. The plate was blocked for an hour with 200 ul of 2% BSA in PBST per well at room temperature with gentle rocking and the 2% BSA in PBST was removed. 50 ul of anti-hGal3 antibody: mab1, mab4, or mab5 (4.2 ug/ml) in 2% BSA in PBST was added to the wells to preincubate for 10 minutes at room temperature with gentle rocking. No antibody was added to the wells of a second control group, "no ab," to preincubate.

After the preincubation with or without anti-Gal3 antibody, 50 ul of biotinylated anti-Gal3 antibodies: mab1, mab4, and mab5 (0.2 ug/ml) in 2% BSA in PBST were added to the wells together and incubated for an hour at room temperature with gentle rocking. The antibodies were not added to the wells of a third control group, "blank," to incubate. Thereafter, the plate was washed three times with 300 μl of PBST per well, and 100 ul of avidin-HRP (1:1000) (Jackson ImmunoResearch) was then added to each well. The plate was again incubated at room temperature for 30 minutes with gentle rocking and then washed three times with 300 μl of PBST per well. 100 ul of TMB substrate (Fisher Scientific, 34029) was then added to each well. The reaction was stopped with 50 ul of 1 M HCl (VWR) per well and the plate was read using a plate reader (Molecular Devices) at absorbance of 450 nm.

Figure 18:
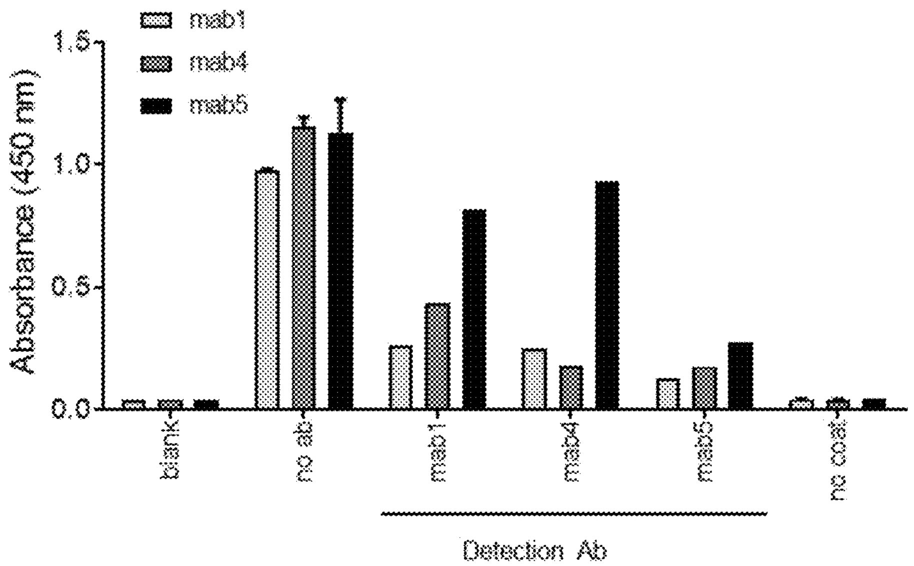
FIG. 18 illustrates ELISA competitive binding assessment of anti-GAL3 antibody binding to GAL3. Results illustrate Gal3-targeted antibodies mab1 (801) and mab4 (804), but not mab5 (805) bi-directionally compete for binding to Gal3.

As shown in FIG. 18, antibody binding plotted as a percent of unblocked control.demonstrated that preincubation with mab1 reduced the binding of mab1, mab4, and mab5 to hGal3 compared to preincubation with an isotype control indicating that these antibodies share some overlapping binding domain. Similarly, mab4 preincubation greatly reduced the later binding of mab1, mab4, and mab5. While mab5 preincubation reduced binding of mab5, it only minimally impacted binding of mab1 and mab4, indicating that the competition was asymmetrical, which is often a consequence of a low affinity antibody.

Example 16. Gal3-TIM-3 Blocking Antibodies Show Distinct Biophysical Characteristics To determine the biophysical characteristics of Gal3 binding antibodies, biolayer interferometry assessments were performed using purified Gal3 protein and various antibodies. Purified antibodies were loaded at 10 ug/mL onto anti-human Fc probes using a Gator (Probe Life, East Palo Alto, CA) for 180 seconds. After balancing in assay buffer for 30 seconds, loaded probes were dipping into human Gal-3 with 1:2 serial dilutions for association, starting with 500 nM. Association was observed for 300 seconds until equilibrium. Probes were then dipped into assay buffers for 300 seconds for dissociation.

Figure 19A:
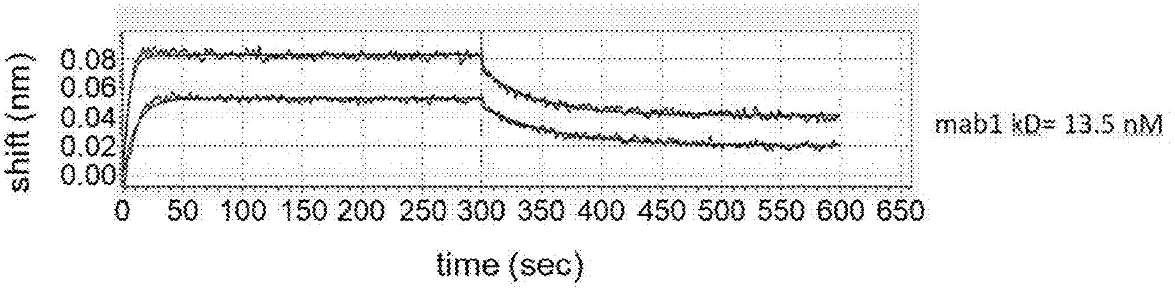
FIGS. 19A-C illustrate biolayer interferometry assessment of anti-Gal3 antibody association and dissociation kinetics with Gal3 (Gal3 binding antibody affinities).
Figure 19B:
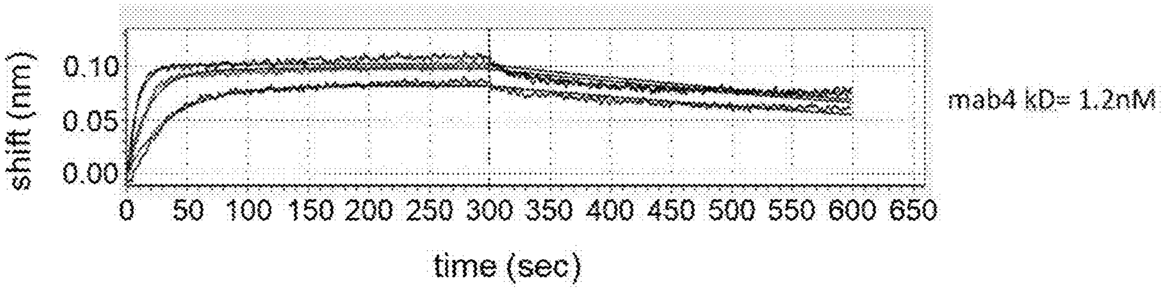
Figure 19C:
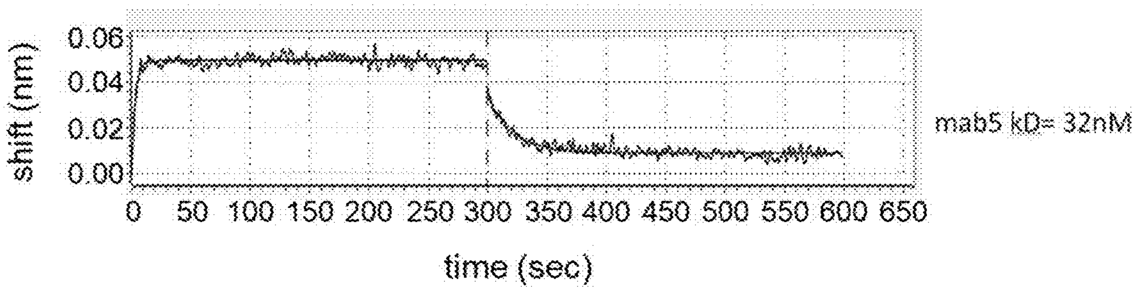

Real time plots of Gal3-binding antibody association and dissociation are depicted in FIG. 19A-C. Antibody mab4 was shown to have the strongest affinity with $K_D$ at 1.2 nM, with a $k_{on}$ of 1.05E+6 $M^{-1}$ $sec^{-1}$ and a $k_{off}$ of 1.32E−3 $sec^{-1}$ (FIG. 19B). Antibody mab1 exhibited the second strongest affinity with $K_D$ at 13.5 nM with a $k_{on}$ of 1.7E+6 $M^{-1}$ $sec^{-1}$ and a $k_{off}$ of 2.29E−2 $sec^{-1}$. Antibody mab5 exhibited the weakest affinity with $K_D$ at 32.3 nM with a $k_{on}$ of 1.41E+6 $M^{-1}$ $sec^{-1}$ and a $k_{off}$ of 4.57 $sec^{-1}$. These binding affinities were qualitatively consistent with the predicted relative affinities from the antibody binning study in Example 15.

Example 17. Gal3-Targeted Antibodies with Gal3-TIM-3 Blocking Activity Activate Antigen-Mediated T-Cell Responses To assess the ability of Gal3-targeted antibodies with Gal3-TIM-3 blocking activity to enhance T-cell mediated responses, a CMV antigen recall assay was used. Human peripheral blood mononuclear cells (PBMCs) (Astarte, donor ID 230) were quickly thawed in 37 C water bath, resuspended in 20 ml of RPMI media with 10% FBS, and centrifuged at 1500 RPM for 5 min. Media was discarded pellet resuspended in 20 ml media and counted by H&E exclusion, and diluted to a final concentration of 4 million/ml in Serum free Media (Lonza). 50 ul of media plus cells (200,000 cells/well) were added to 60 inner wells of a 96 well round bottom plate, and incubated at 37 C for 30 min. Antibodies were added to serum free media to a stock concentration of 4× the final concentration (40 ug/ml). 50 ul of antibodies at 4λ concentration were added directly to the PBMCS and incubated at 37 C for 30 min. After PBMCs were incubated with antibodies for 30 min, 100 ul of CMV (Astarte Biologics, Cat. #1004) at 2× concentration (1 ug/ml) directly to the cells and incubated for 4 days at 37 C. On Day 4, 10 ul of cell supernatant were collected to measure human IFN gamma concentration by ELISA via a human IFN-gamma ELISA kit (Invitrogen).

Figure 20:
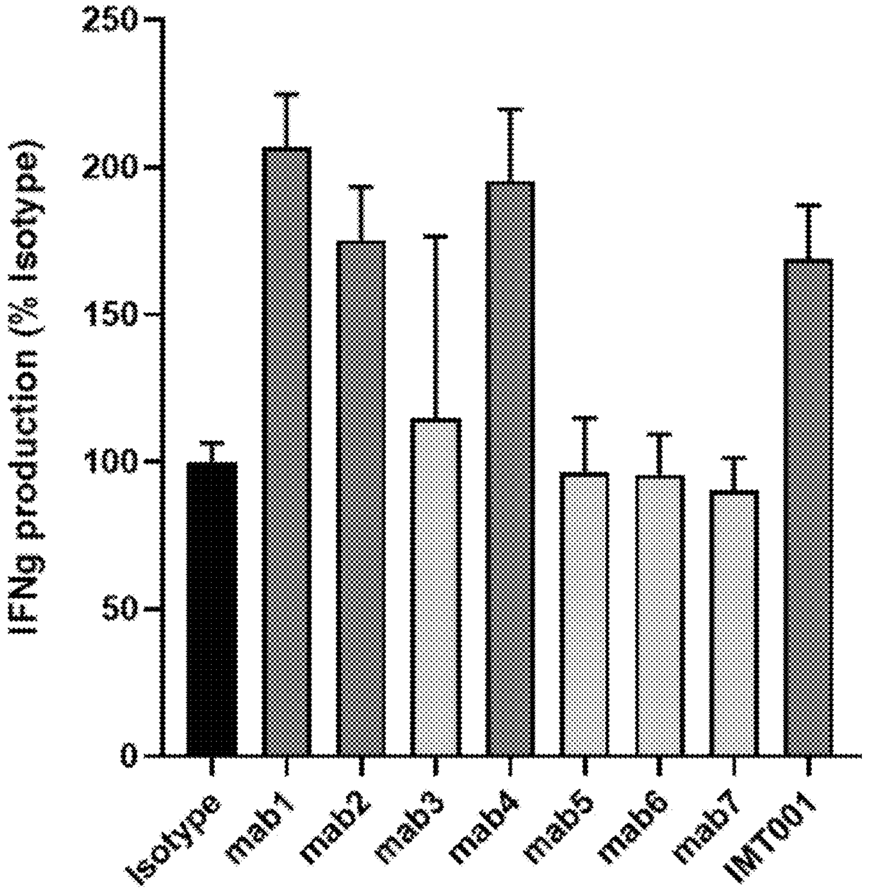
FIG. 20 illustrates CMV antigen recall assay assessment of GAL3 potentiation of T-cell antigen-specific responsiveness. Results illustrate that Gal-3 targeted antibodies exhibit differential activation of T-cells by CMV-induced antigen recall.

As shown in FIG. 20, samples treated with Gal3-targeted antibodies without TIM-3-Gal3 blocking activity, mab6, and mab7 induced similar levels of interferon-g secretion as did isotype-control treated samples. In contrast, Gal3-targeted antibodies with TIM-3-Gal3 blocking activity, mab1, mab2, mab4, and the humanized antibody IMT001 exhibited significantly increased levels of interferon-gamma secretion. Of note, mab5, an antibody with partial Gal3-TIM-3 blocking activity, but relatively low affinity for Gal3, failed to induce significant interferon-gamma secretion, indicating an affinity threshold is required for immune activating properties of Gal3-targeted antibodies. Similarly, mab3, an antibody with partial Gal3-TIM-3 blocking activity produced an equivocal outcome in this T-cell activation assay. Collectively, these data demonstrate the Gal3-targeted antibodies can enhance antigen-specific T-cell activation, and that only those antibodies with the ability to block TIM-3-Gal3 interaction possess this activity.

Example 18: Gal3-TIM-3 Binding Surface

Figure 21B:
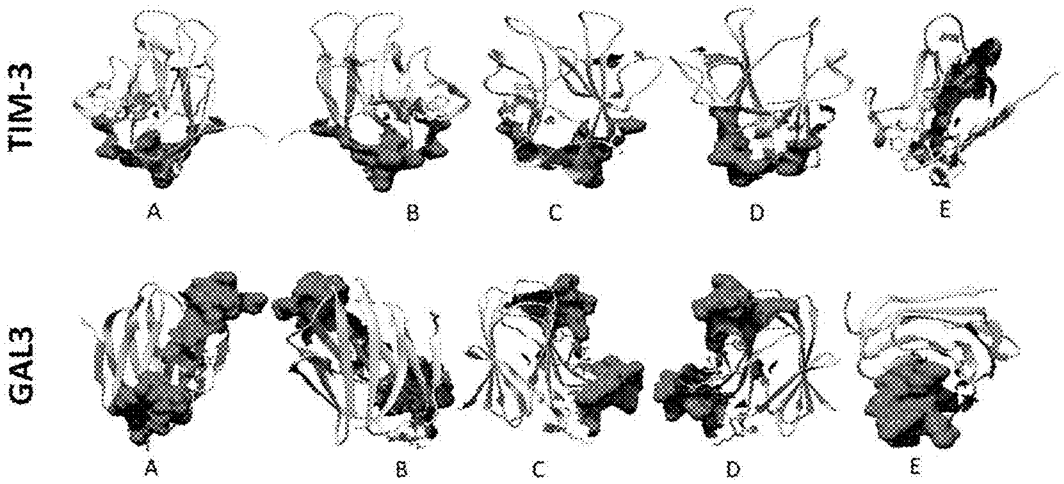
Figure 21C:
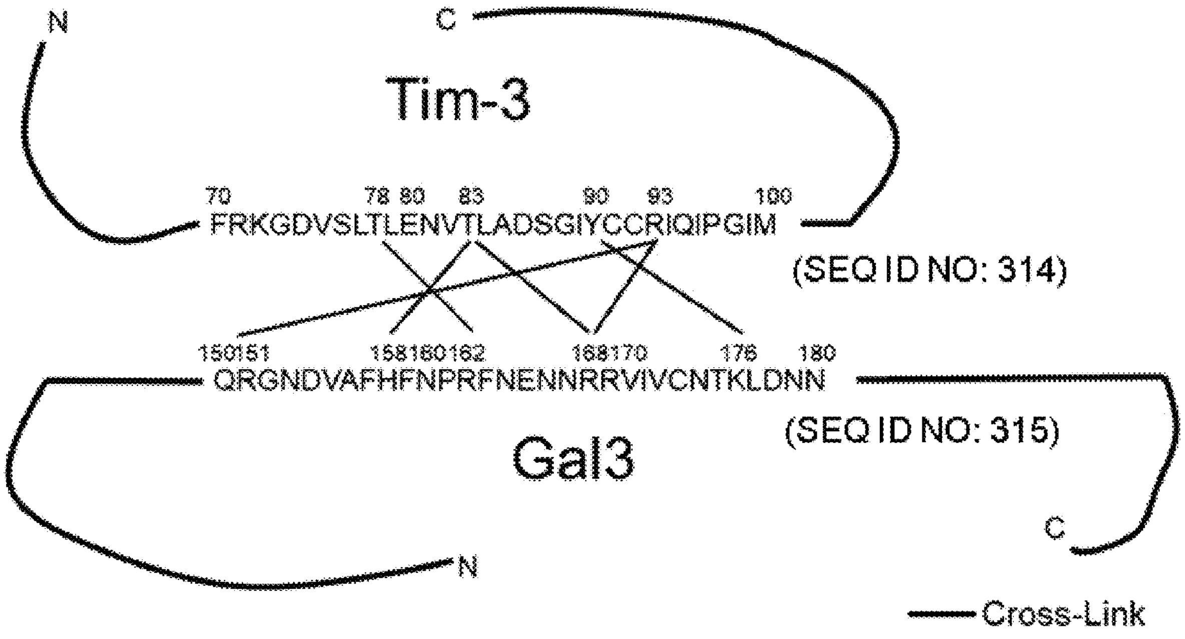

To identify the amino acid residues mediating the interaction between Gal3 and TIM-3, a crosslinked mass spectroscopy was performed. 5 ul of purified Gal3 (4.62 uM) and TIM-3 (3.74 uM) were cross-linked with a K200 MALDI MS analysis kit (CovalX). 9 μl of the cross-linked mixture was added with 1 μl of K200 Stabilizer reagent (2 mg/ml) and incubated at room temperature for 3 hours. The incubated samples were analyzed by High-Mass MALDI analysis immediately after crystallization. For the analysis, the following parameters were applied: Mass Spectrometer: Linear and Positive mode, Ion Source 1:20 kV, Ion Source 2:17 kV, Lens: 12 kV, Pulse Ion Extraction: 400 ns HM4, Gain Voltage: 3.14 kV, Acceleration Voltage: 20 kV. Cross-linked Gal3-TIM-3 products were identified with MH+=26.886 kDa and MH+=34.397 kDa. The cross-linked proteins were digested with trypsin, chymotrypsin, ASPN-N, elastase, or thermolysin to form separate cross-linked peptides (FIG. 21A). The sequences of the cross-linked peptides at the linked sites were determined (FIG. 21A-C). The Gal3-TIM-3 blocking epitopes of Gal3 were not included in the crystal structure models of Gal3 due to intrinsic unstructured features of this region. Note that the amino acid numeration depicted in FIG. 21A reflects the amino acid number in the mature protein after signal peptide processing. See Table 4 which shows the amino acid numbering corresponding to SEQ ID NO: 2.

The amino acid residues in the vicinity of TIM-3 amino acids at positions 73-101 were found to be crosslinked to residues in the vicinity of Gal3 amino acids at 145-184 (FIG. 21A-C). These amino acids were located on the exposed regions of each molecule, suggesting that these regions are involved in the protein-protein interaction of Gal3 and TIM-3. Importantly, the anti-Gal3 antibodies mab1, mab2, mab3, mab4, and mab5, appeared to bind to distinct epitopes as identified in peptide binding assays corresponding to the first 2-21 N-terminal amino acids of Gal3 and residues 52-71 and 72-91 of hGal3 (SEQ ID NO: 1) as described in Example 14, suggesting that a secondary or tertiary structure may be related to the N-terminal regions of Gal3, wherein the region mediates the Gal-TIM-3 interface and binds to the Gal3-TIM-3 blocking antibodies.

Table 4 shows the respective amino acid numberings from FIG. 21A and SEQ ID NO: 2.

TABLE 4

| Residue numbering from FIG. 21A | Corresponding residues of SEQ ID NO: 2 |
|---|---|
| 73-93 | 91-111 |
| 89-99 | 107-117 |
| 64-93 | 82-111 |
| 78-84 | 96-102 |
| 72-104 | 90-122 |
| 82-88 | 100-106 |
| 74-101 | 92-119 |

Example 19: Reduction of Murine Kidney Fibrosis with Anti-Gal3 Antibody

To evaluate the impact of Gal3 inhibition on kidney fibrosis, IMT001 was administered to murine kidney fibrosis disease model. Since IMT001 also exhibits Gal3-TIM-3 blocking activity, the study showed the effect of Gal3-TIM-3 disruption on kidney fibrosis as well.

Unilateral urethral obstruction (UUO) mouse model was created with 8-week old male C57BL/6 mice. The animals were randomly assigned into three groups (n=5); sham, mouse IgG2b control, and IMT001. All animal studies were done in accordance with a protocol approved by the Molecular Medicine Research Institute Institutional Animal Care and Use Committee. On day 0, surgery was performed to ligate the left ureter in each animal. Following the surgery, the animals were administrated intraperitoneally either 10 mg/kg of mIgG2b (BioXCell) or IMT001 on day 1, 5 and 10. The animals in the sham group were left untreated. On day 4, 8 and 15 the animals were humanely sacrificed and left kidney tissues were surgically removed and snap frozen for western blot analysis.

30 mg snap frozen kidney tissue from 14 day treatment UUO group was homogenized in 500 μl of RIPA buffer (Thermo Scientific). The homogenate was left on ice for 10 minutes and then centrifuged at 12000 rpm for 10 min at 4° C. in 1.5 mL Eppendorf tubes. The supernatant containing protein was collected and was quantified by A280 absorbance with a Nanodrop (ThermoFisher). Protein samples were boiled in 4× sample Buffer containing β-mercaptoethanol (Bio-Rad) for 10 min. Equal amounts of protein lysate (20 μl/well; 10 ug/ul) were loaded onto pre-cast SDS-PAGE gels (Bio-Rad) and electrophoretically separated. Separated proteins were transferred to polyvinylidene difluoride membranes followed by blockade with 5% nonfat dry milk in phosphate buffered saline (Fisher Scientific MT21030CM) with 0.5% TWEEN (PBST). The membranes were incubated overnight at 4° C. with primary antibodies targeted against α-smooth muscle actin (SMA) (1:2000 dilution) (Sigma A5228) and fibronectin Fn-EIIIA (1:1000 dilution) (Abcam ab6328). Western blot data were normalized to GAPDH (1:5000 dilution) (Abcam ab181602). After three washes with PBST, the membranes were incubated with respective secondary antibodies conjugated to horseradish peroxidase at a 1:5000 dilution at room temperature for two hours. The membranes were washed three times with PBST and protein bands were detected by enhanced chemiluminescence using standard ECL detection methods as recommended by the manufacturer (Bio-Rad) and developed. GAPDH was used as a loading control reference.

Figure 22:
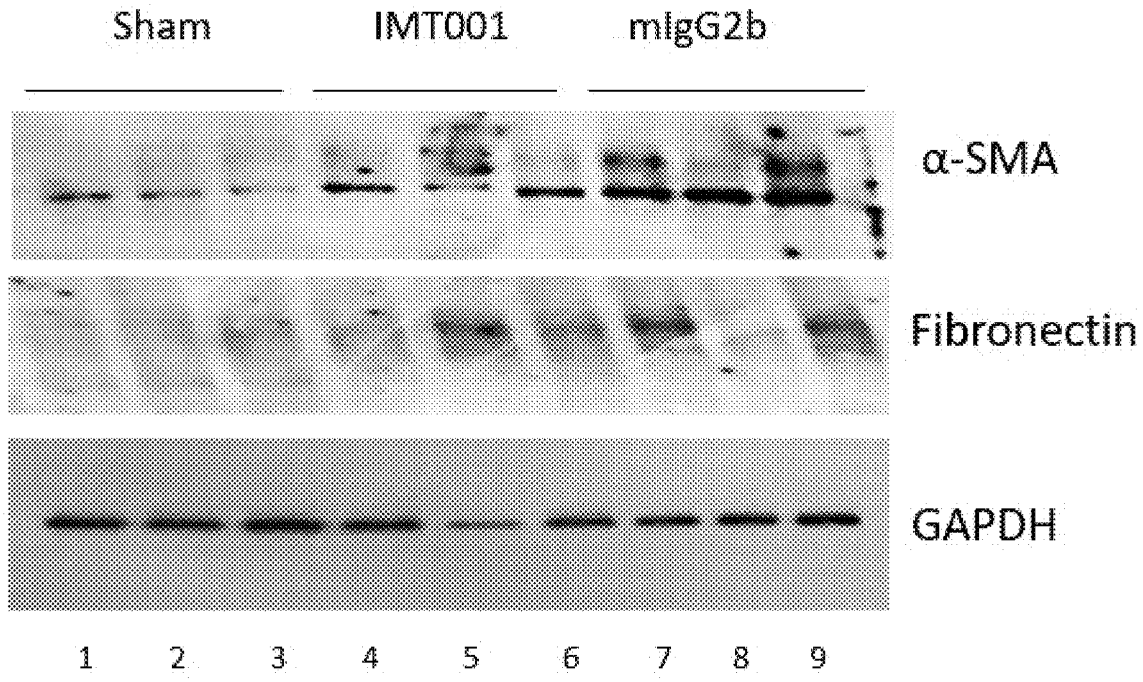
FIG. 22 shows a Western blot analysis of fibrosis markers, alpha-smooth muscle actin (α-SMA) and fibronectin, in kidney tissue lysates from male unilateral urethral obstruction (UUO) mice treated for 14 days with IMT001 and mIgG2b (control) antibodies following uretal ligation, or sham treated without antibody treatment. GAPDH was used as a loading control.

As illustrated in FIG. 22, animals subjected to uretal ligation and treated with a non-specific isotype control antibody, mIgG2b, exhibited an induction of the fibrotic markers a smooth muscle actin (α-SMA) and fibronectin compared to animals treated with a sham surgery (lanes 1-3 vs lanes 7-9). In contrast, animals subjected to uretal ligation and treated with IMT001exhibited reduced expression of both fibrotic markers (lanes 4-6) relative to the IgG2b control (lanes 7-9), appearing more similar to the sham-treated animals. These observations suggested that blocking Gal3 and disrupting Gal3-TIM-3 interaction can reduce kidney fibrosis.

Example 20: Reduction of Murine Liver Fibrosis with Anti-Gal3 Antibody

The Gal3-TIM-3 blocking antibody IMT001 was used on non-obese diabetic and inflammation (N-IF) mouse genetic model of fibrosis to study the effect of Gal3 inhibition on liver fibrosis.

N-IF mice were generated by crossing 24αβNOD mice and NOD.Rag2−/− mouse strains. The N-IF mice were backcrossed with the B6.Rag2−/− mouse strains for 10 generations. Mice (male and female) were separated into two groups: IMT001 antibody treatment group and mIgG2b antibody control group. Antibodies were administered to the animals every fourth day for 40 days, at 10 mg/kg body weight and the animals were subsequently sacrificed. All efforts were made to minimize suffering. Liver and Kidney tissues were collected and snap frozen in liquid nitrogen for western blot analysis. Tissue processing and western blot analysis were performed as in Example 19. GAPDH was used a loading control reference.

Figure 23:
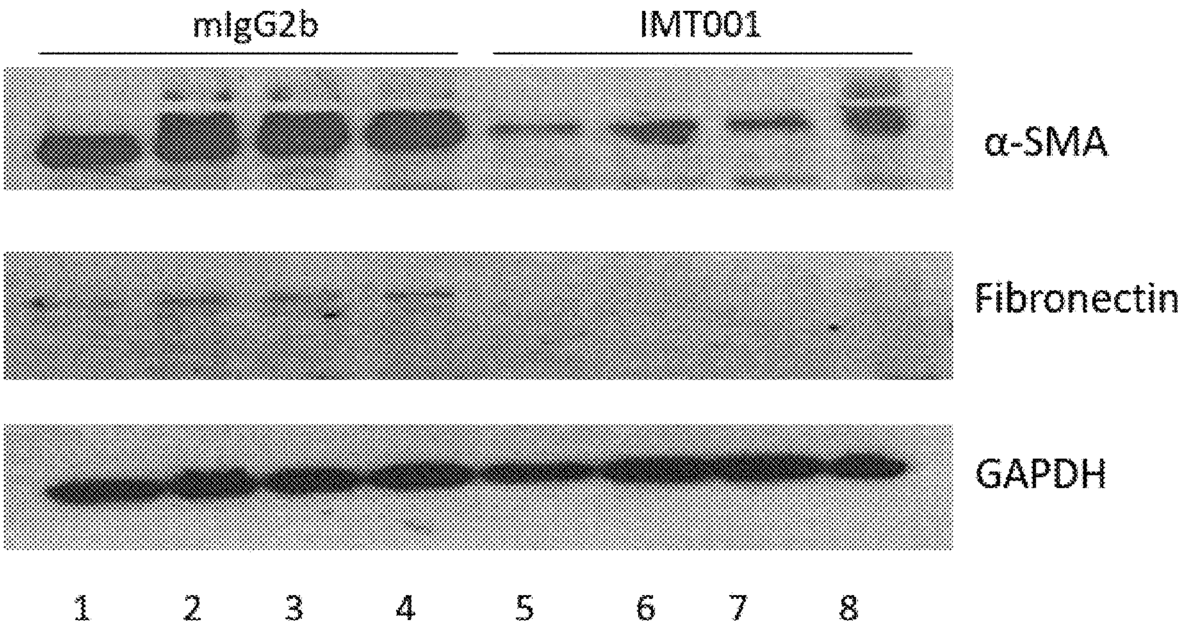
FIG. 23 shows a Western blot analysis fibrosis markers, α-SMA and fibronectin in liver tissue lysates from non-obese diabetic and inflammation (N-IF) mice. The animals were treated with 40 days of IMT001, an anti-Gal3 antibody and mIgG2b (control) antibody. GAPDH was used as a loading control.

The animals treated with Gal3-TIM-3 blocking antibody, IMT001 had significant reductions in the expression of fibrotic markers α-SMA and fibronectin relative to animals treated with mIgG2b isotype control (FIG. 23). These data suggested that Gal3-TIM-3 blockade by IMT001 reduced liver fibrosis in the N-IF model.

Example 21: Effect of Anti-Gal3 Antibodies with/without Gal3-TIM-3 Disrupting Property on Fibrosis To assess effects of anti-Gal3 antibodies with and without Gal3-TIM-3 blocking activity on fibrosis, an in vitro cell culture-based study is conducted.

Normal rat kidney fibroblast cells (NRK-49F) are grown to 80% confluence in RPMI medium containing 10% fetal calf serum and penicillin/streptomycin antibiotics. The culture medium is removed and is replaced with RPMI with penicillin/streptomycin but without fetal calf serum to induce serum starvation for 24 hours, whereupon quiescent cells are treated with control mIgG2b (10 mg/ml), TGF-β1 (1 ng/ml) or Galectin-3 antibody IMT001 (10 mg/ml), and lysed in protein extraction buffer. The lysates are analyzed by Western blotting for the induction of fibroblast-to-myoblast markers of fibrotic disease, including α-SMA and fibronectin, using a GAPDH as a loading control reference. Similarly, Normal human Kidney Proximal tubular cells (HK-2) (ATCC; Rockville, MD) are grown in keratinocyte media, in a humidified incubator at 37° C. under 5% CO2. The cultured cells are treated with either mIgG2b (10 mg/ml), TGF-β1 (1 ng/ml) or IMT001 (10 mg/ml) and are evaluated by Western blotting.

Example 22: Treatment of Patient with Fibrotic Disease

A patient exhibiting jaundice and fluid retention visits a physician. The physician diagnoses the patient with liver fibrosis and prescribes a therapy comprising an anti-Gal3 antibody. The therapy is administered to the patient orally daily for a month at approximately 10 mg/kg of patient's body weight. In some cases, the anti-Gal3 antibody also has Gal3-TIM-3 blocking properties.

Example 23: Induction of Immune System Activation in Human Subjects Using an Anti-Gal3 Antibody Human subjects or patients are optionally selected according to criteria such as immune system irregularity, autoimmune disease, immunodeficiency, immunosuppression, cancer or fibrosis. An anti-Gal3 antibody is administered systemically through parenteral, intravenous, intramuscular, intra-arteriole, intradermal, subcutaneous, intraperitoneal, intraventricular, or intracranial routes. Subjects are monitored for effect on immune system irregularity, autoimmune disease, immunodeficiency, immunosuppression, cancer or fibrosis. Subjects are also monitored by measuring blood, plasma or serum levels of cytokines such as IFNγ, TGF-β, TGF-β1, IL-1β, IL-2, TNF-α, or GM-CSF using methods known in the art, e.g. gas chromatography, liquid chromatography, mass spectrometry, or enzyme-linked immunosorbent assay (ELISA).

Alternatively, white blood cells or TIM-3-enriched white blood cells are isolated from a subject using techniques known in the art, such as centrifugation and fluorescence-activated cell sorting. Isolated white blood cells or TIM-3-enriched white blood cells are contacted with an anti-Gal3 antibody to effect production of at least one cytokine and induce immune activation. Contacted white blood cells or TIM-3-enriched white blood cells can be autologously returned to the subject to treat an immune related disease such as a cancer or a fibrosis. Effects of the treatment can be seen within 1, 2, 3, 4, 5, 6, 7, 8, 9, 10, 11, 12, 13, 14, 15, 16, 17, 18, 19, 20, 21, 22, 23, 24 hours or 1, 2, 3, 4, 5, 6, 7 days, or 1, 2, 3, 4 weeks, or 1, 2, 3, 4, 5, 6, 7, 8, 9, 10, 11, 12 months, or 1, 2, 3, 4, 5, 6, 7, 8, 9, 10 years.

In some embodiments, the administration of the anti-Gal3 antibody to the subject or contacting white blood cells or TIM-3-enriched white blood cells with the anti-Gal3 antibody can reduce an interaction between Gal3 and TIM-3 to less than 99%, less than 95%, less than 90%, less than 80%, less than 78%, less than 70%, less than 66%, less than 60%, less than 56%, less than 52%, less than 50%, less than 40%, less than 30%, less than 29%, less than 27%, less than 20%, less than 19%, less than 17%, less than 10%, less than 5%, less than 4%, less than 3%, less than 2%, or less than 1% of normal.

The anti-Gal3 antibody may be produced and prepared under sterile conditions and under regulated or controlled procedures. In this process, the anti-Gal3 antibody is used in the manufacture of a medicament or composition. The prepared anti-Gal3 antibody is used in the treatment of an immune related disease such as cancer or fibrosis.

Methods for maintaining and ensuring sterility may adhere to good manufacturing practice (GMP), good tissue practice (GTP), good laboratory practice (GLP), and good distribution practice (GDP) standards. Methods for maintaining and ensuring sterility include but are not limited to high-efficiency particulate air (HEPA) filtration, wet or dry heat, radiation, e.g., X-rays, gamma rays, or UV light, sterilizing agents or fumigants, such as ethylene oxide, nitrogen dioxide, ozone, glutaraldehyde, formaldehyde, peracetic acid, chlorine dioxide, or hydrogen peroxide, aseptic filling of sterile containers, packaging in plastic film or wrap, or vacuum sealing.

Example 24: Discovery of Antibodies with GAL3-TIM3 Blocking Activity

To extend the observation made with the original panel of antibodies, an antibody discovery campaign was executed to identify additional GAL3-binding antibodies with the capacity to block the assembly of GAL3 and TIM3. Balb/C, FVB, and CD-1F mice were inoculated at 7 day intervals with 50 ug of GAL3 protein fused to a linker-spaced 6-histidine tag, GAL3-ECD-His, (Acro GA3-H5129; Lot #819-43PS1-5E.) in combination with a TLR agonist adjuvant mix (50 ug MPL, 20 ug CpG, 10 ug Poly (I: C) and 10 pg R848) for 3 repetitions, followed by an inoculation with 50 ug of GAL3-His alone administered subcutaneously to the inguinal, back of the neck and base of the tail sites as well as hock and intraperitoneal sites. Animals were sacrificed in accordance with IACUC protocol and spleen, femurs, and lymph nodes (axillary, accessory axillary, mediastinal, superficial inguinal, iliac, sacral and popliteal) were harvested. A single cell suspension of immunized lymph node (LN), spleen and bone marrow cells were obtained using 2 sterile frosted glass slides in a tissue culture petri dish with 15 mL DMEM. Bone marrow was extracted from femurs via end-cap flushing with a 5 mL syringe fitted with an 18-gauge needle. Cells from 3 animals were pelleted with 5 minutes of centrifugation at 1200 RPM, resuspended in 10 mL of DMEM (GIBCO 10564-011) and nucleated cells were enumerated by hemocytometer count. Cells were pelleted at 1200 RPM and were resuspended in SC-Buffer (PBS, 2% FBS and 1 mM EDTA), and plasma cells were isolated with an EasySep™ Mouse CD138 Positive Selection Kit (StemCell Technologies) with the manufacturer recommended protocol. Enriched CD138-positive cells were pelleted with 5 minutes of centrifugation at 1200 RPM, resuspended in 50 mL electrofusion buffer (Eppendorf 940-00-220-6) and were enumerated. Separately, SP2/0-mIL6 myeloma cells (ATCC CRL2016) were pelleted with 5 minutes of centrifugation at 1200 RPM, resuspended in 50 mL electrofusion buffer and were enumerated. Myeloma cells and CD138-positive plasma cells were combined at a 1:1 ratio, volume was expanded to 50 mL with electrofusion buffer, cells were pelleted with 5 minutes of centrifugation at 1200 RPM and supernatant was discarded. After a repeated step of washing and pelleting in electrofusion buffer, cells were resuspended in electrofusion buffer to a concentration of 10×10^6 cells/ ml, up to 9 mL of cell suspension was added to a BTX electrofusion chamber, and cells were fused with an 800V electrofusion protocol. Fused cells were rested for 5 minutes, transferred to a tissue culture dish containing 40 mL medium MM (DMEM, 15% FBS, 1% glutamax and 1% Pen/Strep), incubated for 1 hour at 37C, 8% CO2, resuspended with a pipette, pelleted with 5 minutes of centrifugation at 1200 RPM, resuspended in ClonaCell HY Liquid HAT Selection Medium (StemCell Technologies), and plated in 96-well tissue culture flat bottomed plates. After 10 days, supernatants were sampled and evaluated for binding to isolated GAL3 by ELISA. 50 ul of 0.1 ug/mL GAL3-ECD-His, (Acro GA3-H5129; Lot #819-43PS1-5E) resuspended in diluent (PBS with 0.5% BSA) was added to each well for 45 minutes, supernatant was discarded and plates were washed with phosphate buffered saline (PBS) with 0.05% Tween20. 50 ul of 1:5 dilution of hybridoma supernatant in diluent was added to each well for 1 hour, followed by 5 successive 300 µl washes with PBS/0.05% Tween20, after which a 1:3000 dilution of goat anti-mouse Fc-specific antibody conjugated to horseradish peroxidase (Novex A16090) in 50 ul of diluent was added to each well for 1 hour followed by 5 successive 300 ul washes with PBS/0.05% Tween20. Following washing, 50 ul of ABTS (Novex #00-202-4) was added to each well for 20-30 minutes, prior to readout on a spectrophotometer (Molecular Devices) at absorbance of 405 nm.

GAL3-binding antibodies were evaluated for their binding affinity by SPR. Kinetics experiments were performed on BiacoreT200 at 25° C. in high performance mode. Ligand proteins, purified antibodies were captured onto a CM5 chip coupled with anti-human Fc or anti-mouse Fc antibody, three antibodies at a time onto flow cell #2, 3, and 4, respectively, while flow cell #1 was used as reference. The analyte Galectin-3 in HBS-EP buffer was injected over all four flow cells at concentrations of 100, 50, 25, 12.5, 6.25, 3.125 and 0 nM at a flow rate of 30 uL/min. The complex was allowed to associate and dissociate for 240 and 300 seconds, respectively. The surfaces were regenerated with a 30 second injection of 10 mM Glycine pH 1.7 (flow rate 30 uL/min). The data were fit to a simple 1:1 interaction model using the global data analysis option available within BiacoreT200 Evaluation software V2.0. The affinity of Gal3 monoclonal antibodies was confirmed to be greater than 30 nM for all antibodies studied (Table 24.1). Antibodies with affinity less than 2E−7 were selected for further characterization.

TABLE 24.1

| Antibody | GAL3-TIM3 Blocking @ 3 ug/mL | hGal-3 KD (M) | Bin | Epitope Mapping |
|---|---|---|---|---|
| mIMT001 | 80% | 1.67E−9 | 1 | 5, 6 |
| 846T.1H2 | 81% | 2.82E−09 | 1 | 5, 6 |
| 13H12.2F8 | 57% | 6.07E−09 | 2 | 6, 7 |
| 19D9.2E5 | 34% | <1.0E−09 | 2 | 6, 7 |
| 14H10.2C9 | 44% | 5.62E−10 | 2 | 6, 7 |
| 2D10.2B2 | 86% | 7.53E−10 | 3 | 6 |
| 4A11.2B5 | 48% | 5.22E−09 | 3 | 6 |
| 846.2H3 | 100% | 1.02E−08 | 3 | 6 |
| 846.1F5 | 90% | 2.73E−09 | 3 | 6 |
| 6H6.2D6 | 82% | 4.86E−09 | 4 | 1, 7 |
| 20H5.A3 | 81% | 3.95E−09 | 4 | 1, 7 |
| 19B5.2E6 | 61% | <1.0E−09 | 4 | 1, 7 |
| 23H9.2E4 | 80% | 4.26E−09 | 4 | 1, 7 |
| 20D11.2C6 | 40% | 2.78E−08 | 5 | 1, 7, 8 |
| 15G7.2A7 | 48% | 1.13E−08 | 5 | 1, 7, 8 |
| 4G2.2G6 | 48% | <1.0E−09 | 6 | 4 |

TABLE 24.1-continued

| Antibody | GAL3-TIM3 Blocking @ 3 ug/mL | hGal-3 KD (M) | Bin | Epitope Mapping |
|---|---|---|---|---|
| 3B11.2G2 | 33% | <1.0E−09 | 7 | 4, 6 |
| 13A12.2E5 | 35% | 8.20E−9 | 7 | 4, 6 |
| 7D8.2D8 | 12% | 2.49E−09 | 8 | 2, 7 |
| 15F10.2D6 | 19% | 2.06E−09 | 8 | 2, 7 |
| 12G5.D7 | 12% | 1.9E−09 | 10 | Non-linear |
| 24D12.2H9 | 0% | 4.13E−09 | 11 | Non-linear |
| 13G4.2F8 | 0% | 2.53E−09 | 12 | Non-linear |
| 9H2.2H1 | 6% | 1.84E−08 | 12 | Non-linear |

Positively scoring wells were evaluated for the ability to block association of GAL3 and TIM3. To identify GAL3-targeted antibodies with the ability to block the interaction of GAL3 and TIM3, purified GAL3 and TIM3 proteins were incubated in the presence of GAL3-immunization hybridoma supernatants described above, or without antibody, and protein interaction was evaluated by ELISA. Human Galectin-3 protein (Acro Biosystems, GA3-H5129) was diluted in PBS (Corning, 21-030-CM) to a concentration of 3 µg/ml and added to the wells of a 96-well ELISA plate (Thermo Fisher, 44-2404-21). After incubating the plate at 4° C. overnight, the plate was washed three times with PBST (PBS with 0.05% Tween 20 [VWR, 0777]). The plate was then blocked for an hour with 2% BSA (EMD Millipore, 126609) in PBST at room temperature with gentle rocking. Thereafter, the 2% BSA in PBST was discarded and antibody or inhibitor (3-fold dilutions beginning at 20 µg/ml, 60 µg/ml, or 180 uM) in 2% BSA in PBST was added to the wells. Afterwards, 2 µg/ml of human TIM3 (Aero Biosystems, TM3-H5229) in 2% BSA in PBST was added to the antibody or inhibitor in the wells in a 1:1 ratio. The plate was incubated for an hour at room temperature with gentle rocking. Thereafter, the plate was washed three times with PBST, and 0.3 ug/ml of human TIM3 Biotinylated Antibody (R&D Systems, BAF2365) in 2% BSA in PBST was added to the wells. The plate was incubated for an hour with gentle rocking and then washed three times with PBST. Avidin-HRP (1:2000) was then added to the wells. The plate was incubated at room temperature for an hour with gentle rocking and then washed three times with PBST. TMB substrate (Thermo Scientific, 34029) was then added to each well. The reaction was stopped with 1M HCl (JT Baker, 5620-02) and read using a plate reader (Molecular Devices) at absorbance of 450 nm.

Figure 24:
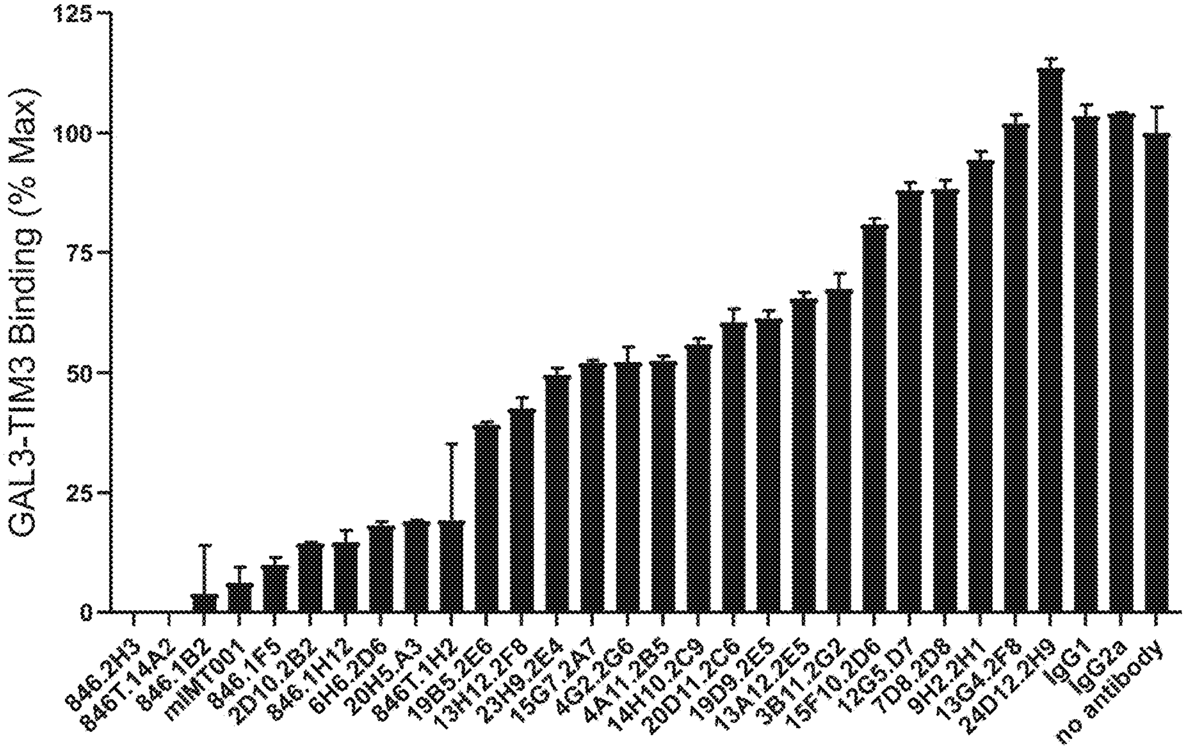
FIG. 24. Galectin-3 targeted antibodies were evaluated for the ability to block the binding of GAL3 and TIM3 by ELISA at 3 μg/mL. Bars represent mean+/−standard deviation.

As depicted in FIG. 24, GAL3-binding antibodies exhibited variable ability to block the associate of GAL3 and TIM3. Some antibodies were able to block the assembly of GAL3 and TIM3 to less than 5% of levels observed in the absence of a GAL3-targeted antibody, including 846.2H3. Other GAL3-binding antibodies blocked the assembly of GAL3 and TIM3 to 5-20% of levels observed in the absence of a GAL3-targeted antibody, including mIMT001, 846.1F5, 2D10.2B2, 6H6.2D6, 20H5.A3, and 846T.1H2. Other GAL3-binding antibodies blocked the assembly of GAL3 and TIM3 to 20-50% of levels observed in the absence of a GAL3-targeted antibody, including 19B5.2E6, 13H12.2F8, and 23H9.2E4. Other GAL3-binding antibodies blocked the assembly of GAL3 and TIM3 to 50-75% of levels observed in the absence of a GAL3-targeted antibody, including 15G7.2A7, 4G2.2G6, 4A11.2B5, 14H10.2C9, 20D11.2C6, 19D9.2E5, 13A12.2E5, and 3B11.2G2. Other GAL3-binding antibodies showed minimal blocking activity towards the assembly of GAL3 and TIM3, reducing binding by 25% or less of TIM3 and GAL3 in the absence of a GAL3-targeted antibody, including 12G5.D7, 7D8.2D8, 9H2.2H1, 13G4.2F8, and 24D12.2H9.

Example 25. Gal3-Targeted Antibodies with and without Gal3-TIM3 Blocking Activity Bind to Distinct Epitopes of Gal3

To identify the epitopes to which Gal3 antibodies with and without Gal3-TIM3 blocking activity bound, a library of 20 amino acid peptides representing portions of Gal3, summarized in Table 24.1, was produced and the ability to bind Gal3 antibodies was evaluated by ELISA.

At least 2 μg/ml of hGal3 peptide in 50 μl of PBS or 0.1 ug/ml of full-length human Gal3 protein (GenScript) and human Galectin-3 protein (Acro Biosystems, GA3-H5129) were diluted in PBS (Corning, 21-030-CM) to concentrations of at least 2 μg/ml or 0.1 ug/ml, respectively, and added to the wells of a 96-well ELISA plate (Thermo Fisher, 44-2404-21). After incubating the plate at 4° C. overnight, the plate was washed three times with PBST (PBS with 0.05% Tween 20 [VWR, 0777]). The plate was then blocked for an hour with 2% BSA (EMD Millipore, 126609) in PBST at room temperature with gentle rocking. Thereafter, the 2% BSA in PBST was discarded and human Galectin-3 hybridoma supernatants or antibodies were diluted in 2% BSA in PBST to concentrations of at least 0.1 ug/ml and added to the wells. The plate was incubated for an hour at room temperature with gentle rocking and then washed three times with PBST. Afterwards, Goat Anti-Mouse IgG-HRP (Jackson ImmunoResearch, 115-036-1461) or Goat Anti-Rat IgG HRP (abcam, ab205720) diluted in 2% BSA in PBST (1:4000) were added to the wells. The plate was incubated for 30 minutes to 1 hour at room temperature with gentle rocking and then washed three times with PBST. TMB substrate (Thermo Scientific, 34029) was then added to each well. The reaction was stopped with 1M HCl (JT Baker, 5620-02) and read using a plate reader (Molecular Devices) at absorbance of 450 nm.

Binding of Gal3-binding antibodies to the peptide array was observed at multiple locations, with the majority of binding observed in peptides 1-8, summarized in Table 25.1. Significantly, all Gal3-binding antibodies with strong TIM3-Gal3 blocking activity exhibited the ability to bind to peptides 4, 5, 6, or 7, corresponding to peptide sequences in the N-terminal domain of Gal3. Specifically, six separate Gal3-binding antibodies with Gal3-TIM3 blocking activity (6H6.2D6, 20H5.A3, 20D11.2C6, 19B5.2E6, 15G7.2A7, 23H9.2E4) all bound peptide 1 of Gal3, corresponding to amino acids 1-20 of Gal3, ADNFSLHDALSGSGNPNPQG (SEQ ID NO: 3). Conversely, no Gal3-targeted antibodies with poor Gal3-TIM3 blocking activity were observed to bind peptide 1. Taken together, these data indicate that binding to Gal3 peptide 1 is predictive of the ability to block the interaction of Gal3 with TIM3. Similarly, three separate Gal3-binding antibodies with Gal3-TIM3 blocking activity (4G2.2G6, 3B11.2G2, and 13A12.2E5) bound peptide 4 of Gal3, corresponding to amino acids 31-50 of Gal3, GAGGYPGASYPGAYPGQAPP (SEQ ID NO: 6). Conversely, no Gal3-targeted antibodies with poor Gal3-TIM3 blocking activity were observed to bind peptide 4. Taken together, these data indicate that binding to Gal3 peptide 4 is predictive of the ability to block the interaction of Gal3 with TIM3. Further, thirteen Gal3-binding antibodies with Gal3-TIM3 blocking activity (mIMT001, 846T.1H2, 13H12.2F8, 19D9.2E5, 14H10.2C9, 2D10.2B2, 4A11.2B5, 846.2H3, 846.1F5, 3B11.2D2, and 13A12.2E5) all bound peptide 6 of Gal3, corresponding to amino acids 51-70 of Gal3, GAYPGQAPPGAYPGAPGAYP (SEQ ID NO: 8). Conversely, no Gal3-targeted antibodies with poor Gal3-TIM3 blocking activity were observed to bind peptide 6. Taken together, these data indicate that binding to Gal3 peptide 6 is predictive of the ability to block the interaction of Gal3 with TIM3. Additionally, eleven Gal3-binding antibodies with Gal3-TIM3 blocking activity (6H6.2D6, 20H5.A3, 20D11.2C6, 13H12.2F8, 19B5.2E6, 23H9.2E4, 15G7.2A7, 19D9.2E5, 14H10.2C9, 7D8.2D8, 15F10.2D6 and 846.14A2) all bound peptide 7 of Gal3, corresponding to amino acids 61-80 of Gal3, AYPGAPGAYPGAPAPGVYPG (SEQ ID NO: 9). Conversely, no Gal3-targeted antibodies with poor Gal3-TIM3 blocking activity were observed to bind peptide 7. Taken together, these data indicate that binding to Gal3 peptide 7 is predictive of the ability to block the interaction of Gal3 with TIM3. In total, these data indicate the binding of anti-Gal3 antibodies to Gal3 peptides 1, 4, 5, 6, and 7 as predictive of the ability to block the interaction of Gal3 and TIM3.

As illustrated in FIG. 25, peptides 4, 5, 6, and 7 share repeated amino acid sequences comprised of proline-glycine (PG) and tyrosine-proline-glycine (YPG), indicating a common feature that may explain the ability of Gal3-targeted antibodies to bind to multiple Gal3 peptides. Further, the amino acid sequence glycine-x-tyrosine-proline-glycine (GxYPG), where x may be the amino acids alanine (A), glycine (G), or valine (V), is shared in peptides 4, 6, and 7, each of which possess two such sequences separated by 3 amino acids. Accordingly, the presence of two GxYPG sequences in close apposition is likely predictive of the ability to bind Gal3-targeted antibodies with the ability to block Gal3 and TIM3. Additionally, the Grantham distance of alanine, glycine, and valine is Ala-Val: 64, Ala-Gly: 60, Val-Gly: 109, thereby predicting that amino acids with similarly low Grantham distances may similarly be able to substitute at the variable region, including proline and threonine.

TABLE 25.2

Galectin-3 peptide sequences

| SEQ ID NO: | Peptide No. | Amino acid sequence |
|---|---|---|
| 3 | 1 | ADNFSLHDALSGSGNPNPQG |
| 4 | 2 | SGSGNPNPQGWPGAWGNQPA |
| 5 | 3 | WPGAWGNQPAGAGGYPGASY |
| 6 | 4 | GAGGYPGASYPGAYPGQAPP |
| 7 | 5 | PGAYPGQAPPGAYPGQAPPG |
| 8 | 6 | GAYPGQAPPGAYPGAPGAYP |
| 9 | 7 | AYPGAPGAYPGAPAPGVYPG |
| 10 | 8 | GAPAPGVYPGPPSGPGAYPS |
| 11 | 9 | PPSGPGAYPSSGQPSATGAY |
| 12 | 10 | SGQPSATGAYPATGPYGAPA |
| 13 | 11 | PATGPYGAPAGPLIVPYNLP |
| 14 | 12 | GPLIVPYNLPLPGGVVPRML |
| 15 | 13 | LPGGVVPRMLITILGTVKPN |
| 16 | 14 | ITILGTVKPNANRIALDFQR |

TABLE 25.2-continued

Galectin-3 peptide sequences

| SEQ ID NO: | Peptide No. | Amino acid sequence |
|---|---|---|
| 17 | 15 | ANRIALDFQRGNDVAFHFNP |
| 18 | 16 | GNDVAFHFNPRFNENNRRVI |
| 19 | 17 | RFNENNRRVIVCNTKLDNNW |
| 20 | 18 | VCNTKLDNNWGREERQSVFP |
| 21 | 19 | GREERQSVFPFESGKPFKIQ |
| 22 | 20 | FESGKPFKIQVLVEPDHFKV |
| 23 | 21 | VLVEPDHFKVAVNDAHLLQY |
| 24 | 22 | AVNDAHLLQYNHRVKKLNEI |
| 25 | 23 | NHRVKKLNEISKLGISGDID |
| 26 | 24 | SKLGISGDIDLTSASYTMI |

Example 26. Gal3-TIM3 Antibodies with Blocking Activity Compete for Binding to Gal3

To determine whether Gal3-binding antibodies with Gal3-TIM3 blocking activity bind to the same or overlapping regions of the Gal3 molecule, antibody binning assays were performed to assess the ability of antibodies to simultaneously bind Gal3. Amine-reactive probes were loaded onto a Gator biosensor (Probe Life, Palo Alto, CA), equilibrated in dH20 for 60 seconds, dipped into 100 μl EDC 0.2M/NHS 0.05M activation buffer for 30 seconds, then dipped into a solution of 20 ug/ul human Gal3-His in 10 mM NaOAc buffer, pH 5 until binding was saturated, and quenched in 1 M ethanolamine pH 8.5 for 300 seconds. Following Gal3-His loading, tips were dipped in 20 μg/mL saturating antibody, then successively dipped into 5 μg/mL competing antibody. As shown in FIG. 26, antibodies with competitive binding profiles were assigned bins and associations to blocking activity were made. Following initial bin assignments, subsequent competition experiments were conducted with representative species from bins establish as described to identify additional members of bins 1 and 3.

12 separate bins of competitive antibody binding patterns to Gal3 were established. Significantly, strong associations between bin and blocking Gal3-TIM3 blocking activity were observed. All antibodies from bins 1, 2, 3, 4, 5, and 6 significantly inhibited Gal3 binding to TIM3, summarized in Table 25.1. In contrast, antibodies in bin 7 and bin 8 were somewhat weaker blockers of Gal3 blocking to TIM3, despite possessing strong affinity to Gal3. Antibodies in bin 10, 11, and 12 uniformly did not have the ability to significantly inhibit the association of Gal3 and TIM3. Thus, the competitive binding bins of 1, 2, 3, 4, 5, and 6 are able to identify the ability of Gal3-binding antibodies to block the assembly of Gal3 and TIM3.

Example 27: Humanized GAL3-TIM3 Blocking Antibodies Block GAL3-TIM3 Binding

Figure 27:
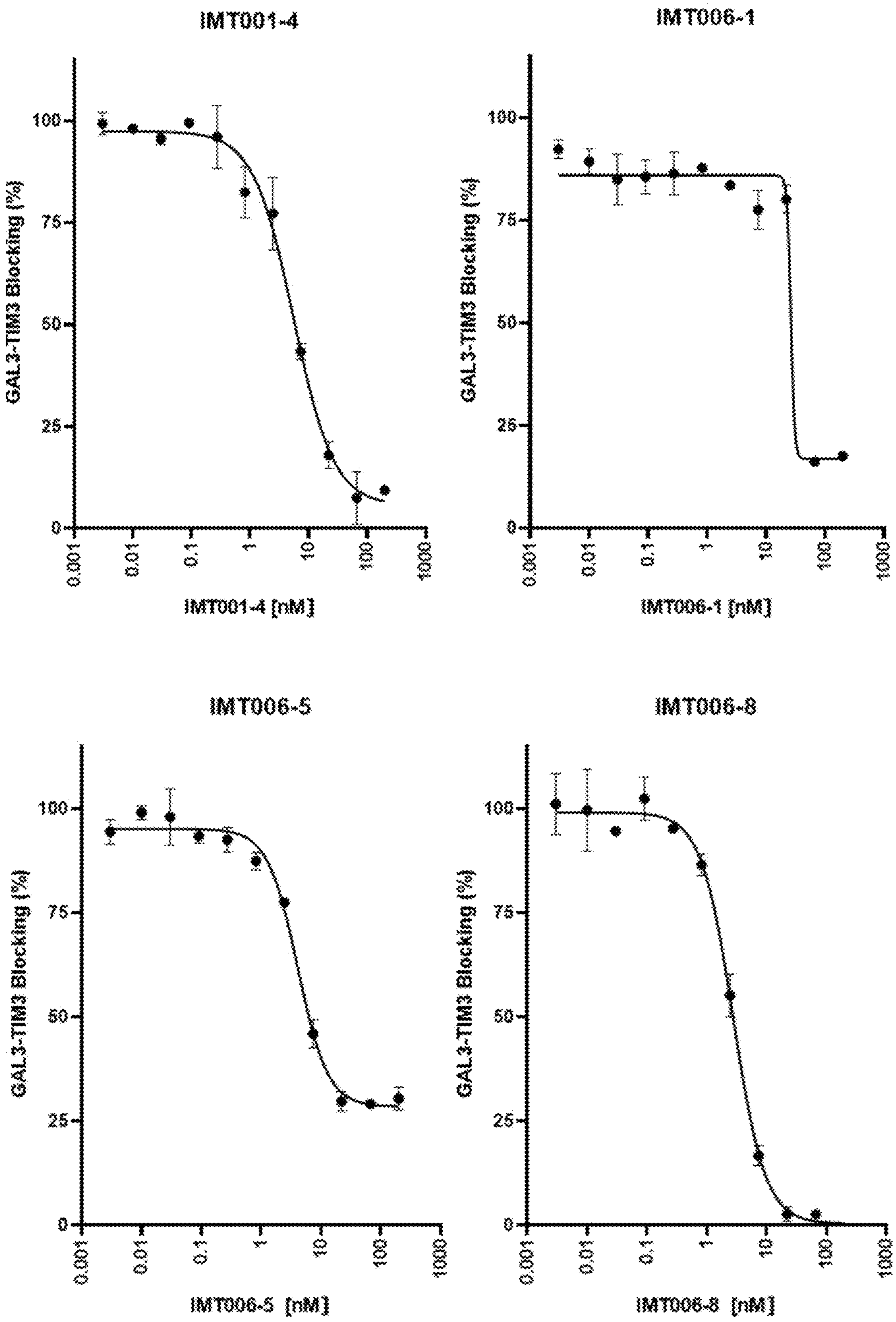
FIG. 27. Humanized anti-GAL3 antibodies were evaluated for blocking of GAL3-TIM3 by ELISA in a titration series. Plotted values represent mean+/−standard deviation.

Humanized variants of GAL3-TIM3 blocking antibodies similarly exhibited the capacity to block the interaction of purified GAL3 and TIM3 as assessed by ELISA, illustrated in FIG. 27. IMT001-4, IMT006-1, IMT006-5, and IMT006-8 exhibited IC50s of 5.6 nM, 26.5 nM, 4.1 nM, and 2.8 nM, respectively.

Example 28: GAL3-TIM3 Blocking Antibodies Exhibit Combination Anti-Tumor Activity with Anti-PD1 or Anti-PD-L1 Antibodies To evaluate the potential for GAL3-TIM3 blocking antibodies to influence tumor biology, studies were conducted in mice bearing MBT-2 bladder tumor xenografts in combination with other antibodies targeting the immunomodulatory checkpoint molecules PD-1 and PD-L1. Briefly, 7-week old female C3H/HeJ mice (Jackson Laboratory) were anesthetized by inhalation anesthetic (3 to 5% Isoflurane in medical grade air) and $1\times10^6$ MBT-2 cells (Sekisui XenoTech, LLC) in 0.1 mL PBS were subcutaneously injected into the right flank by using a syringe with a 25-ga needle. 7 days after tumor implantation, mice were randomly assigned into six groups (n=9-10). Mice were administrated intraperitoneally with isotype control mIgG2b (BioXCell), anti-Gal3 (mIMT001), anti-PD1 (RMP1-14, BioXCell) plus mIgG2b, anti-PD1 (RMP1-14) plus mIMT001, anti-PDL1 (10F.9G2, BioXCell) plus mIgG2b, and anti-PDL1 (10F.9G2) plus mIMT001. Isotype control and anti-Gal3 antibodies were dosed at 20 mg/Kg on day 7, 9, 12, 14 and 16; anti-PD1 (RMP1-14 10 mg/Kg) or anti-PDL1 (10F.9G2, 5 mg/Kg) were dosed on day 8, 12, and 15. Tumor volumes and body weights were monitored twice per week. The animals were humanely sacrificed when tumor volumes or animal health reached IACUC-defined endpoints. Results were expressed as mean±SEM, with statistical analysis performed by two-way ANOVA.

Figure 28B:
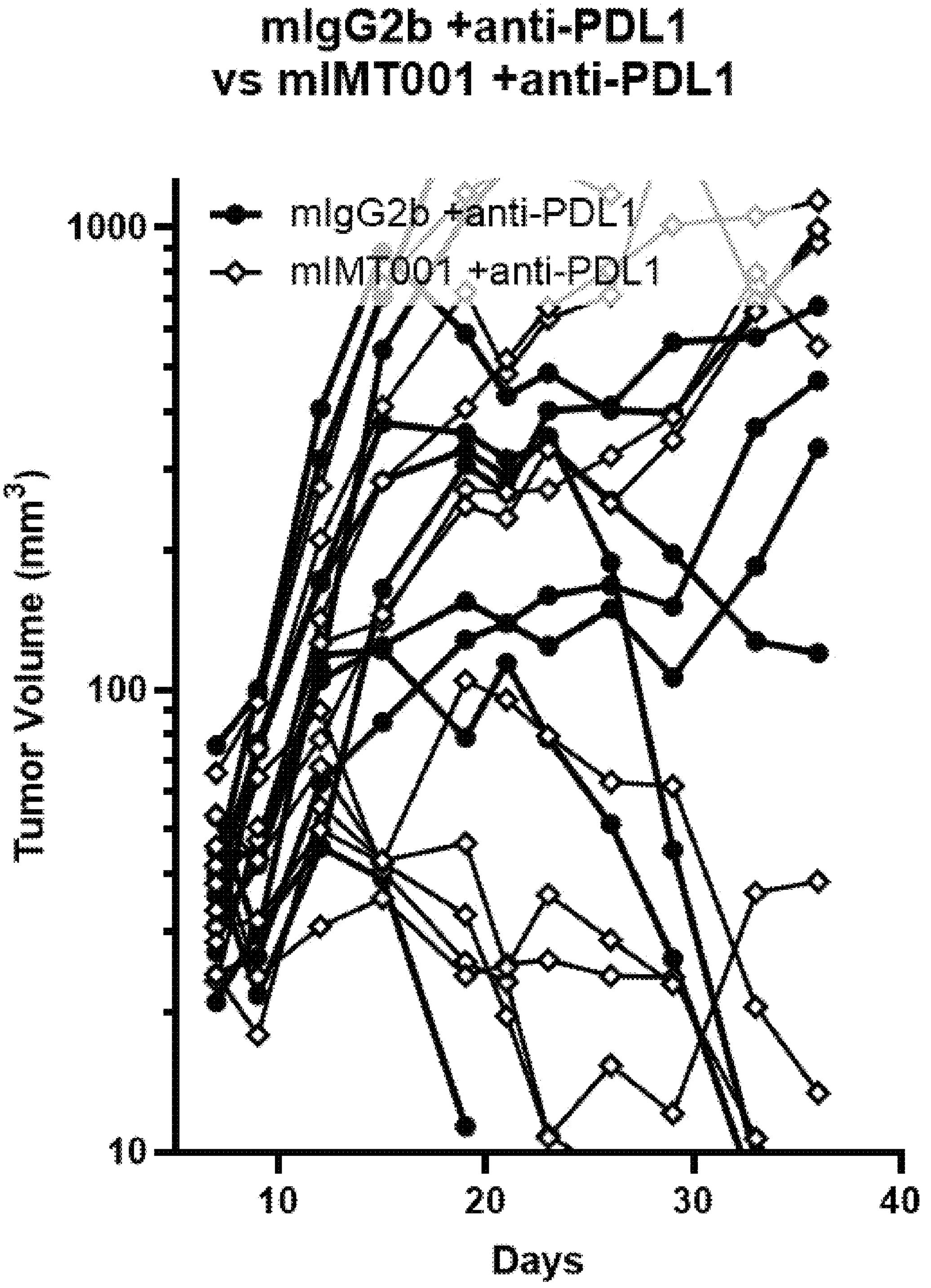

Animals treated with mIMT001 or huIgG4 did not exhibit any significant decrement in tumor volume (data not shown). In contrast, as depicted in FIG. 28, 3/10 animals treated with anti-PD-L1 antibodies exhibited strong anti-tumor responses, as reflected by reductions in tumor volume following treatment (FIGS. 28A-B). Significantly, 5/10 animals treated with the combination of mIMT001 and anti-PD-L1 antibodies exhibited strong anti-tumor responses, representing a 66% increase in response rate relative to animals treated with anti-PD-L1 antibodies alone. These data indicate that the combination of antibodies that block GAL3 and TIM3 with anti-PD-L1 antibodies have significantly increased anti-tumor activity than anti-PD-L1 antibodies do in isolation.

Figure 28D:
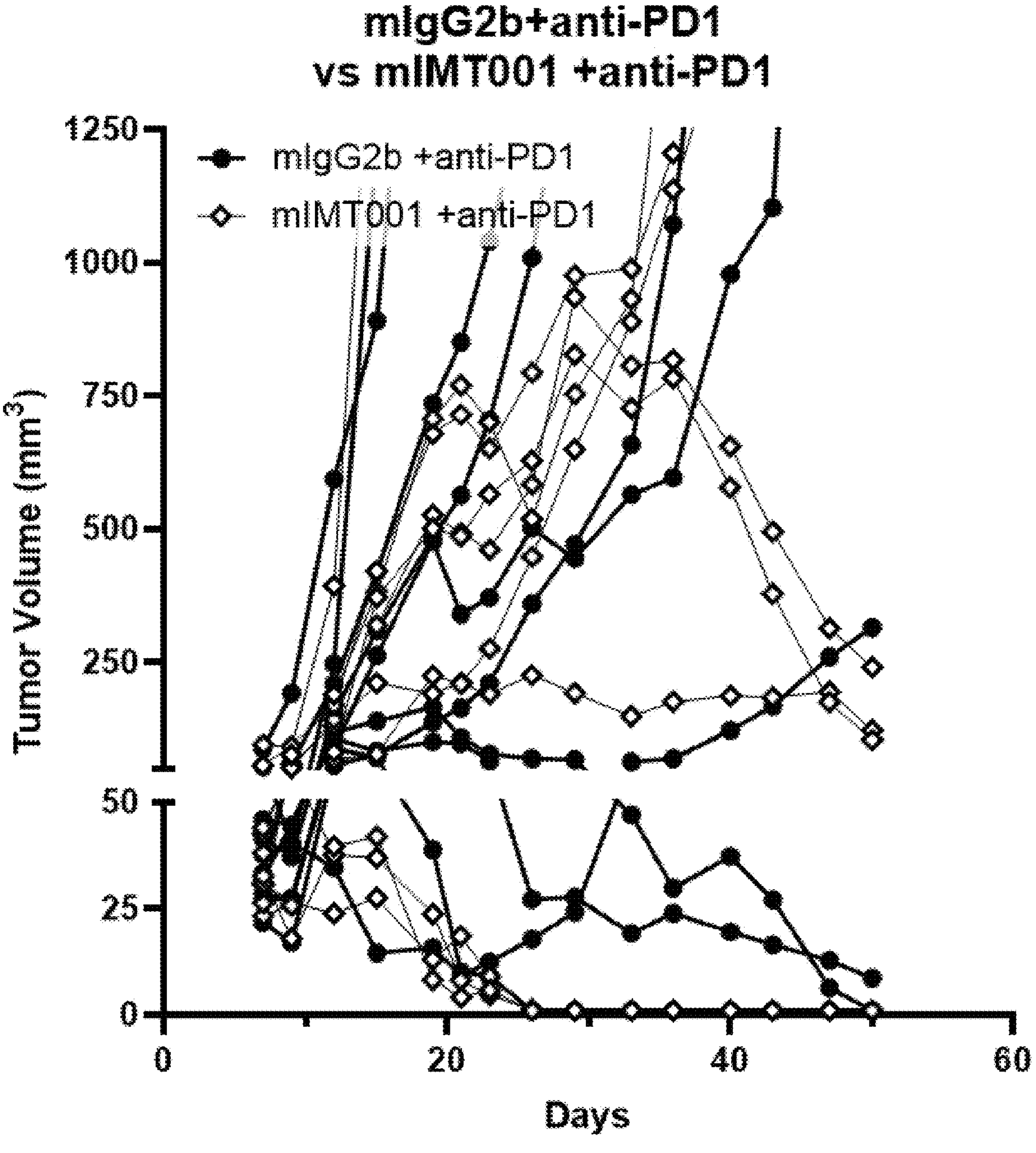

A separate study was conducted to evaluate the activity of mIMT001 in combination with anti-PD-1 antibodies in mice engrafted with subcutaneous MBT-2 tumors. As in the PD-1 study, treatment with isotype control or mIMT001 alone did not reduce tumor volumes (data not shown). In contrast, treatment with anti-PD-1 antibodies resulted in anti-tumor responses in 3/10 animals, as exhibited by significant reductions in tumor volume (FIGS. 28C-D). Significantly, 6/10 animals treated with the combination of mIMT001 and anti-PD-1 antibodies exhibited strong anti-tumor responses, representing a 100% increase in response rate relative to animals treated with anti-PD-1 antibodies alone. These data indicate that the combination of antibodies that block GAL3 and TIM3 with anti-PD-1 antibodies have significantly increased anti-tumor activity than anti-PD-1 antibodies do in isolation. Taken together with the PD-L1 combination study, these data indicate that GAL3-targeted antibodies that can block the interaction of GAL3-TIM3 have the capacity to more generally augment anti-tumor activity induced by interruption of the PD-1-PD-L1 checkpoint.

Example 29: GAL3-TIM3 Blocking Antibodies Exhibit Single-Agent Anti-Tumor Activity in HCC Further studies evaluating the activity of GAL3-TIM3 blocking antibodies were evaluated in the setting of a spontaneous hepatocellular carcinoma (HCC) model induced in STAM-CDAA mice. Briefly, Two-day-old male C57Bl/6 mice were injected by a single subcutaneous injection of 200 ug of streptozotocin to cause islet destruction and then fed CDAA-high fat diet (Research Diet #A06071302) starting at 4 weeks of age and continuing for the entire duration of each study. At 8 weeks of age, mice were divided into two groups (seven mice each). Mice were treated human anti-mIgG4 isotype control (hIgG4, 10 mg/kg) or human anti-Gal3 antibody (IMT001-4, 10 mg/kg) twice a week by intraperitoneal injection for 4 weeks. All animal care and procedures were approved by the Immutics IACUC.

Figure 29A:
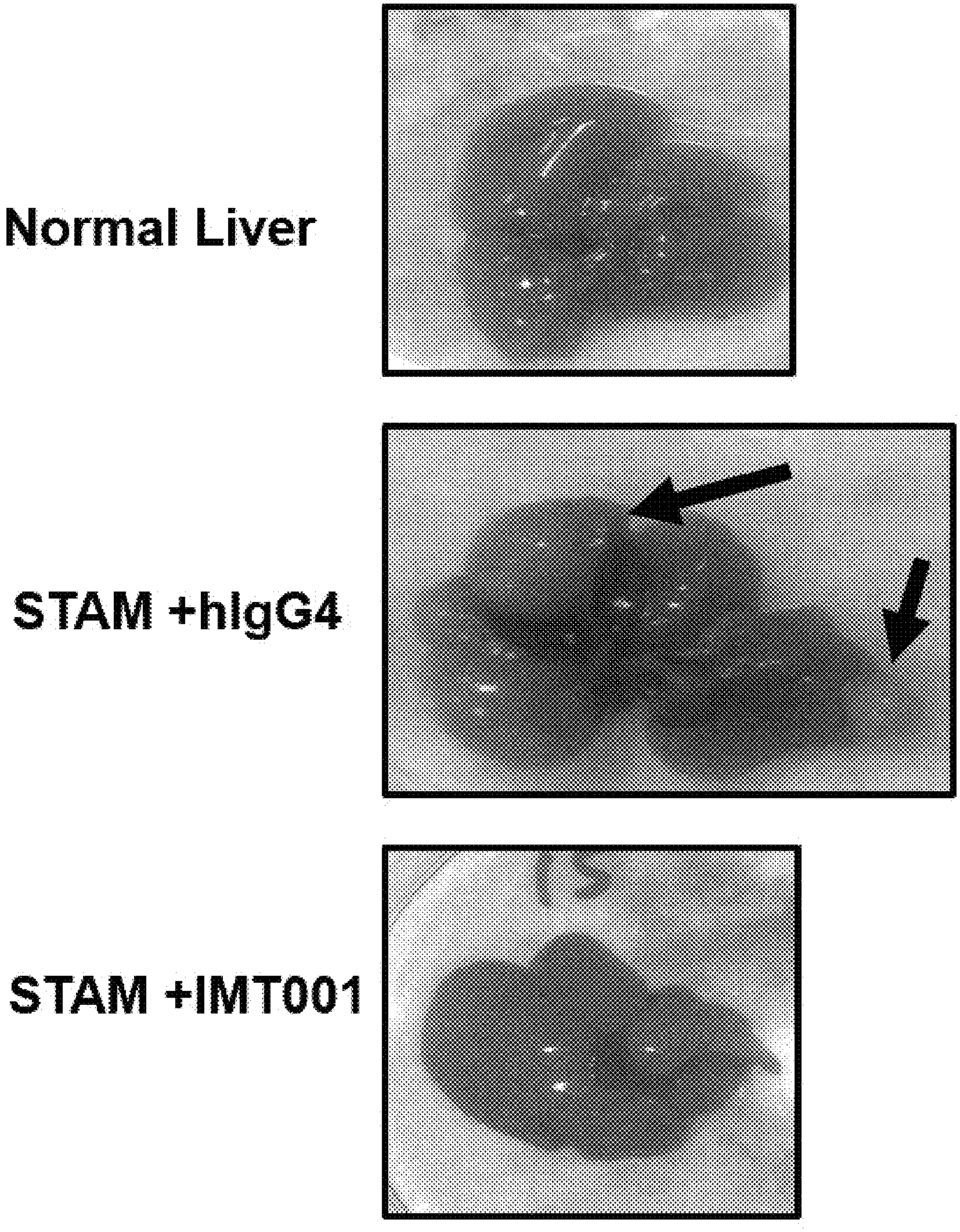
FIGS. 29A-D. Evaluation of hepatocellular carcinoma formation in normal and STAM-CDAA mice treated with human IgG4 (huIgG4) or IMT001-4 by gross histology (FIG. 29A) and enumerated (FIG. 29B). Arrows highlight areas with tumors. Hematoxylin and eosin stained sections of liver samples evaluated for tumor formation (FIG. 29C). Arrows highlight areas with tumors. Quantitation of alpha-fetoprotein in serum of STAM-CDAA mice treated with huIgG4 or IMT001-4 (FIG. 29D). Circles indicate mean values per animal, line indicates mean value per group.
Figure 29B:
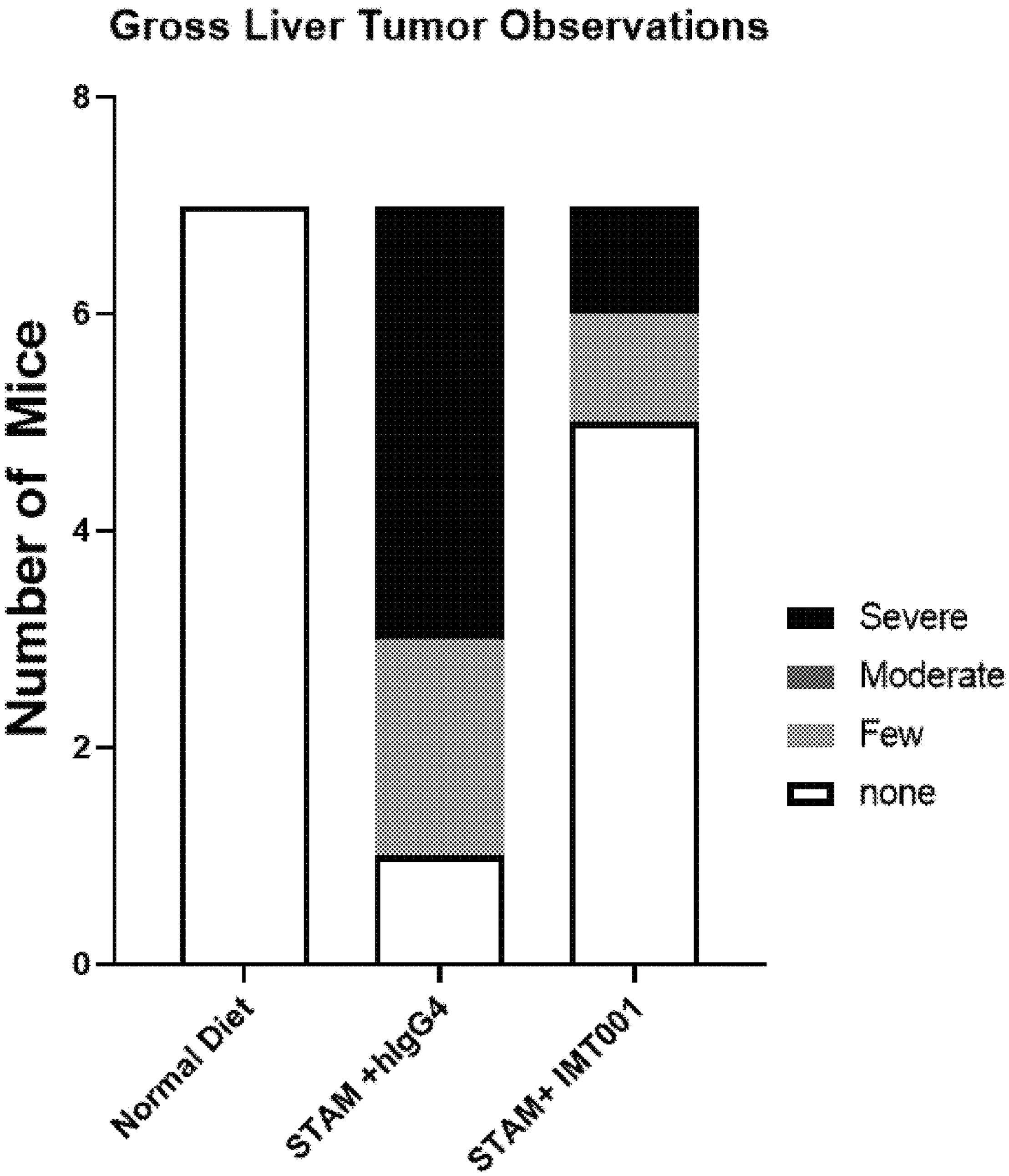

As depicted in FIGS. 29A-B, whereas no tumors were observed in animals kept on a normal diet, STAM-CDAA animals treated with isotype control antibodies exhibited signs of multifocal tumor generation as evident by gross inspection, with severe (>5 tumors per liver) formation noted in 4/7 animals and moderate formation (3-5 tumors per liver) noted in 2/7 animals, whereas only 1/7 was noted to be grossly free of tumors. In contrast, in animals treated with IMT001-4, tumor formation was significantly diminished, with only 1/7 animals exhibiting severe tumor formation, representing a 75% reduction in severe tumor formation and 1/7 animals exhibiting moderate tumor formation, representing a 50% reduction in moderate tumor formation. Correspondingly, IMT001-4 treated animals exhibited no gross signs of tumor formation in 5/7 animals, representing a 400% increase in apparently tumor-free animals.

Microscopic inspection of tumor specimens stained with hematoxylin and eosin was performed to evaluate the histology of the observed tumors. Briefly, livers were fixed in 4% paraformaldehyde (Electron Microscopy Sciences, Cat #15710S) for 24 hours, transferred to 70% EtOH for 72 hours, and samples were subsequently embedded in paraffin. 5 mM samples were cut and mounted on Apex Superior Adhesive Slides (Leica, Cat #3800080), followed by deparaffinization, rehydration in serial ethanol baths, staining in hematoxylin (Cat #HHS32-1L, MilliporeSigma) for 5 min, Define (Leica, Cat #3803590) for 1-minute, bluing buffer (Leica, Cat #3802916) for 1 minute and alcoholic Eosin Y515 (Leica, Cat #3801616) for 30 seconds, prior to their dehydration, clearing and coverslipping (Sakura Finetek, Cat #6500). Brightfield images were acquired under a Revolve microscope (Discover Echo, Inc.).

Figure 29C:
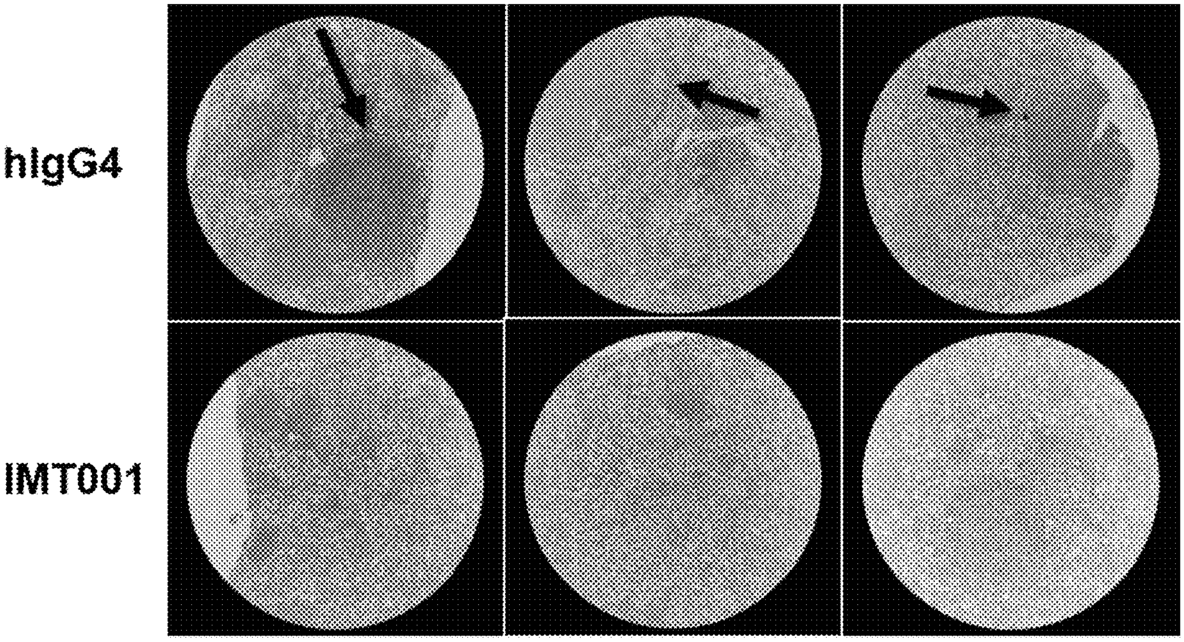

Consistent with the grossly observed tumors in livers from isotype-control treated animals, tissue sections revealed large multifocal regions of dysplastic hepatocytes surrounded by steatotic regions of fatty liver (FIG. 29C). Steatosis was expected as a consequence of the administered diet. Liver sections from IMT001-4 treated animals exhibited significantly fewer regions of dysplastic hepatocyte plaques, with rare representative regions depicted in FIG. 29C. It was noted that in addition to the increased rarity of tumor plaques, the size of tumor regions in IMT001-4 treated animals was also significantly smaller than in control-treated animals.

To more systemically assess the abundance of HCC in STAM-CDAA mice, serum levels of alpha-fetoprotein (AFP), a human clinical biomarker of HCC emergence, were evaluated in isotype- and IMT001-4 treated animals. Serum AFP was assayed by ELISA (R&D systems #MAFP00) according to the manufacturer's instructions.

Figure 29D:
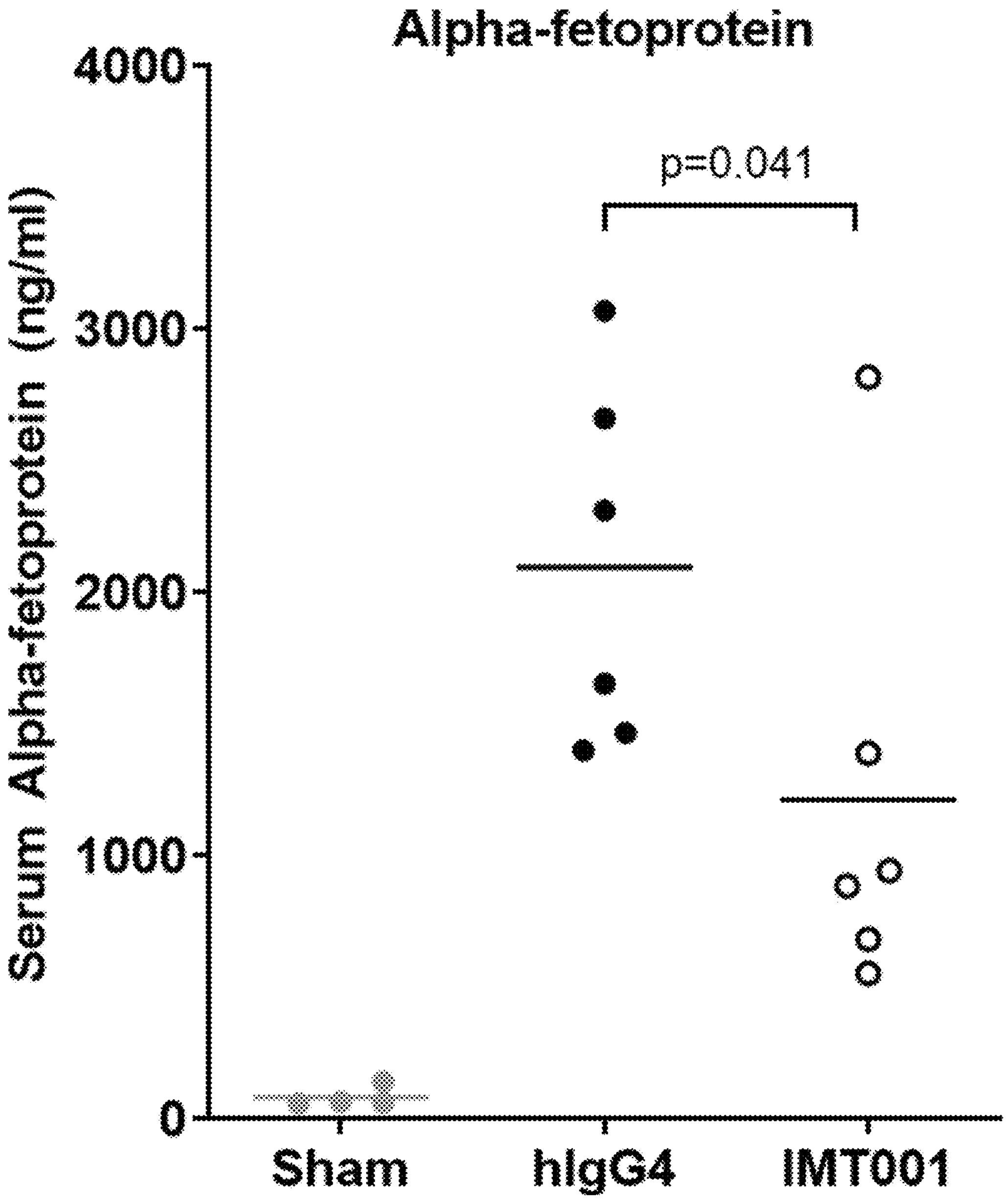

Normal mice exhibited low levels of AFP in serum, however, AFP was significantly elevated in STAM-CDAA mice treated with isotype control, with 3/6 animals exhibiting >2000 ng AFP/mL and 6/6 animals exhibiting >1000 ng AFP/mL (FIG. 29D). In contrast, IMT001-4 treated animals exhibited significantly reduced levels of AFP relative to isotype treated animals, with only 1/6 animals exhibiting >2000 ng AFP/mL, representing a 66% decrease and 2/6 animals exhibiting >1000 ng AFP/mL, also representing a 66% decrease. These data are consistent with the observed frequency and severity of tumor formation as noted by gross observation in FIG. 29A.

Taken together, these data demonstrate that humanized GAL3-TIM3 blocking antibodies can significantly reduce HCC tumor burden, and that these antibodies can have anti-tumor activity as a single agent.

Example 30: IMT001 Reduces Steatosis, Ballooning, and Inflammation in Methionine/Choline Deficient Model of NASH Fibrosis To further investigate the ability of GAL3-TIM3 blocking antibodies to influence liver fibrosis, the methionine-choline deficient (MCD) mouse model of liver fibrosis was employed. Briefly, Six-week-old male C57Bl/6 mice (Jackson Laboratory) were fed either a normal diet (Envigo, #2020X; n=5 mice); or MCD diet (Fisher Scientific, #MP296043910, n=25) for 8 weeks and continuously through the remainder of the study. Mice were divided into three groups (7 mice each) and randomized based on ALT score. Group 1 and 2 were treated mouse anti-mIgG2aLala isotype control (mISO, 10 mg/kg) or mouse anti-Gal3 antibody (mIMT001, 10 mg/kg) twice a week of IP injection for 4 weeks, at which time animals were sacrificed and liver specimens were collected, fixed in 4% paraformaldehyde (Electron Microscopy Sciences, Cat #15710S) for 24 hours, transferred to 70% EtOH for 72 hours, and samples were subsequently embedded in paraffin. 5 mM samples were cut and mounted on Apex Superior Adhesive Slides (Leica, Cat #3800080), followed by deparaffinization, rehydration in serial ethanol baths, staining in hematoxylin (Cat #HHS32-1L, MilliporeSigma) for 5 min, Define (Leica, Cat #3803590) for 1-minute, bluing buffer (Leica, Cat #3802916) for 1 minute and alcoholic Eosin Y515 (Leica, Cat #3801616) for 30 seconds, prior to their dehydration, clearing and coverslipping (Sakura Finetek, Cat #6500). Brightfield images were acquired under a Revolve microscope (Discover Echo, Inc.).

Figure 30A:
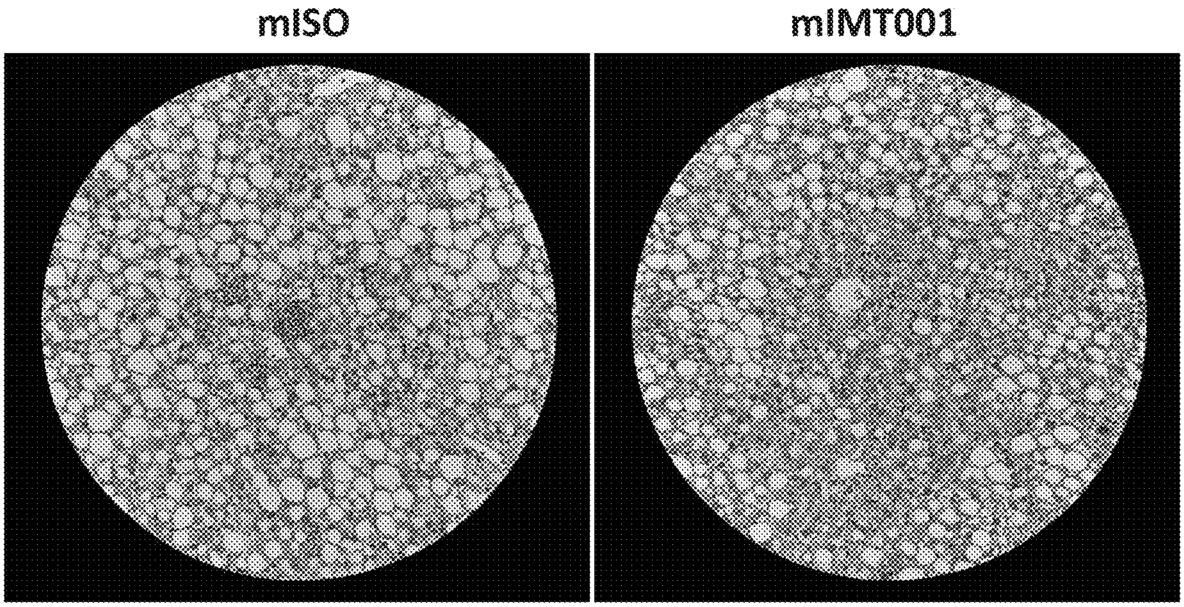
FIGS. 30A-D. Hematoxylin and eosin stained sections of livers from MCD mouse model of NASH liver fibrosis treated with isotype control or mIMT001 (FIG. 30A). Image-based quantification of histological findings measuring steatosis, hepatocellular ballooning, lobular inflammation, or NAFLD Activity Score (NAS) (FIG. 30B). Picosirius red staining of liver specimens from mice treated as in (A), (FIG. 30C). Image based-quantification of Sirius red staining (FIG. 30D). Bars represent mean value of 7 animals+/−standard error of the mean.
Figure 30B:
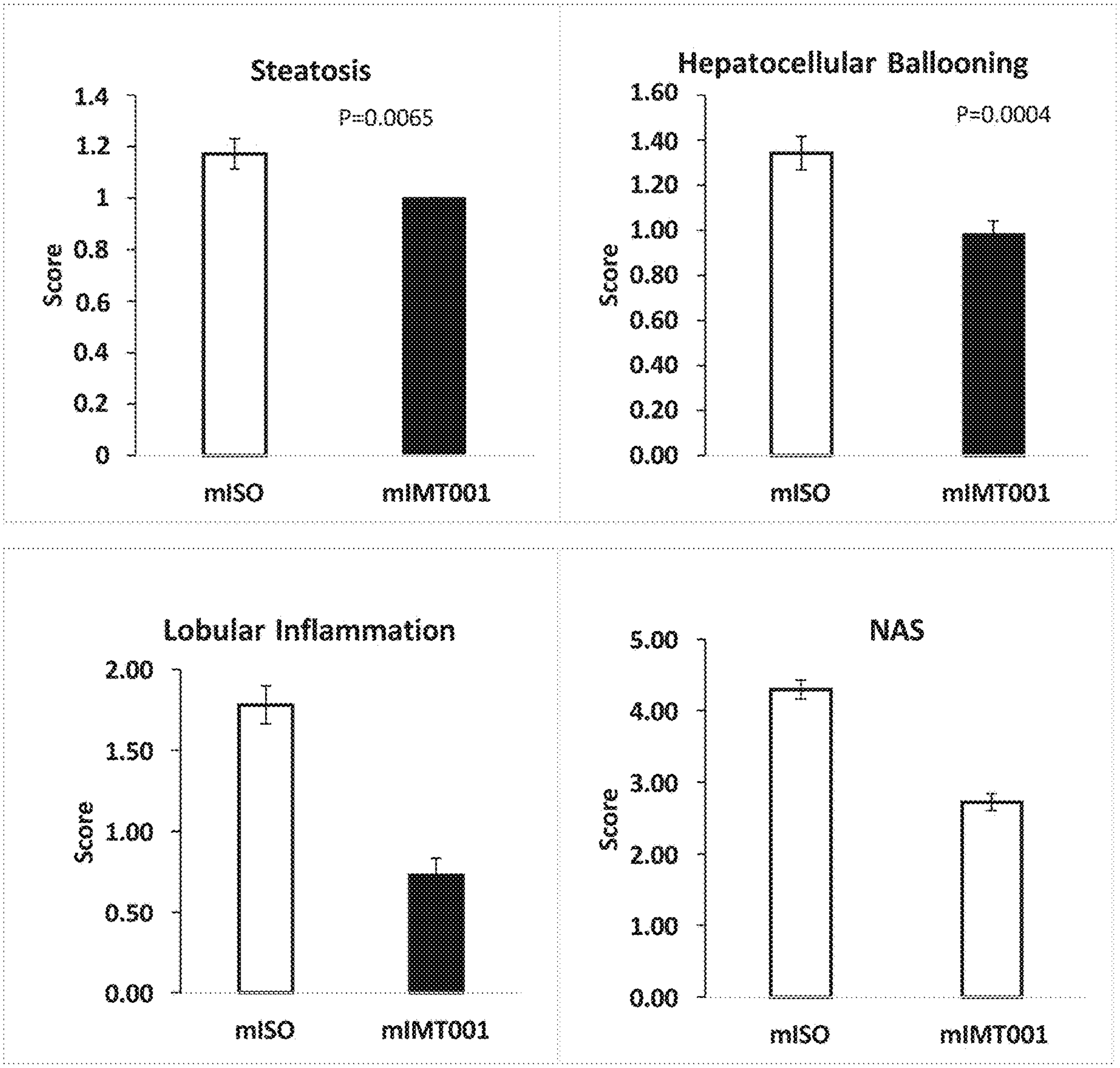
Figure 30C:
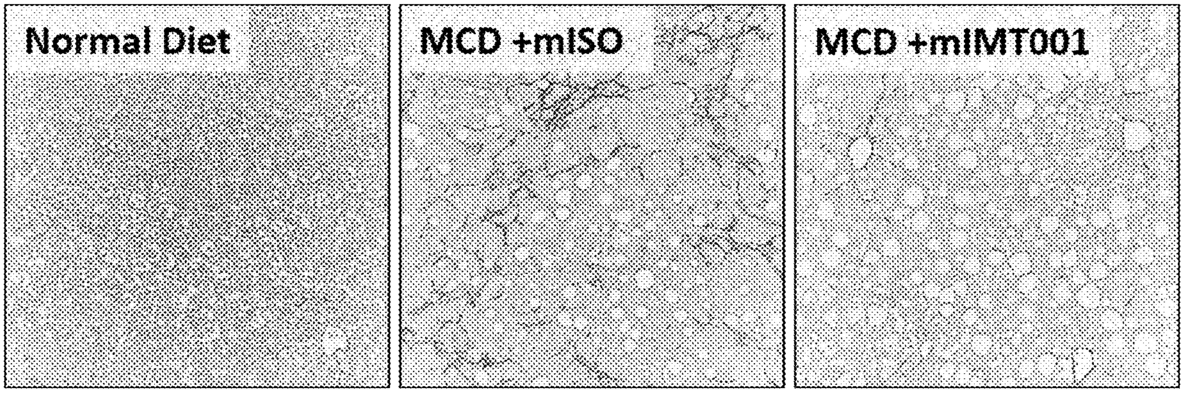

MCD mice treated with isotype control antibody exhibited signs of liver injury typical for this model, including steatosis, evident by the large white areas present in hematoxylin and eosin (H&E) stained liver specimens, hepatocellular ballooning evident by vacuolated apoptotic cells, and the presence of infiltrating immune cells, evident as clusters of largely nuclear cells with little cytoplasm (FIG. 30A). Liver specimens from mIMT001-treated MCD mice exhibited significant reductions in each of these measures of injury. To quantify the difference, image-based quantification was executed, revealing a modest, but statistically significant reduction of steatosis from 1.17 in control-treated specimens to 1 in mIMT001-treated specimens, a 15% reduction (FIG. 30B). Additionally, the presence of apoptotic ballooning cells was reduced from 1.34 in control-treated specimens to 0.98 in mIMT001-treated specimens, a 27% reduction. Further, the presence of infiltrating lobular immune cells was reduced from 1.78 in control-treated specimens to 0.73 in mIMT001-treated specimens a 59% reduction. An integrated NAS score was produced with these measurements, and mIMT001-treated animals exhibited significantly reduced NAS score of 2.72 relative to isotype control treated score of 4.29, a43% reduction. T-tests revealed that these observations were statistically significant both as individual observations and as an integrated NAS score.

To assess fibrosis in these specimens, tissue sections were evaluated for the deposition of fibrotic collagen deposits by picosirius red staining. Briefly, after deparaffinization, liver specimens from isotype control- or IMT001-treated MCD mice were rehydrated in serial ethanol baths, sections were stained in 0.01% Fast green FCF Solution (Cat #1.04022.0025 MilliporeSigma) in saturated picric aqueous solution for 15 minutes at room temperature, followed by 1h incubation at room temperature in 0.04% Fast green FCF/0.1% Sirius red in saturated picric aqueous solution, prior to their dehydration, clearing and mounting. Images were quantitated using ImageJ software (Rasband, W. S., ImageJ, U. S. National Institutes of Health, Bethesda, Maryland, USA, world wide web.imagej.nih.gov/ij/)

Figure 30D:
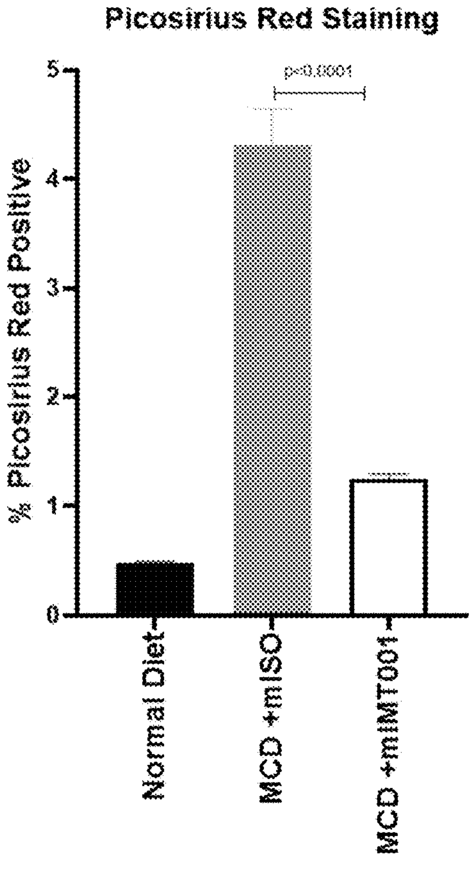

As shown in FIG. 30B, significant fibrosis was evident in liver sections of MCD mice treated with isotype control, as indicated by the presence of abundant picosirius red-positive collagen networks in these specimens. In contrast, liver sections of MCD mice treated with mIMT001 exhibited reduced levels of picosirius-red stained collagen deposits. Image-based quantification of picosirius red sections revealed that staining was reduced from 4.3% of the tissue area in specimens from isotype-control treated animals area to 1.25% of the area in mIMT001-treated specimens, a 71% reduction (FIG. 30D).

These data indicate that GAL3-TIM3 blocking antibodies can reduce liver fibrosis in the murine MCD model of liver fibrosis.

Example 31: IMT001-4 Reduces Liver Fibrosis in CDAA-HFD STAM Mice

To confirm that the observed reduction of liver fibrosis in the MCD mouse model was not unique to this setting, the activity of mIMT001 was explored in the STAM HFD-CDAA mouse model of liver fibrosis. Briefly, Two-day-old male C57Bl/6 mice were injected by a single subcutaneous injection of 200 ug of streptozotocin to cause islet destruction and then fed CDAA-high fat diet (Research Diet #A06071302) starting at 4 weeks of age and continuing for the entire duration of each study. At 8 weeks of age, mice were divided into two groups (seven mice each) based on ALT score. Mice were treated human anti-mIgG4 isotype control (hIgG4, 10 mg/kg) or human anti-Gal3 antibody (IMT001-4, 10 mg/kg) twice a week by intraperitoneal injection for 4 weeks. All animal care and procedures were approved by the Immutics IACUC.

Figure 31A:
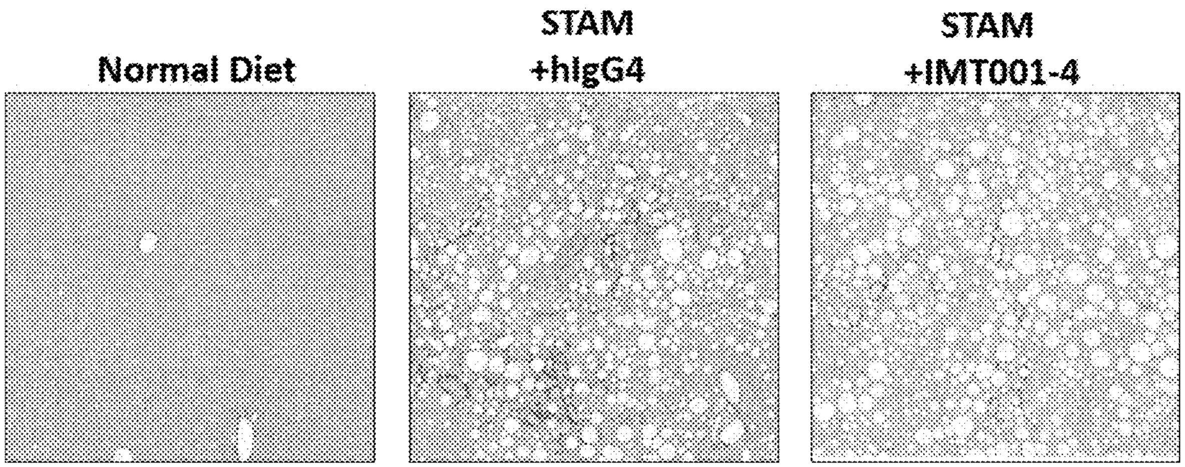
FIG. 31A-B. Picosirius red staining of liver specimens from choline-deficient L-amino defined high fat diet (CDAA-HFD) STAM model of liver fibrosis treated with isotype control or IMT001-4 (FIG. 31A). Image based-quantification of Sirius red staining (FIG. 31B). Bars represent mean value of 5 fields from each of 7 animals+/−standard error of the mean.
Figure 31B:
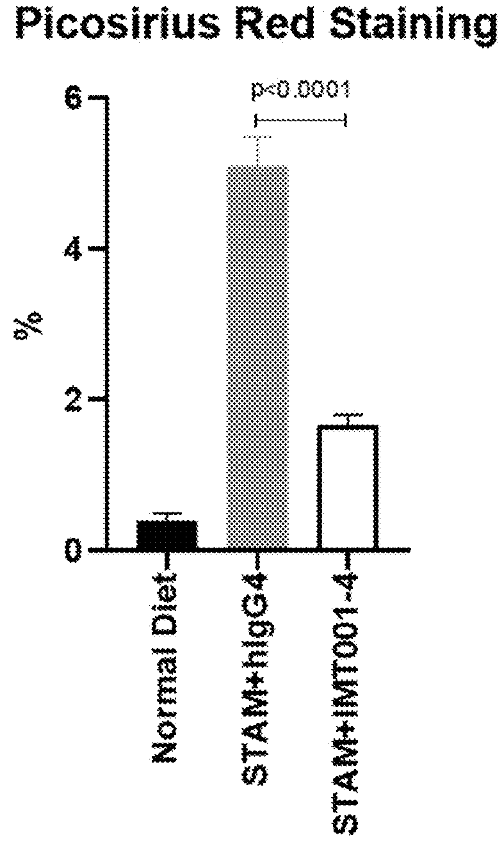

STAM CDAA-HFD mice treated with isotype control antibody exhibited signs of liver injury typical of this model, as evidenced in picosrius-red stained liver sections, which exhibited significant steatosis and the presence of abundant fibrotic collagen deposits (FIG. 31A). Liver specimens from IMT001-4 treated animals exhibited similar levels of steatosis compared to those control treated animals, but levels of picosirius red-positive fibrotic collagen deposits were substantially reduced. Image quantitation analysis of picosirius red staining revealed that whereas STAM CDAA-HFD treated with isotype control antibody exhibited 5.1% area picosirius red staining, this was reduced to 1.66% in specimens from IMT001-treated animals, a 67% reduction (FIG. 31B). These data indicate that GAL3-TIM3 blocking antibodies can reduce liver fibrosis in the murine STAM CDAA-HFD model of liver fibrosis, and taken together with the similar observations from the MCD model of liver fibrosis are strongly suggestive that anti-GAL3 antibodies with TIM3-GAL3 blocking activity have therapeutic potential in human fibrotic disease.

Example 32: Humanized Anti-Gal3 Antibodies Inhibit Kidney Fibrosis in UUO Mouse Model To further evaluate the ability of GAL3-targeted antibodies with the ability to block TIM3-GAL3 assembly to impact fibrosis, we evaluated the impact of humanized IMT001-4 and IMT006-1 in the mouse unilateral ureteral obstruction (UUO) model of kidney fibrosis. Briefly, 8-week-old C57BL/6J male mice were divided into sham, UUO with HuIgG4-, and UUO with HuIMT001-4, HuIMT006-1, and UUO with metformin-treatment. HuIgG4, HuIMT001-4 and HuIMT006-1 were each administered by intraperitoneal route at 10 mg/kg Q2Dx3 whereas metformin (500 mg/kg/day) was administered to mice dissolved in drinking water. In some settings therapeutic antibodies or metformin was administered 1 day before UUO, whereas in other experiments therapeutic antibodies or metformin was administered 1 day after UUO. After 7 days of UUO surgery, mice were sacrificed, left kidney was harvested and fixed with 4% paraformaldehyde for immunohistochemistry (IHC) and blood was collected in Heparin-EDTA tubes for blood biochemistry analysis. Levels of plasma mouse TIM-1/KIM-1/HAVCR were measured using a commercial ELISA kit (Catalog #MKM100; R&D Systems, Minneapolis, MN) according to the protocol provided by the manufacturer. Levels of plasma mouse Lipocalin-2/NGAL were measured using a commercial ELISA kit (Catalog #DY1857; R&D Systems, Minneapolis, MN) according to the protocol provided by the manufacturer. 5 um sections of fixed kidney specimens were produced and processed for picosirius red staining as described for liver specimens above.

Figure 32A:
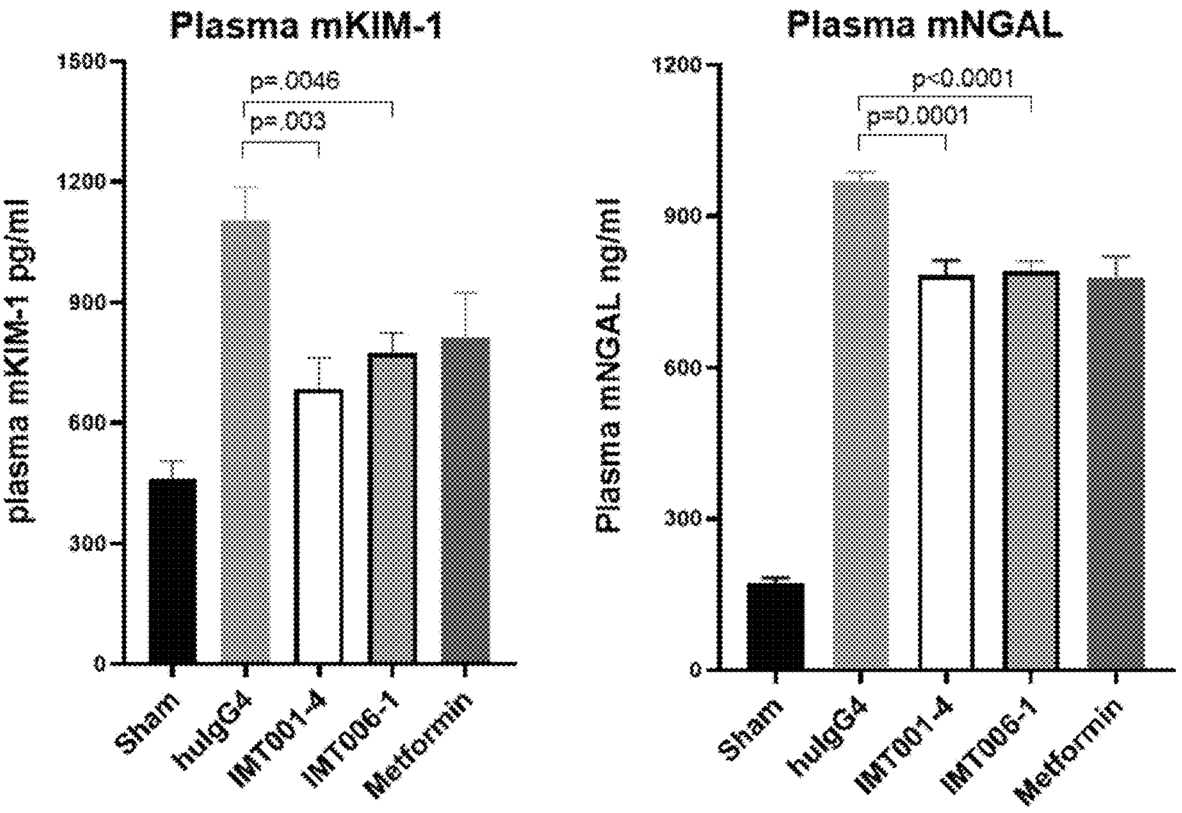
FIGS. 32A-C. Assessment of serum markers of kidney fibrosis KIM-1 and NGAL (FIG. 32A) and picosirius red staining of kidney specimens (FIG. 32B) from mice treated with isotype control, IMT001-4, IMT001-6, or metformin in mouse unilateral ureter obstruction (UUO) model. Image-based Picosirius red staining quantification (FIG. 32C). Bars represent the mean of triplicate assessments from each of seven animals per group+/−standard error of the mean. Points represent individual animal average picosirius red staining, bar indicates mean group value.

In an initial UUO experiment, animals were treated one day before UUO with isotype control antibody, IMT001-4, IMT006-1, or with metformin, a clinically proven modulator of kidney fibrosis. Assessment of KIM-1, a kidney injury marker associated with kidney fibrosis, revealed strong upregulation of KIM-1 in UUO specimens treated with isotype control antibody relative to sham-surgery treated animals, whereas animals treated with IMT001-4, or IMT006-1, KIM-1 levels were significantly reduced relative to controls (FIG. 32A). Metformin also reduced levels of KIM-1, however, due to inter-animal variability within this group the reduction was not statistically significant. Assessment of serum NGAL, another systemic kidney injury marker, demonstrated a similar pattern, wherein isotype-control treated UUO animals exhibited significantly elevated levels relative to sham-treated animals, and IMT001-4 and IMT006-1 treated UUO animals exhibited significant reductions in serum NGAL levels relative to isotype-treated UUO animals. In this setting, metformin proved to significantly impact NGAL levels.

Figure 32B:
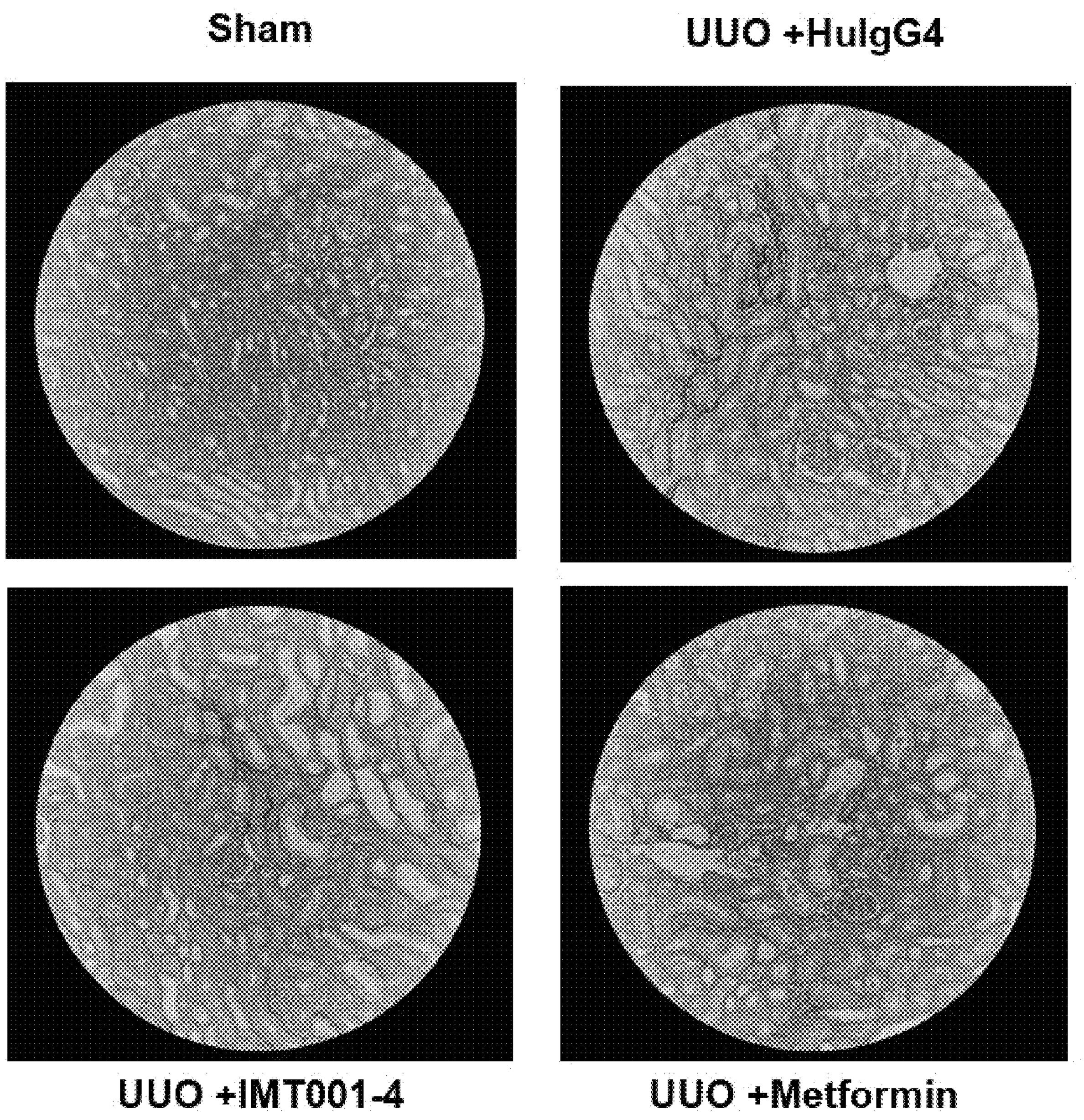
Figure 32C:
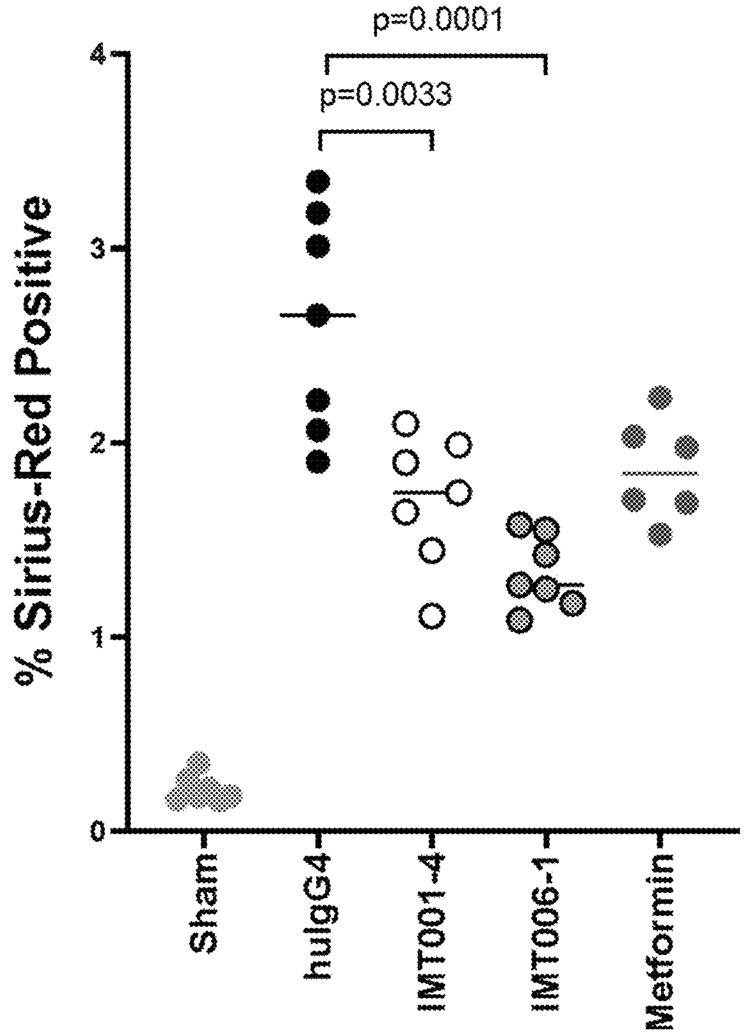

To directly evaluate kidney fibrosis in the UUO model, kidneys from animals treated as above were evaluated for fibrotic deposits by picosirius red staining. UUO animals treated with isotype antibody exhibited characteristic patterns of picosirius red staining (FIG. 32B). In contrast, kidney specimens from UUO mice treated with IMT001-4, IMT001-6, or metformin, showed substantial reductions in picosirius red staining. Image quantification of sections revealed that specimens from UUO treated with isotype exhibited 2.65% picosirius staining, whereas specimens from IMT001-4, IMT006-1, and metformin treated animals exhibited significantly reduced picosirius red staining, at 1.75%, 1.26%, and 1.83%, respectively (FIG. 32C).

Taken together, these observations indicate that humanized antibodies with GAL3-TIM3 blocking activity have anti-fibrotic activity in kidney fibrosis, extending the range of anti-fibrotic activity for GAL3-TIM3 blocking antibodies beyond liver fibrosis.

Figure 33A:
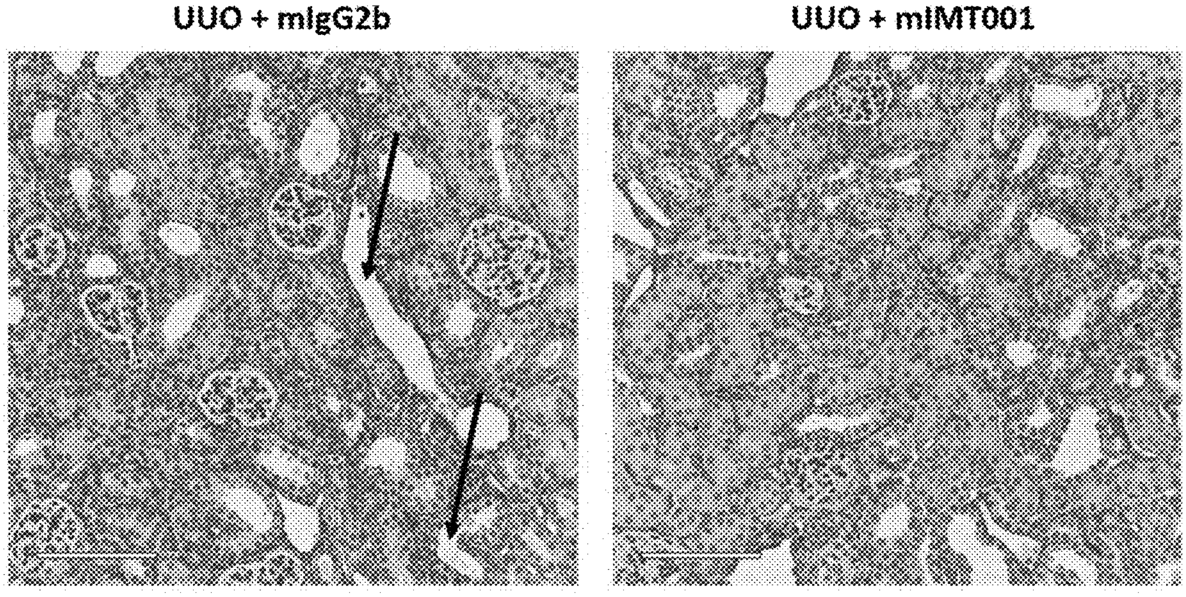
FIG. 33A-B. IHC assessment of Collagen 1a1 (Col1a1) deposition in kidney specimens treated 1 day after UUO treated with isotype control or mIMT001 (FIG. 33A). Black arrows correspond to areas of fibrotic collagen deposition. Image based quantitation (FIG. 33B). Bars represent mean value of 10 fields from each of 7 animals per group+/− standard error of the mean.
Figure 33B:
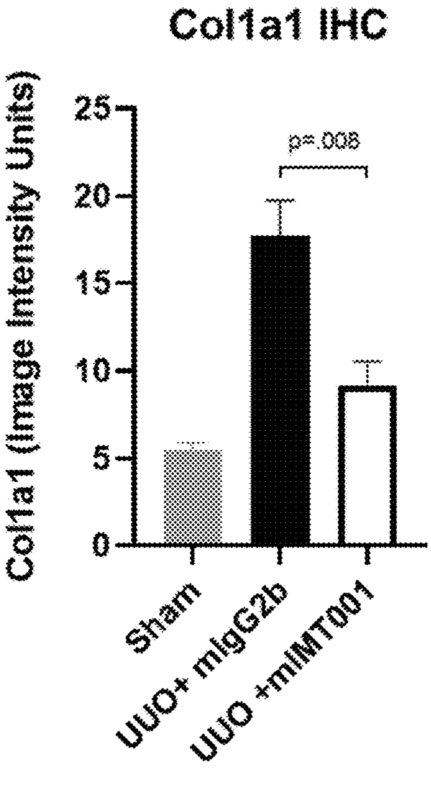

To evaluate the robustness of TIM3-GAL3 blocking antibodies in reducing kidney fibrosis, the ability of mIMT001 to inhibit fibrosis when administered one day after UUO surgery was evaluated. Following UUO surgery and treatment with isotype or control antibodies, kidney specimens were harvested and stained by IHC for Collagen 1a1 (Col1a1), a marker of kidney fibrosis. As shown in FIG. 33A, animals treated with mIMT001 exhibited reduced levels of Col1a1 staining than did specimens from animals treated with isotype control. Image quantification revealed that Col1a1 staining was significantly elevated in isotype-control treated UUO kidney specimens compared to sham control, enumerated at 5.48 intensity units in the former and 17.75 in the latter. Conversely, kidney specimens from mIMT001-treated animals were observed to be significantly reduced to 9.17 intensity units, representing a 48% overall reduction in this marker of fibrosis (FIG. 33B).

Accordingly, GAL3-TIM3 blocking antibodies offer not only a preventative benefit, but also a therapeutic benefit in kidney fibrosis.

Example 33: Anti-Gal3 Antibodies Inhibit Lung Fibrosis in Mouse Bleomycin-Induced Injury Model Fibrosis of the lung represents an additional significant form of fibrotic disease with significant health impacts in humans. To evaluate if the anti-fibrotic effects of GAL3-TIM3 blockade extend into the setting of lung fibrosis, a mouse bleomycin-induced lung fibrosis model was evaluated for sensitivity to mIMT001. Briefly, C57Blck/6 male mice were injected intra-tracheally with 30 ug of Bleomycin Sulfate (MP biomedicals, cat #190306) reconstituted in 50 ul of PBS. Mice were treated on day 18, 20, 22, and 24 with mIgG2b isotype control, anti-GAL3 antibody (mIMT001) (10 mg/kg) by tail vein injection, or small molecule TD139 (Med Chem Express, cat #HY-19940) at 10 uM in 50 ul of Captisol (Med Chem Express, cat #HY-17031) injected intra-tracheally. Mice were sacrificed on day 27 and lungs were surgically dissected and fixed in 4% paraformaldehyde for 24 hours, exchanged into 70% ethanol, and embedded in paraffin. Lung fibrosis in fixed specimens was evaluated by Masson's trichrome staining kit (26367) from Electron Microscopy Sciences (Hatfield, PA). 5 uM lung sections were affixed to glass slides, After deparaffinization, rehydration in serial ethanol baths. Staining was performed by incubating in Bouin's fixative for 1 h at 56 degree, staining with Briebrich Scarlet/acid fuchsin, Phosphomolybdic Acid-Phosphotungstic Acid and Aniline Blue, then differentiated in acetic acid, prior to their dehydration, clearing and mounting.

Figure 34A:
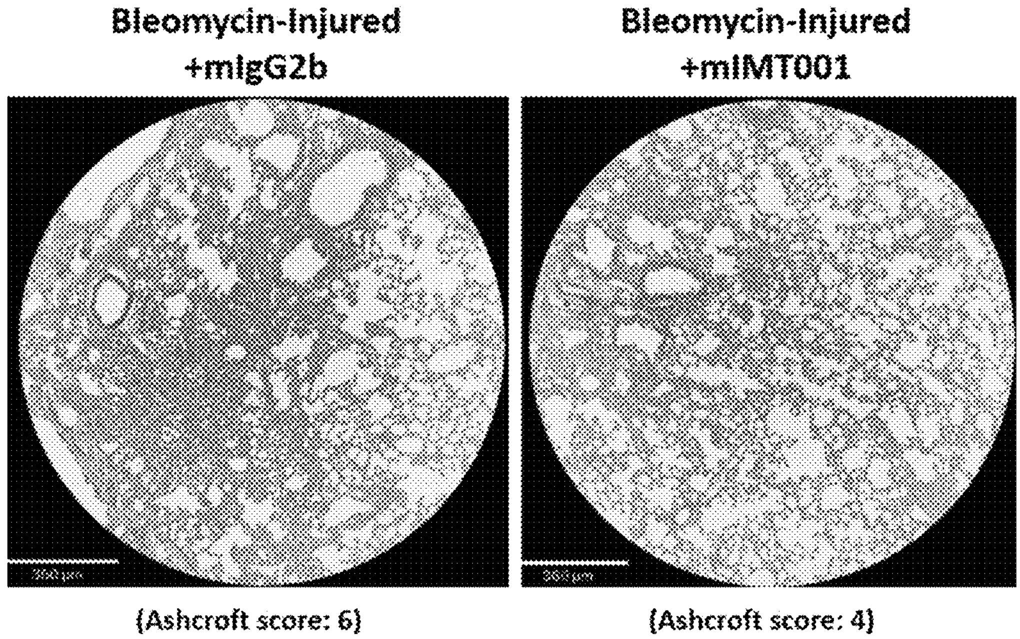
FIG. 34A-B. Masson's trichrome assessment of lung fibrosis in bleomycin-induced lung fibrosis mouse model treated with isotype control or mIMT001 (FIG. 34A). Ashcroft scoring of tissue sections (FIG. 34B). Bars represent the mean of 10 fields from each of 8 animals per group+/−standard error of the mean.
Figure 34B:
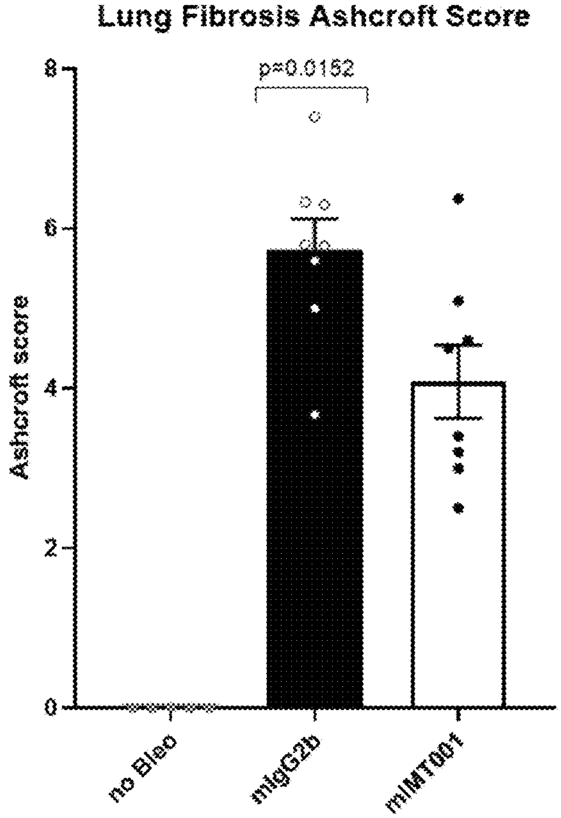

Bleomycin-injured lungs from isotype-control treated mice exhibited morphology typical of lung damage in this model, with substantial pulmonary fibrosis and alveolar scarring evident (FIG. 34A). In contrast, although evidence of injury was present in lungs from bleomycin injured animals treated with mIMT001, fibrosis was substantially reduced compared to isotype control. Lung injury was quantitated by Ashcroft scoring, revealing an average score of 5.74 for lungs from specimens from isotype-control treated animals compared to 4.09 in specimens from mIMT001-treated animals, a statistically significant reduction representing a 29% decrement in fibrotic injury (FIG. 34B). These data indicate that GAL3-targeted GAL3-TIM3 blocking antibodies can improve fibrotic disease in pulmonary fibrosis, extending similar prior observations made in kidney and liver fibrosis.

Example 34: Sequences of Anti-Gal3 Antibodies

Complementarity-determining region (CDR) sequences for the anti-Gal3 disclosed herein were determined. CDRs were mapped using IMGT (world wide web.ebi.ac.uk/ipd/imgt/hla/align.html). Heavy chain CDR (VH) are provided in FIG. 35A, and light chain CDR (VL) are provided in FIG. 35B. Full VH sequences are provided in FIG. 36A, and Full VH sequences are provided in FIG. 36B. Sequences for constant regions are provided in FIG. 37.

Complementarity determining regions of GAL3 binding antibodies from various bins were aligned using Clustal Omega (FIG. 38). Bin 1 antibodies shared significant homology in VH CDR1 and CDR2, as well as in regions of VL CDR1 and CDR3. Bin 2 antibodies shared significant homology in all CDRs examined, with relatively conservative A/S, V/T, H/D, and L/F substitutions observed. Bin 3 antibodies were somewhat more diverse, with significant sequence homology in CDR1, but relatively divergent in other CDR regions. Bin 4 antibodies antibodies shared significant homology in all CDRs examined, with relatively conservative A/T, I/V, D/G, S/N, QK, and V/L substitutions observed. Bin 5 antibodies also shared significant homology in all CDRs, with relatively conservative Y/F, N/K, substitutions observed in addition to less conservative T/I, N/Y substitutions. Finally, bin 7 antibody CDRs were observed to be nearly identical, with a single V/L substitution in VL CDR2 distinguishing 3B11.2G2 from 13A12.2E5. Alignments with any of the other sequences provided in FIG. 35A-B, 36A-B, 37, or 38 can be done with techniques known in the art.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All articles, patents, patent applications, and other publications which have been cited in this disclosure are hereby incorporated herein by reference in each of their entireties.

What is claimed is:

1. An anti-GAL3 antibody or binding fragment thereof, wherein the anti-Gal3 antibody or binding fragment thereof comprises (1) a light chain variable region comprising a VL-CDR1, a VL-CDR2, and a VL-CDR3; and (2) a heavy chain variable region comprising a VH-CDR1, a VH-CDR2, and a VH-CDR3, wherein the VH-CDR1 comprises an amino acid sequence comprising SEQ ID NO: 37, the VH-CDR2 comprises an amino acid sequence comprising SEQ ID NO: 65, the VH-CDR3 comprises an amino acid sequence comprising SEQ ID NO: 93, the VL-CDR1 comprises an amino acid sequence comprising SEQ ID NO: 121, the VL-CDR2 comprises an amino acid sequence comprising RMS, the VL-CDR3 comprises an amino acid sequence comprising SEQ ID NO: 177; or the VH-CDR1 comprises an amino acid sequence comprising SEQ ID NO: 38, the VH-CDR2 comprises an amino acid sequence comprising SEQ ID NO: 66, the VH-CDR3 comprises an amino acid sequence comprising SEQ ID NO: 94, the VL-CDR1 comprises an amino acid sequence comprising SEQ ID NO: 122, the VL-CDR2 comprises an amino acid sequence comprising LVS, the VL-CDR3 comprises an amino acid sequence comprising SEQ ID NO: 178; or the VH-CDR1 comprises an amino acid sequence comprising SEQ ID NO: 39, the VH-CDR2 comprises an amino acid sequence comprising SEQ ID NO: 67, the VH-CDR3 comprises an amino acid sequence comprising SEQ ID NO: 95, the VL-CDR1 comprises an amino acid sequence comprising SEQ ID NO: 123, the VL-CDR2 comprises an amino acid sequence comprising RMS, the VL-CDR3 comprises an amino acid sequence comprising SEQ ID NO: 179; or the VH-CDR1 comprises an amino acid sequence comprising SEQ ID NO: 40, the VH-CDR2 comprises an amino acid sequence comprising SEQ ID NO: 68, the VH-CDR3 comprises an amino acid sequence comprising SEQ ID NO: 96, the VL-CDR1 comprises an amino acid sequence comprising SEQ ID NO: 124, the VL-CDR2 comprises an amino acid sequence comprising LVS, the VL-CDR3 comprises an amino acid sequence comprising SEQ ID NO: 180; or the VH-CDR1 comprises an amino acid sequence comprising SEQ ID NO: 41, the VH-CDR2 comprises an amino acid sequence comprising SEQ ID NO: 69, the VH-CDR3 comprises an amino acid sequence comprising SEQ ID NO: 97, the VL-CDR1 comprises an amino acid sequence comprising SEQ ID NO: 125, the VL-CDR2 comprises an amino acid sequence comprising YTS, the VL-CDR3 comprises an amino acid sequence comprising SEQ ID NO: 181; or the VH-CDR1 comprises an amino acid sequence comprising SEQ ID NO: 42, the VH-CDR2 comprises an amino acid sequence comprising SEQ ID NO: 70, the VH-CDR3 comprises an amino acid sequence comprising SEQ ID NO: 98, the VL-CDR1 comprises an amino acid sequence comprising SEQ ID NO: 126, the VL-CDR2 comprises an amino acid sequence comprising KVS, the VL-CDR3 comprises an amino acid sequence comprising SEQ ID NO: 182; or the VH-CDR1 comprises an amino acid sequence comprising SEQ ID NO: 43, the VH-CDR2 comprises an amino acid sequence comprising SEQ ID NO: 71, the VH-CDR3 comprises an amino acid sequence comprising SEQ ID NO: 99, the VL-CDR1 comprises an amino acid sequence comprising SEQ ID NO: 127, the VL-CDR2 comprises an amino acid sequence comprising HAT, the VL-CDR3 comprises an amino acid sequence comprising SEQ ID NO: 183; or the VH-CDR1 comprises an amino acid sequence comprising SEQ ID NO: 44, the VH-CDR2 comprises an amino acid sequence comprising SEQ ID NO: 72, the VH-CDR3 comprises an amino acid sequence comprising SEQ ID NO: 100, the VL-CDR1 comprises an amino acid sequence comprising SEQ ID NO: 128, the VL-CDR2 comprises an amino acid sequence comprising LLS, the VL-CDR3 comprises an amino acid sequence comprising SEQ ID NO: 184; or the VH-CDR1 comprises an amino acid sequence comprising SEQ ID NO: 45, the VH-CDR2 comprises an amino acid sequence comprising SEQ ID NO: 73, the VH-CDR3 comprises an amino acid sequence comprising SEQ ID NO: 101, the VL-CDR1 comprises an amino acid sequence comprising SEQ ID NO: 129, the VL-CDR2 comprises an amino acid sequence comprising GAS, the VL-CDR3 comprises an amino acid sequence comprising SEQ ID NO: 185; or the VH-CDR1 comprises an amino acid sequence comprising SEQ ID NO: 46, the VH-CDR2 comprises an amino acid sequence comprising SEQ ID NO: 74, the VH-CDR3 comprises an amino acid sequence comprising SEQ ID NO: 102, the VL-CDR1 comprises an amino acid sequence comprising SEQ ID NO: 130, the VL-CDR2 comprises an amino acid sequence comprising LVS, the VL-CDR3 comprises an amino acid sequence comprising SEQ ID NO: 186; or the VH-CDR1 comprises an amino acid sequence comprising SEQ ID NO: 47, the VH-CDR2 comprises an amino acid sequence comprising SEQ ID NO: 75, the VH-CDR3 comprises an amino acid sequence comprising SEQ ID NO: 103, the VL-CDR1 comprises an amino acid sequence comprising SEQ ID NO: 131, the VL-CDR2 comprises an amino acid sequence comprising LVS, the VL-CDR3 comprises an amino acid sequence comprising SEQ ID NO: 187; or the VH-CDR1 comprises an amino acid sequence comprising SEQ ID NO: 48, the VH-CDR2 comprises an amino acid sequence comprising SEQ ID NO: 76, the VH-CDR3 comprises an amino acid sequence comprising SEQ ID NO: 104, the VL-CDR1 comprises an amino acid sequence comprising SEQ ID NO: 132, the VL-CDR2 comprises an amino acid sequence comprising KVS, the VL-CDR3 comprises an amino acid sequence comprising SEQ ID NO: 188; or the VH-CDR1 comprises an amino acid sequence comprising SEQ ID NO: 49, the VH-CDR2 comprises an amino acid sequence comprising SEQ ID NO: 77, the VH-CDR3 comprises an amino acid sequence comprising SEQ ID NO: 105, the VL-CDR1 comprises an amino acid sequence comprising SEQ ID NO: 133, the VL-CDR2 comprises an amino acid sequence comprising KAS, the VL-CDR3 comprises an amino acid sequence comprising SEQ ID NO: 189; or the VH-CDR1 comprises an amino acid sequence comprising SEQ ID NO: 50, the VH-CDR2 comprises an amino acid sequence comprising SEQ ID NO: 78, the VH-CDR3 comprises an amino acid sequence comprising SEQ ID NO: 106, the VL-CDR1 comprises an amino acid sequence comprising SEQ ID NO: 134, the VL-CDR2 comprises an amino acid sequence comprising YAS, the VL-CDR3 comprises an amino acid sequence comprising SEQ ID NO: 190; or the VH-CDR1 comprises an amino acid sequence comprising SEQ ID NO: 51, the VH-CDR2 comprises an amino acid sequence comprising SEQ ID NO: 79, the VH-CDR3 comprises an amino acid sequence comprising SEQ ID NO: 107, the VL-CDR1 comprises an amino acid sequence comprising SEQ ID NO: 135, the VL-CDR2 comprises an amino acid sequence comprising LVS, the VL-CDR3 comprises an amino acid sequence comprising SEQ ID NO: 191; or the VH-CDR1 comprises an amino acid sequence comprising SEQ ID NO: 52, the VH-CDR2 comprises an amino acid sequence comprising SEQ ID NO: 80, the VH-CDR3 comprises an amino acid sequence comprising SEQ ID NO: 108, the VL-CDR1 comprises an amino acid sequence comprising SEQ ID NO: 136, the VL-CDR2 comprises an amino acid sequence comprising KAS, the VL-CDR3 comprises an amino acid sequence comprising SEQ ID NO: 192; or the VH-CDR1 comprises an amino acid sequence comprising SEQ ID NO: 54, the VH-CDR2 comprises an amino acid sequence comprising SEQ ID NO: 82, the VH-CDR3 comprises an amino acid sequence comprising SEQ ID NO: 110, the VL-CDR1 comprises an amino acid sequence comprising SEQ ID NO: 138, the VL-CDR2 comprises an amino acid sequence comprising YAS, the VL-CDR3 comprises an amino acid sequence comprising SEQ ID NO: 194; or the VH-CDR1 comprises an amino acid sequence comprising SEQ ID NO: 55, the VH-CDR2 comprises an amino acid sequence comprising SEQ ID NO: 83, the VH-CDR3 comprises an amino acid sequence comprising SEQ ID NO: 111, the VL-CDR1 comprises an amino acid sequence comprising SEQ ID NO: 139, the VL-CDR2 comprises an amino acid sequence comprising WAS, the VL-CDR3 comprises an amino acid sequence comprising SEQ ID NO: 195; or the VH-CDR1 comprises an amino acid sequence comprising SEQ ID NO: 56, the VH-CDR2 comprises an amino acid sequence comprising SEQ ID NO: 84, the VH-CDR3 comprises an amino acid sequence comprising SEQ ID NO: 112, the VL-CDR1 comprises an amino acid sequence comprising SEQ ID NO: 140, the VL-CDR2 comprises an amino acid sequence comprising WAS, the VL-CDR3 comprises an amino acid sequence comprising SEQ ID NO: 196; or the VH-CDR1 comprises an amino acid sequence comprising SEQ ID NO: 57, the VH-CDR2 comprises an amino acid sequence comprising SEQ ID NO: 85, the VH-CDR3 comprises an amino acid sequence comprising SEQ ID NO: 113, the VL-CDR1 comprises an amino acid sequence comprising SEQ ID NO: 141, the VL-CDR2 comprises an amino acid sequence comprising WAS, the VL-CDR3 comprises an amino acid sequence comprising SEQ ID NO: 197; or the VH-CDR1 comprises an amino acid sequence comprising SEQ ID NO: 58, the VH-CDR2 comprises an amino acid sequence comprising SEQ ID NO: 86, the VH-CDR3 comprises an amino acid sequence comprising SEQ ID NO: 114, the VL-CDR1 comprises an amino acid sequence comprising SEQ ID NO: 142, the VL-CDR2 comprises an amino acid sequence comprising LVC, the VL-CDR3 comprises an amino acid sequence comprising SEQ ID NO: 198; or the VH-CDR1 comprises an amino acid sequence comprising SEQ ID NO: 59, the VH-CDR2 comprises an amino acid sequence comprising SEQ ID NO: 87, the VH-CDR3 comprises an amino acid sequence comprising SEQ ID NO: 115, the VL-CDR1 comprises an amino acid sequence comprising SEQ ID NO: 143, the VL-CDR2 comprises an amino acid sequence comprising WAS, the VL-CDR3 comprises an amino acid sequence comprising SEQ ID NO: 199; or the VH-CDR1 comprises an amino acid sequence comprising SEQ ID NO: 61, the VH-CDR2 comprises an amino acid sequence comprising SEQ ID NO: 89, the VH-CDR3 comprises an amino acid sequence comprising SEQ ID NO: 117, the VL-CDR1 comprises an amino acid sequence comprising SEQ ID NO: 145, the VL-CDR2 comprises an amino acid sequence comprising RMS, the VL-CDR3 comprises an amino acid sequence comprising SEQ ID NO: 201; or the VH-CDR1 comprises an amino acid sequence comprising SEQ ID NO: 63, the VH-CDR2 comprises an amino acid sequence comprising SEQ ID NO: 91, the VH-CDR3 comprises an amino acid sequence comprising SEQ ID NO: 119, the VL-CDR1 comprises an amino acid sequence comprising SEQ ID NO: 147, the VL-CDR2 comprises an amino acid sequence comprising RMS, the VL-CDR3 comprises an amino acid sequence comprising SEQ ID NO: 203; or the VH-CDR1 comprises an amino acid sequence comprising SEQ ID NO: 64, the VH-CDR2 comprises an amino acid sequence comprising SEQ ID NO: 92, the VH-CDR3 comprises an amino acid sequence comprising SEQ ID NO: 120, the VL-CDR1 comprises an amino acid sequence comprising SEQ ID NO: 148, the VL-CDR2 comprises an amino acid sequence comprising SEQ ID NO: 176, the VL-CDR3 comprises an amino acid sequence comprising SEQ ID NO: 204.

2. An anti-GAL3 antibody or binding fragment thereof, wherein the antibody or binding fragment comprises:

a heavy chain sequence comprising SEQ ID NO: 205 and a light chain sequence comprising SEQ ID NO: 233; or a heavy chain sequence comprising SEQ ID NO: 206 and a light chain sequence comprising SEQ ID NO: 234; or a heavy chain sequence comprising SEQ ID NO: 207 and a light chain sequence comprising SEQ ID NO: 235; or a heavy chain sequence comprising SEQ ID NO: 208 and a light chain sequence comprising SEQ ID NO: 236; or a heavy chain sequence comprising SEQ ID NO: 209 and a light chain sequence comprising SEQ ID NO: 237; or a heavy chain sequence comprising SEQ ID NO: 210 and a light chain sequence comprising SEQ ID NO: 238; or a heavy chain sequence comprising SEQ ID NO: 211 and a light chain sequence comprising SEQ ID NO: 239; or a heavy chain sequence comprising SEQ ID NO: 212 and a light chain sequence comprising SEQ ID NO: 240; or a heavy chain sequence comprising SEQ ID NO: 213 and a light chain sequence comprising SEQ ID NO: 241; or a heavy chain sequence comprising SEQ ID NO: 214 and a light chain sequence comprising SEQ ID NO: 242; or a heavy chain sequence comprising SEQ ID NO: 215 and a light chain sequence comprising SEQ ID NO: 243; or a heavy chain sequence comprising SEQ ID NO: 216 and a light chain sequence comprising SEQ ID NO: 244; or a heavy chain sequence comprising SEQ ID NO: 217 and a light chain sequence comprising SEQ ID NO: 245; or a heavy chain sequence comprising SEQ ID NO: 218 and a light chain sequence comprising SEQ ID NO: 246; or a heavy chain sequence comprising SEQ ID NO: 219 and a light chain sequence comprising SEQ ID NO: 247; or a heavy chain sequence comprising SEQ ID NO: 220 and a light chain sequence comprising SEQ ID NO: 248; or a heavy chain sequence comprising SEQ ID NO: 222 and a light chain sequence comprising SEQ ID NO: 250; or a heavy chain sequence comprising SEQ ID NO: 223 and a light chain sequence comprising SEQ ID NO: 251; or a heavy chain sequence comprising SEQ ID NO: 224 and a light chain sequence comprising SEQ ID NO: 252; or a heavy chain sequence comprising SEQ ID NO: 225 and a light chain sequence comprising SEQ ID NO: 253; or a heavy chain sequence comprising SEQ ID NO: 226 and a light chain sequence comprising SEQ ID NO: 254; or a heavy chain sequence comprising SEQ ID NO: 227 and a light chain sequence comprising SEQ ID NO: 255; or a heavy chain sequence comprising SEQ ID NO: 229 and a light chain sequence comprising SEQ ID NO: 257; or a heavy chain sequence comprising SEQ ID NO: 230 and a light chain sequence comprising SEQ ID NO: 258; or a heavy chain sequence comprising SEQ ID NO: 231 and a light chain sequence comprising SEQ ID NO: 259; or a heavy chain sequence comprising SEQ ID NO: 232 and a light chain sequence comprising SEQ ID NO: 260.

3. A method of inducing immune activation, comprising:

contacting a plurality of cells comprising a Gal3-expressing cell and a TIM-3-expressing cell with the anti-Gal3 antibody of claim 1 under conditions to disrupt an interaction between Gal3 and TIM-3, wherein upon binding to the antibody, the Gal3-expressing cell expresses a cytokine which induces immune activation.

4. A method of promoting T cell or Natural Killer (NK) cell proliferation, comprising:

contacting a plurality of cells comprising T cells, NK cells, and a Gal3-expressing cell with the anti-Gal3 antibody or binding fragment thereof of claim 1 under conditions to effect proliferation of T cells and/or NK cells in the plurality of cells.

5. A method of inducing immune activation, comprising:

contacting a plurality of cells comprising a Gal3-expressing cell and a TIM-3-expressing cell with the anti-Gal3 antibody or binding fragment thereof of claim 1 under conditions to disrupt an interaction between Gal3 and TIM-3, wherein the Gal3-TIM-3 interaction is reduced to less than 70%, less than 60%, less than 59%, less than 50%, less than 40%, less than 34%, less than 30%, less than 20%, less than 14%, less than 10%, less than 7%, less than 5%, less than 4%, or less than 1%.

* * * * *

SEQUENCE LISTING

```
Sequence total quantity: 315
SEQ ID NO: 1            moltype = AA  length = 250
FEATURE                 Location/Qualifiers
source                  1..250
                        mol_type = protein
                        organism = Homo sapiens
SEQUENCE: 1
MADNFSLHDA LSGSGNPNPQ GWPGAWGNQP AGAGGYPGAS YPGAYPGQAP PGAYPGQAPP  60
GAYPGAPGAY PGAPAPGVYP GPPSGPGAYP SSGQPSATGA YPATGPYGAP AGPLIVPYNL  120
PLPGGVVPRM LITILGTVKP NANRIALDFQ RGNDVAFHFN PRFNENNRRV IVCNTKLDNN  180
WGREERQSVF PFESGKPFKI QVLVEPDHFK VAVNDAHLLQ YNHRVKKLNE ISKLGISGDI  240
DLTSASYTMI                                                         250

SEQ ID NO: 2            moltype = AA  length = 301
FEATURE                 Location/Qualifiers
source                  1..301
                        mol_type = protein
                        organism = Homo sapiens
SEQUENCE: 2
MFSHLPFDCV LLLLLLLLTR SSEVEYRAEV GQNAYLPCFY TPAAPGNLVP VCWGKGACPV  60
FECGNVVLRT DERDVNYWTS RYWLNGDFRK GDVSLTIENV TLADSGIYCC RIQIPGIMND  120
EKFNLKLVIK PAKVTPAPTR QRDFTAAFPR MLTTRGHGPA ETQTLGSLPD INLTQISTLA  180
NELRDSRLAN DLRDSGATIR IGIYIGAGIC AGLALALIFG ALIFKWYSHS KEKIQNLSLI  240
SLANLPPSGL ANAVAEGIRS EENIYTIEEN VYEVEEPNEY YCYVSSRQQP SQPLGCRFAM  300
P                                                                  301
```

```
SEQ ID NO: 3            moltype = AA  length = 20
FEATURE                 Location/Qualifiers
source                  1..20
                        mol_type = protein
                        organism = Homo sapiens
SEQUENCE: 3
ADNFSLHDAL SGSGNPNPQG                                               20

SEQ ID NO: 4            moltype = AA  length = 20
FEATURE                 Location/Qualifiers
source                  1..20
                        mol_type = protein
                        organism = Homo sapiens
SEQUENCE: 4
SGSGNPNPQG WPGAWGNQPA                                               20

SEQ ID NO: 5            moltype = AA  length = 20
FEATURE                 Location/Qualifiers
source                  1..20
                        mol_type = protein
                        organism = Homo sapiens
SEQUENCE: 5
WPGAWGNQPA GAGGYPGASY                                               20

SEQ ID NO: 6            moltype = AA  length = 20
FEATURE                 Location/Qualifiers
source                  1..20
                        mol_type = protein
                        organism = Homo sapiens
SEQUENCE: 6
GAGGYPGASY PGAYPGQAPP                                               20

SEQ ID NO: 7            moltype = AA  length = 20
FEATURE                 Location/Qualifiers
source                  1..20
                        mol_type = protein
                        organism = Homo sapiens
SEQUENCE: 7
PGAYPGQAPP GAYPGQAPPG                                               20

SEQ ID NO: 8            moltype = AA  length = 20
FEATURE                 Location/Qualifiers
source                  1..20
                        mol_type = protein
                        organism = Homo sapiens
SEQUENCE: 8
GAYPGQAPPG AYPGAPGAYP                                               20

SEQ ID NO: 9            moltype = AA  length = 20
FEATURE                 Location/Qualifiers
source                  1..20
                        mol_type = protein
                        organism = Homo sapiens
SEQUENCE: 9
AYPGAPGAYP GAPAPGVYPG                                               20

SEQ ID NO: 10           moltype = AA  length = 20
FEATURE                 Location/Qualifiers
source                  1..20
                        mol_type = protein
                        organism = Homo sapiens
SEQUENCE: 10
GAPAPGVYPG PPSGPGAYPS                                               20

SEQ ID NO: 11           moltype = AA  length = 20
FEATURE                 Location/Qualifiers
source                  1..20
                        mol_type = protein
                        organism = Homo sapiens
SEQUENCE: 11
PPSGPGAYPS SGQPSATGAY                                               20

SEQ ID NO: 12           moltype = AA  length = 20
FEATURE                 Location/Qualifiers
source                  1..20
                        mol_type = protein
                        organism = Homo sapiens
SEQUENCE: 12
```

```
SGQPSATGAY PATGPYGAPA                                                    20

SEQ ID NO: 13            moltype = AA  length = 20
FEATURE                  Location/Qualifiers
source                   1..20
                         mol_type = protein
                         organism = Homo sapiens
SEQUENCE: 13
PATGPYGAPA GPLIVPYNLP                                                    20

SEQ ID NO: 14            moltype = AA  length = 20
FEATURE                  Location/Qualifiers
source                   1..20
                         mol_type = protein
                         organism = Homo sapiens
SEQUENCE: 14
GPLIVPYNLP LPGGVVPRML                                                    20

SEQ ID NO: 15            moltype = AA  length = 20
FEATURE                  Location/Qualifiers
source                   1..20
                         mol_type = protein
                         organism = Homo sapiens
SEQUENCE: 15
LPGGVVPRML ITILGTVKPN                                                    20

SEQ ID NO: 16            moltype = AA  length = 20
FEATURE                  Location/Qualifiers
source                   1..20
                         mol_type = protein
                         organism = Homo sapiens
SEQUENCE: 16
ITILGTVKPN ANRIALDFQR                                                    20

SEQ ID NO: 17            moltype = AA  length = 20
FEATURE                  Location/Qualifiers
source                   1..20
                         mol_type = protein
                         organism = Homo sapiens
SEQUENCE: 17
ANRIALDFQR GNDVAFHFNP                                                    20

SEQ ID NO: 18            moltype = AA  length = 20
FEATURE                  Location/Qualifiers
source                   1..20
                         mol_type = protein
                         organism = Homo sapiens
SEQUENCE: 18
GNDVAFHFNP RFNENNRRVI                                                    20

SEQ ID NO: 19            moltype = AA  length = 20
FEATURE                  Location/Qualifiers
source                   1..20
                         mol_type = protein
                         organism = Homo sapiens
SEQUENCE: 19
RFNENNRRVI VCNTKLDNNW                                                    20

SEQ ID NO: 20            moltype = AA  length = 20
FEATURE                  Location/Qualifiers
source                   1..20
                         mol_type = protein
                         organism = Homo sapiens
SEQUENCE: 20
VCNTKLDNNW GREERQSVFP                                                    20

SEQ ID NO: 21            moltype = AA  length = 20
FEATURE                  Location/Qualifiers
source                   1..20
                         mol_type = protein
                         organism = Homo sapiens
SEQUENCE: 21
GREERQSVFP FESGKPFKIQ                                                    20

SEQ ID NO: 22            moltype = AA  length = 20
FEATURE                  Location/Qualifiers
source                   1..20
                         mol_type = protein
                         organism = Homo sapiens
```

```
SEQUENCE: 22
FESGKPFKIQ VLVEPDHFKV                                              20

SEQ ID NO: 23           moltype = AA  length = 20
FEATURE                 Location/Qualifiers
source                  1..20
                        mol_type = protein
                        organism = Homo sapiens
SEQUENCE: 23
VLVEPDHFKV AVNDAHLLQY                                              20

SEQ ID NO: 24           moltype = AA  length = 20
FEATURE                 Location/Qualifiers
source                  1..20
                        mol_type = protein
                        organism = Homo sapiens
SEQUENCE: 24
AVNDAHLLQY NHRVKKLNEI                                              20

SEQ ID NO: 25           moltype = AA  length = 20
FEATURE                 Location/Qualifiers
source                  1..20
                        mol_type = protein
                        organism = Homo sapiens
SEQUENCE: 25
NHRVKKLNEI SKLGISGDID                                              20

SEQ ID NO: 26           moltype = AA  length = 19
FEATURE                 Location/Qualifiers
source                  1..19
                        mol_type = protein
                        organism = Homo sapiens
SEQUENCE: 26
SKLGISGDID LTSASYTMI                                               19

SEQ ID NO: 27           moltype = AA  length = 10
FEATURE                 Location/Qualifiers
source                  1..10
                        mol_type = protein
                        organism = Homo sapiens
SEQUENCE: 27
PGAYPGQAPP                                                         10

SEQ ID NO: 28           moltype = AA  length = 10
FEATURE                 Location/Qualifiers
source                  1..10
                        mol_type = protein
                        organism = Homo sapiens
SEQUENCE: 28
GQAPPGAYPG                                                         10

SEQ ID NO: 29           moltype = AA  length = 11
FEATURE                 Location/Qualifiers
source                  1..11
                        mol_type = protein
                        organism = Homo sapiens
SEQUENCE: 29
GAYPGQAPPG A                                                       11

SEQ ID NO: 30           moltype = AA  length = 10
FEATURE                 Location/Qualifiers
source                  1..10
                        mol_type = protein
                        organism = Homo sapiens
SEQUENCE: 30
APPGAYPGAP                                                         10

SEQ ID NO: 31           moltype = AA  length = 9
FEATURE                 Location/Qualifiers
source                  1..9
                        mol_type = protein
                        organism = Homo sapiens
SEQUENCE: 31
YPGAPGAYP                                                          9

SEQ ID NO: 32           moltype = AA  length = 6
FEATURE                 Location/Qualifiers
source                  1..6
                        mol_type = protein
```

```
                          organism = Homo sapiens
SEQUENCE: 32
APPGAY                                                                   6

SEQ ID NO: 33             moltype = AA  length = 6
FEATURE                   Location/Qualifiers
source                    1..6
                          mol_type = protein
                          organism = Homo sapiens
SEQUENCE: 33
GAYPGQ                                                                   6

SEQ ID NO: 34             moltype = AA  length = 6
FEATURE                   Location/Qualifiers
source                    1..6
                          mol_type = protein
                          organism = Homo sapiens
SEQUENCE: 34
PGQAPP                                                                   6

SEQ ID NO: 35             moltype = DNA  length = 958
FEATURE                   Location/Qualifiers
source                    1..958
                          mol_type = unassigned DNA
                          organism = Homo sapiens
SEQUENCE: 35
gcccgcagca cctcctcgcc agcagccgtc cggagccagc caacgagcgg aaaatggcag  60
acaatttttc gctccatgat gcgttatctg ggtctggaaa cccaaaccct caaggatggc  120
ctggcgcatg gggaaccag  cctgctgggg caggggggcta cccaggggct tcctatcctg  180
gggcctaccc cgggcaggca cccccagggg cttatcctgg acaggcacct ccaggcgcct  240
accctggagc acctggagct tatcccggag cacctgcacc tggagtctac ccagggccac  300
ccagcggccc tggggcctac ccatcttctg gacagccaag tgccaccgga gcctaccctg  360
ccactggccc ctatggcgcc cctgctgggc cactgattgt gccttataac ctgcctttgc  420
ctgggggagt ggtgcctcgc atgctgataa caattctggg cacggtgaag cccaatgcaa  480
acagaattgc tttagatttc caaagaggga atgatgttgc cttccacttt aacccacgct  540
tcaatgagaa caacaggaga gtcattgttt gcaatacaaa gctggataat aactggggaa  600
gggaagaaag acagtcggtt ttcccatttg aaagtgggaa accattcaaa atacaagtac  660
tggttgaacc tgaccacttc aaggttgcag tgaatgatgc tcacttgttg cagtacaatc  720
atcgggttaa aaaactcaat gaaatcagca aactgggaat ttctggtgac atagacctca  780
ccagtgcttc atataccatg atataatctg aaaggggcag attaaaaaaa aaaaaagaat  840
ctaaacctta catgtgtaaa ggtttcatgt tcactgtgag tgaaaatttt tacattcatc  900
aatatccctc ttgtaagtca tctacttaat aaatattaca gtgaattacc tgtctcaa    958

SEQ ID NO: 36             moltype = DNA  length = 2237
FEATURE                   Location/Qualifiers
source                    1..2237
                          mol_type = unassigned DNA
                          organism = Homo sapiens
SEQUENCE: 36
atttggagag ttaaaactgt gcctaacaga ggtgtcctct gacttttctt ctgcaagctc  60
catgttttca catcttccct ttgactgtgt cctgctgctg ctgctgctac tacttacaag  120
gtcctcagaa gtggaataca gagcggaggt cggtcagaat gcctatctgc cctgcttcta  180
caccccagcc gccccaggga acctcgtgcc cgtctgctgg ggcaaaggag cctgtcctgt  240
gtttgaatgt ggcaacgtgg tgctcaggac tgatgaaagg gatgtgaatt attggacatc  300
cagatactgg ctaaatgggg atttccgcaa aggagatgtg tccctgacca tagagaatgt  360
gactctagca gacagtggga tctactgctg ccggatccaa atcccaggca taatgaatga  420
tgaaaaattt aacctgaagt tggtcatcaa accagccaag gtcacccctg caccgactcg  480
gcagagagac ttcactgcag cctttccaag gatgcttacc accaggggac atggcccagc  540
agagacacag acactgggga gcctccctga tataaatcta acacaaatat ccacattggc  600
caatgagtta cgggactcta gattggccaa tgacttacgg gactctggag caaccatcag  660
aataggcatc tacatcggag cagggatctg tgctgggctg gctctggctc ttatcttcgg  720
cgctttaatt ttcaaatggt attctcatag caaagagaag atacagaatt taagcctcat  780
ctctttggcc aacctccctc cctcaggatt ggcaaatgca gtagcagagg gaattcgctc  840
agaagaaaac atctatacca ttgaagagaa cgtatatgaa gtggaggagc ccaatgagta  900
ttattgctat gtcagcagca ggcagcaacc ctcacaacct ttgggttgtc gctttgcaat  960
gccatagatc caaccacctt atttttgagc ttggtgtttt gtctttttca gaaactatga  1020
gctgtgtcac ctgactggtt ttggaggttc tgtccactgc tatggagcag agttttccca  1080
ttttcagaag ataatgactc acatgggaat tgaactggga cctgcactga acttaaacag  1140
gcatgtcatt gcctctgtat ttaagccaac agagttaccc aacccagaga ctgttaatca  1200
tggatgttag agctcaaacg ggcttttata tacactagga attcttgacg tggggtctct  1260
ggagctccag gaaattcggg cacatcatat gtccatgaaa cttcagataa actagggaaa  1320
actgggtgct gaggtgaaag cataactttt ttggcacaga aagtctaaag gggccactga  1380
ttttcaaaga gatctgtgat ccctttttgt tttttgtttt tgagatggag tcttgctctg  1440
ttgcccaggc tggagtgcaa tggcacaatc tcggctcact gcaagctccg cctcctgggt  1500
tcaagcgatt ctcctgcctc agcctcctga gtggctggga ttacaggcat gcaccaccat  1560
gcccagctaa tttgttgtat ttttagtaga gacagggttt caccatgttg gccagtgtgg  1620
tctcaaactc ctgacctcat gatttgcctg cctcggcctc ccaaagcact gggattacag  1680
gcgtgagcca cccacatccag ccagtgatcc ttaaaagatt aagagatgac tggaccaggt  1740
ctaccttgat cttgaagatt cccttggaat gttgagattt aggcttattt gagcactgcc  1800
```

```
tgcccaactg tcagtgccag tgcatagccc ttcttttgtc tcccttatga agactgccct  1860
gcagggctga gatgtggcag gagctcccag ggaaaaacga agtgcatttg attggtgtgt  1920
attggccaag ttttgcttgt tgtgtgcttg aaagaaaata tctctgacca acttctgtat  1980
tcgtggacca aactgaagct atatttttca cagaagaaga agcagtgacg gggacacaaa  2040
ttctgttgcc tggtggaaag aaggcaaagg ccttcagcaa tctatattac cagcgctgga  2100
tcctttgaca gagagtggtc cctaaactta aatttcaaga cggtataggc ttgatctgtc  2160
ttgcttattg ttgccccctg cgcctagcac aattctgaca cacaattgga acttactaaa  2220
aatttttttt tactgtt                                                 2237

SEQ ID NO: 37          moltype = AA  length = 7
FEATURE                Location/Qualifiers
REGION                 1..7
                       note = VH CDR1 of 2D10.2B2
source                 1..7
                       mol_type = protein
                       organism = synthetic construct
SEQUENCE: 37
GYTFTDY                                                            7

SEQ ID NO: 38          moltype = AA  length = 7
FEATURE                Location/Qualifiers
REGION                 1..7
                       note = VH CDR1 of 3B11.2G2
source                 1..7
                       mol_type = protein
                       organism = synthetic construct
SEQUENCE: 38
GYKFKTY                                                            7

SEQ ID NO: 39          moltype = AA  length = 7
FEATURE                Location/Qualifiers
REGION                 1..7
                       note = VH CDR1 of 4A11.2B5
source                 1..7
                       mol_type = protein
                       organism = synthetic construct
SEQUENCE: 39
GYSFTNY                                                            7

SEQ ID NO: 40          moltype = AA  length = 7
FEATURE                Location/Qualifiers
REGION                 1..7
                       note = VH CDR1 of 4G2.2G6
source                 1..7
                       mol_type = protein
                       organism = synthetic construct
SEQUENCE: 40
GYTFTTY                                                            7

SEQ ID NO: 41          moltype = AA  length = 7
FEATURE                Location/Qualifiers
REGION                 1..7
                       note = VH CDR1 of 6H6.2D6
source                 1..7
                       mol_type = protein
                       organism = synthetic construct
SEQUENCE: 41
GYTFTTY                                                            7

SEQ ID NO: 42          moltype = AA  length = 7
FEATURE                Location/Qualifiers
REGION                 1..7
                       note = VH CDR1 of 7D8.2D8
source                 1..7
                       mol_type = protein
                       organism = synthetic construct
SEQUENCE: 42
GFTFSSY                                                            7

SEQ ID NO: 43          moltype = AA  length = 7
FEATURE                Location/Qualifiers
REGION                 1..7
                       note = VH CDR1 of 12G5.D7
source                 1..7
                       mol_type = protein
                       organism = synthetic construct
SEQUENCE: 43
GYTFTDY                                                            7
```

```
SEQ ID NO: 44           moltype = AA  length = 7
FEATURE                 Location/Qualifiers
REGION                  1..7
                        note = VH CDR1 of 13A12.2E5
source                  1..7
                        mol_type = protein
                        organism = synthetic construct
SEQUENCE: 44
GYKFKTY                                                     7

SEQ ID NO: 45           moltype = AA  length = 7
FEATURE                 Location/Qualifiers
REGION                  1..7
                        note = VH CDR1 of 13G4.2F8
source                  1..7
                        mol_type = protein
                        organism = synthetic construct
SEQUENCE: 45
GYTFTSY                                                     7

SEQ ID NO: 46           moltype = AA  length = 7
FEATURE                 Location/Qualifiers
REGION                  1..7
                        note = VH CDR1 of 13H12.2F8
source                  1..7
                        mol_type = protein
                        organism = synthetic construct
SEQUENCE: 46
GYTFTTY                                                     7

SEQ ID NO: 47           moltype = AA  length = 7
FEATURE                 Location/Qualifiers
REGION                  1..7
                        note = VH CDR1 of 14H10.2C9
source                  1..7
                        mol_type = protein
                        organism = synthetic construct
SEQUENCE: 47
GYTFTTY                                                     7

SEQ ID NO: 48           moltype = AA  length = 7
FEATURE                 Location/Qualifiers
REGION                  1..7
                        note = VH CDR1 of 15F10.2D6
source                  1..7
                        mol_type = protein
                        organism = synthetic construct
SEQUENCE: 48
GFAFSSY                                                     7

SEQ ID NO: 49           moltype = AA  length = 7
FEATURE                 Location/Qualifiers
REGION                  1..7
                        note = VH CDR1 of 15G7.2A7
source                  1..7
                        mol_type = protein
                        organism = synthetic construct
SEQUENCE: 49
GYTFTDY                                                     7

SEQ ID NO: 50           moltype = AA  length = 7
FEATURE                 Location/Qualifiers
REGION                  1..7
                        note = VH CDR1 of 19B5.2E6
source                  1..7
                        mol_type = protein
                        organism = synthetic construct
SEQUENCE: 50
GYTFTTY                                                     7

SEQ ID NO: 51           moltype = AA  length = 7
FEATURE                 Location/Qualifiers
REGION                  1..7
                        note = VH CDR1 of 19D9.2E5
source                  1..7
                        mol_type = protein
                        organism = synthetic construct
SEQUENCE: 51
GYTFTTY                                                     7
```

```
SEQ ID NO: 52           moltype = AA  length = 7
FEATURE                 Location/Qualifiers
REGION                  1..7
                        note = VH CDR1 of 20D11.2C6
source                  1..7
                        mol_type = protein
                        organism = synthetic construct
SEQUENCE: 52
GYTFTDF                                                                7

SEQ ID NO: 53           moltype = AA  length = 7
FEATURE                 Location/Qualifiers
REGION                  1..7
                        note = VH CDR1 of 20H5.A3
source                  1..7
                        mol_type = protein
                        organism = synthetic construct
SEQUENCE: 53
GYAFTTY                                                                7

SEQ ID NO: 54           moltype = AA  length = 7
FEATURE                 Location/Qualifiers
REGION                  1..7
                        note = VH CDR1 of 23H9.2E4
source                  1..7
                        mol_type = protein
                        organism = synthetic construct
SEQUENCE: 54
GYTFTTY                                                                7

SEQ ID NO: 55           moltype = AA  length = 7
FEATURE                 Location/Qualifiers
REGION                  1..7
                        note = VH CDR1 of 24D12.2H9
source                  1..7
                        mol_type = protein
                        organism = synthetic construct
SEQUENCE: 55
GFSLTSY                                                                7

SEQ ID NO: 56           moltype = AA  length = 8
FEATURE                 Location/Qualifiers
REGION                  1..8
                        note = VH CDR1 of 846.1F5
source                  1..8
                        mol_type = protein
                        organism = synthetic construct
SEQUENCE: 56
GYTFTNYG                                                               8

SEQ ID NO: 57           moltype = AA  length = 8
FEATURE                 Location/Qualifiers
REGION                  1..8
                        note = VH CDR1 of 846.2H3
source                  1..8
                        mol_type = protein
                        organism = synthetic construct
SEQUENCE: 57
GYTFTNYG                                                               8

SEQ ID NO: 58           moltype = AA  length = 8
FEATURE                 Location/Qualifiers
REGION                  1..8
                        note = VH CDR1 of 846T.1H2
source                  1..8
                        mol_type = protein
                        organism = synthetic construct
SEQUENCE: 58
GYTFTNYG                                                               8

SEQ ID NO: 59           moltype = AA  length = 7
FEATURE                 Location/Qualifiers
REGION                  1..7
                        note = VH CDR1 of 9H2.2H10
source                  1..7
                        mol_type = protein
                        organism = synthetic construct
SEQUENCE: 59
```

```
GYTFTNY                                                     7

SEQ ID NO: 60          moltype = AA  length = 7
FEATURE                Location/Qualifiers
REGION                 1..7
                       note = VH CDR1 of IMT001-4
source                 1..7
                       mol_type = protein
                       organism = synthetic construct
SEQUENCE: 60
GYTFTNY                                                     7

SEQ ID NO: 61          moltype = AA  length = 7
FEATURE                Location/Qualifiers
REGION                 1..7
                       note = VH CDR1 of IMT006-1
source                 1..7
                       mol_type = protein
                       organism = synthetic construct
SEQUENCE: 61
GYSFTNY                                                     7

SEQ ID NO: 62          moltype = AA  length = 7
FEATURE                Location/Qualifiers
REGION                 1..7
                       note = VH CDR1 of IMT006-5
source                 1..7
                       mol_type = protein
                       organism = synthetic construct
SEQUENCE: 62
GYSFTNY                                                     7

SEQ ID NO: 63          moltype = AA  length = 7
FEATURE                Location/Qualifiers
REGION                 1..7
                       note = VH CDR1 of IMT006-8
source                 1..7
                       mol_type = protein
                       organism = synthetic construct
SEQUENCE: 63
GYSFTNY                                                     7

SEQ ID NO: 64          moltype = AA  length = 7
FEATURE                Location/Qualifiers
REGION                 1..7
                       note = VH CDR1 of mIMT001
source                 1..7
                       mol_type = protein
                       organism = synthetic construct
SEQUENCE: 64
GYTFTNY                                                     7

SEQ ID NO: 65          moltype = AA  length = 8
FEATURE                Location/Qualifiers
REGION                 1..8
                       note = VH CDR2 of 2D10.2B2
source                 1..8
                       mol_type = protein
                       organism = synthetic construct
SEQUENCE: 65
IYPGSNDT                                                    8

SEQ ID NO: 66          moltype = AA  length = 8
FEATURE                Location/Qualifiers
REGION                 1..8
                       note = VH CDR2 of 3B11.2G2
source                 1..8
                       mol_type = protein
                       organism = synthetic construct
SEQUENCE: 66
INTYSGVP                                                    8

SEQ ID NO: 67          moltype = AA  length = 8
FEATURE                Location/Qualifiers
REGION                 1..8
                       note = VH CDR2 of 4A11.2B5
source                 1..8
                       mol_type = protein
                       organism = synthetic construct
```

```
SEQUENCE: 67
IYPGSGNT                                                                8

SEQ ID NO: 68           moltype = AA  length = 8
FEATURE                 Location/Qualifiers
REGION                  1..8
                        note = VH CDR2 of 4G2.2G6
source                  1..8
                        mol_type = protein
                        organism = synthetic construct
SEQUENCE: 68
INTHSGVP                                                                8

SEQ ID NO: 69           moltype = AA  length = 8
FEATURE                 Location/Qualifiers
REGION                  1..8
                        note = VH CDR2 of 6H6.2D6
source                  1..8
                        mol_type = protein
                        organism = synthetic construct
SEQUENCE: 69
INTYSGVP                                                                8

SEQ ID NO: 70           moltype = AA  length = 8
FEATURE                 Location/Qualifiers
REGION                  1..8
                        note = VH CDR2 of 7D8.2D8
source                  1..8
                        mol_type = protein
                        organism = synthetic construct
SEQUENCE: 70
ISDGGIYT                                                                8

SEQ ID NO: 71           moltype = AA  length = 8
FEATURE                 Location/Qualifiers
REGION                  1..8
                        note = VH CDR2 of 12G5.D7
source                  1..8
                        mol_type = protein
                        organism = synthetic construct
SEQUENCE: 71
IYPGTGNT                                                                8

SEQ ID NO: 72           moltype = AA  length = 8
FEATURE                 Location/Qualifiers
REGION                  1..8
                        note = VH CDR2 of 13A12.2E5
source                  1..8
                        mol_type = protein
                        organism = synthetic construct
SEQUENCE: 72
INTYSGVP                                                                8

SEQ ID NO: 73           moltype = AA  length = 8
FEATURE                 Location/Qualifiers
REGION                  1..8
                        note = VH CDR2 of 13G4.2F8
source                  1..8
                        mol_type = protein
                        organism = synthetic construct
SEQUENCE: 73
IHPNSGST                                                                8

SEQ ID NO: 74           moltype = AA  length = 8
FEATURE                 Location/Qualifiers
REGION                  1..8
                        note = VH CDR2 of 13H12.2F8
source                  1..8
                        mol_type = protein
                        organism = synthetic construct
SEQUENCE: 74
INTYSGVP                                                                8

SEQ ID NO: 75           moltype = AA  length = 8
FEATURE                 Location/Qualifiers
REGION                  1..8
                        note = VH CDR2 of 14H10.2C9
source                  1..8
                        mol_type = protein
```

```
                        organism = synthetic construct
SEQUENCE: 75
INTYSGVP                                                              8

SEQ ID NO: 76           moltype = AA  length = 8
FEATURE                 Location/Qualifiers
REGION                  1..8
                        note = VH CDR2 of 15F10.2D6
source                  1..8
                        mol_type = protein
                        organism = synthetic construct
SEQUENCE: 76
ISDGGVYT                                                              8

SEQ ID NO: 77           moltype = AA  length = 8
FEATURE                 Location/Qualifiers
REGION                  1..8
                        note = VH CDR2 of 15G7.2A7
source                  1..8
                        mol_type = protein
                        organism = synthetic construct
SEQUENCE: 77
INPNNGGT                                                              8

SEQ ID NO: 78           moltype = AA  length = 8
FEATURE                 Location/Qualifiers
REGION                  1..8
                        note = VH CDR2 of 19B5.2E6
source                  1..8
                        mol_type = protein
                        organism = synthetic construct
SEQUENCE: 78
INTYSGVP                                                              8

SEQ ID NO: 79           moltype = AA  length = 8
FEATURE                 Location/Qualifiers
REGION                  1..8
                        note = VH CDR2 of 19D9.2E5
source                  1..8
                        mol_type = protein
                        organism = synthetic construct
SEQUENCE: 79
INTYSGVP                                                              8

SEQ ID NO: 80           moltype = AA  length = 8
FEATURE                 Location/Qualifiers
REGION                  1..8
                        note = VH CDR2 of 20D11.2C6
source                  1..8
                        mol_type = protein
                        organism = synthetic construct
SEQUENCE: 80
INPKNGGI                                                              8

SEQ ID NO: 81           moltype = AA  length = 8
FEATURE                 Location/Qualifiers
REGION                  1..8
                        note = VH CDR2 of 20H5.A3
source                  1..8
                        mol_type = protein
                        organism = synthetic construct
SEQUENCE: 81
VNTYSGVP                                                              8

SEQ ID NO: 82           moltype = AA  length = 8
FEATURE                 Location/Qualifiers
REGION                  1..8
                        note = VH CDR2 of 23H9.2E4
source                  1..8
                        mol_type = protein
                        organism = synthetic construct
SEQUENCE: 82
INTYSGVP                                                              8

SEQ ID NO: 83           moltype = AA  length = 7
FEATURE                 Location/Qualifiers
REGION                  1..7
                        note = VH CDR2 of 24D12.2H9
source                  1..7
```

```
                        mol_type = protein
                        organism = synthetic construct
SEQUENCE: 83
IWSGGST                                                7

SEQ ID NO: 84           moltype = AA  length = 8
FEATURE                 Location/Qualifiers
REGION                  1..8
                        note = VH CDR2 of 846.1F5
source                  1..8
                        mol_type = protein
                        organism = synthetic construct
SEQUENCE: 84
INTYTGEP                                               8

SEQ ID NO: 85           moltype = AA  length = 8
FEATURE                 Location/Qualifiers
REGION                  1..8
                        note = VH CDR2 of 846.2H3
source                  1..8
                        mol_type = protein
                        organism = synthetic construct
SEQUENCE: 85
INTYTGEP                                               8

SEQ ID NO: 86           moltype = AA  length = 8
FEATURE                 Location/Qualifiers
REGION                  1..8
                        note = VH CDR2 of 846T.1H2
source                  1..8
                        mol_type = protein
                        organism = synthetic construct
SEQUENCE: 86
INTNTGES                                               8

SEQ ID NO: 87           moltype = AA  length = 8
FEATURE                 Location/Qualifiers
REGION                  1..8
                        note = VH CDR2 of 9H2.2H10
source                  1..8
                        mol_type = protein
                        organism = synthetic construct
SEQUENCE: 87
IDPSDSET                                               8

SEQ ID NO: 88           moltype = AA  length = 6
FEATURE                 Location/Qualifiers
REGION                  1..6
                        note = VH CDR2 of IMT001-4
source                  1..6
                        mol_type = protein
                        organism = synthetic construct
SEQUENCE: 88
NTNTGE                                                 6

SEQ ID NO: 89           moltype = AA  length = 8
FEATURE                 Location/Qualifiers
REGION                  1..8
                        note = VH CDR2 of IMT006-1
source                  1..8
                        mol_type = protein
                        organism = synthetic construct
SEQUENCE: 89
IYPGSGNT                                               8

SEQ ID NO: 90           moltype = AA  length = 8
FEATURE                 Location/Qualifiers
REGION                  1..8
                        note = VH CDR2 of IMT006-5
source                  1..8
                        mol_type = protein
                        organism = synthetic construct
SEQUENCE: 90
IYPGSGNT                                               8

SEQ ID NO: 91           moltype = AA  length = 8
FEATURE                 Location/Qualifiers
REGION                  1..8
                        note = VH CDR2 of IMT006-8
```

```
source                  1..8
                        mol_type = protein
                        organism = synthetic construct
SEQUENCE: 91
IYPGSGNT                                                                  8

SEQ ID NO: 92           moltype = AA  length = 6
FEATURE                 Location/Qualifiers
REGION                  1..6
                        note = VH CDR2 of mIMT001
source                  1..6
                        mol_type = protein
                        organism = synthetic construct
SEQUENCE: 92
NTNTGE                                                                    6

SEQ ID NO: 93           moltype = AA  length = 13
FEATURE                 Location/Qualifiers
REGION                  1..13
                        note = VH CDR3 of 2D10.2B2
source                  1..13
                        mol_type = protein
                        organism = synthetic construct
SEQUENCE: 93
ANYFGCSGWF FDV                                                            13

SEQ ID NO: 94           moltype = AA  length = 12
FEATURE                 Location/Qualifiers
REGION                  1..12
                        note = VH CDR3 of 3B11.2G2
source                  1..12
                        mol_type = protein
                        organism = synthetic construct
SEQUENCE: 94
ARDGNYGDPM DY                                                             12

SEQ ID NO: 95           moltype = AA  length = 9
FEATURE                 Location/Qualifiers
REGION                  1..9
                        note = VH CDR3 of 4A11.2B5
source                  1..9
                        mol_type = protein
                        organism = synthetic construct
SEQUENCE: 95
STAPGGFDV                                                                 9

SEQ ID NO: 96           moltype = AA  length = 12
FEATURE                 Location/Qualifiers
REGION                  1..12
                        note = VH CDR3 of 4G2.2G6
source                  1..12
                        mol_type = protein
                        organism = synthetic construct
SEQUENCE: 96
TRDGNDGDAM DN                                                             12

SEQ ID NO: 97           moltype = AA  length = 9
FEATURE                 Location/Qualifiers
REGION                  1..9
                        note = VH CDR3 of 6H6.2D6
source                  1..9
                        mol_type = protein
                        organism = synthetic construct
SEQUENCE: 97
ARGPYAMDY                                                                 9

SEQ ID NO: 98           moltype = AA  length = 6
FEATURE                 Location/Qualifiers
REGION                  1..6
                        note = VH CDR3 of 7D8.2D8
source                  1..6
                        mol_type = protein
                        organism = synthetic construct
SEQUENCE: 98
VRDGGY                                                                    6

SEQ ID NO: 99           moltype = AA  length = 15
FEATURE                 Location/Qualifiers
REGION                  1..15
```

```
                        note = VH CDR3 of 12G5.D7
source                  1..15
                        mol_type = protein
                        organism = synthetic construct
SEQUENCE: 99
ARFAYYYGSG GYFDY                                                      15

SEQ ID NO: 100          moltype = AA  length = 12
FEATURE                 Location/Qualifiers
REGION                  1..12
                        note = VH CDR3 of 13A12.2E5
source                  1..12
                        mol_type = protein
                        organism = synthetic construct
SEQUENCE: 100
ARDGNYGDPM DY                                                         12

SEQ ID NO: 101          moltype = AA  length = 12
FEATURE                 Location/Qualifiers
REGION                  1..12
                        note = VH CDR3 of 13G4.2F8
source                  1..12
                        mol_type = protein
                        organism = synthetic construct
SEQUENCE: 101
TRWGIYYYAR DY                                                         12

SEQ ID NO: 102          moltype = AA  length = 10
FEATURE                 Location/Qualifiers
REGION                  1..10
                        note = VH CDR3 of 13H12.2F8
source                  1..10
                        mol_type = protein
                        organism = synthetic construct
SEQUENCE: 102
AVPYEYDGAY                                                            10

SEQ ID NO: 103          moltype = AA  length = 10
FEATURE                 Location/Qualifiers
REGION                  1..10
                        note = VH CDR3 of 14H10.2C9
source                  1..10
                        mol_type = protein
                        organism = synthetic construct
SEQUENCE: 103
STPYEYDGAY                                                            10

SEQ ID NO: 104          moltype = AA  length = 6
FEATURE                 Location/Qualifiers
REGION                  1..6
                        note = VH CDR3 of 15F10.2D6
source                  1..6
                        mol_type = protein
                        organism = synthetic construct
SEQUENCE: 104
VRDGGY                                                                6

SEQ ID NO: 105          moltype = AA  length = 8
FEATURE                 Location/Qualifiers
REGION                  1..8
                        note = VH CDR3 of 15G7.2A7
source                  1..8
                        mol_type = protein
                        organism = synthetic construct
SEQUENCE: 105
TSGYGFPY                                                              8

SEQ ID NO: 106          moltype = AA  length = 9
FEATURE                 Location/Qualifiers
REGION                  1..9
                        note = VH CDR3 of 19B5.2E6
source                  1..9
                        mol_type = protein
                        organism = synthetic construct
SEQUENCE: 106
ARGPYAMDY                                                             9

SEQ ID NO: 107          moltype = AA  length = 10
FEATURE                 Location/Qualifiers
```

```
REGION                 1..10
                       note = VH CDR3 of 19D9.2E5
source                 1..10
                       mol_type = protein
                       organism = synthetic construct
SEQUENCE: 107
ATPYEYDGAY                                                                  10

SEQ ID NO: 108         moltype = AA  length = 8
FEATURE                Location/Qualifiers
REGION                 1..8
                       note = VH CDR3 of 20D11.2C6
source                 1..8
                       mol_type = protein
                       organism = synthetic construct
SEQUENCE: 108
TSGYGFPY                                                                    8

SEQ ID NO: 109         moltype = AA  length = 9
FEATURE                Location/Qualifiers
REGION                 1..9
                       note = VH CDR3 of 20H5.A3
source                 1..9
                       mol_type = protein
                       organism = synthetic construct
SEQUENCE: 109
ARGPYAMDY                                                                   9

SEQ ID NO: 110         moltype = AA  length = 9
FEATURE                Location/Qualifiers
REGION                 1..9
                       note = VH CDR3 of 23H9.2E4
source                 1..9
                       mol_type = protein
                       organism = synthetic construct
SEQUENCE: 110
ARGPYAMDY                                                                   9

SEQ ID NO: 111         moltype = AA  length = 14
FEATURE                Location/Qualifiers
REGION                 1..14
                       note = VH CDR3 of 24D12.2H9
source                 1..14
                       mol_type = protein
                       organism = synthetic construct
SEQUENCE: 111
AKSPDGYDVA WFGY                                                             14

SEQ ID NO: 112         moltype = AA  length = 15
FEATURE                Location/Qualifiers
REGION                 1..15
                       note = VH CDR3 of 846.1F5
source                 1..15
                       mol_type = protein
                       organism = synthetic construct
SEQUENCE: 112
ARWGGYDGDY YAMDY                                                            15

SEQ ID NO: 113         moltype = AA  length = 15
FEATURE                Location/Qualifiers
REGION                 1..15
                       note = VH CDR3 of 846.2H3
source                 1..15
                       mol_type = protein
                       organism = synthetic construct
SEQUENCE: 113
ARWGGYDGDY YAMDY                                                            15

SEQ ID NO: 114         moltype = AA  length = 11
FEATURE                Location/Qualifiers
REGION                 1..11
                       note = VH CDR3 of 846T.1H2
source                 1..11
                       mol_type = protein
                       organism = synthetic construct
SEQUENCE: 114
QPGGVTGTLT T                                                                11

SEQ ID NO: 115         moltype = AA  length = 8
```

```
FEATURE                Location/Qualifiers
REGION                 1..8
                       note = VH CDR3 of 9H2.2H10
source                 1..8
                       mol_type = protein
                       organism = synthetic construct
SEQUENCE: 115
ARHGYYDY                                                              8

SEQ ID NO: 116         moltype = AA  length = 9
FEATURE                Location/Qualifiers
REGION                 1..9
                       note = VH CDR3 of IMT001-4
source                 1..9
                       mol_type = protein
                       organism = synthetic construct
SEQUENCE: 116
APYDNFFAY                                                             9

SEQ ID NO: 117         moltype = AA  length = 9
FEATURE                Location/Qualifiers
REGION                 1..9
                       note = VH CDR3 of IMT006-1
source                 1..9
                       mol_type = protein
                       organism = synthetic construct
SEQUENCE: 117
STAPGGFDV                                                             9

SEQ ID NO: 118         moltype = AA  length = 9
FEATURE                Location/Qualifiers
REGION                 1..9
                       note = VH CDR3 of IMT006-5
source                 1..9
                       mol_type = protein
                       organism = synthetic construct
SEQUENCE: 118
STAPGGFDV                                                             9

SEQ ID NO: 119         moltype = AA  length = 9
FEATURE                Location/Qualifiers
REGION                 1..9
                       note = VH CDR3 of IMT006-8
source                 1..9
                       mol_type = protein
                       organism = synthetic construct
SEQUENCE: 119
STAPGGFDV                                                             9

SEQ ID NO: 120         moltype = AA  length = 9
FEATURE                Location/Qualifiers
REGION                 1..9
                       note = VH CDR3 of mIMT001
source                 1..9
                       mol_type = protein
                       organism = synthetic construct
SEQUENCE: 120
APYDNFFAY                                                             9

SEQ ID NO: 121         moltype = AA  length = 11
FEATURE                Location/Qualifiers
REGION                 1..11
                       note = VL CDR1 of 2D10.2B2
source                 1..11
                       mol_type = protein
                       organism = synthetic construct
SEQUENCE: 121
KSLLHSDGIT Y                                                          11

SEQ ID NO: 122         moltype = AA  length = 11
FEATURE                Location/Qualifiers
REGION                 1..11
                       note = VL CDR1 of 3B11.2G2
source                 1..11
                       mol_type = protein
                       organism = synthetic construct
SEQUENCE: 122
QSLLYTNGKT Y                                                          11
```

```
SEQ ID NO: 123          moltype = AA  length = 11
FEATURE                 Location/Qualifiers
REGION                  1..11
                        note = VL CDR1 of 4A11.2B5
source                  1..11
                        mol_type = protein
                        organism = synthetic construct
SEQUENCE: 123
KSLLHSDGIT Y                                                       11

SEQ ID NO: 124          moltype = AA  length = 11
FEATURE                 Location/Qualifiers
REGION                  1..11
                        note = VL CDR1 of 4G2.2G6
source                  1..11
                        mol_type = protein
                        organism = synthetic construct
SEQUENCE: 124
QSLLYTDGKT Y                                                       11

SEQ ID NO: 125          moltype = AA  length = 6
FEATURE                 Location/Qualifiers
REGION                  1..6
                        note = VL CDR1 of 6H6.2D6
source                  1..6
                        mol_type = protein
                        organism = synthetic construct
SEQUENCE: 125
QGISNY                                                             6

SEQ ID NO: 126          moltype = AA  length = 11
FEATURE                 Location/Qualifiers
REGION                  1..11
                        note = VL CDR1 of 7D8.2D8
source                  1..11
                        mol_type = protein
                        organism = synthetic construct
SEQUENCE: 126
QSIVHSNGNT Y                                                       11

SEQ ID NO: 127          moltype = AA  length = 6
FEATURE                 Location/Qualifiers
REGION                  1..6
                        note = VL CDR1 of 12G5.D7
source                  1..6
                        mol_type = protein
                        organism = synthetic construct
SEQUENCE: 127
QGINSN                                                             6

SEQ ID NO: 128          moltype = AA  length = 11
FEATURE                 Location/Qualifiers
REGION                  1..11
                        note = VL CDR1 of 13A12.2E5
source                  1..11
                        mol_type = protein
                        organism = synthetic construct
SEQUENCE: 128
QSLLYTNGKT Y                                                       11

SEQ ID NO: 129          moltype = AA  length = 6
FEATURE                 Location/Qualifiers
REGION                  1..6
                        note = VL CDR1 of 13G4.2F8
source                  1..6
                        mol_type = protein
                        organism = synthetic construct
SEQUENCE: 129
QNVGTN                                                             6

SEQ ID NO: 130          moltype = AA  length = 11
FEATURE                 Location/Qualifiers
REGION                  1..11
                        note = VL CDR1 of 13H12.2F8
source                  1..11
                        mol_type = protein
                        organism = synthetic construct
SEQUENCE: 130
QSLFHSDGKT Y                                                       11
```

```
SEQ ID NO: 131          moltype = AA  length = 11
FEATURE                 Location/Qualifiers
REGION                  1..11
                        note = VL CDR1 of 14H10.2C9
source                  1..11
                        mol_type = protein
                        organism = synthetic construct
SEQUENCE: 131
QSLFDSDGKT Y                                                            11

SEQ ID NO: 132          moltype = AA  length = 11
FEATURE                 Location/Qualifiers
REGION                  1..11
                        note = VL CDR1 of 15F10.2D6
source                  1..11
                        mol_type = protein
                        organism = synthetic construct
SEQUENCE: 132
QSIVHNNGNT Y                                                            11

SEQ ID NO: 133          moltype = AA  length = 6
FEATURE                 Location/Qualifiers
REGION                  1..6
                        note = VL CDR1 of 15G7.2A7
source                  1..6
                        mol_type = protein
                        organism = synthetic construct
SEQUENCE: 133
QNINIW                                                                  6

SEQ ID NO: 134          moltype = AA  length = 6
FEATURE                 Location/Qualifiers
REGION                  1..6
                        note = VL CDR1 of 19B5.2E6
source                  1..6
                        mol_type = protein
                        organism = synthetic construct
SEQUENCE: 134
QGINNY                                                                  6

SEQ ID NO: 135          moltype = AA  length = 11
FEATURE                 Location/Qualifiers
REGION                  1..11
                        note = VL CDR1 of 19D9.2E5
source                  1..11
                        mol_type = protein
                        organism = synthetic construct
SEQUENCE: 135
QSLLHSDGKT Y                                                            11

SEQ ID NO: 136          moltype = AA  length = 6
FEATURE                 Location/Qualifiers
REGION                  1..6
                        note = VL CDR1 of 20D11.2C6
source                  1..6
                        mol_type = protein
                        organism = synthetic construct
SEQUENCE: 136
QNIYIW                                                                  6

SEQ ID NO: 137          moltype = AA  length = 6
FEATURE                 Location/Qualifiers
REGION                  1..6
                        note = VL CDR1 of 20H5.A3
source                  1..6
                        mol_type = protein
                        organism = synthetic construct
SEQUENCE: 137
QDISNY                                                                  6

SEQ ID NO: 138          moltype = AA  length = 6
FEATURE                 Location/Qualifiers
REGION                  1..6
                        note = VL CDR1 of 23H9.2E4
source                  1..6
                        mol_type = protein
                        organism = synthetic construct
SEQUENCE: 138
```

```
QGINNY                                                                    6

SEQ ID NO: 139          moltype = AA  length = 6
FEATURE                 Location/Qualifiers
REGION                  1..6
                        note = VL CDR1 of 24D12.2H9
source                  1..6
                        mol_type = protein
                        organism = synthetic construct
SEQUENCE: 139
QDVRTA                                                                    6

SEQ ID NO: 140          moltype = AA  length = 12
FEATURE                 Location/Qualifiers
REGION                  1..12
                        note = VL CDR1 of 846.1F5
source                  1..12
                        mol_type = protein
                        organism = synthetic construct
SEQUENCE: 140
QSVLYSSNQK NY                                                             12

SEQ ID NO: 141          moltype = AA  length = 12
FEATURE                 Location/Qualifiers
REGION                  1..12
                        note = VL CDR1 of 846.2H3
source                  1..12
                        mol_type = protein
                        organism = synthetic construct
SEQUENCE: 141
QSVLYSSNQK NY                                                             12

SEQ ID NO: 142          moltype = AA  length = 11
FEATURE                 Location/Qualifiers
REGION                  1..11
                        note = VL CDR1 of 846T.1H2
SITE                    3
                        note = misc_feature - Xaa can be any naturally occurring
                         amino acid
SITE                    7
                        note = misc_feature - Xaa can be any naturally occurring
                         amino acid
source                  1..11
                        mol_type = protein
                        organism = synthetic construct
SEQUENCE: 142
QSXKYSXGKT Y                                                              11

SEQ ID NO: 143          moltype = AA  length = 6
FEATURE                 Location/Qualifiers
REGION                  1..6
                        note = VL CDR1 of 9H2.2H10
source                  1..6
                        mol_type = protein
                        organism = synthetic construct
SEQUENCE: 143
QDVSTA                                                                    6

SEQ ID NO: 144          moltype = AA  length = 16
FEATURE                 Location/Qualifiers
REGION                  1..16
                        note = VL CDR1 of IMT001-4
source                  1..16
                        mol_type = protein
                        organism = synthetic construct
SEQUENCE: 144
RSSKSLLYKD GKTYLN                                                         16

SEQ ID NO: 145          moltype = AA  length = 11
FEATURE                 Location/Qualifiers
REGION                  1..11
                        note = VL CDR1 of IMT006-1
source                  1..11
                        mol_type = protein
                        organism = synthetic construct
SEQUENCE: 145
KSLLHSDGIT Y                                                              11

SEQ ID NO: 146          moltype = AA  length = 11
```

```
FEATURE                Location/Qualifiers
REGION                 1..11
                       note = VL CDR1 of IMT006-5
source                 1..11
                       mol_type = protein
                       organism = synthetic construct
SEQUENCE: 146
KSLLHSDGIT Y                                                      11

SEQ ID NO: 147         moltype = AA  length = 11
FEATURE                Location/Qualifiers
REGION                 1..11
                       note = VL CDR1 of IMT006-8
source                 1..11
                       mol_type = protein
                       organism = synthetic construct
SEQUENCE: 147
KSLLHSDGIT Y                                                      11

SEQ ID NO: 148         moltype = AA  length = 16
FEATURE                Location/Qualifiers
REGION                 1..16
                       note = VL CDR1 of mIMT001
source                 1..16
                       mol_type = protein
                       organism = synthetic construct
SEQUENCE: 148
RSSKSLLYKD GKTYLN                                                 16

SEQ ID NO: 149         moltype =   length =
SEQUENCE: 149
000

SEQ ID NO: 150         moltype =   length =
SEQUENCE: 150
000

SEQ ID NO: 151         moltype =   length =
SEQUENCE: 151
000

SEQ ID NO: 152         moltype =   length =
SEQUENCE: 152
000

SEQ ID NO: 153         moltype =   length =
SEQUENCE: 153
000

SEQ ID NO: 154         moltype =   length =
SEQUENCE: 154
000

SEQ ID NO: 155         moltype =   length =
SEQUENCE: 155
000

SEQ ID NO: 156         moltype =   length =
SEQUENCE: 156
000

SEQ ID NO: 157         moltype =   length =
SEQUENCE: 157
000

SEQ ID NO: 158         moltype =   length =
SEQUENCE: 158
000

SEQ ID NO: 159         moltype =   length =
SEQUENCE: 159
000

SEQ ID NO: 160         moltype =   length =
SEQUENCE: 160
000

SEQ ID NO: 161         moltype =   length =
SEQUENCE: 161
```

```
000

SEQ ID NO: 162          moltype =   length =
SEQUENCE: 162
000

SEQ ID NO: 163          moltype =   length =
SEQUENCE: 163
000

SEQ ID NO: 164          moltype =   length =
SEQUENCE: 164
000

SEQ ID NO: 165          moltype =   length =
SEQUENCE: 165
000

SEQ ID NO: 166          moltype =   length =
SEQUENCE: 166
000

SEQ ID NO: 167          moltype =   length =
SEQUENCE: 167
000

SEQ ID NO: 168          moltype =   length =
SEQUENCE: 168
000

SEQ ID NO: 169          moltype =   length =
SEQUENCE: 169
000

SEQ ID NO: 170          moltype =   length =
SEQUENCE: 170
000

SEQ ID NO: 171          moltype =   length =
SEQUENCE: 171
000

SEQ ID NO: 172          moltype = AA  length = 7
FEATURE                 Location/Qualifiers
REGION                  1..7
                        note = VL CDR2 of IMT001-4
source                  1..7
                        mol_type = protein
                        organism = synthetic construct
SEQUENCE: 172
LMSTHAS                                                                 7

SEQ ID NO: 173          moltype =   length =
SEQUENCE: 173
000

SEQ ID NO: 174          moltype =   length =
SEQUENCE: 174
000

SEQ ID NO: 175          moltype =   length =
SEQUENCE: 175
000

SEQ ID NO: 176          moltype = AA  length = 7
FEATURE                 Location/Qualifiers
REGION                  1..7
                        note = VL CDR2 of mIMT001
source                  1..7
                        mol_type = protein
                        organism = synthetic construct
SEQUENCE: 176
LMSTHAS                                                                 7

SEQ ID NO: 177          moltype = AA  length = 9
FEATURE                 Location/Qualifiers
REGION                  1..9
                        note = VL CDR3 of 2D10.2B2
source                  1..9
```

```
                        mol_type = protein
                        organism = synthetic construct
SEQUENCE: 177
AQMIEFPLT                                                   9

SEQ ID NO: 178          moltype = AA  length = 9
FEATURE                 Location/Qualifiers
REGION                  1..9
                        note = VL CDR3 of 3B11.2G2
source                  1..9
                        mol_type = protein
                        organism = synthetic construct
SEQUENCE: 178
LQSTHFPLT                                                   9

SEQ ID NO: 179          moltype = AA  length = 9
FEATURE                 Location/Qualifiers
REGION                  1..9
                        note = VL CDR3 of 4A11.2B5
source                  1..9
                        mol_type = protein
                        organism = synthetic construct
SEQUENCE: 179
AQMLEFPLT                                                   9

SEQ ID NO: 180          moltype = AA  length = 9
FEATURE                 Location/Qualifiers
REGION                  1..9
                        note = VL CDR3 of 4G2.2G6
source                  1..9
                        mol_type = protein
                        organism = synthetic construct
SEQUENCE: 180
LQSTHFPLT                                                   9

SEQ ID NO: 181          moltype = AA  length = 9
FEATURE                 Location/Qualifiers
REGION                  1..9
                        note = VL CDR3 of 6H6.2D6
source                  1..9
                        mol_type = protein
                        organism = synthetic construct
SEQUENCE: 181
QQYSELPYT                                                   9

SEQ ID NO: 182          moltype = AA  length = 9
FEATURE                 Location/Qualifiers
REGION                  1..9
                        note = VL CDR3 of 7D8.2D8
source                  1..9
                        mol_type = protein
                        organism = synthetic construct
SEQUENCE: 182
FQGSHVPLT                                                   9

SEQ ID NO: 183          moltype = AA  length = 9
FEATURE                 Location/Qualifiers
REGION                  1..9
                        note = VL CDR3 of 12G5.D7
source                  1..9
                        mol_type = protein
                        organism = synthetic construct
SEQUENCE: 183
VQYAQFPPT                                                   9

SEQ ID NO: 184          moltype = AA  length = 9
FEATURE                 Location/Qualifiers
REGION                  1..9
                        note = VL CDR3 of 13A12.2E5
source                  1..9
                        mol_type = protein
                        organism = synthetic construct
SEQUENCE: 184
LQSTHFPLT                                                   9

SEQ ID NO: 185          moltype = AA  length = 9
FEATURE                 Location/Qualifiers
REGION                  1..9
                        note = VL CDR3 of 13G4.2F8
```

```
source                1..9
                      mol_type = protein
                      organism = synthetic construct
SEQUENCE: 185
EQYSNFPLT                                                                9

SEQ ID NO: 186        moltype = AA  length = 9
FEATURE               Location/Qualifiers
REGION                1..9
                      note = VL CDR3 of 13H12.2F8
source                1..9
                      mol_type = protein
                      organism = synthetic construct
SEQUENCE: 186
WQGTHFPLT                                                                9

SEQ ID NO: 187        moltype = AA  length = 9
FEATURE               Location/Qualifiers
REGION                1..9
                      note = VL CDR3 of 14H10.2C9
source                1..9
                      mol_type = protein
                      organism = synthetic construct
SEQUENCE: 187
WQGTHFPLT                                                                9

SEQ ID NO: 188        moltype = AA  length = 9
FEATURE               Location/Qualifiers
REGION                1..9
                      note = VL CDR3 of 15F10.2D6
source                1..9
                      mol_type = protein
                      organism = synthetic construct
SEQUENCE: 188
FQGSHVPLT                                                                9

SEQ ID NO: 189        moltype = AA  length = 9
FEATURE               Location/Qualifiers
REGION                1..9
                      note = VL CDR3 of 15G7.2A7
source                1..9
                      mol_type = protein
                      organism = synthetic construct
SEQUENCE: 189
LQGQSYPLT                                                                9

SEQ ID NO: 190        moltype = AA  length = 9
FEATURE               Location/Qualifiers
REGION                1..9
                      note = VL CDR3 of 19B5.2E6
source                1..9
                      mol_type = protein
                      organism = synthetic construct
SEQUENCE: 190
QQYSQVPYT                                                                9

SEQ ID NO: 191        moltype = AA  length = 9
FEATURE               Location/Qualifiers
REGION                1..9
                      note = VL CDR3 of 19D9.2E5
source                1..9
                      mol_type = protein
                      organism = synthetic construct
SEQUENCE: 191
WQGTHFPLT                                                                9

SEQ ID NO: 192        moltype = AA  length = 9
FEATURE               Location/Qualifiers
REGION                1..9
                      note = VL CDR3 of 20D11.2C6
source                1..9
                      mol_type = protein
                      organism = synthetic construct
SEQUENCE: 192
LQGQSYPLT                                                                9

SEQ ID NO: 193        moltype = AA  length = 9
FEATURE               Location/Qualifiers
REGION                1..9
```

```
                        note = VL CDR3 of 20H5.A3
source                  1..9
                        mol_type = protein
                        organism = synthetic construct
SEQUENCE: 193
QQYSKLPYT                                                         9

SEQ ID NO: 194          moltype = AA  length = 9
FEATURE                 Location/Qualifiers
REGION                  1..9
                        note = VL CDR3 of 23H9.2E4
source                  1..9
                        mol_type = protein
                        organism = synthetic construct
SEQUENCE: 194
QQYSQVPYT                                                         9

SEQ ID NO: 195          moltype = AA  length = 9
FEATURE                 Location/Qualifiers
REGION                  1..9
                        note = VL CDR3 of 24D12.2H9
source                  1..9
                        mol_type = protein
                        organism = synthetic construct
SEQUENCE: 195
QQYSSYPWT                                                         9

SEQ ID NO: 196          moltype = AA  length = 8
FEATURE                 Location/Qualifiers
REGION                  1..8
                        note = VL CDR3 of 846.1F5
source                  1..8
                        mol_type = protein
                        organism = synthetic construct
SEQUENCE: 196
HQYLSSLT                                                          8

SEQ ID NO: 197          moltype = AA  length = 8
FEATURE                 Location/Qualifiers
REGION                  1..8
                        note = VL CDR3 of 846.2H3
source                  1..8
                        mol_type = protein
                        organism = synthetic construct
SEQUENCE: 197
HQYLSSLT                                                          8

SEQ ID NO: 198          moltype = AA  length = 9
FEATURE                 Location/Qualifiers
REGION                  1..9
                        note = VL CDR3 of 846T.1H2
SITE                    7
                        note = misc_feature - Xaa can be any naturally occurring
                         amino acid
source                  1..9
                        mol_type = protein
                        organism = synthetic construct
SEQUENCE: 198
VQGPHFXHT                                                         9

SEQ ID NO: 199          moltype = AA  length = 9
FEATURE                 Location/Qualifiers
REGION                  1..9
                        note = VL CDR3 of 9H2.2H10
source                  1..9
                        mol_type = protein
                        organism = synthetic construct
SEQUENCE: 199
QQHYTTPLT                                                         9

SEQ ID NO: 200          moltype = AA  length = 9
FEATURE                 Location/Qualifiers
REGION                  1..9
                        note = VL CDR3 of IMT001-4
source                  1..9
                        mol_type = protein
                        organism = synthetic construct
SEQUENCE: 200
QQLVDYPLT                                                         9
```

```
SEQ ID NO: 201         moltype = AA  length = 9
FEATURE                Location/Qualifiers
REGION                 1..9
                       note = VL CDR3 of IMT006-1
source                 1..9
                       mol_type = protein
                       organism = synthetic construct
SEQUENCE: 201
AQMLEFPLT                                                          9

SEQ ID NO: 202         moltype = AA  length = 9
FEATURE                Location/Qualifiers
REGION                 1..9
                       note = VL CDR3 of IMT006-5
source                 1..9
                       mol_type = protein
                       organism = synthetic construct
SEQUENCE: 202
AQMLEFPLT                                                          9

SEQ ID NO: 203         moltype = AA  length = 9
FEATURE                Location/Qualifiers
REGION                 1..9
                       note = VL CDR3 of IMT006-8
source                 1..9
                       mol_type = protein
                       organism = synthetic construct
SEQUENCE: 203
AQMLEFPLT                                                          9

SEQ ID NO: 204         moltype = AA  length = 9
FEATURE                Location/Qualifiers
REGION                 1..9
                       note = VL CDR3 of mIMT001
source                 1..9
                       mol_type = protein
                       organism = synthetic construct
SEQUENCE: 204
QQLVDYPLT                                                          9

SEQ ID NO: 205         moltype = AA  length = 120
FEATURE                Location/Qualifiers
REGION                 1..120
                       note = VH of 2D10.2B2
source                 1..120
                       mol_type = protein
                       organism = synthetic construct
SEQUENCE: 205
QVQLQQSGPE LVKPGASVKI SCKASGYTFT DYYINWVKQR PGQGLEWIGW IYPGSNDTKY  60
NEKFKGKATL TVDTSSSTAY MQLGSLTSED SAVYFCANYF GCSGWFFDVW GTGTTVTVSS  120

SEQ ID NO: 206         moltype = AA  length = 119
FEATURE                Location/Qualifiers
REGION                 1..119
                       note = VH of 3B11.2G2
source                 1..119
                       mol_type = protein
                       organism = synthetic construct
SEQUENCE: 206
QIQLVQSGPE LKKPGETVKI SCKTSGYKFK TYVMSWVKQA PGKALKWMGW INTYSGVPTY  60
ADDFKGRFAF SLETSASTAY LEIINLKNED TATYFCARDG NYGDPMDYWG QGTSVTVSS   119

SEQ ID NO: 207         moltype = AA  length = 116
FEATURE                Location/Qualifiers
REGION                 1..116
                       note = VH of 4A11.2B5
source                 1..116
                       mol_type = protein
                       organism = synthetic construct
SEQUENCE: 207
QVQLQQSGPE LVKPGASVKI SCKASGYSFT NYYIHWVKQR PGQGLEWIGW IYPGSGNTNY  60
NEKFKGKATL TADTSSSTTN MQLSSLTSED SAVYYCSTAP GGFDVWGSGT TVTVSS      116

SEQ ID NO: 208         moltype = AA  length = 119
FEATURE                Location/Qualifiers
REGION                 1..119
                       note = VH of 4G2.2G6
source                 1..119
```

```
                        mol_type = protein
                        organism = synthetic construct
SEQUENCE: 208
QIQLVQSGPD LKKPGETVKI SCKASGYTFT TYVMSWVKQA PGKDLKWMGW INTHSGVPTY  60
ADDFKGRFDF SLETSANTAF LQINNLKNED TATYFCTRDG NDGDAMDNWG QGTSVTVSS   119

SEQ ID NO: 209          moltype = AA  length = 116
FEATURE                 Location/Qualifiers
REGION                  1..116
                        note = VH of 6H6.2D6
source                  1..116
                        mol_type = protein
                        organism = synthetic construct
SEQUENCE: 209
QIQLVQSGPE LKKPGETVKI SCKASGYTFT TYGMSWVKQA PGKGLKWMAW INTYSGVPTY  60
ADDFKGRFAF SLETSASTAY LQINNLTNED TATYFCARGP YAMDYWGQGT SVTVSS      116

SEQ ID NO: 210          moltype = AA  length = 113
FEATURE                 Location/Qualifiers
REGION                  1..113
                        note = VH of 7D8.2D8
source                  1..113
                        mol_type = protein
                        organism = synthetic construct
SEQUENCE: 210
EVQLVESGGG LVKPGGSLKL SCAASGFTFS SYAMSWVRQT PEKRLEWVAT ISDGGIYTYY  60
PDNVKGRFTI SRDNAKNNLF LQMSHLKSED TAMYYCVRDG GYWGQGTTLT VSS         113

SEQ ID NO: 211          moltype = AA  length = 122
FEATURE                 Location/Qualifiers
REGION                  1..122
                        note = VH of 12G5.D7
source                  1..122
                        mol_type = protein
                        organism = synthetic construct
SEQUENCE: 211
QVQLKQSGAE LVRPGASVKL SCKASGYTFT DYYINWVKQR PGQGLEWIAR IYPGTGNTDY  60
NEKFKGRATL TAEKSSSTAY MQLSSLTSED SAVYFCARFA YYYGSGGYFD YWGHGTTLTV  120
SS                                                                122

SEQ ID NO: 212          moltype = AA  length = 119
FEATURE                 Location/Qualifiers
REGION                  1..119
                        note = VH of 13A12.2E5
source                  1..119
                        mol_type = protein
                        organism = synthetic construct
SEQUENCE: 212
QIQLVQSGPE LKKPGETVKI SCKTSGYKFK TYVMSWVKQA PGKALKWMGW INTYSGVPTY  60
ADDFKGRFAF SLETSASTAY LEIINLKNED TATYFCARDG NYGDPMDYWG QGTSVTVSS   119

SEQ ID NO: 213          moltype = AA  length = 119
FEATURE                 Location/Qualifiers
REGION                  1..119
                        note = VH of 13G4.2F8
source                  1..119
                        mol_type = protein
                        organism = synthetic construct
SEQUENCE: 213
QVQLQQPGAE LVKPGASVKL SCKASGYTFT SYWMHWVKQR PGQGLEWIGM IHPNSGSTDY  60
NEKFKNKATL NVDKSSSTAY IQLSSLTSED SAVYYCTRWG IYYYARDYWG QGTTLTVSS   119

SEQ ID NO: 214          moltype = AA  length = 117
FEATURE                 Location/Qualifiers
REGION                  1..117
                        note = VH of 13H12.2F8
source                  1..117
                        mol_type = protein
                        organism = synthetic construct
SEQUENCE: 214
QIQLVQSGPE LKKPGETVKI SCKASGYTFT TYGMSWVKQA PGKGLKWMGW INTYSGVPTY  60
ADDFKGRFAF SLETSASTAY LQINNLKNED TATYFCAVPY EYDGAYWGQG TLVTVSA     117

SEQ ID NO: 215          moltype = AA  length = 117
FEATURE                 Location/Qualifiers
REGION                  1..117
                        note = VH of 14H10.2C9
source                  1..117
                        mol_type = protein
```

```
                         organism = synthetic construct
SEQUENCE: 215
QIQLVQSGPE LKKPGETVKI SCKASGYTFT TYGMGWVKQA PGKDLKWMGW INTYSGVPTY  60
ADDFKGRFAF SLETSASTAY LQISNLKNED TATYFCSTPY EYDGAYWGQG TLVTVSA     117

SEQ ID NO: 216           moltype = AA  length = 113
FEATURE                  Location/Qualifiers
REGION                   1..113
                         note = VH of 15F10.2D6
source                   1..113
                         mol_type = protein
                         organism = synthetic construct
SEQUENCE: 216
EVQLVESGGG LVKPGGSLKL SCAASGFAFS SYAMSWVRQT PEKRLEWVAT ISDGGVYTYY  60
TDHVKGRFTI SRDNAEDNLY LQMSHLKSED TAMYYCVRDG GYWGQGTTLT VSS         113

SEQ ID NO: 217           moltype = AA  length = 115
FEATURE                  Location/Qualifiers
REGION                   1..115
                         note = VH of 15G7.2A7
source                   1..115
                         mol_type = protein
                         organism = synthetic construct
SEQUENCE: 217
EVQLQQSGPE LVKPGASVKI SCKASGYTFT DYYMNWVKQS HGKSLEWIGD INPNNGGTNY  60
NQKFKGKATL TVDKSSSTAY MELRSLTSED SAVYYCTSGY GFPYWGQGTL VTVSA       115

SEQ ID NO: 218           moltype = AA  length = 116
FEATURE                  Location/Qualifiers
REGION                   1..116
                         note = VH of 19B5.2E6
source                   1..116
                         mol_type = protein
                         organism = synthetic construct
SEQUENCE: 218
QIQLVQSGPE LKKPGETVKI SCKASGYTFT TYAMSWVKQA PGKGLKWMGW INTYSGVPTY  60
ADDLKGRFAF SLETSASTAY LQINNLKNED TATYFCARGP YAMDYWGQGT SVTVSS      116

SEQ ID NO: 219           moltype = AA  length = 117
FEATURE                  Location/Qualifiers
REGION                   1..117
                         note = VH of 19D9.2E5
source                   1..117
                         mol_type = protein
                         organism = synthetic construct
SEQUENCE: 219
QIQLVQSGPE LKKPGETVKI SCKASGYTFT TYGMGWVKQA PGKGLKWMGW INTYSGVPTY  60
ADDFKGRFAF SLETSTSTAY LQINNLKNED MATYFCATPY EYDGAYWGQG TLVTVSA     117

SEQ ID NO: 220           moltype = AA  length = 115
FEATURE                  Location/Qualifiers
REGION                   1..115
                         note = VH of 20D11.2C6
source                   1..115
                         mol_type = protein
                         organism = synthetic construct
SEQUENCE: 220
EVQLQQSGPE LVKPGASVKI SCKASGYTFT DFYINWVKQS HGKSLEWIGD INPKNGGINY  60
NPKFKIKATL TVDKSSSTSY MDLRGLTSED SAVYYCTSGY GFPYWGQGTL VTVSA       115

SEQ ID NO: 221           moltype = AA  length = 116
FEATURE                  Location/Qualifiers
REGION                   1..116
                         note = VH of 20H5.A3
source                   1..116
                         mol_type = protein
                         organism = synthetic construct
SEQUENCE: 221
QIQLVQSGPE LKKPGESVKI SCKASGYAFT TYGMSWVQQA PGKGLKWMGW VNTYSGVPTC  60
ADDFKGRFAF SLETSASTAY LQINNLRNED TATYFCARGP YAMDYWGQGT SVTVSS      116

SEQ ID NO: 222           moltype = AA  length = 116
FEATURE                  Location/Qualifiers
REGION                   1..116
                         note = VH of 23H9.2E4
source                   1..116
                         mol_type = protein
                         organism = synthetic construct
SEQUENCE: 222
```

```
QIQLVQSGPE LKKPGETVKI SCKASGYTFT TYAMSWVKQA PGKGLKWMGW INTYSGVPTY  60
ADDLKGRFAF SLETSASTAY LQINNLKNED TATYFCARGP YAMDYWGQGT SVTVSS      116

SEQ ID NO: 223         moltype = AA  length = 120
FEATURE                Location/Qualifiers
REGION                 1..120
                       note = VH of 24D12.2H9
source                 1..120
                       mol_type = protein
                       organism = synthetic construct
SEQUENCE: 223
QVQLKQSGPG LVQPSQSLSI TCTVSGFSLT SYGVHWVRQA PGKGLEWLGV IWSGGSTDYN  60
AAFMSRLSIS KDNSKSQVFF KMNSLQADDT AIYYCAKSPD GYDVAWFGYW GQGTLVTVSA  120

SEQ ID NO: 224         moltype = AA  length = 122
FEATURE                Location/Qualifiers
REGION                 1..122
                       note = VH of 846.1F5
source                 1..122
                       mol_type = protein
                       organism = synthetic construct
SEQUENCE: 224
QIQLVQSGPE LKKPGETVKI SCKASGYTFT NYGMNWVKQA PGKGLKWMGW INTYTGEPSY  60
ADDFKGRFAF SLETSASTAY LQINNLKNED MATYFCARWG GYDGDYYAMD YWGQGTSVTV  120
SS                                                                 122

SEQ ID NO: 225         moltype = AA  length = 122
FEATURE                Location/Qualifiers
REGION                 1..122
                       note = VH of 846.2H3
source                 1..122
                       mol_type = protein
                       organism = synthetic construct
SEQUENCE: 225
QIQLVQSGPE LKKPGETVKI SCKASGYTFT NYGMNWVKQA PGKGLKWMGW INTYTGEPSY  60
ADDFKGRFAF SLETSASTAY LQINNLKNED MATYFCARWG GYDGDYYAMD YWGQGTSVTV  120
SS                                                                 122

SEQ ID NO: 226         moltype = AA  length = 118
FEATURE                Location/Qualifiers
REGION                 1..118
                       note = VH of 846T.1H2
source                 1..118
                       mol_type = protein
                       organism = synthetic construct
SEQUENCE: 226
QIQLVQSGPE LKKPGETVKI SCKASGYTFT NYGMNWVKQA PGKGLKWMGW INTNTGEPTY  60
AEEFKGRFAF SLETSASTAY LQINNLKNED TATYFCATGG GNWDFDYWGQ GTTLTVSS    118

SEQ ID NO: 227         moltype = AA  length = 115
FEATURE                Location/Qualifiers
REGION                 1..115
                       note = VH of 9H2.2H10
source                 1..115
                       mol_type = protein
                       organism = synthetic construct
SEQUENCE: 227
QVQLQQPGAE LVGPGSSVKL SCKASGYTFT NYWIHWVKQR PLQGLEWIGN IDPSDSETHY  60
NQKFKDKATL TVDKSSSTAY MQLSSLTSED SAVYYCARHG YYDYWGQGTT LTVSS       115

SEQ ID NO: 228         moltype = AA  length = 116
FEATURE                Location/Qualifiers
REGION                 1..116
                       note = VH of IMT001-4
source                 1..116
                       mol_type = protein
                       organism = synthetic construct
SEQUENCE: 228
QVQLVQSGSE LKKPGASVKV SCKASGYTFT NYGMNWVRQA PGQGLKWMGW INTNTGEPTY  60
VEEFTGRFVF SLETSVSTAY LQISSLKAED TAVYFCAPYD NFFAYWGQGT TVTVSS      116

SEQ ID NO: 229         moltype = AA  length = 116
FEATURE                Location/Qualifiers
REGION                 1..116
                       note = VH of IMT006-1
source                 1..116
                       mol_type = protein
                       organism = synthetic construct
SEQUENCE: 229
```

```
QVQLVQSGAE VKKPGASVKV SCKASGYSFT NYYMHWVRQA PGQGLEWMGW IYPGSGNTNY  60
NEKFQGRVTM TADTSISTAY MELSRLRSDD TAVYYCSTAP GGFDVWGQGT TVTVSS      116

SEQ ID NO: 230         moltype = AA  length = 116
FEATURE                Location/Qualifiers
REGION                 1..116
                       note = VH of IMT006-5
source                 1..116
                       mol_type = protein
                       organism = synthetic construct
SEQUENCE: 230
QVQLVQSGAE VKKPGASVKV SCKASGYSFT NYYMHWVRQA PGQRLEWMGW IYPGSGNTNY  60
NEKFQGRVTI TADTSASTAY MELSSLRSED TAVYYCSTAP GGFDVWGQGT TVTVSS      116

SEQ ID NO: 231         moltype = AA  length = 116
FEATURE                Location/Qualifiers
REGION                 1..116
                       note = VH of IMT006-8
source                 1..116
                       mol_type = protein
                       organism = synthetic construct
SEQUENCE: 231
QVQLVQSGAE VKKPGASVKV SCKASGYSFT NYYIHWVRQA PGQRLEWMGW IYPGSGNTNY  60
NEKFQGRVTL TADTSASTTY MELSSLRSED TAVYYCSTAP GGFDVWGQGT TVTVSS      116

SEQ ID NO: 232         moltype = AA  length = 116
FEATURE                Location/Qualifiers
REGION                 1..116
                       note = VH of mIMT001
source                 1..116
                       mol_type = protein
                       organism = synthetic construct
SEQUENCE: 232
QIQLVQSGPE LKKPGETVKI SCKASGYTFT NYGMNWVKQA PGKGLKWMGW INTNTGEPTY  60
VEEFKGRFAF SLETSASTAY LQINNLKNED TATYFCAPYD NFFAYWGQGT LVTVSA      116

SEQ ID NO: 233         moltype = AA  length = 112
FEATURE                Location/Qualifiers
REGION                 1..112
                       note = VL of 2D10.2B2
source                 1..112
                       mol_type = protein
                       organism = synthetic construct
SEQUENCE: 233
DIVMTQAAFS NPVTLGTSAS ISCRSSKSLL HSDGITYLYW YLQRPGQSPQ LLIYRMSNLA  60
SGVPDRFSGS GSGTDFTLRI SRVEAEDVGV YYCAQMIEFP LTFGAGTILE LK          112

SEQ ID NO: 234         moltype = AA  length = 112
FEATURE                Location/Qualifiers
REGION                 1..112
                       note = VL of 3B11.2G2
source                 1..112
                       mol_type = protein
                       organism = synthetic construct
SEQUENCE: 234
DVVMTQTPLT LSVAIGQPAS ISCKSSQSLL YTNGKTYLNW LLQRPGQSPK RLIYLVSKLD  60
SGVPDRFSGS GSGTDFTLKI SRVEAEDLGV YYCLQSTHFP LTFGAGTKLE LK          112

SEQ ID NO: 235         moltype = AA  length = 112
FEATURE                Location/Qualifiers
REGION                 1..112
                       note = VL of 4A11.2B5
source                 1..112
                       mol_type = protein
                       organism = synthetic construct
SEQUENCE: 235
DIVMTQAAFS NPVTLGTSAS ISCRSSKSLL HSDGITYLYW YLQRPGQSPQ LLIYRMSNLA  60
SGVPDRFSGS GSGTDFTLRI SRVEAEDVGV YYCAQMLEFP LTFGAGTKLE LK          112

SEQ ID NO: 236         moltype = AA  length = 112
FEATURE                Location/Qualifiers
REGION                 1..112
                       note = VL of 4G2.2G6
source                 1..112
                       mol_type = protein
                       organism = synthetic construct
SEQUENCE: 236
DVVMTQTPLT LSVTIGQPAS ISCKSSQSLL YTDGKTYLSW FLQRPGQSPK RLIYLVSKLD  60
SGVPDRFSGS GSGTDFTLKI SRVEAEDLGV YYCLQSTHFP LTFGAGTKLE VK          112
```

```
SEQ ID NO: 237         moltype = AA  length = 107
FEATURE                Location/Qualifiers
REGION                 1..107
                       note = VL of 6H6.2D6
source                 1..107
                       mol_type = protein
                       organism = synthetic construct
SEQUENCE: 237
DIQMTQTTSS LSASLGDRVT ISCSASQGIS NYLNWYQQKP DGTVKLLIYY TSSLHSGVPS  60
RFSGSGSGTD YSLTISNLEP EDIATYYCQQ YSELPYTFGS GTKLEIK              107

SEQ ID NO: 238         moltype = AA  length = 112
FEATURE                Location/Qualifiers
REGION                 1..112
                       note = VL of 7D8.2D8
source                 1..112
                       mol_type = protein
                       organism = synthetic construct
SEQUENCE: 238
DVLMTQTPLS LPVSLGDQAS ISCRSSQSIV HSNGNTYLEW YLQKPGQSPK LLIYKVSNRF  60
SGVPDRFSGS GSGTDFTLKI SRVEAEDLGV YYCFQGSHVP LTFGAGTKLE LK         112

SEQ ID NO: 239         moltype = AA  length = 107
FEATURE                Location/Qualifiers
REGION                 1..107
                       note = VL of 12G5.D7
source                 1..107
                       mol_type = protein
                       organism = synthetic construct
SEQUENCE: 239
DILMTQSPSS MSVSLGDTVS ITCHASQGIN SNMGWLQQKP GKSFKGLIYH ATNLEDGVPS  60
RFSGSGSGAD YSLTISSLES EDFADYYCVQ YAQFPPTFGS GTKLEIK              107

SEQ ID NO: 240         moltype = AA  length = 112
FEATURE                Location/Qualifiers
REGION                 1..112
                       note = VL of 13A12.2E5
source                 1..112
                       mol_type = protein
                       organism = synthetic construct
SEQUENCE: 240
DVVMTQTPLT LSVAIGQPAS ISCKSSQSLL YTNGKTYLNW LLQRPGQSPK RLIYLLSKLD  60
SGVPDRFSAS GSGTDFTLKI SRVEAEDLGV YYCLQSTHFP LTFGAGTKLE MK         112

SEQ ID NO: 241         moltype = AA  length = 107
FEATURE                Location/Qualifiers
REGION                 1..107
                       note = VL of 13G4.2F8
source                 1..107
                       mol_type = protein
                       organism = synthetic construct
SEQUENCE: 241
DIVMTQSQKF MSTSVGERVS ITCKASQNVG TNVAWYQQKA GQSLELLIYG ASNRHTGVPD  60
RFTGSGSGTD FTLTITNVQS EDMTNYFCEQ YSNFPLTFGA GTKLELK              107

SEQ ID NO: 242         moltype = AA  length = 112
FEATURE                Location/Qualifiers
REGION                 1..112
                       note = VL of 13H12.2F8
source                 1..112
                       mol_type = protein
                       organism = synthetic construct
SEQUENCE: 242
DVVMTQTPLT LSVTIGQPAS ISCKSSQSLF HSDGKTYLNW LLQRPGQSPK RLIYLVSKLD  60
SGVPDRFTGS GSGTDFTLKI SRVEAEDLGV YYCWQGTHFP LTFGAGTKLE MK         112

SEQ ID NO: 243         moltype = AA  length = 112
FEATURE                Location/Qualifiers
REGION                 1..112
                       note = VL of 14H10.2C9
source                 1..112
                       mol_type = protein
                       organism = synthetic construct
SEQUENCE: 243
DVVMTQTPLT LSVTIGQPAS ISCKSSQSLF DSDGKTYLNW LLQRPGQSPK RLIYLVSKLD  60
SGVPDRFTGS GSGTDFTLKI SRVEAEDLGV YYCWQGTHFP LTFGAGTKLE MK         112

SEQ ID NO: 244         moltype = AA  length = 112
```

```
FEATURE                 Location/Qualifiers
REGION                  1..112
                        note = VL of 15F10.2D6
source                  1..112
                        mol_type = protein
                        organism = synthetic construct
SEQUENCE: 244
DVLMTQTPLS LPVSLGDQAS ISCRSSQSIV HNNGNTYLEW YLQKPGQSPK LLIYKVSNRF  60
SGVPDRFSGS GSGTDFTLKI SRVEAEDLGV YYCFQGSHVP LTFGGGTKLE LK          112

SEQ ID NO: 245          moltype = AA  length = 107
FEATURE                 Location/Qualifiers
REGION                  1..107
                        note = VL of 15G7.2A7
source                  1..107
                        mol_type = protein
                        organism = synthetic construct
SEQUENCE: 245
DIQMNQSPSS LSASLGDTIS ITCRASQNIN IWLSWYQQKP GNIPQLLIYK ASNLHTGVPS  60
RFSGSGSGTD FTLTISSLQP EDIATYYCLQ GQSYPLTFGA GTKLVMK               107

SEQ ID NO: 246          moltype = AA  length = 107
FEATURE                 Location/Qualifiers
REGION                  1..107
                        note = VL of 19B5.2E6
source                  1..107
                        mol_type = protein
                        organism = synthetic construct
SEQUENCE: 246
DIQMTQTTSS LSASLGDRVT ISCSASQGIN NYLNWYQQKP DGTVKLLIYY ASSLHSGVPS  60
RFSGSGSGTD YSLTISNLEP EDIATYYCQQ YSQVPYTFGS GTKLEIK               107

SEQ ID NO: 247          moltype = AA  length = 112
FEATURE                 Location/Qualifiers
REGION                  1..112
                        note = VL of 19D9.2E5
source                  1..112
                        mol_type = protein
                        organism = synthetic construct
SEQUENCE: 247
DVVMTQTPLT LSVTIGQPAS ISCKSSQSLL HSDGKTYLNW LLQRPGQPPK RLMYLVSTLD  60
SGVPDRFTGS GSGTDFTLKI SRVEAEDLGV YYCWQGTHFP LTFGAGTKPE LK          112

SEQ ID NO: 248          moltype = AA  length = 107
FEATURE                 Location/Qualifiers
REGION                  1..107
                        note = VL of 20D11.2C6
source                  1..107
                        mol_type = protein
                        organism = synthetic construct
SEQUENCE: 248
DIQMNQSPSS LSASLGDTIT ITCRASQNIY IWLSWYQQKP GNIPKLLIYK ASNLHTGVPS  60
RFSGSGSGTD FTLTISTLQP EDIATYFCLQ GQSYPLTFGA GTKLEMK               107

SEQ ID NO: 249          moltype = AA  length = 107
FEATURE                 Location/Qualifiers
REGION                  1..107
                        note = VL of 20H5.A3
source                  1..107
                        mol_type = protein
                        organism = synthetic construct
SEQUENCE: 249
DIQMTQTTSS LSASLGDRVT INCSASQDIS NYLNWYQQKP DGTVKLLIYY TSSLLSGVPS  60
RFSGSGSGTD YSLTISNLEP EDIATYFCQQ YSKLPYTFGS GTHLEIK               107

SEQ ID NO: 250          moltype = AA  length = 107
FEATURE                 Location/Qualifiers
REGION                  1..107
                        note = VL of 23H9.2E4
source                  1..107
                        mol_type = protein
                        organism = synthetic construct
SEQUENCE: 250
DIQMTQTTSS LSASLGDRVT ISCSASQGIN NYLNWYQQKP DGTVKLLIYY ASSLHSGVPS  60
RFSGSGSGTD YSLTISNLEP EDIATYYCQQ YSQVPYTFGS GTKLEIK               107

SEQ ID NO: 251          moltype = AA  length = 107
FEATURE                 Location/Qualifiers
REGION                  1..107
```

```
                        note = VL of 24D12.2H9
source                  1..107
                        mol_type = protein
                        organism = synthetic construct
SEQUENCE: 251
DIVMTQSHKF MSTSVGDRVS ITCKASQDVR TAVAWYQQKP GQSPKLLIYW ASTRHTGVPD  60
RFTGSGSGTD FTLTLSNVQS EDLADYFCQQ YSSYPWTFGG GTKLEIK               107

SEQ ID NO: 252          moltype = AA  length = 112
FEATURE                 Location/Qualifiers
REGION                  1..112
                        note = VL of 846.1F5
source                  1..112
                        mol_type = protein
                        organism = synthetic construct
SEQUENCE: 252
NIMMTQSPSS LAVSAGEKVT MSCKSSQSVL YSSNQKNYLA WYQQKPGQSP KLLIYWASTR  60
ESGVPDRFTG SGSGTDFTLT ISSVQPEDLA VYYCHQYLSS LTFGAGTKLE LK          112

SEQ ID NO: 253          moltype = AA  length = 112
FEATURE                 Location/Qualifiers
REGION                  1..112
                        note = VL of 846.2H3
source                  1..112
                        mol_type = protein
                        organism = synthetic construct
SEQUENCE: 253
NIMMTQSPSS LAVSAGEKVT MSCKSSQSVL YSSNQKNYLA WYQQKPGQSP KLLIYWASTR  60
ESGVPDRFTG SGSGTDFTLT ISSVQPEDLA VYYCHQYLSS LTFGAGTKLE LK          112

SEQ ID NO: 254          moltype = AA  length = 112
FEATURE                 Location/Qualifiers
REGION                  1..112
                        note = VL of 846T.1H2
source                  1..112
                        mol_type = protein
                        organism = synthetic construct
SEQUENCE: 254
DVVMTQTPLT LSVTIGQPAS ISCKSSQSLL YSNGKTYLNW LLQRPGQSPK RLIYLVSKLD  60
SGVPDRFTGS GSGTDFTLKI SRVEAEDLGV YYCVQGTHFP QTFGGGTKLE IK          112

SEQ ID NO: 255          moltype = AA  length = 107
FEATURE                 Location/Qualifiers
REGION                  1..107
                        note = VL of 9H2.2H10
source                  1..107
                        mol_type = protein
                        organism = synthetic construct
SEQUENCE: 255
DIVMTQSHKF MSTSVGDRVS ITCKASQDVS TAVAWYQQKP GQSPKLLIYW ASTRHTGVPD  60
RFTGSGSGTD YTLTISSVQA EDLALYYCQQ HYTTPLTFGA GTKLELK               107

SEQ ID NO: 256          moltype = AA  length = 112
FEATURE                 Location/Qualifiers
REGION                  1..112
                        note = VL of IMT001-4
source                  1..112
                        mol_type = protein
                        organism = synthetic construct
SEQUENCE: 256
DIVLTQSPLS LPVTPGEPAS ISCRSSKSLL YKDGKTYLNW FLQKPGQSPQ LLIYLMSTHA  60
SGVPDRFSGS GSGTDFTLKI SRVEAEDVGV YYCQQLVDYP LTFGGGTKLE IK          112

SEQ ID NO: 257          moltype = AA  length = 112
FEATURE                 Location/Qualifiers
REGION                  1..112
                        note = VL of IMT006-1
source                  1..112
                        mol_type = protein
                        organism = synthetic construct
SEQUENCE: 257
DIVMTQTPLS LSVTPGQPAS ISCKSSKSLL HSDGITYLYW YLQKPGQSPQ LLIYRMSNLA  60
SGVPDRFSGS GSGTDFTLKI SRVEAEDVGV YYCAQMLEFP LTFGQGTKLE IK          112

SEQ ID NO: 258          moltype = AA  length = 112
FEATURE                 Location/Qualifiers
REGION                  1..112
                        note = VL of IMT006-5
source                  1..112
```

```
                        mol_type = protein
                        organism = synthetic construct
SEQUENCE: 258
DIVMTQTPLS LSVTPGQPAS ISCKSSKSLL HSDGITYLYW YLQKPGQSPQ LLIYRMSNLA  60
SGVPDRFSGS GSGTDFTLKI SRVEAEDVGV YYCAQMLEFP LTFGQGTKLE IK          112

SEQ ID NO: 259          moltype = AA  length = 112
FEATURE                 Location/Qualifiers
REGION                  1..112
                        note = VL of IMT006-8
source                  1..112
                        mol_type = protein
                        organism = synthetic construct
SEQUENCE: 259
DIVMTQSPLS LPVTPGEPAS ISCRSSKSLL HSDGITYLYW YLQKPGQSPQ LLIYRMSNLA  60
SGVPDRFSGS GSGTDFTLKI SRVEAEDVGV YYCAQMLEFP LTFGQGTKLE IK          112

SEQ ID NO: 260          moltype = AA  length = 112
FEATURE                 Location/Qualifiers
REGION                  1..112
                        note = VL of mIMT001
source                  1..112
                        mol_type = protein
                        organism = synthetic construct
SEQUENCE: 260
DIVITQDELS NPVTSGESVS ISCRSSKSLL YKDGKTYLNW FLQRPGQSPQ LLIYLMSTHA  60
SGVSDRFSGS GSGTDFTLEI SRVKAEDVGV YYCQQLVDYP LTFGAGTKLE LK          112

SEQ ID NO: 261          moltype = AA  length = 461
FEATURE                 Location/Qualifiers
REGION                  1..461
                        note = hIgG4 (S228P) Constant of IMT001-4
source                  1..461
                        mol_type = protein
                        organism = synthetic construct
SEQUENCE: 261
MGSTAILGLL LAVLQGVCAQ VQLVQSGSEL KKPGASVKVS CKASGYTFTN YGMNWVRQAP  60
GQGLKWMGWI NTNTGEPTYV EEFTGRFVFS LETSVSTAYL QISSLKAEDT AVYFCAPYDN  120
FFAYWGQGTT VTVSSASTKG PSVFPLAPCS RSTSESTAAL GCLVKDYFPE PVTVSWNSGA  180
LTSGVHTFPA VLQSSGLYSL SSVVTVPSSS LGTKTYTCNV DHKPSNTKVD KRVESKYGPP  240
CPPCPAPEFL GGPSVFLFPP KPKDTLMISR TPEVTCVVVD VSQEDPEVQF NWYVDGVEVH  300
NAKTKPREEQ FNSTYRVVSV LTVLHQDWLN GKEYKCKVSN KGLPSSIEKT ISKAKGQPRE  360
PQVYTLPPSQ EEMTKNQVSL TCLVKGFYPS DIAVEWESNG QPENNYKTTP PVLDSDGSFF  420
LYSRLTVDKS RWQEGNVFSC SVMHEALHNH YTQKSLSLSL G                      461

SEQ ID NO: 262          moltype = AA  length = 241
FEATURE                 Location/Qualifiers
REGION                  1..241
                        note = hKappa Constant of IMT001-4
source                  1..241
                        mol_type = protein
                        organism = synthetic construct
SEQUENCE: 262
MDMRVPAQLL GLLLLWLRGA RCDIVLTQSP LSLPVTPGEP ASISCRSSKS LLYKDGKTYL  60
NWFLQKPGQS PQLLIYLMST HASGVPDRFS GSGSGTDFTL KISRVEAEDV GVYYCQQLVD  120
YPLTFGGGTK LEIKRTVAAP SVFIFPPSDE QLKSGTASVV CLLNNFYPRE AKVQWKVDNA  180
LQSGNSQESV TEQDSKDSTY SLSSTLTLSK ADYEKHKVYA CEVTHQGLSS PVTKSFNRGE  240
C                                                                  241

SEQ ID NO: 263          moltype = AA  length = 466
FEATURE                 Location/Qualifiers
REGION                  1..466
                        note = hIgG4 (S228P) Constant of IMT006-4
source                  1..466
                        mol_type = protein
                        organism = synthetic construct
SEQUENCE: 263
MDPKGSLSWR ILLFLSLAFE LSYGQVQLVQ SGAEVKKPGA SVKVSCKASG YSFTNYYMHW  60
VRQAPGQGLE WMGWIYPGSG NTNYNEKFQG RVTMTADTSI STAYMELSRL RSDDTAVYYC  120
STAPGGFDVW GQGTTVTVSS ASTKGPSVFP LAPCSRSTSE STAALGCLVK DYFPEPVTVS  180
WNSGALTSGV HTFPAVLQSS GLYSLSSVVT VPSSSLGTKT YTCNVDHKPS NTKVDKRVES  240
KYGPPCPPCP APEFLGGPSV FLFPPKPKDT LMISRTPEVT CVVVDVSQED PEVQFNWYVD  300
GVEVHNAKTK PREEQFNSTY RVVSVLTVLH QDWLNGKEYK CKVSNKGLPS SIEKTISKAK  360
GQPREPQVYT LPPSQEEMTK NQVSLTCLVK GFYPSDIAVE WESNGQPENN YKTTPPVLDS  420
DGSFFLYSRL TVDKSRWQEG NVFSCSVMHE ALHNHYTQKS LSLSLG                 466

SEQ ID NO: 264          moltype = AA  length = 239
FEATURE                 Location/Qualifiers
REGION                  1..239
```

```
                         note = hKappa Constant of IMT006-4
source                   1..239
                         mol_type = protein
                         organism = synthetic construct
SEQUENCE: 264
METDTLLLWV LLLWVPGSTG DIVMTQTPLS LSVTPGQPAS ISCKSSKSLL HSDGITYLYW  60
YLQKPGQSPQ LLIYRMSNLA SGVPDRFSGS GSGTDFTLKI SRVEAEDVGV YYCAQMLEFP  120
LTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 265           moltype = AA  length = 466
FEATURE                  Location/Qualifiers
REGION                   1..466
                         note = hIgG4 (S228P) Constant of IMT006-5
source                   1..466
                         mol_type = protein
                         organism = synthetic construct
SEQUENCE: 265
MDPKGSLSWR ILLFLSLAFE LSYGQVQLVQ SGAEVKKPGA SVKVSCKASG YSFTNYYMHW  60
VRQAPGQRLE WMGWIYPGSG NTNYNEKFQG RVTITADTSA STAYMELSSL RSEDTAVYYC  120
STAPGGFDVW GQGTTVTVSS ASTKGPSVFP LAPCSRSTSE STAALGCLVK DYFPEPVTVS  180
WNSGALTSGV HTFPAVLQSS GLYSLSSVVT VPSSSLGTKT YTCNVDHKPS NTKVDKRVES  240
KYGPPCPPCP APEFLGGPSV FLFPPKPKDT LMISRTPEVT CVVVDVSQED PEVQFNWYVD  300
GVEVHNAKTK PREEQFNSTY RVVSVLTVLH QDWLNGKEYK CKVSNKGLPS SIEKTISKAK  360
GQPREPQVYT LPPSQEEMTK NQVSLTCLVK GFYPSDIAVE WESNGQPENN YKTTPPVLDS  420
DGSFFLYSRL TVDKSRWQEG NVFSCSVMHE ALHNHYTQKS LSLSLG                466

SEQ ID NO: 266           moltype = AA  length = 239
FEATURE                  Location/Qualifiers
REGION                   1..239
                         note = hKappa Constant of IMT006-5
source                   1..239
                         mol_type = protein
                         organism = synthetic construct
SEQUENCE: 266
METDTLLLWV LLLWVPGSTG DIVMTQTPLS LSVTPGQPAS ISCKSSKSLL HSDGITYLYW  60
YLQKPGQSPQ LLIYRMSNLA SGVPDRFSGS GSGTDFTLKI SRVEAEDVGV YYCAQMLEFP  120
LTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 267           moltype = AA  length = 466
FEATURE                  Location/Qualifiers
REGION                   1..466
                         note = hIgG4 (S228P) Constant of IMT006-8
source                   1..466
                         mol_type = protein
                         organism = synthetic construct
SEQUENCE: 267
MDPKGSLSWR ILLFLSLAFE LSYGQVQLVQ SGAEVKKPGA SVKVSCKASG YSFTNYYIHW  60
VRQAPGQRLE WMGWIYPGSG NTNYNEKFQG RVTLTADTSA STTYMELSSL RSEDTAVYYC  120
STAPGGFDVW GQGTTVTVSS ASTKGPSVFP LAPCSRSTSE STAALGCLVK DYFPEPVTVS  180
WNSGALTSGV HTFPAVLQSS GLYSLSSVVT VPSSSLGTKT YTCNVDHKPS NTKVDKRVES  240
KYGPPCPPCP APEFLGGPSV FLFPPKPKDT LMISRTPEVT CVVVDVSQED PEVQFNWYVD  300
GVEVHNAKTK PREEQFNSTY RVVSVLTVLH QDWLNGKEYK CKVSNKGLPS SIEKTISKAK  360
GQPREPQVYT LPPSQEEMTK NQVSLTCLVK GFYPSDIAVE WESNGQPENN YKTTPPVLDS  420
DGSFFLYSRL TVDKSRWQEG NVFSCSVMHE ALHNHYTQKS LSLSLG                466

SEQ ID NO: 268           moltype = AA  length = 239
FEATURE                  Location/Qualifiers
REGION                   1..239
                         note = hKappa Constant of IMT006-8
source                   1..239
                         mol_type = protein
                         organism = synthetic construct
SEQUENCE: 268
METDTLLLWV LLLWVPGSTG DIVMTQSPLS LPVTPGEPAS ISCRSSKSLL HSDGITYLYW  60
YLQKPGQSPQ LLIYRMSNLA SGVPDRFSGS GSGTDFTLKI SRVEAEDVGV YYCAQMLEFP  120
LTFGQGTKLE IKRTVAAPSV FIFPPSDEQL KSGTASVVCL LNNFYPREAK VQWKVDNALQ  180
SGNSQESVTE QDSKDSTYSL SSTLTLSKAD YEKHKVYACE VTHQGLSSPV TKSFNRGEC   239

SEQ ID NO: 269           moltype = AA  length = 8
FEATURE                  Location/Qualifiers
REGION                   1..8
                         note = Synthetic
SITE                     8
                         note = MISC_FEATURE - X = G or absent
source                   1..8
                         mol_type = protein
                         organism = synthetic construct
```

```
SEQUENCE: 269
GYTFTNYX                                                    8

SEQ ID NO: 270          moltype = AA  length = 8
FEATURE                 Location/Qualifiers
REGION                  1..8
                        note = Synthetic
SITE                    1
                        note = MISC_FEATURE - X = I or absent
SITE                    8
                        note = MISC_FEATURE - X =S or absent
source                  1..8
                        mol_type = protein
                        organism = synthetic construct
SEQUENCE: 270
XNTNTGEX                                                    8

SEQ ID NO: 271          moltype =   length =
SEQUENCE: 271
000

SEQ ID NO: 272          moltype = AA  length = 16
FEATURE                 Location/Qualifiers
REGION                  1..16
                        note = Synthetic
SITE                    1
                        note = MISC_FEATURE - X = R or absent
SITE                    2
                        note = MISC_FEATURE - X = S or absent
SITE                    3
                        note = MISC_FEATURE - X = S or absent
SITE                    4
                        note = MISC_FEATURE - X = K or Q
SITE                    9
                        note = MISC_FEATURE - X = S or K
SITE                    10
                        note = MISC_FEATURE - X = N or D
SITE                    15
                        note = MISC_FEATURE - X = L or absent
SITE                    16
                        note = MISC_FEATURE - X = N or absent
source                  1..16
                        mol_type = protein
                        organism = synthetic construct
SEQUENCE: 272
XXXXSLLYXX GKTYXX                                           16

SEQ ID NO: 273          moltype =   length =
SEQUENCE: 273
000

SEQ ID NO: 274          moltype =   length =
SEQUENCE: 274
000

SEQ ID NO: 275          moltype = AA  length = 7
FEATURE                 Location/Qualifiers
REGION                  1..7
                        note = Synthetic
source                  1..7
                        mol_type = protein
                        organism = synthetic construct
SEQUENCE: 275
GYTFTTY                                                     7

SEQ ID NO: 276          moltype = AA  length = 8
FEATURE                 Location/Qualifiers
REGION                  1..7
                        note = Synthetic
source                  1..8
                        mol_type = protein
                        organism = synthetic construct
SEQUENCE: 276
INTYSGVP                                                    8

SEQ ID NO: 277          moltype = AA  length = 10
FEATURE                 Location/Qualifiers
REGION                  1..10
                        note = Synthetic
```

```
SITE                  1
                      note = MISC_FEATURE - X = A or S
SITE                  2
                      note = MISC_FEATURE - X = V or T
source                1..10
                      mol_type = protein
                      organism = synthetic construct
SEQUENCE: 277
XXPYEYDGAY                                                    10

SEQ ID NO: 278        moltype = AA  length = 11
FEATURE               Location/Qualifiers
REGION                1..11
                      note = Synthetic
SITE                  4
                      note = MISC_FEATURE - X = L or F
SITE                  5
                      note = MISC_FEATURE - X = D or H
source                1..11
                      mol_type = protein
                      organism = synthetic construct
SEQUENCE: 278
QSLXXSDGKT Y                                                  11

SEQ ID NO: 279        moltype =   length =
SEQUENCE: 279
000

SEQ ID NO: 280        moltype = AA  length = 9
FEATURE               Location/Qualifiers
REGION                1..9
                      note = Synthetic
source                1..9
                      mol_type = protein
                      organism = synthetic construct
SEQUENCE: 280
WQGTHFPLT                                                     9

SEQ ID NO: 281        moltype = AA  length = 8
FEATURE               Location/Qualifiers
REGION                1..8
                      note = Synthetic
SITE                  3
                      note = MISC_FEATURE - X = S or T
SITE                  6
                      note = MISC_FEATURE - X = D or N
SITE                  8
                      note = MISC_FEATURE - X = G or absent
source                1..8
                      mol_type = protein
                      organism = synthetic construct
SEQUENCE: 281
GYXFTXYX                                                      8

SEQ ID NO: 282        moltype =   length =
SEQUENCE: 282
000

SEQ ID NO: 283        moltype =   length =
SEQUENCE: 283
000

SEQ ID NO: 284        moltype =   length =
SEQUENCE: 284
000

SEQ ID NO: 285        moltype =   length =
SEQUENCE: 285
000

SEQ ID NO: 286        moltype =   length =
SEQUENCE: 286
000

SEQ ID NO: 287        moltype = AA  length = 7
FEATURE               Location/Qualifiers
REGION                1..7
                      note = Synthetic
SITE                  3
```

```
                         note = MISC_FEATURE - X = A or T
source                   1..7
                         mol_type = protein
                         organism = synthetic construct
SEQUENCE: 287
GYXFTTY                                                                    7

SEQ ID NO: 288           moltype = AA  length = 8
FEATURE                  Location/Qualifiers
REGION                   1..8
                         note = Synthetic
SITE                     1
                         note = MISC_FEATURE - X = I or V
source                   1..8
                         mol_type = protein
                         organism = synthetic construct
SEQUENCE: 288
XNTYSGVP                                                                   8

SEQ ID NO: 289           moltype = AA  length = 9
FEATURE                  Location/Qualifiers
REGION                   1..9
                         note = Synthetic
source                   1..9
                         mol_type = protein
                         organism = synthetic construct
SEQUENCE: 289
ARGPYAMDY                                                                  9

SEQ ID NO: 290           moltype = AA  length = 6
FEATURE                  Location/Qualifiers
REGION                   1..6
                         note = Synthetic
SITE                     2
                         note = MISC_FEATURE - X = G or D
SITE                     4
                         note = MISC_FEATURE - X = S or N
source                   1..6
                         mol_type = protein
                         organism = synthetic construct
SEQUENCE: 290
QXIXNY                                                                     6

SEQ ID NO: 291           moltype =   length =
SEQUENCE: 291
000

SEQ ID NO: 292           moltype = AA  length = 9
FEATURE                  Location/Qualifiers
REGION                   1..9
                         note = Synthetic
SITE                     5
                         note = MISC_FEATURE - X = E, Q or K
SITE                     6
                         note = MISC_FEATURE - X = L or V
source                   1..9
                         mol_type = protein
                         organism = synthetic construct
SEQUENCE: 292
QQYSXXPYT                                                                  9

SEQ ID NO: 293           moltype = AA  length = 7
FEATURE                  Location/Qualifiers
REGION                   1..7
                         note = Synthetic
SITE                     7
                         note = MISC_FEATURE - X = F or Y
source                   1..7
                         mol_type = protein
                         organism = synthetic construct
SEQUENCE: 293
GYTFTDX                                                                    7

SEQ ID NO: 294           moltype = AA  length = 8
FEATURE                  Location/Qualifiers
REGION                   1..8
                         note = Synthetic
SITE                     4
                         note = MISC_FEATURE - X = N or K
```

```
source                1..8
                      mol_type = protein
                      organism = synthetic construct
SEQUENCE: 294
INPXNGGI                                                        8

SEQ ID NO: 295        moltype = AA  length = 8
FEATURE               Location/Qualifiers
REGION                1..8
                      note = Synthetic
source                1..8
                      mol_type = protein
                      organism = synthetic construct
SEQUENCE: 295
TSGYGFPY                                                        8

SEQ ID NO: 296        moltype = AA  length = 6
FEATURE               Location/Qualifiers
REGION                1..6
                      note = Synthetic
SITE                  4
                      note = MISC_FEATURE - X = N or Y
source                1..6
                      mol_type = protein
                      organism = synthetic construct
SEQUENCE: 296
QNIXIW                                                          6

SEQ ID NO: 297        moltype =   length =
SEQUENCE: 297
000

SEQ ID NO: 298        moltype = AA  length = 9
FEATURE               Location/Qualifiers
REGION                1..9
                      note = Synthetic
source                1..9
                      mol_type = protein
                      organism = synthetic construct
SEQUENCE: 298
LQGQSYPLT                                                       9

SEQ ID NO: 299        moltype = AA  length = 7
FEATURE               Location/Qualifiers
REGION                1..7
                      note = Synthetic
source                1..7
                      mol_type = protein
                      organism = synthetic construct
SEQUENCE: 299
GYKFKTY                                                         7

SEQ ID NO: 300        moltype = AA  length = 8
FEATURE               Location/Qualifiers
REGION                1..8
                      note = Synthetic
source                1..8
                      mol_type = protein
                      organism = synthetic construct
SEQUENCE: 300
INTYSGVP                                                        8

SEQ ID NO: 301        moltype = AA  length = 12
FEATURE               Location/Qualifiers
REGION                1..12
                      note = Synthetic
source                1..12
                      mol_type = protein
                      organism = synthetic construct
SEQUENCE: 301
ARDGNYGDPM DY                                                   12

SEQ ID NO: 302        moltype = AA  length = 11
FEATURE               Location/Qualifiers
REGION                1..11
                      note = Synthetic
source                1..11
                      mol_type = protein
                      organism = synthetic construct
```

```
SEQUENCE: 302
QSLLYTNGKT Y                                                    11

SEQ ID NO: 303          moltype =   length =
SEQUENCE: 303
000

SEQ ID NO: 304          moltype = AA  length = 9
FEATURE                 Location/Qualifiers
REGION                  1..9
                        note = Synthetic
source                  1..9
                        mol_type = protein
                        organism = synthetic construct
SEQUENCE: 304
LQSTHFPLT                                                       9

SEQ ID NO: 305          moltype = AA  length = 45
FEATURE                 Location/Qualifiers
REGION                  1..45
                        note = Tim-3/Gal3 crosslink 1
REGION                  1..21
                        note = MISC_FEATURE - Tim-3 fragment
SITE                    11
                        note = MISC_FEATURE - Tim-3 crosslink residue
REGION                  22..45
                        note = MISC_FEATURE - Gal3 fragment
SITE                    35
                        note = MISC_FEATURE - Gal3 crosslink residue
source                  1..45
                        mol_type = protein
                        organism = synthetic construct
SEQUENCE: 305
GDVSLTIENV TLADSGIYCC RIALDFQRGN DVAFHFNPRF NENNR               45

SEQ ID NO: 306          moltype = AA  length = 19
FEATURE                 Location/Qualifiers
REGION                  1..19
                        note = Tim-3/Gal3 crosslink 2
REGION                  1..11
                        note = MISC_FEATURE - Tim-3 fragment
SITE                    5
                        note = MISC_FEATURE - Tim-3 crosslink residue
REGION                  12..19
                        note = MISC_FEATURE - Gal3 fragment
SITE                    14
                        note = MISC_FEATURE - Gal3 crosslink residue
source                  1..19
                        mol_type = protein
                        organism = synthetic construct
SEQUENCE: 306
IYCCRIQIPG IFQRGNDVA                                            19

SEQ ID NO: 307          moltype = AA  length = 47
FEATURE                 Location/Qualifiers
REGION                  1..47
                        note = Tim-3/Gal3 crosslink 3
REGION                  1..30
                        note = MISC_FEATURE - Tim-3 fragment
SITE                    15
                        note = MISC_FEATURE - Tim-3 crosslink residue
REGION                  31..47
                        note = MISC_FEATURE - Gal3 fragment
SITE                    41
                        note = MISC_FEATURE - Gal3 crosslink residue
source                  1..47
                        mol_type = protein
                        organism = synthetic construct
SEQUENCE: 307
YWLNGDFRKG DVSLTIENVT LADSGIYCCR GNDVAFHFNP RFNENNR             47

SEQ ID NO: 308          moltype = AA  length = 25
FEATURE                 Location/Qualifiers
REGION                  1..25
                        note = Tim-3/Gal3 crosslink 4
REGION                  1..7
                        note = MISC_FEATURE - Tim-3 fragment
SITE                    6
                        note = MISC_FEATURE - Tim-3 crosslink residue
```

```
REGION                8..25
                      note = MISC_FEATURE - Gal3 fragment
SITE                  16
                      note = MISC_FEATURE - Gal3 crosslink residue
source                1..25
                      mol_type = protein
                      organism = synthetic construct
SEQUENCE: 308
TIENVTLNPR FNENNRRVIV CNTKL                                       25

SEQ ID NO: 309        moltype = AA  length = 40
FEATURE               Location/Qualifiers
REGION                1..40
                      note = Tim-3/Gal3 crosslink 5
REGION                1..33
                      note = MISC_FEATURE - Tim-3 fragment
SITE                  12
                      note = MISC_FEATURE - Tim-3 crosslink residue
REGION                34..40
                      note = MISC_FEATURE - Gal3 fragment
SITE                  39
                      note = MISC_FEATURE - Gal3 crosslink residue
source                1..40
                      mol_type = protein
                      organism = synthetic construct
SEQUENCE: 309
KGDVSLTIEN VTLADSGIYC CRIQIPGIMN DEKFNENNRR                       40

SEQ ID NO: 310        moltype = AA  length = 40
FEATURE               Location/Qualifiers
REGION                1..40
                      note = Tim-3/Gal3 crosslink 6
REGION                1..33
                      note = MISC_FEATURE - Tim-3 fragment
SITE                  22
                      note = MISC_FEATURE - Tim-3 crosslink residue
REGION                34..40
                      note = MISC_FEATURE - Gal3 fragment
SITE                  39
                      note = MISC_FEATURE - Gal3 crosslink residue
source                1..40
                      mol_type = protein
                      organism = synthetic construct
SEQUENCE: 310
KGDVSLTIEN VTLADSGIYC CRIQIPGIMN DEKFNENNRR                       40

SEQ ID NO: 311        moltype = AA  length = 14
FEATURE               Location/Qualifiers
REGION                1..14
                      note = Tim-3/Gal3 crosslink 7
REGION                1..7
                      note = MISC_FEATURE - Tim-3 fragment
SITE                  2
                      note = MISC_FEATURE - Tim-3 crosslink residue
REGION                8..14
                      note = MISC_FEATURE - Gal3 fragment
SITE                  13
                      note = MISC_FEATURE - Gal3 crosslink residue
source                1..14
                      mol_type = protein
                      organism = synthetic construct
SEQUENCE: 311
VTLADSGFNE NNRR                                                   14

SEQ ID NO: 312        moltype = AA  length = 16
FEATURE               Location/Qualifiers
REGION                1..16
                      note = Tim-3/Gal3 crosslink 8
REGION                1..7
                      note = MISC_FEATURE - Tim-3 fragment
SITE                  2
                      note = MISC_FEATURE - Tim-3 crosslink residue
REGION                8..16
                      note = MISC_FEATURE - Gal3 fragment
SITE                  13
                      note = MISC_FEATURE - Gal3 crosslink residue
source                1..16
                      mol_type = protein
                      organism = synthetic construct
```

-continued

```
SEQUENCE: 312
VTLADSGFNE NNRRVI                                               16

SEQ ID NO: 313          moltype = AA  length = 48
FEATURE                 Location/Qualifiers
REGION                  1..48
                        note = Tim-3/Gal3 crosslink 9
REGION                  1..28
                        note = MISC_FEATURE - Tim-3 fragment
SITE                    17
                        note = MISC_FEATURE - Tim-3 crosslink residue
REGION                  29..48
                        note = MISC_FEATURE - Gal3 fragment
SITE                    40
                        note = MISC_FEATURE - Gal3 crosslink residue
source                  1..48
                        mol_type = protein
                        organism = synthetic construct
SEQUENCE: 313
DVSLTIENVT LADSGIYCCR IQIPGIMNEN NRRVIVCNTK LDNNWGRE            48

SEQ ID NO: 314          moltype = AA  length = 31
FEATURE                 Location/Qualifiers
REGION                  1..31
                        note = Human Tim-3 70-100
source                  1..31
                        mol_type = protein
                        organism = synthetic construct
SEQUENCE: 314
FRKGDVSLTI ENVTLADSGI YCCRIQIPGI M                              31

SEQ ID NO: 315          moltype = AA  length = 31
FEATURE                 Location/Qualifiers
REGION                  1..31
                        note = Human Gal3 150-180
source                  1..31
                        mol_type = protein
                        organism = synthetic construct
SEQUENCE: 315
QRGNDVAFHF NPRFNENNRR VIVCNTKLDN N                              31
```